US010689443B2

(12) United States Patent
Wang et al.

(10) Patent No.: US 10,689,443 B2
(45) Date of Patent: Jun. 23, 2020

(54) HUMANIZED MONOCLONAL ANTIBODIES AND METHODS OF USE FOR THE DIAGNOSIS AND TREATMENT OF COLON AND PANCREAS CANCER

(71) Applicant: PRECISION BIOLOGICS, INC., Rockville, MD (US)

(72) Inventors: Xue-Ping Wang, Port Washington, NY (US); Philip M. Arlen, Bethesda, MD (US)

(73) Assignee: PRECISION BIOLOGICS, INC., Rockville, MD (US)

( * ) Notice: Subject to any disclaimer, the term of this patent is extended or adjusted under 35 U.S.C. 154(b) by 0 days.

(21) Appl. No.: 15/934,526

(22) Filed: Mar. 23, 2018

(65) Prior Publication Data

US 2018/0265583 A1 Sep. 20, 2018

Related U.S. Application Data

(62) Division of application No. 14/655,982, filed as application No. PCT/US2013/078290 on Dec. 30, 2013, now Pat. No. 9,938,344.

(60) Provisional application No. 61/747,067, filed on Dec. 28, 2012.

(51) Int. Cl.

| | |
|---|---|
| ***C07K 16/00*** | (2006.01) |
| ***C07K 16/28*** | (2006.01) |
| ***G01N 33/574*** | (2006.01) |
| ***A61K 39/395*** | (2006.01) |
| ***A61K 45/06*** | (2006.01) |
| *A61K 39/00* | (2006.01) |

(52) U.S. Cl.

CPC ...... *C07K 16/2806* (2013.01); *A61K 39/3955* (2013.01); *A61K 45/06* (2013.01); *C07K 16/2803* (2013.01); *G01N 33/57419* (2013.01); *G01N 33/57438* (2013.01); *G01N 33/57484* (2013.01); *A61K 2039/505* (2013.01); *C07K 2317/24* (2013.01); *C07K 2317/34* (2013.01); *C07K 2317/732* (2013.01); *C07K 2317/734* (2013.01); *C07K 2317/92* (2013.01); *G01N 2333/70507* (2013.01)

(58) Field of Classification Search

None

See application file for complete search history.

(56) References Cited

U.S. PATENT DOCUMENTS

| | | | | |
|---|---|---|---|---|
| 5,530,101 | A * | 6/1996 | Queen | C07K 16/00 424/133.1 |
| RE39,760 | E | 8/2007 | Tsang et al. | |
| 7,314,622 | B2 | 1/2008 | Arlen et al. | |
| 7,763,720 | B2 | 7/2010 | Arlen et al. | |
| 7,829,678 | B2 | 11/2010 | Bristol et al. | |
| 8,470,326 | B2 * | 6/2013 | Arlen | C07K 16/303 424/155.1 |
| 8,524,456 | B2 | 9/2013 | Bristol et al. | |
| 8,535,667 | B2 | 9/2013 | Arlen et al. | |
| 8,802,090 | B2 | 8/2014 | Bristol et al. | |
| 9,034,588 | B2 | 5/2015 | Arlen et al. | |
| 2006/0228363 | A1 | 10/2006 | Arlen et al. | |
| 2008/0031873 | A1 | 2/2008 | Fasick et al. | |
| 2008/0200654 | A1 | 8/2008 | Kataoka et al. | |
| 2008/0227965 | A1 | 9/2008 | Arlen et al. | |
| 2011/0158902 | A1 | 6/2011 | Arlen et al. | |
| 2014/0369926 | A1 | 12/2014 | Bristol et al. | |
| 2015/0104464 | A1 | 4/2015 | Arlen et al. | |

FOREIGN PATENT DOCUMENTS

| | | |
|---|---|---|
| WO | WO2002/074251 * | 9/2002 |
| WO | WO 2002074251 | 9/2002 |
| WO | WO 2006004950 | 1/2006 |
| WO | WO 2006028197 | 3/2006 |
| WO | WO 2011163401 | 12/2011 |

OTHER PUBLICATIONS

Apantaku et al. (Breast cancer diagnosis and screening, American Family Physician 2000) (Year: 2000).*

Martin et al (Journal of the National Cancer Institute, vol. 92, No. 14: pp. 1126-1135, Jul. 19, 2000) (Year: 2000).*

NCBI, GenBank accession No. 3NZH_L, Oct. 10, 2012.

NCBI, GenBank accession No. ABH10632.1, Aug. 14, 2006.

Arlen M, et al. "The therapeutic value of monoclonal antibodies directed against immunogenic tumor glycoproteins," J Cancer. Nov. 3, 2010;1:209-22.

Rudikoff S, et al. "Single amino acid substitution altering antigen-binding specificity," Proc Natl Acad Sci U S A. Mar. 1982;79(6):1979-83.

MacCallum R, et al. "Antibody-antigen interactions: contact analysis and binding site topography," J Mol Biol. Oct. 11, 1996;262(5):732-45.

De Pascalis, et al. "Grafting of "abbreviated" complementarity-determining regions containing specificity-determining residues essential for ligand contact to engineer a less immunogenic humanized monoclonal antibody." J Immunol. Sep. 15, 2002;169(6): 3076-84.

Casset, F, et al. "A peptide mimetic of an anti-CD4 monoclonal antibody by rational design." Biochem Biophys Res Commun. Jul. 18, 2003;307(1):198-205.

Vajdos, F., et al. "Comprehensive functional maps of the antigen-binding site of an anti-ErbB2 antibody obtained with shotgun scanning mutagenesis." J Mol Biol. Jul. 5, 2002,320(2): 415-28.

Chen, Y, et al. "Selection and analysis of an optimized anti-VEGF antibody: crystal structure of an affinity-matured Fab in complex with antigen." J Mol Biol. Nov. 5, 1999;293(4):865-81.

(Continued)

*Primary Examiner* — Meera Natarajan

(74) *Attorney, Agent, or Firm* — Robin L. Teskin; Baker, Donelson, Bearman, Caldwell & Berkowitz PC

(57) ABSTRACT

This invention relates to humanized antibodies that selectively bind the 31.1 epitope on the A33 protein differentially expressed in cancers including, lung cancer, ovarian cancer, pancreas cancer, breast cancer, and colon cancer, and diagnostic and therapeutic usages.

18 Claims, 13 Drawing Sheets

Specification includes a Sequence Listing.

(56) References Cited

OTHER PUBLICATIONS

Wu, H, et al. "Humanization of a murine monoclonal antibody by simultaneous optimization of framework and CDR residues." J Mol Biol. Nov. 19, 1999:294(1):151-62.
Padian et al. "Structure of an antibody-antigen complex: crystal structure of the HyHEL_10 Fab-lysozyme complex," Proc Natl Acad Sci U S A. Aug. 1989;86(15):5938-42.
Lamminmaki et al. "Crystal structure of a recombinanat anti-estradiol Fab fragment in complex with 17beta-estradiol," J Biol. Chem. Sep. 28, 2001;276(39):36687-94. Epub Jul. 12, 2001.

* cited by examiner

FIGURE 1A
cdr31.1-HC

QIQLVQSGAEVKKPGASVKVSCKASGYTFTNYGMNWVKQAPGKGLKWMGWINTYTGEPTYADDFKGRFAFTLD
TSISTAYMELSRLRSDDTAVYFCARAYYGKYFDYWGQGTTVTVSSASTKGPSVFPLAPSSKSTSGGTA
ALGCLVKDYFPEPVTVSWNSGALTSGVHTFPAVLQSSGPYSLSSVVTVPSSSLGTQTYICN
VNHKPSNTKVDKKVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGFYPSDIAVEWESN
GQPENNYKTMPPVLDSDGSFFLYSKLTVDKSRWQQGNVFSCSVMHEALHNHYTQKSLSLSP
GK

FIGURE 1B
abb31.1-HC

QIQLVQSGAEVKKPGASVKVSCKASGYTFTNYGMNWVRQAPGKGLEWMGWINTYTGEPTYAQKFQGRVTFTLD
TSISTAYMELSRLRSDDTAVYFCARAYYGKYFDYWGQGTTVTVSSASTKGPSVFPLAPSSKSTSGGTA
ALGCLVKDYFPEPVTVSWNSGALTSGVHTFPAVLQSSGPYSLSSVVTVPSSSLGTQTYICN
VNHKPSNTKVDKKVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGFYPSDIAVEWESN
GQPENNYKTMPPVLDSDGSFFLYSKLTVDKSRWQQGNVFSCSVMHEALHNHYTQKSLSLSP
GK

FIGURE 1C
sdr31.1-HC

QIQLVQSGAEVKKPGASVKVSCKASGYTFTNYGMNWVRQAPGKGLEWMGWINPYTGEPTYAQKFQGRVTFTLD
TSISTAYMELSRLRSDDTAVYFCARAYYGKYFDYWGQGTTVTVSSASTKGPSVFPLAPSSKSTSGGTA
ALGCLVKDYFPEPVTVSWNSGALTSGVHTFPAVLQSSGPYSLSSVVTVPSSSLGTQTYICN
VNHKPSNTKVDKKVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGFYPSDIAVEWESN
GQPENNYKTMPPVLDSDGSFFLYSKLTVDKSRWQQGNVFSCSVMHEALHNHYTQKSLSLSP
GK

FIGURE 1D
ven31.1-HC

QIQLVQSGPEVKKPGASVKISCKASGYTFTNYGMNWVKQAPGQGLKWMGWINTYTGEPTYADDFKGRFAFT
LDTSISTAYLEISRLRSDDTAVYFCARAYYGKYFDYWGQGTTLTVSSASTKGPSVFPLAPSSKSTSGGTAA
LGCLVKDYFPEPVTVSWNSGALTSGVHTFPAVLQSSGPYSLSSVVTVPSSSLGTQTYICNVNHKPSNTKVD
KKVEPKSCDKTHTCPPCPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREPQVYTLPPS
RDELTKNQVSLTCLVKGFYPSDIAVEWESNGQPENNYKTMPPVLDSDGSFFLYSKLTVDKSRWQQGNVFSC
SVMHEALHNHYTQKSLSLSPGK

FIGURE 1E

```
alignment position            1......... 11........ 21........ 31........ 41........

cdr31.1-HC            1       QIQLVQSGAE VKKPGASVKV SCKASGYTFT NYGMNWVKQA PGKGLKWMGW
abb31.1-HC            1       QIQLVQSGAE VKKPGASVKV SCKASGYTFT NYGMNWVRQA PGKGLEWMGW
sdr31.1-HC            1       QIQLVQSGAE VKKPGASVKV SCKASGYTFT NYGMNWVRQA PGKGLEWMGW
ven31.1-HC            1       QIQLVQSGPE VKKPGASVKI SCKASGYTFT NYGMNWVKQA PGQGLKWMGW
                                                      CDR1

alignment position            51........ 61........ 71........ 81........ 91........

cdr31.1-HC           51       INTYTGEPTY ADDFKGRFAF TLDTSISTAY MELSRLRSDD TAVYFCARAY
abb31.1-HC           51       INTYTGEPTY AQKFQGRVTF TLDTSISTAY MELSRLRSDD TAVYFCARAY
sdr31.1-HC           51       INPYTGEPTY AQKFQGRVTF TLDTSISTAY MELSRLRSDD TAVYFCARAY
ven31.1-HC           51       INTYTGEPTY ADDFKGRFAF TLDTSISTAY LEISRLRSDD TAVYFCARAY
                                     CDR2

alignment position            101....... 111....... 121....... 131....... 141.......

cdr31.1-HC          101       YGKYFDYWGQ GTTVTVSSAS TKGPSVFPLA PSSKSTSGGT AALGCLVKDY
abb31.1-HC          101       YGKYFDYWGQ GTTVTVSSAS TKGPSVFPLA PSSKSTSGGT AALGCLVKDY
sdr31.1-HC          101       YGKYFDYWGQ GTTVTVSSAS TKGPSVFPLA PSSKSTSGGT AALGCLVKDY
ven31.1-HC          101       YGKYFDYWGQ GTTLTVSSAS TKGPSVFPLA PSSKSTSGGT AALGCLVKDY
                              CDR3

alignment position            151....... 161....... 171....... 181....... 191.......

cdr31.1-HC          151       FPEPVTVSWN SGALTSGVHT FPAVLQSSGP YSLSSVVTVP SSSLGTQTYI
abb31.1-HC          151       FPEPVTVSWN SGALTSGVHT FPAVLQSSGP YSLSSVVTVP SSSLGTQTYI
sdr31.1-HC          151       FPEPVTVSWN SGALTSGVHT FPAVLQSSGP YSLSSVVTVP SSSLGTQTYI
ven31.1-HC          151       FPEPVTVSWN SGALTSGVHT FPAVLQSSGP YSLSSVVTVP SSSLGTQTYI

alignment position            201....... 211....... 221....... 231....... 241.......

cdr31.1-HC          201       CNVNHKPSNT KVDKKVEPKS CDKTHTCPPC PAPELLGGPS VFLFPPKPKD
abb31.1-HC          201       CNVNHKPSNT KVDKKVEPKS CDKTHTCPPC PAPELLGGPS VFLFPPKPKD
sdr31.1-HC          201       CNVNHKPSNT KVDKKVEPKS CDKTHTCPPC PAPELLGGPS VFLFPPKPKD
ven31.1-HC          201       CNVNHKPSNT KVDKKVEPKS CDKTHTCPPC PAPELLGGPS VFLFPPKPKD

alignment position            251....... 261....... 271....... 281....... 291.......

cdr31.1-HC          251       TLMISRTPEV TCVVVDVSHE DPEVKFNWYV DGVEVHNAKT KPREEQYNST
abb31.1-HC          251       TLMISRTPEV TCVVVDVSHE DPEVKFNWYV DGVEVHNAKT KPREEQYNST
sdr31.1-HC          251       TLMISRTPEV TCVVVDVSHE DPEVKFNWYV DGVEVHNAKT KPREEQYNST
ven31.1-HC          251       TLMISRTPEV TCVVVDVSHE DPEVKFNWYV DGVEVHNAKT KPREEQYNST

alignment position            301....... 311....... 321....... 331....... 341.......

cdr31.1-HC          301       YRVVSVLTVL HQDWLNGKEY KCKVSNKALP APIEKTISKA KGQPREPQVY
abb31.1-HC          301       YRVVSVLTVL HQDWLNGKEY KCKVSNKALP APIEKTISKA KGQPREPQVY
sdr31.1-HC          301       YRVVSVLTVL HQDWLNGKEY KCKVSNKALP APIEKTISKA KGQPREPQVY
ven31.1-HC          301       YRVVSVLTVL HQDWLNGKEY KCKVSNKALP APIEKTISKA KGQPREPQVY

alignment position            351....... 361....... 371....... 381....... 391.......

cdr31.1-HC          351       TLPPSRDELT KNQVSLTCLV KGFYPSDIAV EWESNGQPEN NYKTMPPVLD
abb31.1-HC          351       TLPPSRDELT KNQVSLTCLV KGFYPSDIAV EWESNGQPEN NYKTMPPVLD
sdr31.1-HC          351       TLPPSRDELT KNQVSLTCLV KGFYPSDIAV EWESNGQPEN NYKTMPPVLD
ven31.1-HC          351       TLPPSRDELT KNQVSLTCLV KGFYPSDIAV EWESNGQPEN NYKTMPPVLD

alignment position            401....... 411....... 421....... 431....... 441.....

cdr31.1-HC          401       SDGSFFLYSK LTVDKSRWQQ GNVFSCSVMH EALHNHYTQK SLSLSPGK
abb31.1-HC          401       SDGSFFLYSK LTVDKSRWQQ GNVFSCSVMH EALHNHYTQK SLSLSPGK
sdr31.1-HC          401       SDGSFFLYSK LTVDKSRWQQ GNVFSCSVMH EALHNHYTQK SLSLSPGK
ven31.1-HC          401       SDGSFFLYSK LTVDKSRWQQ GNVFSCSVMH EALHNHYTQK SLSLSPGK
```

FIGURE 2A
cdr31.1-LC

SIVMTQSPSSLSASVGDRVTITCKASQSVSNDVAWYQQKPGQSPKLLIYYASNRYTGVPDRFSGSGYGTDFTLTISS
LQPEDFAVYFCQQDYSSPLTFGAGTKLEIKRTVAAPSVFIFPPSDEQLKSGTASVVCLLNNFYPREAKV
QWKVDNALQSGNSQESVTEQDSKDSTYSLSSTLTLSKADYEKHKVYACEVTHQGLSSPVTKSFN
RGEC

FIGURE 2B
abb31.1-LC

SIQMTQSPSSLSASVGDRVTITCRASQSVSNDVAWYQQKPGQSPKLLIYYASNRYSGVPDRFSGSGYGTDFTLTISS
LQPEDFAVYFCQQDYSSPLTFGAGTKLEIKRTVAAPSVFIFPPSDEQLKSGTASVVCLLNNFYPREAKV
QWKVDNALQSGNSQESVTEQDSKDSTYSLSSTLTLSKADYEKHKVYACEVTHQGLSSPVTKSFN
RGEC

FIGURE 2C
sdr31.1-LC

SIQMTQSPSSLSASVGDRVTITCRASQSISNDLAWYQQKPGQSPKLLIYYASNRYTGVPDRFSGSGYGTDFTLTISS
LQPEDFAVYFCQQDYSSPLTFGAGTKLEIKRTVAAPSVFIFPPSDEQLKSGTASVVCLLNNFYPREAKV
QWKVDNALQSGNSQESVTEQDSKDSTYSLSSTLTLSKADYEKHKVYACEVTHQGLSSPVTKSFN
RGEC

FIGURE 2D
ven31.1-LC

SIVMTQSPSSLSVSVGDRVTITCKASQSVSNDVAWYQQKPGQSPKLLIYYASNRYTGVPDRFSGSGYGTDF
TFTISSVQPEDLAVYFCQQDYSSPLTFGAGTKLELKRTVAAPSVFIFPPSDEQLKSGTASVVCLLNNFYPR
EAKVQWKVDNALQSGNSQESVTEQDSKDSTYSLSSTLTLSKADYEKHKVYACEVTHQGLSSPVTKSFNRGE
C

FIGURE 2E

```
alignment position          1......... 11........ 21........ 31........ 41........

cdr31.1-LC             1    SIVMTQSPSS LSASVGDRVT ITCKASQSVS NDVAWYQQKP GQSPKLLIYY
abb31.1-LC             1    SIQMTQSPSS LSASVGDRVT ITCRASQSVS NDVAWYQQKP GQSPKLLIYY
sdr31.1-LC             1    SIQMTQSPSS LSASVGDRVT ITCRASQSIS NDLAWYQQKP GQSPKLLIYY
ven31.1-LC             1    SIVMTQSPSS LSVSVGDRVT ITCKASQSVS NDVAWYQQKP GQSPKLLIYY
                                                       CDR1

alignment position          51........ 61........ 71........ 81........ 91........

cdr31.1-LC            51    ASNRYTGVPD RFSGSGYGTD FTLTISSLQP EDFAVYFCQQ DYSSPLTFGA
abb31.1-LC            51    ASNRYSGVPD RFSGSGYGTD FTLTISSLQP EDFAVYFCQQ DYSSPLTFGA
sdr31.1-LC            51    ASNRYTGVPD RFSGSGYGTD FTLTISSLQP EDFAVYFCQQ DYSSPLTFGA
ven31.1-LC            51    ASNRYTGVPD RFSGSGYGTD FTFTISSVQP EDLAVYFCQQ DYSSPLTFGA
                              CDR2                                       CDR3

alignment position          101....... 111....... 121....... 131....... 141.......

cdr31.1-LC           101    GTKLEIKRTV AAPSVFIFPP SDEQLKSGTA SVVCLLNNFY PREAKVQWKV
abb31.1-LC           101    GTKLEIKRTV AAPSVFIFPP SDEQLKSGTA SVVCLLNNFY PREAKVQWKV
sdr31.1-LC           101    GTKLEIKRTV AAPSVFIFPP SDEQLKSGTA SVVCLLNNFY PREAKVQWKV
ven31.1-LC           101    GTKLELKRTV AAPSVFIFPP SDEQLKSGTA SVVCLLNNFY PREAKVQWKV

alignment position          151....... 161....... 171....... 181....... 191.......

cdr31.1-LC           151    DNALQSGNSQ ESVTEQDSKD STYSLSSTLT LSKADYEKHK VYACEVTHQG
abb31.1-LC           151    DNALQSGNSQ ESVTEQDSKD STYSLSSTLT LSKADYEKHK VYACEVTHQG
sdr31.1-LC           151    DNALQSGNSQ ESVTEQDSKD STYSLSSTLT LSKADYEKHK VYACEVTHQG
ven31.1-LC           151    DNALQSGNSQ ESVTEQDSKD STYSLSSTLT LSKADYEKHK VYACEVTHQG

alignment position          201....... 211.

cdr31.1-LC           201    LSSPVTKSFN RGEC
abb31.1-LC           201    LSSPVTKSFN RGEC
sdr31.1-LC           201    LSSPVTKSFN RGEC
ven31.1-LC           201    LSSPVTKSFN RGEC
```

Frozen colon ca met to liver # 45942

SEQUENCE LISTING

```
<160> NUMBER OF SEQ ID NOS: 94

<210> SEQ ID NO 1
<211> LENGTH: 307
<212> TYPE: PRT
<213> ORGANISM: Artificial Sequence
<220> FEATURE:
<223> OTHER INFORMATION: NPC-1 antigen (variant 1)

<400> SEQUENCE: 1

Thr Thr His Ser Gln Pro Val Thr Arg Asp Cys His Leu Arg Cys Thr
1               5                   10                  15

Trp Thr Lys Trp Phe Asp Val Asp Phe Pro Ser Pro Gly Pro His Gly
            20                  25                  30

Gly Asp Lys Glu Thr Tyr Asn Asn Ile Ile Arg Ser Gly Glu Lys Ile
        35                  40                  45

Cys Arg Arg Pro Glu Glu Ile Thr Arg Leu Gln Cys Arg Ala Glu Ser
    50                  55                  60
```

```
His Pro Glu Val Ser Ile Glu His Leu Gly Gln Val Val Gln Cys Ser
65                  70                  75                  80

Arg Glu Glu Gly Leu Val Cys Arg Asn Gln Asp Gln Gln Gly Pro Phe
                85                  90                  95

Lys Met Cys Leu Asn Tyr Glu Val Arg Val Leu Cys Cys Glu Thr Pro
            100                 105                 110

Lys Gly Cys Pro Val Thr Ser Thr Pro Val Thr Ala Pro Ser Thr Pro
        115                 120                 125

Ser Gly Arg Ala Thr Ser Pro Thr Gln Ser Thr Ser Ser Trp Gln Lys
    130                 135                 140

Ser Arg Thr Thr Thr Leu Val Thr Thr Ser Thr Thr Ser Thr Pro Gln
145                 150                 155                 160

Thr Ser Thr Thr Ser Ala Pro Thr Thr Ser Thr Thr Ser Ala Pro Thr
                165                 170                 175

Thr Ser Thr Thr Ser Ala Pro Thr Thr Ser Thr Thr Ser Thr Pro Gln
            180                 185                 190

Thr Ser Ile Ser Ser Ala Pro Thr Ser Ser Thr Thr Ser Ala Pro Thr
        195                 200                 205

Ser Ser Thr Ile Ser Ala Arg Thr Thr Ser Ile Ile Ser Ala Pro Thr
    210                 215                 220

Thr Ser Thr Thr Ser Ser Pro Thr Thr Ser Thr Thr Ser Ala Thr Thr
225                 230                 235                 240

Thr Ser Thr Thr Ser Ala Pro Thr Ser Ser Thr Thr Ser Thr Pro Gln
                245                 250                 255

Thr Ser Lys Thr Ser Ala Ala Thr Ser Ser Thr Thr Ser Ser Ser Gly
            260                 265                 270

Thr Thr Pro Ser Pro Val Thr Thr Thr Ser Thr Ala Ser Val Ser Lys
        275                 280                 285

Thr Ser Thr Ser His Val Ser Val Ser Lys Thr Thr His Ser Gln Pro
    290                 295                 300

Val Thr Arg
305


<210> SEQ ID NO 2
<211> LENGTH: 281
<212> TYPE: PRT
<213> ORGANISM: Artificial Sequence
<220> FEATURE:
<223> OTHER INFORMATION: NPC-1 antigen (variant 2)

<400> SEQUENCE: 2

Gly Thr His Thr Thr Pro Val Thr Arg Asn Cys His Pro Arg Cys Thr
1               5                   10                  15

Trp Thr Lys Trp Phe Asp Val Asp Phe Pro Ser Pro Gly Pro His Gly
            20                  25                  30

Gly Asp Lys Glu Thr Tyr Asn Asn Ile Ile Arg Ser Gly Glu Lys Ile
        35                  40                  45

Cys Arg Arg Pro Glu Glu Ile Thr Arg Leu Gln Cys Arg Ala Lys Ser
    50                  55                  60

His Pro Glu Val Ser Ile Glu His Leu Gly Gln Val Val Gln Cys Ser
65                  70                  75                  80

Arg Glu Glu Gly Leu Val Cys Arg Asn Gln Asp Gln Gln Gly Pro Phe
                85                  90                  95

Lys Met Cys Leu Asn Tyr Glu Val Arg Val Leu Cys Cys Glu Thr Pro
            100                 105                 110
```

```
Arg Gly Cys Pro Val Thr Ser Thr Pro Val Thr Ala Pro Ser Thr Pro
        115                 120                 125

Ser Gly Arg Ala Ile Ser Pro Thr Gln Ser Thr Ser Ser Trp Gln Lys
    130                 135                 140

Ser Arg Thr Thr Thr Leu Val Thr Thr Ser Thr Thr Ser Thr Pro Gln
145                 150                 155                 160

Thr Ser Thr Thr Tyr Ala His Thr Thr Ser Thr Thr Ser Ala Pro Thr
                165                 170                 175

Ala Arg Thr Thr Ser Ala Pro Thr Thr Arg Thr Thr Ser Ala Ser Pro
            180                 185                 190

Ala Ser Thr Thr Ser Gly Pro Gly Asn Thr Pro Ser Pro Val Pro Thr
        195                 200                 205

Thr Ser Thr Ile Ser Ala Pro Thr Thr Ser Ile Thr Ser Ala Pro Thr
    210                 215                 220

Thr Ser Thr Thr Ser Ala Pro Thr Ser Ser Thr Thr Ser Ala Pro Thr
225                 230                 235                 240

Thr Ser Thr Thr Ser Ala Pro Thr Ser Ser Thr Thr Ser Ser Pro Gln
                245                 250                 255

Thr Ser Thr Thr Ser Ala Pro Thr Thr Ser Thr Thr Ser Gly Pro Gly
            260                 265                 270

Thr Thr Pro Ser Pro Val Pro Thr Thr
        275                 280


<210> SEQ ID NO 3
<211> LENGTH: 16
<212> TYPE: PRT
<213> ORGANISM: Artificial Sequence
<220> FEATURE:
<223> OTHER INFORMATION: MUC5AC NPC-1 epitope (1)

<400> SEQUENCE: 3

Thr Thr Ser Thr Thr Ser Ala Pro Thr Thr Ser Thr Thr Ser Ala Pro
1               5                   10                  15


<210> SEQ ID NO 4
<211> LENGTH: 15
<212> TYPE: PRT
<213> ORGANISM: Artificial Sequence
<220> FEATURE:
<223> OTHER INFORMATION: MUC5AC NPC-1 epitope (2)

<400> SEQUENCE: 4

Gly Cys Pro Val Thr Ser Thr Pro Val Thr Ala Pro Ser Thr Pro
1               5                   10                  15


<210> SEQ ID NO 5
<211> LENGTH: 92
<212> TYPE: PRT
<213> ORGANISM: Artificial Sequence
<220> FEATURE:
<223> OTHER INFORMATION: CEACAM5 16C3 epitope
<220> FEATURE:
<221> NAME/KEY: MISC_FEATURE
<222> LOCATION: (8)..(67)
<223> OTHER INFORMATION: Xaa can be any amino acid

<400> SEQUENCE: 5

Gly Pro Asp Ala Pro Thr Ile Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30
```

```
Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Gly Ser Tyr Thr Cys Gln Ala His Asn Ser Asp Thr Gly
65                  70                  75                  80

Leu Asn Arg Thr Thr Val Thr Thr Ile Thr Val Tyr
                85                  90


<210> SEQ ID NO 6
<211> LENGTH: 7
<212> TYPE: PRT
<213> ORGANISM: Artificial Sequence
<220> FEATURE:
<223> OTHER INFORMATION: CEACAM 16C3 epitope N-terminal flanking peptide

<400> SEQUENCE: 6

Gly Pro Asp Ala Pro Thr Ile
1               5


<210> SEQ ID NO 7
<211> LENGTH: 25
<212> TYPE: PRT
<213> ORGANISM: Artificial Sequence
<220> FEATURE:
<223> OTHER INFORMATION: CEACAM5 16C3 C-terminal flanking peptide

<400> SEQUENCE: 7

Gly Ser Tyr Thr Cys Gln Ala His Asn Ser Asp Thr Gly Leu Asn Arg
1               5                   10                  15

Thr Thr Val Thr Thr Ile Thr Val Tyr
            20                  25


<210> SEQ ID NO 8
<211> LENGTH: 92
<212> TYPE: PRT
<213> ORGANISM: Artificial Sequence
<220> FEATURE:
<223> OTHER INFORMATION: CEACAM6 16C3 epitope
<220> FEATURE:
<221> NAME/KEY: MISC_FEATURE
<222> LOCATION: (8)..(67)
<223> OTHER INFORMATION: Xaa can be any amino acid

<400> SEQUENCE: 8

Gly Pro Asp Gly Pro Thr Ile Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Gly Ser Tyr Met Cys Gln Ala His Asn Ser Ala Thr Gly
65                  70                  75                  80

Leu Asn Arg Thr Thr Val Thr Met Ile Thr Val Ser
                85                  90


<210> SEQ ID NO 9
<211> LENGTH: 25
<212> TYPE: PRT
<213> ORGANISM: Artificial Sequence
<220> FEATURE:
```

-continued

<223> OTHER INFORMATION: CEACAM6 C-terminal flanking peptide

<400> SEQUENCE: 9

```
Gly Ser Tyr Met Cys Gln Ala His Asn Ser Ala Thr Gly Leu Asn Arg
1               5                   10                  15

Thr Thr Val Thr Met Ile Thr Val Ser
            20                  25
```

<210> SEQ ID NO 10
<211> LENGTH: 319
<212> TYPE: PRT
<213> ORGANISM: Homo sapiens
<220> FEATURE:
<223> OTHER INFORMATION: A33 antigen

<400> SEQUENCE: 10

```
Met Val Gly Lys Met Trp Pro Val Leu Trp Thr Leu Cys Ala Val Arg
1               5                   10                  15

Val Thr Val Asp Ala Ile Ser Val Glu Thr Pro Gln Asp Val Leu Arg
            20                  25                  30

Ala Ser Gln Gly Lys Ser Val Thr Leu Pro Cys Thr Tyr His Thr Ser
        35                  40                  45

Thr Ser Ser Arg Glu Gly Leu Ile Gln Trp Asp Lys Leu Leu Leu Thr
    50                  55                  60

His Thr Glu Arg Val Val Ile Trp Pro Phe Ser Asn Lys Asn Tyr Ile
65                  70                  75                  80

His Gly Glu Leu Tyr Lys Asn Arg Val Ser Ile Ser Asn Asn Ala Glu
                85                  90                  95

Gln Ser Asp Ala Ser Ile Thr Ile Asp Gln Leu Thr Met Ala Asp Asn
            100                 105                 110

Gly Thr Tyr Glu Cys Ser Val Ser Leu Met Ser Asp Leu Glu Gly Asn
        115                 120                 125

Thr Lys Ser Arg Val Arg Leu Leu Val Leu Val Pro Pro Ser Lys Pro
    130                 135                 140

Glu Cys Gly Ile Glu Gly Glu Thr Ile Ile Gly Asn Asn Ile Gln Leu
145                 150                 155                 160

Thr Cys Gln Ser Lys Glu Gly Ser Pro Thr Pro Gln Tyr Ser Trp Lys
                165                 170                 175

Arg Tyr Asn Ile Leu Asn Gln Glu Gln Pro Leu Ala Gln Pro Ala Ser
            180                 185                 190

Gly Gln Pro Val Ser Leu Lys Asn Ile Ser Thr Asp Thr Ser Gly Tyr
        195                 200                 205

Tyr Ile Cys Thr Ser Ser Asn Glu Glu Gly Thr Gln Phe Cys Asn Ile
    210                 215                 220

Thr Val Ala Val Arg Ser Pro Ser Met Asn Val Ala Leu Tyr Val Gly
225                 230                 235                 240

Ile Ala Val Gly Val Val Ala Ala Leu Ile Ile Ile Gly Ile Ile Ile
                245                 250                 255

Tyr Cys Cys Cys Cys Arg Gly Lys Asp Asp Asn Thr Glu Asp Lys Glu
            260                 265                 270

Asp Ala Arg Pro Asn Arg Glu Ala Tyr Glu Glu Pro Pro Glu Gln Leu
        275                 280                 285

Arg Glu Leu Ser Arg Glu Arg Glu Glu Glu Asp Asp Tyr Arg Gln Glu
    290                 295                 300

Glu Gln Arg Ser Thr Gly Arg Glu Ser Pro Asp His Leu Asp Gln
305                 310                 315
```

<210> SEQ ID NO 11
<211> LENGTH: 56
<212> TYPE: PRT
<213> ORGANISM: Artificial Sequence
<220> FEATURE:
<223> OTHER INFORMATION: A33 antigen mass spec fragment 1

<400> SEQUENCE: 11

```
Ala Ser Gln Gly Lys Ser Val Thr Leu Pro Cys Thr Tyr His Thr Ser
1               5                   10                  15

Thr Ser Ser Arg Glu Gly Leu Ile Gln Trp Asp Lys Leu Leu Leu Thr
            20                  25                  30

His Thr Glu Arg Val Val Ile Trp Pro Phe Ser Asn Lys Asn Tyr Ile
        35                  40                  45

His Gly Glu Leu Tyr Lys Asn Arg
    50                  55
```

<210> SEQ ID NO 12
<211> LENGTH: 67
<212> TYPE: PRT
<213> ORGANISM: Artificial Sequence
<220> FEATURE:
<223> OTHER INFORMATION: A33 antigen mass spec fragment 2

<400> SEQUENCE: 12

```
Val Arg Leu Leu Val Leu Val Pro Pro Ser Lys Pro Glu Cys Gly Ile
1               5                   10                  15

Glu Gly Glu Thr Ile Ile Gly Asn Asn Ile Gln Leu Thr Cys Gln Ser
            20                  25                  30

Lys Glu Gly Ser Pro Thr Pro Gln Tyr Ser Trp Lys Arg Tyr Asn Ile
        35                  40                  45

Leu Asn Gln Glu Gln Pro Leu Ala Gln Pro Ala Ser Gly Gln Pro Val
    50                  55                  60

Ser Leu Lys
65
```

<210> SEQ ID NO 13
<211> LENGTH: 55
<212> TYPE: PRT
<213> ORGANISM: Artificial Sequence
<220> FEATURE:
<223> OTHER INFORMATION: A33 antigen mass spec fragment 3

<400> SEQUENCE: 13

```
Asp Asp Asn Thr Glu Asp Lys Glu Asp Ala Arg Pro Asn Arg Glu Ala
1               5                   10                  15

Tyr Glu Glu Pro Pro Glu Gln Leu Arg Glu Leu Ser Arg Glu Arg Glu
            20                  25                  30

Glu Glu Asp Asp Tyr Arg Gln Glu Glu Gln Arg Ser Thr Gly Arg Glu
        35                  40                  45

Ser Pro Asp His Leu Asp Gln
    50                  55
```

<210> SEQ ID NO 14
<211> LENGTH: 965
<212> TYPE: DNA
<213> ORGANISM: Artificial Sequence
<220> FEATURE:
<223> OTHER INFORMATION: NPC-1 antibody light chain

<400> SEQUENCE: 14

-continued

```
atgagaatac cattaattag ctagggacca aaattcaaag acaaaatgga ttttcaggtg     60

cagattttca gcttcctgct aatcagtgcc tcagtcatac tgtccagagg acaagttgtt    120

ctcacccagt ctccagtaat catgtctgca tctccagggg agaaggtcac catgacctgc    180

agtgccagct caagtataag ttacatgtac tggtaccagc agaagccagg cacctccccc    240

aaaagatgga tttatgacac atccaaactg gcttctggag tccctgctcg cttcagtggc    300

agtgggtctg ggacctctta ttctctcaca atcagcaaca tggaggctgg agatgctgcc    360

acttattact gccatcagcg ggattcttac ccatggacgt tcggtggagg caccaacctg    420

gaaatcaaac gggctgatgc tgcaccaact gtatccatct tcccaccatc cagtgagcag    480

ttaacatctg gaggtgcctc agtcgtgtgc ttcttgaaca acttctaccc caaagacatc    540

aatgtcaagt ggaagattga tggcagtgaa cgacaaaatg gcgtcctgaa cagttggact    600

gatcaggaca gcaaagacag cacctacagc atgagcagca ccctcacgtt gaccaaggac    660

gagtatgaac gacataacag ctatacctgt gaggccactc acaagacatc aacttcaccc    720

attgtcaaga gcttcaacag gaatgagtgt tagagacaaa ggtcctgaga cgccaccacc    780

agctccccag ctccatccta tcttcccttc taaggtcttg gaggcttccc cacaagcgac    840

ctaccactgt tgcggtgctc caaacctcct ccccacctcc ttctcctcct cctccctttc    900

cttggctttt atcatgctaa tatttgcaga aaatattcaa taaagtgagt ctttgcactt    960

gaaaa                                                                965


<210> SEQ ID NO 15
<211> LENGTH: 235
<212> TYPE: PRT
<213> ORGANISM: Artificial Sequence
<220> FEATURE:
<223> OTHER INFORMATION: NPC-1 antibody light chain
<220> FEATURE:
<221> NAME/KEY: MISC_FEATURE
<222> LOCATION: (46)..(55)
<223> OTHER INFORMATION: CDR1
<220> FEATURE:
<221> NAME/KEY: MISC_FEATURE
<222> LOCATION: (71)..(77)
<223> OTHER INFORMATION: CDR2
<220> FEATURE:
<221> NAME/KEY: MISC_FEATURE
<222> LOCATION: (110)..(118)
<223> OTHER INFORMATION: CDR3

<400> SEQUENCE: 15

Met Asp Phe Gln Val Gln Ile Phe Ser Phe Leu Leu Ile Ser Ala Ser
1               5                   10                  15

Val Ile Leu Ser Arg Gly Gln Val Val Leu Thr Gln Ser Pro Val Ile
            20                  25                  30

Met Ser Ala Ser Pro Gly Glu Lys Val Thr Met Thr Cys Ser Ala Ser
        35                  40                  45

Ser Ser Ile Ser Tyr Met Tyr Trp Tyr Gln Gln Lys Pro Gly Thr Ser
    50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Asn Met Glu Ala Gly Asp Ala Ala Thr Tyr Tyr Cys His Gln Arg
            100                 105                 110

Asp Ser Tyr Pro Trp Thr Phe Gly Gly Gly Thr Asn Leu Glu Ile Lys
```

```
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235


<210> SEQ ID NO 16
<211> LENGTH: 10
<212> TYPE: PRT
<213> ORGANISM: Artificial Sequence
<220> FEATURE:
<223> OTHER INFORMATION: NPC-1 light chain CDR1

<400> SEQUENCE: 16

Ser Ala Ser Ser Ser Ile Ser Tyr Met Tyr
1               5                   10


<210> SEQ ID NO 17
<211> LENGTH: 7
<212> TYPE: PRT
<213> ORGANISM: Artificial Sequence
<220> FEATURE:
<223> OTHER INFORMATION: NPC-1 light chain CDR2

<400> SEQUENCE: 17

Asp Thr Ser Lys Leu Ala Ser
1               5


<210> SEQ ID NO 18
<211> LENGTH: 9
<212> TYPE: PRT
<213> ORGANISM: Artificial Sequence
<220> FEATURE:
<223> OTHER INFORMATION: NPC-1 antibody light chain CDR3

<400> SEQUENCE: 18

His Gln Arg Asp Ser Tyr Pro Trp Thr
1               5


<210> SEQ ID NO 19
<211> LENGTH: 1520
<212> TYPE: DNA
<213> ORGANISM: Artificial Sequence
<220> FEATURE:
<223> OTHER INFORMATION: NPC-1 antibody heavy chain

<400> SEQUENCE: 19

ttttccatcc tcttctcata gagcctccat cagaccatgg ctgtcctggc actgctcctc     60

tgcctggtga cattcccaag ctgtgtcctg tcccaggtgc agctgaagga gtcaggacct    120

gacctggtgg cgccctcaca gagcctgtcc atcacatgca ctgtctcagg attctcatta    180

agcaaatttg gtgtaaactg ggttcgccag cctccaggaa agggtctgga gtggctggga    240
```

```
gtaatatggg gtgacgggag cacaagttat aattcaggtc tcatatcaag actgagcatc    300

agcaaggaga actccaagag ccaggttttc ttaaaactga acagtctgca agctgatgac    360

acagccacat actactgtgt caaaccgggg ggtgactact ggggtcacgg aacctcagtc    420

accgtctcct cagccaaaac gacaccccca tctgtctatc cactggcccc tggatctgct    480

gcccaaacta actccatggt gaccctggga tgcctggtca agggctattt ccctgagcca    540

gtgacagtga cctggaactc tggatccctg tccagcggtg tgcacacctt cccagctgtc    600

ctgcagtctg acctctacac tctgagcagc tcagtgactg tcccctccag cacctggccc    660

agcgagaccg tcacctgcaa cgttgcccac ccggccagca gcaccaaggt ggacaagaaa    720

attgtgccca gggattgtgg ttgtaagcct tgcatatgta cagtcccaga agtatcatct    780

gtcttcatct tccccccaaa gcccaaggat gtgctcacca ttactctgac tcctaaggtc    840

acgtgtgttg tggtagacat cagcaaggat gatcccgagg tccagttcag ctggtttgta    900

gatgtggagg tgcacacagc tcagacgcaa ccccgggagg agcagttcaa cagcactttc    960

cgctcagtca gtgaacttcc catcatgcac caggactggc tcaatggcaa ggagttcaaa   1020

tgcagggtca acagtgcagc tttccctgcc cccatcgaga aaaccatctc caaaaccaaa   1080

ggcagaccga aggctccaca ggtgtacacc attccacctc ccaaggagca gatggccaag   1140

gataaagtca gtctgacctg catgataaca gacttcttcc ctgaagacat tactgtggag   1200

tggcagtgga atgggcagcc agcggagaac tacaagaaca ctcagcccat catggacaca   1260

gatggctctt acttcgtcta cagcaagctc aatgtgcaga agagcaactg ggaggcagga   1320

aatactttca cctgctctgt gttacatgag ggcctgcaca accaccatac tgagaagagc   1380

ctctcccact ctcctggtaa atgatcccag tgtccttgga gccctctggt cctacaggac   1440

tctgacacct acctccaccc ctccctgtat aaataaagca cccagcactg ccttgggacc   1500

ctgcaaaaaa aaaaaaaaaa                                                1520
```

<210> SEQ ID NO 20
<211> LENGTH: 456
<212> TYPE: PRT
<213> ORGANISM: Artificial Sequence
<220> FEATURE:
<223> OTHER INFORMATION: NPC-1 antibody heavy chain
<220> FEATURE:
<221> NAME/KEY: MISC_FEATURE
<222> LOCATION: (49)..(54)
<223> OTHER INFORMATION: CDR1
<220> FEATURE:
<221> NAME/KEY: MISC_FEATURE
<222> LOCATION: (69)..(84)
<223> OTHER INFORMATION: CDR2
<220> FEATURE:
<221> NAME/KEY: MISC_FEATURE
<222> LOCATION: (114)..(121)
<223> OTHER INFORMATION: CDR3

<400> SEQUENCE: 20

```
Met Ala Val Leu Ala Leu Leu Leu Cys Leu Val Thr Phe Pro Ser Cys
1               5                   10                  15

Val Leu Ser Gln Val Gln Leu Lys Glu Ser Gly Pro Asp Leu Val Ala
            20                  25                  30

Pro Ser Gln Ser Leu Ser Ile Thr Cys Thr Val Ser Gly Phe Ser Leu
        35                  40                  45

Ser Lys Phe Gly Val Asn Trp Val Arg Gln Pro Pro Gly Lys Gly Leu
    50                  55                  60
```

```
Glu Trp Leu Gly Val Ile Trp Gly Asp Gly Ser Thr Ser Tyr Asn Ser
65                  70                  75                  80

Gly Leu Ile Ser Arg Leu Ser Ile Ser Lys Glu Asn Ser Lys Ser Gln
                85                  90                  95

Val Phe Leu Lys Leu Asn Ser Leu Gln Ala Asp Asp Thr Ala Thr Tyr
            100                 105                 110

Tyr Cys Val Lys Pro Gly Gly Asp Tyr Trp Gly His Gly Thr Ser Val
        115                 120                 125

Thr Val Ser Ser Ala Lys Thr Thr Pro Pro Ser Val Tyr Pro Leu Ala
    130                 135                 140

Pro Gly Ser Ala Ala Gln Thr Asn Ser Met Val Thr Leu Gly Cys Leu
145                 150                 155                 160

Val Lys Gly Tyr Phe Pro Glu Pro Val Thr Val Thr Trp Asn Ser Gly
                165                 170                 175

Ser Leu Ser Ser Gly Val His Thr Phe Pro Ala Val Leu Gln Ser Asp
            180                 185                 190

Leu Tyr Thr Leu Ser Ser Ser Val Thr Val Pro Ser Ser Thr Trp Pro
        195                 200                 205

Ser Glu Thr Val Thr Cys Asn Val Ala His Pro Ala Ser Ser Thr Lys
    210                 215                 220

Val Asp Lys Lys Ile Val Pro Arg Asp Cys Gly Cys Lys Pro Cys Ile
225                 230                 235                 240

Cys Thr Val Pro Glu Val Ser Ser Val Phe Ile Phe Pro Pro Lys Pro
                245                 250                 255

Lys Asp Val Leu Thr Ile Thr Leu Thr Pro Lys Val Thr Cys Val Val
            260                 265                 270

Val Asp Ile Ser Lys Asp Asp Pro Glu Val Gln Phe Ser Trp Phe Val
        275                 280                 285

Asp Asp Val Glu Val His Thr Ala Gln Thr Gln Pro Arg Glu Glu Gln
    290                 295                 300

Phe Asn Ser Thr Phe Arg Ser Val Ser Glu Leu Pro Ile Met His Gln
305                 310                 315                 320

Asp Trp Leu Asn Gly Lys Glu Phe Lys Cys Arg Val Asn Ser Ala Ala
                325                 330                 335

Phe Pro Ala Pro Ile Glu Lys Thr Ile Ser Lys Thr Lys Gly Arg Pro
            340                 345                 350

Lys Ala Pro Gln Val Tyr Thr Ile Pro Pro Pro Lys Glu Gln Met Ala
        355                 360                 365

Lys Asp Lys Val Ser Leu Thr Cys Met Ile Thr Asp Phe Phe Pro Glu
    370                 375                 380

Asp Ile Thr Val Glu Trp Gln Trp Asn Gly Gln Pro Ala Glu Asn Tyr
385                 390                 395                 400

Lys Asn Thr Gln Pro Ile Met Asp Thr Asp Gly Ser Tyr Phe Val Tyr
                405                 410                 415

Ser Lys Leu Asn Val Gln Lys Ser Asn Trp Glu Ala Gly Asn Thr Phe
            420                 425                 430

Thr Cys Ser Val Leu His Glu Gly Leu His Asn His His Thr Glu Lys
        435                 440                 445

Ser Leu Ser His Ser Pro Gly Lys
    450                 455

<210> SEQ ID NO 21
<211> LENGTH: 6
<212> TYPE: PRT
```

<213> ORGANISM: Artificial Sequence
<220> FEATURE:
<223> OTHER INFORMATION: NPC-1 antibody heavy chain CDR1

<400> SEQUENCE: 21

Ser Lys Phe Gly Val Asn
1 5

<210> SEQ ID NO 22
<211> LENGTH: 16
<212> TYPE: PRT
<213> ORGANISM: Artificial Sequence
<220> FEATURE:
<223> OTHER INFORMATION: NPC-1 heavy chain CDR2

<400> SEQUENCE: 22

Val Ile Trp Gly Asp Gly Ser Thr Ser Tyr Asn Ser Gly Leu Ile Ser
1 5 10 15

<210> SEQ ID NO 23
<211> LENGTH: 8
<212> TYPE: PRT
<213> ORGANISM: Artificial Sequence
<220> FEATURE:
<223> OTHER INFORMATION: NPC-1 antibody heavy chain CDR3

<400> SEQUENCE: 23

Cys Val Lys Pro Gly Gly Asp Tyr
1 5

<210> SEQ ID NO 24
<211> LENGTH: 737
<212> TYPE: DNA
<213> ORGANISM: Artificial Sequence
<220> FEATURE:
<223> OTHER INFORMATION: NPC-1 Chi-antibody light chain

<400> SEQUENCE: 24
gcatagatct gccaccatgg actttcaggt ccagatattt agctttctat tgattagcgc 60
ctctgtcatt ctgagtaggg ggcaggtggt gctcacccag tctccagtga tcatgtcagc 120
ctcaccagga gaaaaagtga ctatgacctg ctcagcatcc tccagcatca gttacatgta 180
ctggtaccag cagaagccag gcacctcgcc caagcgttgg atctacgata cttccaagct 240
ggcaagtggg gtacccgcac gcttcagtgg aagtggctcc ggaacctcgt acagtttgac 300
catttcaaat atggaagctg gggacgcagc tacatattat tgccaccaga gagactccta 360
cccgtggacc ttcggaggcg gtactaattt agagatcaag aggaccgtag ccgctccttc 420
cgtgttcatc tttcccccctt ccgacgaaca actgaaaagc ggtacagcct ccgtggtttg 480
tctgctgaac aacttctacc cccgggaggc taaagttcag tggaaggttg acaatgctct 540
gcagtcaggc aactctcaag agagcgtcac ggagcaagat agcaaagatt ctacatattc 600
tctctcttct acacttacac ttagcaaggc cgattatgag aagcacaagg tgtatgcctg 660
cgaggtgact catcagggtc tttcttctcc tgtcactaaa agcttcaacc gaggcgaatg 720
ttgatgaaga tcttacg 737

<210> SEQ ID NO 25
<211> LENGTH: 235
<212> TYPE: PRT
<213> ORGANISM: Artificial Sequence
<220> FEATURE:
<223> OTHER INFORMATION: NPC-1 chi-antibody light chain with signal
peptide

```
<220> FEATURE:
<221> NAME/KEY: SIGNAL
<222> LOCATION: (1)..(22)
<220> FEATURE:
<221> NAME/KEY: MISC_FEATURE
<222> LOCATION: (46)..(55)
<223> OTHER INFORMATION: CDR1
<220> FEATURE:
<221> NAME/KEY: MISC_FEATURE
<222> LOCATION: (71)..(77)
<223> OTHER INFORMATION: CDR2
<220> FEATURE:
<221> NAME/KEY: MISC_FEATURE
<222> LOCATION: (110)..(118)
<223> OTHER INFORMATION: CDR3

<400> SEQUENCE: 25

Met Asp Phe Gln Val Gln Ile Phe Ser Phe Leu Leu Ile Ser Ala Ser
1               5                   10                  15

Val Ile Leu Ser Arg Gly Gln Val Val Leu Thr Gln Ser Pro Val Ile
            20                  25                  30

Met Ser Ala Ser Pro Gly Glu Lys Val Thr Met Thr Cys Ser Ala Ser
        35                  40                  45

Ser Ser Ile Ser Tyr Met Tyr Trp Tyr Gln Gln Lys Pro Gly Thr Ser
    50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Asn Met Glu Ala Gly Asp Ala Ala Thr Tyr Tyr Cys His Gln Arg
            100                 105                 110

Asp Ser Tyr Pro Trp Thr Phe Gly Gly Gly Thr Asn Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235


<210> SEQ ID NO 26
<211> LENGTH: 10
<212> TYPE: PRT
<213> ORGANISM: Artificial Sequence
<220> FEATURE:
<223> OTHER INFORMATION: NPC-1 chi-antibody light chain CDR1

<400> SEQUENCE: 26

Ser Ala Ser Ser Ser Ile Ser Tyr Met Tyr
1               5                   10


<210> SEQ ID NO 27
<211> LENGTH: 7
```

<212> TYPE: PRT
<213> ORGANISM: Artificial Sequence
<220> FEATURE:
<223> OTHER INFORMATION: NPC-1 chi-antibody light chain CDR2

<400> SEQUENCE: 27

Asp Thr Ser Lys Leu Ala Ser
1 5

<210> SEQ ID NO 28
<211> LENGTH: 9
<212> TYPE: PRT
<213> ORGANISM: Artificial Sequence
<220> FEATURE:
<223> OTHER INFORMATION: NPC-1 chi-antibody light chain CDR3

<400> SEQUENCE: 28

His Gln Arg Asp Ser Tyr Pro Trp Thr
1 5

<210> SEQ ID NO 29
<211> LENGTH: 1418
<212> TYPE: DNA
<213> ORGANISM: Artificial Sequence
<220> FEATURE:
<223> OTHER INFORMATION: NPC-1 chi-antibody heavy chain

<400> SEQUENCE: 29
gagcggtacc gccaccatgg cagtgctggc ccttcttcta tgtctggtga ccttcccatc 60
ctgcgtcctg agccaggtac aactgaagga gtcgggccca gacctagtgg ctccgtcaca 120
atcactctcc attacgtgca ctgtctccgg cttctctttg tctaaattcg gcgtgaattg 180
ggtgcgacag ccccccggga aggggcttga gtggttagga gttatctggg gtgacggctc 240
aaccagctac aactcaggac taatctcacg cttgtcaatt tcaaaggaga attcaaagtc 300
tcaggtgttc cttaagctca actcgctgca agccgacgat accgcaacct attactgcgt 360
caaacctggc ggggactact ggggccatgg cacctccgtc acagtgagtt ccgcatccac 420
aaagggtccc agtgtttttc ctttggcgcc ctctagcaaa tcgacatctg gcggcacagc 480
cgcacttggg tgcttggtta aagactactt ccccgaaccg gtgacagtat cttggaactc 540
tggcgctctt accagcggag ttcatacctt ccctgccgta ttacagtcta gcgggcccta 600
ctccctctcc tctgtcgtga cagtcccaag ctcttctctg ggaactcaaa cctacatctg 660
caatgtgaac cataaaccta gcaacacgaa agtggacaaa aaggtcgaac ccaagagttg 720
cgacaagaca cacacctgcc ctccttgtcc tgctccagag ctcctcggcg gacctagcgt 780
tttcttgttc cctccgaaac caaaggacac cttgatgatt tctcggaccc ccgaggtgac 840
atgtgtagta gttgatgtct cccacgagga ccctgaggtc aagtttaatt ggtatgtgga 900
cggtgtggag gtccacaacg ccaaaacaaa accacgggag gaacagtaca attccacata 960
tagggtggtg agcgtcctta ccgtcctgca tcaggattgg ttaaatggta aggagtataa 1020
gtgtaaggtg tctaacaagg ctctgcctgc tcccatcgaa aaaactataa gtaaggccaa 1080
aggacagccc agggaacctc aggtgtatac tcttccaccc agtagagatg agctgactaa 1140
aaaccaggtg tccctgactt gtctggtgaa gggattttac ccatccgata tcgccgtgga 1200
atgggagtcc aacggacagc cagaaaacaa ttataaaact atgccaccag tgctggatag 1260
tgatggtagt ttttttctgt acagtaagct gactgttgat aagagtagat ggcagcaggg 1320
taatgttttt agttgtagcg ttatgcacga agctctgcac aatcactata ctcagaagag 1380

-continued cctgagcctg agccccggta agtgatgagg taccgagc 1418

<210> SEQ ID NO 30
<211> LENGTH: 462
<212> TYPE: PRT
<213> ORGANISM: Artificial Sequence
<220> FEATURE:
<223> OTHER INFORMATION: NPC-1 chi-antibody heavy chain
<220> FEATURE:
<221> NAME/KEY: SIGNAL
<222> LOCATION: (1)..(19)

<400> SEQUENCE: 30

```
Met Ala Val Leu Ala Leu Leu Leu Cys Leu Val Thr Phe Pro Ser Cys
1               5                   10                  15

Val Leu Ser Gln Val Gln Leu Lys Glu Ser Gly Pro Asp Leu Val Ala
            20                  25                  30

Pro Ser Gln Ser Leu Ser Ile Thr Cys Thr Val Ser Gly Phe Ser Leu
        35                  40                  45

Ser Lys Phe Gly Val Asn Trp Val Arg Gln Pro Pro Gly Lys Gly Leu
    50                  55                  60

Glu Trp Leu Gly Val Ile Trp Gly Asp Gly Ser Thr Ser Tyr Asn Ser
65                  70                  75                  80

Gly Leu Ile Ser Arg Leu Ser Ile Ser Lys Glu Asn Ser Lys Ser Gln
                85                  90                  95

Val Phe Leu Lys Leu Asn Ser Leu Gln Ala Asp Asp Thr Ala Thr Tyr
            100                 105                 110

Tyr Cys Val Lys Pro Gly Gly Asp Tyr Trp Gly His Gly Thr Ser Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Pro Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
```

```
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Met Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460


<210> SEQ ID NO 31
<211> LENGTH: 10
<212> TYPE: PRT
<213> ORGANISM: Artificial Sequence
<220> FEATURE:
<223> OTHER INFORMATION: NPC-1 chi-antibody heavy chain CDR1

<400> SEQUENCE: 31

Gly Phe Ser Leu Ser Lys Phe Gly Val Asn
1               5                   10


<210> SEQ ID NO 32
<211> LENGTH: 16
<212> TYPE: PRT
<213> ORGANISM: Artificial Sequence
<220> FEATURE:
<223> OTHER INFORMATION: NPC-1 chi-antibody heavy chain CDR2

<400> SEQUENCE: 32

Val Ile Trp Gly Asp Gly Ser Thr Ser Tyr Asn Ser Gly Leu Ile Ser
1               5                   10                  15


<210> SEQ ID NO 33
<211> LENGTH: 5
<212> TYPE: PRT
<213> ORGANISM: Artificial Sequence
<220> FEATURE:
<223> OTHER INFORMATION: NPC-1 chi-antibody heavy chain CDR3

<400> SEQUENCE: 33

Pro Gly Gly Asp Tyr
1               5


<210> SEQ ID NO 34
<211> LENGTH: 735
<212> TYPE: DNA
<213> ORGANISM: Artificial Sequence
<220> FEATURE:
<223> OTHER INFORMATION: Humanized NEO 103 light chain

<400> SEQUENCE: 34

aagcttgcca ccatgaagta cctgctgccc accgctgctg ctggcttgct gctgctggca      60

gctcagcctg ccatggccga gatcgtgctg acccagtctc ctggcaccct gtctctgagc     120

cctggcgaga gagctaccct gtcctgctcc gcctcctcca gcatctccta catgtactgg     180

tatcagcaga agcccggcca ggcccctcgg ctgctgatct acgatacctc caagctggcc     240
```

```
tccggcatcc ccgacagatt ctccggctct ggctctggca ccgacttcac cctgaccatc    300

tcccggctgg aacccgagga cttcgccgtg tactactgcc accagcggga ctcctacccc    360

tggacctttg gccagggcac caagctggaa atcaagcgga ccgtggccgc tccctccgtg    420

ttcatcttcc caccttccga cgagcagctg aagtccggca ccgcttctgt cgtgtgcctg    480

ctgaacaact tctacccccg cgaggccaag gtgcagtgga aggtggacaa cgccctgcag    540

tccggcaact cccaggaatc cgtgaccgag caggactcca aggacagcac ctactccctg    600

tcctctaccc tgaccctgtc caaggccgac tacgagaagc acaaggtgta cgcctgcgaa    660

gtgacccacc agggcctgtc tagccccgtg accaagtctt tcaaccgggg cgagtgctga    720

tgaggatcct gatga                                                      735
```

<210> SEQ ID NO 35
<211> LENGTH: 239
<212> TYPE: PRT
<213> ORGANISM: Artificial Sequence
<220> FEATURE:
<223> OTHER INFORMATION: Humanized NEO 103 light chain

<400> SEQUENCE: 35

```
Lys Leu Ala Thr Met Lys Tyr Leu Leu Pro Thr Ala Ala Ala Gly Leu
1               5                   10                  15

Leu Leu Leu Ala Ala Gln Pro Ala Met Ala Glu Ile Val Leu Thr Gln
            20                  25                  30

Ser Pro Gly Thr Leu Ser Leu Ser Pro Gly Glu Arg Ala Thr Leu Ser
        35                  40                  45

Cys Ser Ala Ser Ser Ser Ile Ser Tyr Met Tyr Trp Tyr Gln Gln Lys
    50                  55                  60

Pro Gly Gln Ala Pro Arg Leu Leu Ile Tyr Asp Thr Ser Lys Leu Ala
65                  70                  75                  80

Ser Gly Ile Pro Asp Arg Phe Ser Gly Ser Gly Ser Gly Thr Asp Phe
                85                  90                  95

Thr Leu Thr Ile Ser Arg Leu Glu Pro Glu Asp Phe Ala Val Tyr Tyr
            100                 105                 110

Cys His Gln Arg Asp Ser Tyr Pro Trp Thr Phe Gly Gln Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 36
<211> LENGTH: 1437
<212> TYPE: DNA
<213> ORGANISM: Artificial Sequence
<220> FEATURE:
<223> OTHER INFORMATION: Humanized NEO 103 heavy chain

<400> SEQUENCE: 36

```
aagcttgcca ccatggacct gctgtgcaag aacatgaagc acctgtggtt ctttctgctg     60

ctggtggccg ctcccagatg ggtgctgtct caggtgcagc tggtggaatc tggccctggc    120

ctggtgcagc cttccagatc cctgtctctg acctgctcct ccagcggctt cagcctgtcc    180

aagttcggcg tgaactgggt gcgacagcct cctggcaagg gcctggaatg ggtgggagtg    240

atctggggcg acggctccac ctcctacaac tccggcctga tctccagagt gaccatctcc    300

cgggacacct ccaagaacca gctgttcctg aagatggact ccctgaccgc cgaggacacc    360

gccgtgtact actgtgctag acctggcggc gactactggg gccagggcac aacagtgacc    420

gtgtcctccg cttccaccaa gggcccctct gtgtttcctc tggcccccte cagcaagtcc    480

acctctggtg gaactgccgc tctgggctgc ctcgtgaagg actacttccc cgagcccgtg    540

acagtgtcct ggaactctgg cgctctgacc tccggcgtgc acacctttcc agctgtgctg    600

cagtccagcg gcctgtactc cctgtcctcc gtcgtgaccg tgccttccag ctctctgggc    660

acccagacct acatctgcaa cgtgaaccac aagccctcca ataccaaggt ggacaagaag    720

gtggaaccca agtcctgcga caagacccac acctgtcccc cttgtcctgc ccctgaactg    780

ctgggcggac cttccgtgtt cctgttcccc ccaaagccca aggacaccct gatgatctcc    840

cggacccccg aagtgacctg cgtggtggtg gatgtgtccc acgaggaccc tgaagtgaag    900

ttcaattggt acgtggacgg cgtggaagtg cacaacgcca agaccaagcc tagagaggaa    960

cagtacaact ccacctaccg ggtggtgtcc gtgctgaccg tgctgcatca ggactggctg   1020

aacggcaaag agtacaagtg caaggtgtcc aacaaggccc tgcctgcccc catcgaaaag   1080

accatcagca aggctaaggg ccagccccgc gagccccagg tgtacacact gcctccatcc   1140

cgggaagaga tgaccaagaa tcaggtgtcc ctgacctgtc tcgtgaaagg cttctacccc   1200

tccgatatcg ccgtggaatg ggagtccaac ggccagcccg agaacaacta caagaccacc   1260

ccccctgtgc tggactccga cggctcattc ttcctgtaca gcaagctgac agtggacaag   1320

tcccggtggc agcagggcaa cgtgttctcc tgctccgtga tgcacgaggc cctgcacaac   1380

cactacaccc agaagtccct gtccctgagc cccggcaagt gatgatgagg atcctga      1437
```

<210> SEQ ID NO 37
<211> LENGTH: 473
<212> TYPE: PRT
<213> ORGANISM: Artificial Sequence
<220> FEATURE:
<223> OTHER INFORMATION: Humanized NEO 103 heavy chain

<400> SEQUENCE: 37

```
Lys Leu Ala Thr Met Asp Leu Leu Cys Lys Asn Met Lys His Leu Trp
1               5                   10                  15

Phe Phe Leu Leu Leu Val Ala Ala Pro Arg Trp Val Leu Ser Gln Val
            20                  25                  30

Gln Leu Val Glu Ser Gly Pro Gly Leu Val Gln Pro Ser Arg Ser Leu
        35                  40                  45

Ser Leu Thr Cys Ser Ser Ser Gly Phe Ser Leu Ser Lys Phe Gly Val
    50                  55                  60

Asn Trp Val Arg Gln Pro Pro Gly Lys Gly Leu Glu Trp Val Gly Val
65                  70                  75                  80

Ile Trp Gly Asp Gly Ser Thr Ser Tyr Asn Ser Gly Leu Ile Ser Arg
```

-continued

```
                85                  90                  95

Val Thr Ile Ser Arg Asp Thr Ser Lys Asn Gln Leu Phe Leu Lys Met
            100                 105                 110

Asp Ser Leu Thr Ala Glu Asp Thr Ala Val Tyr Tyr Cys Ala Arg Pro
        115                 120                 125

Gly Gly Asp Tyr Trp Gly Gln Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470
```

<210> SEQ ID NO 38
<211> LENGTH: 963
<212> TYPE: DNA
<213> ORGANISM: Artificial Sequence

```
<220> FEATURE:
<223> OTHER INFORMATION: 16C3 antibody light chain

<400> SEQUENCE: 38

gcggggcagc ctcacacaga acacacacag atatgggtgt acccactcag ctcctgttgc      60

tgtggcttac agtcgtagtt gtcagatgtg acatccagat gactcagtct ccagcttcac     120

tgtctgcatc tgtgggagaa actgtcacca tcacatgtgg agcaagtgag aatatttacg     180

gtgctttaaa ttggtatcag cggaaacagg gaaaatctcc tcagctcctg atttatggcg     240

caagtaattt ggcagatggc atgtcatcga ggttcagtgg cagtggatct ggtagacagt     300

attctctcaa gatcagtagc ctgcatcctg acgatgttgc aacgtattac tgtcaaaatg     360

tattaagtag tccgtacacg ttcggagggg ggaccaagct ggaaataaaa cgggctgatg     420

ctgcaccaac tgtatccatc ttcccaccat ccagtgagca gttaacatct ggaggtgcct     480

cagtcgtgtg cttcttgaac aacttctacc ccaaagacat caatgtcaag tggaagattg     540

atggcagtga acgacaaaat ggcgtcctga acagttggac tgatcaggac agcaaagaca     600

gcacctacag catgagcagc accctcacgt tgaccaagga cgagtatgaa cgacataaca     660

gctatacctg tgaggccact cacaagacac caacttcacc cattgtcaag agcttcaaca     720

ggaatgagtg ttagagacaa aggtcctgag acgccaccac cagctcccca gctccatcct     780

atcttccctt ctaaggtctt ggaggcttcc ccacaagcga ctaccactgt tgcggtgctc     840

caaacctcct ccccacctcc ttctcctcct cctccctttc cttggctttt atcatgctaa     900

tatttgcaga aaatattcaa taaagtgatc tttgcacaaa aaaaaaaaaa aaaaaaaaaa     960

aaa                                                                   963


<210> SEQ ID NO 39
<211> LENGTH: 107
<212> TYPE: PRT
<213> ORGANISM: Artificial Sequence
<220> FEATURE:
<223> OTHER INFORMATION: 16C3 antibody light chain
<220> FEATURE:
<221> NAME/KEY: MISC_FEATURE
<222> LOCATION: (22)..(32)
<223> OTHER INFORMATION: CDR1
<220> FEATURE:
<221> NAME/KEY: MISC_FEATURE
<222> LOCATION: (48)..(54)
<223> OTHER INFORMATION: CDR2
<220> FEATURE:
<221> NAME/KEY: MISC_FEATURE
<222> LOCATION: (86)..(95)
<223> OTHER INFORMATION: CDR3

<400> SEQUENCE: 39

Leu Met Thr Gln Ser Pro Ala Ser Leu Ser Ala Ser Val Gly Glu Thr
1               5                   10                  15

Val Thr Ile Thr Cys Gly Ala Ser Glu Asn Ile Tyr Gly Ala Leu Asn
            20                  25                  30

Trp Tyr Gln Arg Lys Gln Gly Lys Ser Pro Gln Leu Leu Ile Tyr Gly
        35                  40                  45

Ala Ser Asn Leu Ala Asp Gly Met Ser Ser Arg Phe Ser Gly Ser Gly
    50                  55                  60

Ser Gly Arg Gln Tyr Ser Leu Lys Ile Ser Ser Leu His Pro Asp Asp
65                  70                  75                  80

Val Ala Thr Tyr Tyr Cys Gln Asn Val Leu Ser Ser Pro Tyr Thr Phe
                85                  90                  95
```

Gly Gly Gly Thr Lys Leu Glu Ile Lys Lys Gly
100 105

<210> SEQ ID NO 40
<211> LENGTH: 11
<212> TYPE: PRT
<213> ORGANISM: Artificial Sequence
<220> FEATURE:
<223> OTHER INFORMATION: 16C3 light chain CDR1

<400> SEQUENCE: 40

Gly Ala Ser Glu Asn Ile Tyr Gly Ala Leu Asn
1 5 10

<210> SEQ ID NO 41
<211> LENGTH: 7
<212> TYPE: PRT
<213> ORGANISM: Artificial Sequence
<220> FEATURE:
<223> OTHER INFORMATION: 16C3 antibody light chain CDR2

<400> SEQUENCE: 41

Gly Ala Ser Asn Leu Ala Asp
1 5

<210> SEQ ID NO 42
<211> LENGTH: 10
<212> TYPE: PRT
<213> ORGANISM: Artificial Sequence
<220> FEATURE:
<223> OTHER INFORMATION: 16C3 antibody light chain CDR3

<400> SEQUENCE: 42

Cys Gln Asn Val Leu Ser Ser Pro Tyr Thr
1 5 10

<210> SEQ ID NO 43
<211> LENGTH: 1575
<212> TYPE: DNA
<213> ORGANISM: Artificial Sequence
<220> FEATURE:
<223> OTHER INFORMATION: 16C3 antibody heavy chain

<400> SEQUENCE: 43
acgcgggaca cagtagtctc tacagtcaca ggagtacaca ggacattgcc atgggttgga 60
gctgtatcat cttctttctg gtagcaacag ctacaggtgt gcactcccag gtccagctgc 120
agcagtctgg gcctgaggtg gtgaggcctg ggtctcagt gaagatttcc tgcaagggtt 180
ccggctacac attcactgat tatgctatgc actgggtgaa gcagagtcat gcaaagagtc 240
tcgagtggat tggacttatt agtacttaca gtggtgatac aaagtacaac cagaatttaa 300
gggcaaggcc acaatgactg tagacaaatc ctccaacaca gcctatatgg aacttgccag 360
attgacatct gaggattctg ccatctatta ctgtgcaaga ggggattatt ccggtagtag 420
gtactggttt gcttactggg gccaagggac tctggtcact gtctctgcag ccaaaacgac 480
acccccatct gtctatccac tggcccctgg atctgctgcc caaactaact ccatggtgac 540
cctgggatgc ctggtcaagg gctatttccc tgagccagtg acagtgacct ggaactctgg 600
atccctgtcc agcggtgtgc acaccttccc agctgttcct gcagtctgac ctctacactc 660
tgagcagctc agtgactgtc ccctccagca cctggcccag cgagaccgtc acctgcaacg 720
ttgcccaccc ggccagcagc accaaggtgg acaagaaaat tgtgcccagg gattgtggtt 780
gtaagccttg catatgtaca gtcccagaag tatcatctgt cttcatcttc cccccaaagc 840

```
ccaaggatgt gctcaccatt actctgactc ctaaggtcac gtgtgttgtg gtagacatca    900

gcaaggatga tcccgaggtc cagttcagct ggtttgtaga tgatgtggag gtgcacacag    960

ctcagacgca accccgggag gagcagttca acagcacttt ccgctcagtc agtgaacttc   1020

ccatcatgca ccaggactgg ctcaatggca aggagttcaa atgcagggtc aacagtgcag   1080

ctttccctgc ccccatcgag aaaaccatct ccaaaaccaa aggcagaccg aaggctccac   1140

aggtgtacac cattccacct cccaaggagc agatggccaa ggataaagtc agtctgacct   1200

gcatgataac agacttcttc cctgaagaca ttactgtgga gtggcagtgg aatgggcagc   1260

cagcggagaa ctacaagaac actcagccca tcatggacac agatggctct tacttcgtct   1320

acagcaagct caatgtgcag aagagcaact gggaggcagg aaatactttc acctgctctg   1380

tgttacatga gggcctgcac aaccaccata ctgagaagag cctctcccac tctcctggta   1440

aatgatccca gtgtccttgg agccctctgg ccctacagga ctttgacacc tacctccacc   1500

cctccctgta taaataaagc acccagcact gcctcgggac cctgcataaa aaaaaaaaaa   1560

aaaaaaaaaa aaaaa                                                    1575
```

```
<210> SEQ ID NO 44
<211> LENGTH: 116
<212> TYPE: PRT
<213> ORGANISM: Artificial Sequence
<220> FEATURE:
<223> OTHER INFORMATION: 16C3 antibody heavy chain
<220> FEATURE:
<221> NAME/KEY: MISC_FEATURE
<222> LOCATION: (23)..(32)
<223> OTHER INFORMATION: CDR1
<220> FEATURE:
<221> NAME/KEY: MISC_FEATURE
<222> LOCATION: (47)..(63)
<223> OTHER INFORMATION: CDR2
<220> FEATURE:
<221> NAME/KEY: MISC_FEATURE
<222> LOCATION: (96)..(107)
<223> OTHER INFORMATION: CDR3

<400> SEQUENCE: 44

Leu Glu Glu Ser Gly Pro Glu Val Val Arg Pro Gly Val Ser Val Lys
1               5                   10                  15

Ile Ser Cys Lys Gly Ser Gly Tyr Thr Phe Thr Asp Tyr Ala Met His
            20                  25                  30

Trp Val Lys Gln Ser His Ala Lys Ser Leu Glu Trp Ile Gly Leu Ile
        35                  40                  45

Ser Thr Tyr Ser Gly Asp Thr Lys Tyr Asn Gln Asn Phe Lys Gly Lys
    50                  55                  60

Ala Thr Met Thr Val Asp Lys Ser Ser Asn Thr Ala Tyr Met Glu Leu
65                  70                  75                  80

Ala Arg Leu Thr Ser Glu Asp Ser Ala Ile Tyr Tyr Cys Ala Arg Gly
                85                  90                  95

Asp Tyr Ser Gly Ser Arg Tyr Trp Phe Ala Tyr Trp Gly Gln Gly Thr
            100                 105                 110

Thr Val Thr Arg
        115


<210> SEQ ID NO 45
<211> LENGTH: 10
<212> TYPE: PRT
<213> ORGANISM: Artificial Sequence
<220> FEATURE:
```

<223> OTHER INFORMATION: 16C3 antibody heavy chain CDR1

<400> SEQUENCE: 45

```
Gly Tyr Thr Phe Thr Asp Tyr Ala Met His
1               5                   10
```

<210> SEQ ID NO 46
<211> LENGTH: 17
<212> TYPE: PRT
<213> ORGANISM: Artificial Sequence
<220> FEATURE:
<223> OTHER INFORMATION: 16C3 antibody heavy chain CDR2

<400> SEQUENCE: 46

```
Leu Ile Ser Thr Tyr Ser Gly Asp Thr Lys Tyr Asn Gln Asn Phe Lys
1               5                   10                  15

Gly
```

<210> SEQ ID NO 47
<211> LENGTH: 12
<212> TYPE: PRT
<213> ORGANISM: Artificial Sequence
<220> FEATURE:
<223> OTHER INFORMATION: 16C3 antibody heavy chain CDR3

<400> SEQUENCE: 47

```
Gly Asp Tyr Ser Gly Ser Arg Tyr Trp Phe Ala Tyr
1               5                   10
```

<210> SEQ ID NO 48
<211> LENGTH: 107
<212> TYPE: PRT
<213> ORGANISM: Artificial Sequence
<220> FEATURE:
<223> OTHER INFORMATION: 16C3 antibody light chain (ven16C3)

<400> SEQUENCE: 48

```
Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45

Tyr Gly Ala Ser Asn Leu Ala Asp Gly Met Pro Ser Arg Phe Ser Gly
    50                  55                  60

Ser Gly Ser Gly Arg Gln Tyr Thr Leu Thr Ile Ser Ser Leu Gln Pro
65                  70                  75                  80

Glu Asp Val Ala Thr Tyr Tyr Cys Gln Asn Val Leu Ser Ser Pro Tyr
                85                  90                  95

Thr Phe Gly Gly Gly Thr Lys Leu Glu Ile Lys
            100                 105
```

<210> SEQ ID NO 49
<211> LENGTH: 107
<212> TYPE: PRT
<213> ORGANISM: Artificial Sequence
<220> FEATURE:
<223> OTHER INFORMATION: 16C3 antibody light chain (cdr16C3)

<400> SEQUENCE: 49

```
Asp Ile Gln Met Thr Gln Ser Pro Ser Ser Leu Ser Ala Ser Val Gly
1               5                   10                  15
```

-continued

Asp Arg Val Thr Ile Thr Cys Gly Ala Ser Glu Asn Ile Tyr Gly Ala
20 25 30

Leu Asn Trp Tyr Gln Arg Lys Pro Gly Lys Ser Pro Lys Leu Leu Ile
35 40 45

Tyr Gly Ala Ser Asn Leu Ala Asp Gly Met Pro Ser Arg Phe Ser Gly
50 55 60

Ser Gly Ser Gly Arg Gln Tyr Thr Leu Thr Ile Ser Ser Leu Gln Pro
65 70 75 80

Glu Asp Val Ala Thr Tyr Tyr Cys Gln Asn Val Leu Ser Ser Pro Tyr
85 90 95

Thr Phe Gly Gly Gly Thr Lys Leu Glu Ile Lys
100 105

<210> SEQ ID NO 50
<211> LENGTH: 107
<212> TYPE: PRT
<213> ORGANISM: Artificial Sequence
<220> FEATURE:
<223> OTHER INFORMATION: 16C3 antibody light chain (abb16C3)

<400> SEQUENCE: 50

Asp Ile Gln Met Thr Gln Ser Pro Ser Ser Leu Ser Ala Ser Val Gly
1 5 10 15

Asp Arg Val Thr Ile Thr Cys Gln Ala Ser Glu Asn Ile Tyr Gly Ala
20 25 30

Leu Asn Trp Tyr Gln Arg Lys Pro Gly Lys Ser Pro Lys Leu Leu Ile
35 40 45

Tyr Gly Ala Ser Asn Leu Ala Thr Gly Met Pro Ser Arg Phe Ser Gly
50 55 60

Ser Gly Ser Gly Thr Asp Tyr Thr Phe Thr Ile Ser Ser Leu Gln Pro
65 70 75 80

Glu Asp Ile Ala Thr Tyr Tyr Cys Gln Asn Val Leu Ser Ser Pro Tyr
85 90 95

Thr Phe Gly Gly Gly Thr Lys Leu Glu Ile Lys
100 105

<210> SEQ ID NO 51
<211> LENGTH: 107
<212> TYPE: PRT
<213> ORGANISM: Artificial Sequence
<220> FEATURE:
<223> OTHER INFORMATION: 16C3 antibody light chain (sdr16C3)

<400> SEQUENCE: 51

Asp Ile Gln Met Thr Gln Ser Pro Ser Ser Leu Ser Ala Ser Val Gly
1 5 10 15

Asp Arg Val Thr Ile Thr Cys Gln Ala Ser Glu Asn Ile Tyr Gly Ala
20 25 30

Leu Asn Trp Tyr Gln Arg Lys Pro Gly Lys Ser Pro Lys Leu Leu Ile
35 40 45

Tyr Gly Ala Ser Asn Leu Ala Thr Gly Met Pro Ser Arg Phe Ser Gly
50 55 60

Ser Gly Ser Gly Arg Gln Tyr Thr Phe Thr Ile Ser Ser Leu Gln Pro
65 70 75 80

Glu Asp Ile Ala Thr Tyr Tyr Cys Gln Gln Val Leu Ser Ser Pro Tyr
85 90 95

Thr Phe Gly Gly Gly Thr Lys Leu Glu Ile Lys
100 105

<210> SEQ ID NO 52
<211> LENGTH: 107
<212> TYPE: PRT
<213> ORGANISM: Artificial Sequence
<220> FEATURE:
<223> OTHER INFORMATION: 16C3 antibody light chain (fra16C3)

<400> SEQUENCE: 52

```
Asp Ile Gln Met Thr Gln Ser Pro Ser Ser Leu Ser Ala Ser Val Gly
1               5                   10                  15

Asp Arg Val Thr Ile Thr Cys Cys Ala Ser Glu Asn Ile Tyr Gly Ala
            20                  25                  30

Leu Asn Trp Tyr Gln Arg Lys Pro Gly Lys Ser Pro Asn Leu Leu Ile
        35                  40                  45

Tyr Gly Ala Ser Asn Leu Ala Asp Gly Met Pro Ser Arg Phe Ser Gly
    50                  55                  60

Ser Gly Ser Gly Arg Gln Tyr Thr Leu Thr Ile Ser Ser Leu Gln Pro
65                  70                  75                  80

Glu Asp Val Ala Thr Tyr Tyr Cys Gln Asn Val Leu Ser Ser Pro Tyr
                85                  90                  95

Thr Phe Gly Gly Gly Thr Lys Leu Glu Ile Lys
            100                 105
```

<210> SEQ ID NO 53
<211> LENGTH: 121
<212> TYPE: PRT
<213> ORGANISM: Artificial Sequence
<220> FEATURE:
<223> OTHER INFORMATION: 16C3 antibody heavy chain (ven16C3)

<400> SEQUENCE: 53

```
Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Leu Ile Ser Thr Tyr Ser Gly Asp Thr Lys Tyr Asn Gln Asn Phe
    50                  55                  60

Lys Gly Lys Ala Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120
```

<210> SEQ ID NO 54
<211> LENGTH: 121
<212> TYPE: PRT
<213> ORGANISM: Artificial Sequence
<220> FEATURE:
<223> OTHER INFORMATION: 16C3 antibody heavy chain (cdr16C3)

<400> SEQUENCE: 54

```
Gln Val Gln Leu Gln Gln Ser Gly Pro Glu Val Val Arg Pro Gly Val
1               5                   10                  15
```

```
Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Leu Ile Ser Thr Tyr Ser Gly Asp Thr Lys Tyr Asn Gln Asn Phe
    50                  55                  60

Lys Gly Lys Ala Thr Met Thr Val Asp Thr Ser Ile Ser Thr Ala Tyr
65                  70                  75                  80

Met Glu Leu Ser Arg Leu Arg Ser Asp Asp Thr Ala Ile Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120


<210> SEQ ID NO 55
<211> LENGTH: 121
<212> TYPE: PRT
<213> ORGANISM: Artificial Sequence
<220> FEATURE:
<223> OTHER INFORMATION: 16C3 antibody heavy chain (abb16C3)

<400> SEQUENCE: 55

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Leu Ile Ser Thr Tyr Ser Gly Asp Thr Lys Tyr Ser Gln Lys Phe
    50                  55                  60

Gln Gly Arg Val Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120


<210> SEQ ID NO 56
<211> LENGTH: 121
<212> TYPE: PRT
<213> ORGANISM: Artificial Sequence
<220> FEATURE:
<223> OTHER INFORMATION: 16C3 antibody heavy chain (sdr16C3)

<400> SEQUENCE: 56

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Leu Ile Ser Thr Tyr Ser Gly Asp Thr Lys Tyr Asn Gln Lys Phe
    50                  55                  60

Gln Gly Lys Ala Thr Met Thr Val Asp Lys Ser Ala Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120
```

<210> SEQ ID NO 57
<211> LENGTH: 121
<212> TYPE: PRT
<213> ORGANISM: Artificial Sequence
<220> FEATURE:
<223> OTHER INFORMATION: 16C3 antibody heavy chain (fra16C3)

<400> SEQUENCE: 57

```
Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Leu Ile Ser Thr Tyr Ser Gly Asp Thr Lys Tyr Asn Gln Asn Phe
    50                  55                  60

Lys Gly Lys Ala Thr Met Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120
```

<210> SEQ ID NO 58
<211> LENGTH: 702
<212> TYPE: DNA
<213> ORGANISM: Artificial Sequence
<220> FEATURE:
<223> OTHER INFORMATION: h16C3-Abb* light chain

<400> SEQUENCE: 58

```
atgggcgtgc ccacccagct gctgctgctg tggctgaccg tggtggtggt gcggtgcgac     60

atccagatga cccagtcccc tagctctctg agcgcctccg tgggcgacag ggtgaccatc    120

acctgccaag cctctgagaa catctacggc gccctgaact ggtaccagag gaagcccggc    180

aagagcccca agctgctgat ctacggcgcc tctaacctgg ccaccggcat gcctagccgg    240

ttctccggct ccggcagcgg caccgactac accttcacca tctcctccct gcaacccgag    300

gacatcgcca cctactactg ccagcaggtg ctgtcctccc cctacacctt cggcggcggc    360

accaaactgg agatcaagcg gaccgtggcc gcccccagcg tgttcatctt cccccccctct    420

gacgagcagc tgaagtccgg caccgcctct gtggtgtgcc tgctgaacaa cttctacccc    480

agggaggcca aggtccagtg gaaggtggac aacgccctgc agtccggcaa cagccaggag    540

tctgtgaccg agcaggactc caaggactcc acctacagcc tgtctagcac cctgaccctg    600

tccaaggccg actacgagaa gcacaaggtg tacgcctgcg aggtgaccca ccagggcctg    660

tccagccctg tgaccaagtc cttcaacagg ggcgagtgct ga                       702
```

-continued

<210> SEQ ID NO 59
<211> LENGTH: 233
<212> TYPE: PRT
<213> ORGANISM: Artificial Sequence
<220> FEATURE:
<223> OTHER INFORMATION: h16C3-Abb* light chain
<220> FEATURE:
<221> NAME/KEY: MISC_FEATURE
<222> LOCATION: (43)..(53)
<223> OTHER INFORMATION: CDR1
<220> FEATURE:
<221> NAME/KEY: MISC_FEATURE
<222> LOCATION: (69)..(75)
<223> OTHER INFORMATION: CDR2
<220> FEATURE:
<221> NAME/KEY: MISC_FEATURE
<222> LOCATION: (108)..(116)
<223> OTHER INFORMATION: CDR3

<400> SEQUENCE: 59

```
Met Gly Val Pro Thr Gln Leu Leu Leu Leu Trp Leu Thr Val Val Val
1               5                   10                  15

Val Arg Cys Asp Ile Gln Met Thr Gln Ser Pro Ser Ser Leu Ser Ala
            20                  25                  30

Ser Val Gly Asp Arg Val Thr Ile Thr Cys Gln Ala Ser Glu Asn Ile
        35                  40                  45

Tyr Gly Ala Leu Asn Trp Tyr Gln Arg Lys Pro Gly Lys Ser Pro Lys
    50                  55                  60

Leu Leu Ile Tyr Gly Ala Ser Asn Leu Ala Thr Gly Met Pro Ser Arg
65                  70                  75                  80

Phe Ser Gly Ser Gly Ser Gly Thr Asp Tyr Thr Phe Thr Ile Ser Ser
                85                  90                  95

Leu Gln Pro Glu Asp Ile Ala Thr Tyr Tyr Cys Gln Gln Val Leu Ser
            100                 105                 110

Ser Pro Tyr Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 60
<211> LENGTH: 11
<212> TYPE: PRT
<213> ORGANISM: Artificial Sequence
<220> FEATURE:
<223> OTHER INFORMATION: h16C3-Abb* light chain CDR1

<400> SEQUENCE: 60

```
Gln Ala Ser Glu Asn Ile Tyr Gly Ala Leu Asn
1               5                   10
```

<210> SEQ ID NO 61
<211> LENGTH: 7
<212> TYPE: PRT
<213> ORGANISM: Artificial Sequence
<220> FEATURE:
<223> OTHER INFORMATION: h16C3-Abb* light chain CDR2

<400> SEQUENCE: 61

Gly Ala Ser Asn Leu Ala Thr
1               5

<210> SEQ ID NO 62
<211> LENGTH: 9
<212> TYPE: PRT
<213> ORGANISM: Artificial Sequence
<220> FEATURE:
<223> OTHER INFORMATION: h16C3-Abb* light chain CDR3

<400> SEQUENCE: 62

Gln Gln Val Leu Ser Ser Pro Tyr Thr
1               5

<210> SEQ ID NO 63
<211> LENGTH: 1413
<212> TYPE: DNA
<213> ORGANISM: Artificial Sequence
<220> FEATURE:
<223> OTHER INFORMATION: h16C3-Abb* heavy chain

<400> SEQUENCE: 63
atgggctggt cctgcatcat cttcttcctg gtggccaccg ccaccggcgt gcacagccag 60
gtgcagcttg tgcagagcgg cgccgaggtg aagaagcccg gcgccagcgt gaaggtgtcc 120
tgcaaggcct ccggctacac cttcaccgac tacgccatgc actgggtgcg gcaggccccc 180
ggccagcggc tggagtggat gggcctgatc agcacctact ctggcgacac caagtacaac 240
cagaacttcc agggccgggt gaccatgacc gtggacaaga gcgccagcac cgcctacatg 300
gagctgtcct ccctgaggtc tgaggacacc gccgtgtact actgcgcccg gggcgactac 360
agcggcagcc ggtactggtt cgcctactgg ggccagggca ccctggtgac cgtgtccagc 420
gcctctacca agggccccag cgtgtttccc ctggcccctt cctccaaaag caccagcggc 480
ggtaccgccg ccctgggctg cctggtgaag gactacttcc ccgagcccgt gaccgtgagc 540
tggaactccg gcgccctgac cagcggcgtg cacaccttcc ctgccgtgct gcaaagctcc 600
ggcctgtact ccctgagctc tgtggtgacc gtgccctcca gctccctggg cacccagacc 660
tacatctgca acgtgaacca caagcccagc aacaccaagg tggacaagaa ggtggagcct 720
aagtcttgcg acaagaccca cacctgcccc ccttgccctg cccctgagct gctgggcggc 780
cccagcgtgt tcctgttccc tcccaagccc aaggacaccc tgatgatctc ccggacccct 840
gaggtgacct gcgtggtggt ggatgtgagc cacgaggatc ctgaagtgaa gttcaattgg 900
tatgtggatg gcgtggaggt gcacaacgcc aagaccaagc cccgggagga gcagtacaac 960
agcacctaca gggtggtgtc cgtgctgacc gtgctgcacc aggactggct gaacggcaag 1020
gagtacaagt gcaaggtgtc caacaaggcc ctgcccgccc ccatcgagaa gaccatctcc 1080
aaggccaagg gccagccccg ggagccccag gtgtacaccc tgcctcccag ccgggacgag 1140
ctgaccaaga accaggtgtc cctgacctgc ctggtgaagg gcttctaccc ctctgacatc 1200
gccgtggagt gggagagcaa cggccagccc gagaacaact acaagaccac cccccccgtg 1260
ctggactccg acggctcctt cttcctgtac tctaagctga ccgtggacaa gtcccgctgg 1320

```
cagcagggca acgtgttcag ctgctccgtg atgcacgagg ccctgcacaa ccactacacc   1380

cagaagagcc tgagcctgtc tcccggcaag tga                                1413


<210> SEQ ID NO 64
<211> LENGTH: 470
<212> TYPE: PRT
<213> ORGANISM: Artificial Sequence
<220> FEATURE:
<223> OTHER INFORMATION: h16C3-Abb* heavy chain
<220> FEATURE:
<221> NAME/KEY: MISC_FEATURE
<222> LOCATION: (45)..(54)
<223> OTHER INFORMATION: CDR1
<220> FEATURE:
<221> NAME/KEY: MISC_FEATURE
<222> LOCATION: (70)..(85)
<223> OTHER INFORMATION: CDR2
<220> FEATURE:
<221> NAME/KEY: MISC_FEATURE
<222> LOCATION: (118)..(129)
<223> OTHER INFORMATION: CDR3

<400> SEQUENCE: 64

Met Gly Trp Ser Cys Ile Ile Phe Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Ala Met His Trp Val Arg Gln Ala Pro Gly Gln Arg Leu
    50                  55                  60

Glu Trp Met Gly Leu Ile Ser Thr Tyr Ser Gly Asp Thr Lys Tyr Asn
65                  70                  75                  80

Gln Asn Phe Gln Gly Arg Val Thr Met Thr Val Asp Lys Ser Ala Ser
                85                   90                  95

Thr Ala Tyr Met Glu Leu Ser Ser Leu Arg Ser Glu Asp Thr Ala Val
            100                 105                 110

Tyr Tyr Cys Ala Arg Gly Asp Tyr Ser Gly Ser Arg Tyr Trp Phe Ala
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
```

-continued

```
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470


<210> SEQ ID NO 65
<211> LENGTH: 10
<212> TYPE: PRT
<213> ORGANISM: Artificial Sequence
<220> FEATURE:
<223> OTHER INFORMATION: h16C3-Abb* heavy chain CDR1

<400> SEQUENCE: 65

Gly Tyr Thr Phe Thr Asp Tyr Ala Met His
1               5                   10


<210> SEQ ID NO 66
<211> LENGTH: 16
<212> TYPE: PRT
<213> ORGANISM: Artificial Sequence
<220> FEATURE:
<223> OTHER INFORMATION: h16C3-Abb* heavy chain CDR2

<400> SEQUENCE: 66

Ile Ser Thr Tyr Ser Gly Asp Thr Lys Tyr Asn Gln Asn Phe Gln Gly
1               5                   10                  15


<210> SEQ ID NO 67
<211> LENGTH: 12
<212> TYPE: PRT
<213> ORGANISM: Artificial Sequence
<220> FEATURE:
<223> OTHER INFORMATION: h16C3-Abb* heavy chain CDR3

<400> SEQUENCE: 67

Gly Asp Tyr Ser Gly Ser Arg Tyr Trp Phe Ala Tyr
1               5                   10


<210> SEQ ID NO 68
```

<211> LENGTH: 236
<212> TYPE: PRT
<213> ORGANISM: Artificial Sequence
<220> FEATURE:
<223> OTHER INFORMATION: humanized 31.1 antibody light chain

<400> SEQUENCE: 68

Met Lys Tyr Leu Leu Pro Thr Ala Ala Ala Gly Leu Leu Leu Leu Ala
1               5                   10                  15

Ala Gln Pro Ala Met Ala Glu Ile Val Met Thr Gln Ser Pro Leu Ser
            20                  25                  30

Leu Pro Val Ser Pro Gly Glu Pro Ala Ser Ile Ser Cys Lys Ala Ser
        35                  40                  45

Gln Ser Val Ser Asn Asp Val Ala Trp Tyr Leu Gln Lys Pro Gly Gln
    50                  55                  60

Ser Pro Lys Leu Leu Ile Tyr Tyr Ala Ser Asn Arg Tyr Thr Gly Val
65                  70                  75                  80

Pro Asp Arg Phe Ser Gly Ser Gly Ser Gly Thr Asp Phe Thr Leu Lys
                85                  90                  95

Ile Ser Arg Val Glu Ala Glu Asp Leu Gly Val Tyr Tyr Cys Gln Gln
            100                 105                 110

Asp Tyr Ser Ser Pro Leu Thr Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 69
<211> LENGTH: 467
<212> TYPE: PRT
<213> ORGANISM: Artificial Sequence
<220> FEATURE:
<223> OTHER INFORMATION: humanized 31.1 antibody heavy chain

<400> SEQUENCE: 69

Met Asp Trp Thr Trp Arg Ile Leu Phe Leu Val Ala Ala Ala Thr Gly
1               5                   10                  15

Ala Gln Ala Gln Val Gln Leu Val Gln Ser Gly Pro Glu Leu Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Lys Gly Leu
    50                  55                  60

Glu Trp Met Gly Trp Ile Asn Thr Tyr Thr Gly Glu Pro Thr Tyr Ala
65                  70                  75                  80

Asp Asp Phe Lys Gly Arg Phe Ser Met Ser Leu Asp Thr Ser Thr Ser

```
                85                  90                  95

Thr Ala Tyr Leu Gln Ile Ser Ser Leu Lys Ser Glu Asp Thr Ala Val
            100                 105                 110

Tyr Phe Cys Ala Arg Ala Tyr Tyr Gly Lys Tyr Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465
```

<210> SEQ ID NO 70
<211> LENGTH: 738
<212> TYPE: DNA
<213> ORGANISM: Artificial Sequence
<220> FEATURE:
<223> OTHER INFORMATION: humanized NEO 302 light chain

<400> SEQUENCE: 70

```
aagcttgcca ccatgaagta cctgctgccc accgctgctg ctggcttgct gctgctggca      60

gctcagcctg ccatggccga gatcgtgatg acccagtccc ctctgtccct gcctgtgtct     120

cctggcgagc ctgcctccat ctcctgcaag gcctcccagt ccgtgtccaa cgacgtggcc     180

tggtatctgc agaagcctgg ccagtccccc aagctgctga tctactacgc ctccaaccgg     240

tacaccggcg tgcccgacag attctccggc tctggctctg gcaccgactt caccctgaag     300

atctcccggg tggaagccga ggacctgggc gtgtactact gtcagcagga ctactcctcc     360

cccctgacct ttggccaggg caccaagctg gaaatcaagc ggaccgtggc cgctccctcc     420

gtgttcatct tcccaccttc cgacgagcag ctgaagtccg gcaccgcttc tgtcgtgtgc     480

ctgctgaaca acttctaccc ccgcgaggcc aaggtgcagt ggaaggtgga caacgccctg     540

cagtccggca actcccagga atccgtgacc gagcaggact ccaaggacag cacctactcc     600

ctgtccagca ccctgaccct gtccaaggcc gactacgaga agcacaaggt gtacgcctgc     660

gaagtgaccc accagggcct gtctagcccc gtgaccaagt ctttcaaccg gggcgagtgc     720

tgatgatgag gatcctga                                                   738
```

<210> SEQ ID NO 71
<211> LENGTH: 240
<212> TYPE: PRT
<213> ORGANISM: Artificial Sequence
<220> FEATURE:
<223> OTHER INFORMATION: humanized NEO 302 light chain

<400> SEQUENCE: 71

```
Lys Leu Ala Thr Met Lys Tyr Leu Leu Pro Thr Ala Ala Ala Gly Leu
1               5                   10                  15

Leu Leu Leu Ala Ala Gln Pro Ala Met Ala Glu Ile Val Met Thr Gln
            20                  25                  30

Ser Pro Leu Ser Leu Pro Val Ser Pro Gly Glu Pro Ala Ser Ile Ser
        35                  40                  45

Cys Lys Ala Ser Gln Ser Val Ser Asn Asp Val Ala Trp Tyr Leu Gln
    50                  55                  60

Lys Pro Gly Gln Ser Pro Lys Leu Leu Ile Tyr Tyr Ala Ser Asn Arg
65                  70                  75                  80

Tyr Thr Gly Val Pro Asp Arg Phe Ser Gly Ser Gly Ser Gly Thr Asp
                85                  90                  95

Phe Thr Leu Lys Ile Ser Arg Val Glu Ala Glu Asp Leu Gly Val Tyr
            100                 105                 110

Tyr Cys Gln Gln Asp Tyr Ser Ser Pro Leu Thr Phe Gly Gln Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205
```

-continued

```
Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 72
<211> LENGTH: 1431
<212> TYPE: DNA
<213> ORGANISM: Artificial Sequence
<220> FEATURE:
<223> OTHER INFORMATION: humanized NEO 302 heavy chain

<400> SEQUENCE: 72

```
aagcttgcca ccatggactg gacctggcgc atcctgtttc tggtggccgc tgctacaggc     60
gcccaggctc aggtgcagct ggtgcagtct ggacccgagc tgaagaaacc tggcgcctcc    120
gtgaaggtgt cctgcaaggc ttccggctac acctttacca actacggcat gaactgggtg    180
cgacaggccc ctggcaaggg cctggaatgg atgggctgga tcaacaccta caccggcgag    240
cccacctacg ccgacgactt caagggccgg ttctccatgt ccctggacac ctccaccagc    300
accgcctacc tgcagatctc cagcctgaag tccgaggata ccgccgtgta cttctgcgcc    360
agagcctact acggcaagta cttcgactac tggggccagg gcaccctcgt gaccgtgtcc    420
tctgcttcta ccaagggccc ctccgtgttc cctctggccc cttccagcaa gtctacctct    480
ggcggcacag ccgctctggg ctgcctcgtg aaggactact tccccgagcc cgtgacagtg    540
tcttggaact ctggcgccct gacctccggc gtgcacacct ttccagctgt gctgcagtcc    600
tccggcctgt actccctgtc ctccgtcgtg actgtgccct ccagctctct gggcacccag    660
acctacatct gcaacgtgaa ccacaagccc tccaacacca aggtggacaa gaaggtggaa    720
cccaagtcct gcgacaagac ccacacctgt ccccccttgtc ctgcccctga actgctgggc    780
ggacccagcg tgttcctgtt ccccccaaag cccaaggaca ccctgatgat ctcccggacc    840
cccgaagtga cctgcgtggt ggtggatgtg tctcacgagg accctgaagt gaagttcaat    900
tggtacgtgg acggcgtgga agtgcacaac gccaagacca agcctagaga ggaacagtac    960
aactccacct accgggtggt gtccgtgctg accgtgctgc accaggattg gctgaacggc   1020
aaagagtaca agtgcaaggt gtccaacaag gccctgcctg cccccatcga aaagaccatc   1080
tccaaggcca agggccagcc ccgggaaccc caggtgtaca cactgccccc tagcagggac   1140
gagctgacca agaaccaggt gtccctgacc tgtctcgtga aaggcttcta cccctccgat   1200
atcgccgtgg aatgggagtc caacggccag cctgagaaca actacaagac cacccccccct   1260
gtgctggact ccgacggctc attcttcctg tacagcaagc tgacagtgga caagtcccgg   1320
tggcagcagg gcaacgtgtt ctcctgctcc gtgatgcacg aggccctgca caaccactac   1380
acccagaagt ccctgtccct gagccccggc aagtgatgat gaggatcctg a            1431
```

<210> SEQ ID NO 73
<211> LENGTH: 471
<212> TYPE: PRT
<213> ORGANISM: Artificial Sequence
<220> FEATURE:
<223> OTHER INFORMATION: humanized NEO 302 heavy chain

<400> SEQUENCE: 73

```
Lys Leu Ala Thr Met Asp Trp Thr Trp Arg Ile Leu Phe Leu Val Ala
1               5                   10                  15

Ala Ala Thr Gly Ala Gln Ala Gln Val Gln Leu Val Gln Ser Gly Pro
```

```
            20                  25                  30

Glu Leu Lys Lys Pro Gly Ala Ser Val Lys Val Ser Cys Lys Ala Ser
        35                  40                  45

Gly Tyr Thr Phe Thr Asn Tyr Gly Met Asn Trp Val Arg Gln Ala Pro
    50                  55                  60

Gly Lys Gly Leu Glu Trp Met Gly Trp Ile Asn Thr Tyr Thr Gly Glu
65                  70                  75                  80

Pro Thr Tyr Ala Asp Asp Phe Lys Gly Arg Phe Ser Met Ser Leu Asp
                85                  90                  95

Thr Ser Thr Ser Thr Ala Tyr Leu Gln Ile Ser Ser Leu Lys Ser Glu
            100                 105                 110

Asp Thr Ala Val Tyr Phe Cys Ala Arg Ala Tyr Tyr Gly Lys Tyr Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445
```

```
Cys Ser Val Met His Glu Ala Leu His Asn His Tyr Thr Gln Lys Ser
    450                 455                 460

Leu Ser Leu Ser Pro Gly Lys
465                 470


<210> SEQ ID NO 74
<211> LENGTH: 448
<212> TYPE: PRT
<213> ORGANISM: Artificial Sequence
<220> FEATURE:
<223> OTHER INFORMATION: NEO-303 antibody Heavy Chain (cdr31.1)
<220> FEATURE:
<221> NAME/KEY: MISC_FEATURE
<222> LOCATION: (1)..(118)
<223> OTHER INFORMATION: Variable region
<220> FEATURE:
<221> NAME/KEY: MISC_FEATURE
<222> LOCATION: (25)..(35)
<223> OTHER INFORMATION: CDR1
<220> FEATURE:
<221> NAME/KEY: MISC_FEATURE
<222> LOCATION: (50)..(70)
<223> OTHER INFORMATION: CDR2
<220> FEATURE:
<221> NAME/KEY: MISC_FEATURE
<222> LOCATION: (99)..(108)
<223> OTHER INFORMATION: CDR3

<400> SEQUENCE: 74

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Thr Leu Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Ala Arg Ala Tyr Tyr Gly Lys Tyr Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Pro Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
```

245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Leu Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Met Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 75
<211> LENGTH: 448
<212> TYPE: PRT
<213> ORGANISM: Artificial Sequence
<220> FEATURE:
<223> OTHER INFORMATION: NEO-303 antibody Heavy Chain (abb31.1)
<220> FEATURE:
<221> NAME/KEY: MISC_FEATURE
<222> LOCATION: (1)..(118)
<223> OTHER INFORMATION: Variable region
<220> FEATURE:
<221> NAME/KEY: MISC_FEATURE
<222> LOCATION: (25)..(35)
<223> OTHER INFORMATION: CDR1
<220> FEATURE:
<221> NAME/KEY: MISC_FEATURE
<222> LOCATION: (50)..(70)
<223> OTHER INFORMATION: CDR2
<220> FEATURE:
<221> NAME/KEY: MISC_FEATURE
<222> LOCATION: (99)..(108)
<223> OTHER INFORMATION: CDR3

<400> SEQUENCE: 75

Gln Ile Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Gly Met Asn Trp Val Arg Gln Ala Pro Gly Lys Gly Leu Glu Trp Met
35 40 45

Gly Trp Ile Asn Thr Tyr Thr Gly Glu Pro Thr Tyr Ala Gln Lys Phe
50 55 60

Gln Gly Arg Val Thr Phe Thr Leu Asp Thr Ser Ile Ser Thr Ala Tyr
65 70 75 80

-continued

```
Met Glu Leu Ser Arg Leu Arg Ser Asp Asp Thr Ala Val Tyr Phe Cys
                85                  90                  95

Ala Arg Ala Tyr Tyr Gly Lys Tyr Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Pro Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Met Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 76
<211> LENGTH: 448
<212> TYPE: PRT
<213> ORGANISM: Artificial Sequence
<220> FEATURE:
<223> OTHER INFORMATION: NEO-303 antibody Heavy Chain (sdr31.1)
<220> FEATURE:
<221> NAME/KEY: MISC_FEATURE
<222> LOCATION: (1)..(118)

-continued

<223> OTHER INFORMATION: Variable region
<220> FEATURE:
<221> NAME/KEY: MISC_FEATURE
<222> LOCATION: (25)..(35)
<223> OTHER INFORMATION: CDR1
<220> FEATURE:
<221> NAME/KEY: MISC_FEATURE
<222> LOCATION: (50)..(70)
<223> OTHER INFORMATION: CDR2
<220> FEATURE:
<221> NAME/KEY: MISC_FEATURE
<222> LOCATION: (99)..(108)
<223> OTHER INFORMATION: CDR3

<400> SEQUENCE: 76

```
Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Pro Tyr Thr Gly Glu Pro Thr Tyr Ala Gln Lys Phe
    50                  55                  60

Gln Gly Arg Val Thr Phe Thr Leu Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Ala Arg Ala Tyr Tyr Gly Lys Tyr Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Pro Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335
```

-continued

```
Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Met Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 77
<211> LENGTH: 448
<212> TYPE: PRT
<213> ORGANISM: Artificial Sequence
<220> FEATURE:
<223> OTHER INFORMATION: NEO-303 antibody Heavy Chain (ven31.1)
<220> FEATURE:
<221> NAME/KEY: MISC_FEATURE
<222> LOCATION: (1)..(118)
<223> OTHER INFORMATION: Variable region
<220> FEATURE:
<221> NAME/KEY: MISC_FEATURE
<222> LOCATION: (25)..(35)
<223> OTHER INFORMATION: CDR1
<220> FEATURE:
<221> NAME/KEY: MISC_FEATURE
<222> LOCATION: (50)..(70)
<223> OTHER INFORMATION: CDR2
<220> FEATURE:
<221> NAME/KEY: MISC_FEATURE
<222> LOCATION: (99)..(108)
<223> OTHER INFORMATION: CDR3

<400> SEQUENCE: 77

Gln Ile Gln Leu Val Gln Ser Gly Pro Glu Val Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Thr Leu Asp Thr Ser Ile Ser Thr Ala Tyr
65                  70                  75                  80

Leu Glu Ile Ser Arg Leu Arg Ser Asp Asp Thr Ala Val Tyr Phe Cys
                85                  90                  95

Ala Arg Ala Tyr Tyr Gly Lys Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Pro Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Met Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 78
<211> LENGTH: 11
<212> TYPE: PRT
<213> ORGANISM: Artificial Sequence
<220> FEATURE:
<223> OTHER INFORMATION: NEO-303 antibody Heavy Chain CDR1

<400> SEQUENCE: 78

Ser Gly Tyr Thr Phe Thr Asn Tyr Gly Met Asn
1               5                   10


<210> SEQ ID NO 79
<211> LENGTH: 21
<212> TYPE: PRT
<213> ORGANISM: Artificial Sequence
<220> FEATURE:
<223> OTHER INFORMATION: NEO-303 antibody Heavy Chain CDR2

<400> SEQUENCE: 79

Trp Ile Asn Thr Tyr Thr Gly Glu Pro Thr Tyr Ala Asp Asp Phe Lys
1               5                   10                  15

Gly Arg Phe Ala Phe
```

20

<210> SEQ ID NO 80
<211> LENGTH: 21
<212> TYPE: PRT
<213> ORGANISM: Artificial Sequence
<220> FEATURE:
<223> OTHER INFORMATION: NEO-303 antibody Heavy Chain CDR2

<400> SEQUENCE: 80

Trp Ile Asn Thr Tyr Thr Gly Glu Pro Thr Tyr Ala Gln Lys Phe Gln
1 5 10 15

Gly Arg Val Thr Phe
20

<210> SEQ ID NO 81
<211> LENGTH: 21
<212> TYPE: PRT
<213> ORGANISM: Artificial Sequence
<220> FEATURE:
<223> OTHER INFORMATION: NEO-303 antibody Heavy Chain CDR2

<400> SEQUENCE: 81

Trp Ile Asn Pro Tyr Thr Gly Glu Pro Thr Tyr Ala Gln Lys Phe Gln
1 5 10 15

Gly Arg Val Thr Phe
20

<210> SEQ ID NO 82
<211> LENGTH: 21
<212> TYPE: PRT
<213> ORGANISM: Artificial Sequence
<220> FEATURE:
<223> OTHER INFORMATION: NEO-303 antibody Heavy Chain CDR2

<400> SEQUENCE: 82

Trp Ile Asn Thr Tyr Thr Gly Glu Pro Thr Tyr Ala Asp Asp Phe Lys
1 5 10 15

Gly Arg Phe Ala Phe
20

<210> SEQ ID NO 83
<211> LENGTH: 10
<212> TYPE: PRT
<213> ORGANISM: Artificial Sequence
<220> FEATURE:
<223> OTHER INFORMATION: NEO-303 antibody Heavy Chain CDR3

<400> SEQUENCE: 83

Ala Tyr Tyr Gly Lys Tyr Phe Asp Tyr Trp
1 5 10

<210> SEQ ID NO 84
<211> LENGTH: 214
<212> TYPE: PRT
<213> ORGANISM: Artificial Sequence
<220> FEATURE:
<223> OTHER INFORMATION: NEO-303 antibody light chain (cdr31.1)
<220> FEATURE:
<221> NAME/KEY: MISC_FEATURE
<222> LOCATION: (1)..(107)
<223> OTHER INFORMATION: Variable region
<220> FEATURE:
<221> NAME/KEY: MISC_FEATURE
<222> LOCATION: (21)..(34)
<223> OTHER INFORMATION: CDR1
<220> FEATURE:

```
<221> NAME/KEY: MISC_FEATURE
<222> LOCATION: (50)..(56)
<223> OTHER INFORMATION: CDR2
<220> FEATURE:
<221> NAME/KEY: MISC_FEATURE
<222> LOCATION: (89)..(97)
<223> OTHER INFORMATION: CDR3

<400> SEQUENCE: 84

Ser Ile Val Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Val Tyr Phe Cys Gln Gln Asp Tyr Ser Ser Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 85
<211> LENGTH: 214
<212> TYPE: PRT
<213> ORGANISM: Artificial Sequence
<220> FEATURE:
<223> OTHER INFORMATION: NEO-303 antibody light chain (abb31.1)
<220> FEATURE:
<221> NAME/KEY: MISC_FEATURE
<222> LOCATION: (1)..(107)
<223> OTHER INFORMATION: Variable region
<220> FEATURE:
<221> NAME/KEY: MISC_FEATURE
<222> LOCATION: (21)..(34)
<223> OTHER INFORMATION: CDR1
<220> FEATURE:
<221> NAME/KEY: MISC_FEATURE
<222> LOCATION: (50)..(56)
<223> OTHER INFORMATION: CDR2
<220> FEATURE:
<221> NAME/KEY: MISC_FEATURE
<222> LOCATION: (89)..(97)
<223> OTHER INFORMATION: CDR3

<400> SEQUENCE: 85

Ser Ile Gln Met Thr Gln Ser Pro Ser Ser Leu Ser Ala Ser Val Gly
```

```
1               5                   10                  15

Asp Arg Val Thr Ile Thr Cys Arg Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Ser Gly Val Pro Asp Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Val Tyr Phe Cys Gln Gln Asp Tyr Ser Ser Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 86
<211> LENGTH: 214
<212> TYPE: PRT
<213> ORGANISM: Artificial Sequence
<220> FEATURE:
<223> OTHER INFORMATION: NEO-303 antibody light chain (sdr31.1)
<220> FEATURE:
<221> NAME/KEY: MISC_FEATURE
<222> LOCATION: (1)..(107)
<223> OTHER INFORMATION: Variable region
<220> FEATURE:
<221> NAME/KEY: MISC_FEATURE
<222> LOCATION: (21)..(34)
<223> OTHER INFORMATION: CDR1
<220> FEATURE:
<221> NAME/KEY: MISC_FEATURE
<222> LOCATION: (50)..(56)
<223> OTHER INFORMATION: CDR2
<220> FEATURE:
<221> NAME/KEY: MISC_FEATURE
<222> LOCATION: (89)..(97)
<223> OTHER INFORMATION: CDR3

<400> SEQUENCE: 86

Ser Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asp
            20                  25                  30

Leu Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Ser Gly
    50                  55                  60
```

```
Ser Gly Tyr Gly Thr Asp Phe Thr Leu Thr Ile Ser Ser Leu Gln Pro
65                  70                  75                  80

Glu Asp Phe Ala Val Tyr Phe Cys Gln Gln Asp Tyr Ser Ser Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 87
<211> LENGTH: 214
<212> TYPE: PRT
<213> ORGANISM: Artificial Sequence
<220> FEATURE:
<223> OTHER INFORMATION: NEO-303 antibody light chain (ven31.1)
<220> FEATURE:
<221> NAME/KEY: MISC_FEATURE
<222> LOCATION: (1)..(107)
<223> OTHER INFORMATION: Variable region
<220> FEATURE:
<221> NAME/KEY: MISC_FEATURE
<222> LOCATION: (21)..(34)
<223> OTHER INFORMATION: CDR1
<220> FEATURE:
<221> NAME/KEY: MISC_FEATURE
<222> LOCATION: (50)..(56)
<223> OTHER INFORMATION: CDR2
<220> FEATURE:
<221> NAME/KEY: MISC_FEATURE
<222> LOCATION: (89)..(97)
<223> OTHER INFORMATION: CDR3

<400> SEQUENCE: 87

Ser Ile Val Met Thr Gln Ser Pro Ser Ser Leu Ser Val Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Ser Gly
    50                  55                  60

Ser Gly Tyr Gly Thr Asp Phe Thr Phe Thr Ile Ser Ser Val Gln Pro
65                  70                  75                  80

Glu Asp Leu Ala Val Tyr Phe Cys Gln Gln Asp Tyr Ser Ser Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125
```

-continued

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 88
<211> LENGTH: 14
<212> TYPE: PRT
<213> ORGANISM: Artificial Sequence
<220> FEATURE:
<223> OTHER INFORMATION: NEO-303 antibody light chain CDR1

<400> SEQUENCE: 88

Ile Thr Cys Lys Ala Ser Gln Ser Val Ser Asn Asp Val Ala
1               5                   10


<210> SEQ ID NO 89
<211> LENGTH: 14
<212> TYPE: PRT
<213> ORGANISM: Artificial Sequence
<220> FEATURE:
<223> OTHER INFORMATION: NEO-303 antibody light chain CDR1

<400> SEQUENCE: 89

Ile Thr Cys Arg Ala Ser Gln Ser Val Ser Asn Asp Val Ala
1               5                   10


<210> SEQ ID NO 90
<211> LENGTH: 14
<212> TYPE: PRT
<213> ORGANISM: Artificial Sequence
<220> FEATURE:
<223> OTHER INFORMATION: NEO-303 antibody light chain CDR1

<400> SEQUENCE: 90

Ile Thr Cys Arg Ala Ser Gln Ser Ile Ser Asn Asp Leu Ala
1               5                   10


<210> SEQ ID NO 91
<211> LENGTH: 7
<212> TYPE: PRT
<213> ORGANISM: Artificial Sequence
<220> FEATURE:
<223> OTHER INFORMATION: NEO-303 antibody light chain CDR2

<400> SEQUENCE: 91

Tyr Ala Ser Asn Arg Tyr Thr
1               5


<210> SEQ ID NO 92
<211> LENGTH: 7
<212> TYPE: PRT
<213> ORGANISM: Artificial Sequence
<220> FEATURE:
<223> OTHER INFORMATION: NEO-303 antibody light chain CDR2
```

-continued

```
<400> SEQUENCE: 92

Tyr Ala Ser Asn Arg Tyr Ser
1               5


<210> SEQ ID NO 93
<211> LENGTH: 9
<212> TYPE: PRT
<213> ORGANISM: Artificial Sequence
<220> FEATURE:
<223> OTHER INFORMATION: NEO-303 antibody light chain CDR3

<400> SEQUENCE: 93

Gln Gln Asp Tyr Ser Ser Pro Leu Thr
1               5


<210> SEQ ID NO 94
<211> LENGTH: 19
<212> TYPE: PRT
<213> ORGANISM: Artificial Sequence
<220> FEATURE:
<223> OTHER INFORMATION: 31.1 epitope

<400> SEQUENCE: 94

Ser Pro Thr Pro Gln Tyr Ser Trp Lys Arg Tyr Asn Ile Leu Asn Gln
1               5                   10                  15

Glu Gln Pro
```

HUMANIZED MONOCLONAL ANTIBODIES AND METHODS OF USE FOR THE DIAGNOSIS AND TREATMENT OF COLON AND PANCREAS CANCER

CROSS-REFERENCE TO RELATED APPLICATIONS

This application is a divisional of U.S. application Ser. No. 14/655,982, which has a 371(c) date of Jun. 26, 2015, which is a U.S. Nat'l Phase Appl. of Int'l Appl. No. PCT/US2013/078290, filed Dec. 30, 2013, which claims the benefit of U.S. Provisional Appl. No. 61/747,067, filed Dec. 28, 2012, each of which is hereby incorporated by reference in its entirety.

The sequence listing in the file named "43282o3003.txt" having a size of 112,560 bytes that was created May 23, 2018 is hereby incorporated by reference in its entirety.

BACKGROUND

Prostate cancer, lung cancer, and colorectal cancer are the three most common cancers among men. Lung cancer, prostate cancer, liver cancer, and colorectal cancer are the leading causes of cancer deaths among men. Breast cancer, lung cancer, and colorectal cancer are the three most common cancers among women. Lung cancer, breast cancer, and colorectal cancer are the leading causes of cancer death among women. Example, each year in the United States alone, more than 43,000 people are diagnosed with pancreas cancer. While there have been many advancements in cancer detection and therapy over the last two decades, the current options for early detection and treatment of cancer are limited.

Despite medical advances in cancer detection and survival, there is need for early detection strategies and treatment regimens to reduce cancer morbidity and mortality. Monoclonal antibodies have proven to be efficacious in the improvement of cancer therapies as evidenced by the U.S. Food and Drug Administration (FDA) approval of such agents as ARZERRA® (ofatumumab), AVASTIN® (bevacizumab), BEXXAR® (tositumomab), CAMPATH® (alemtuzumab), ERBITUX® (cetuximab), HERCEPTIN® (trastuzumab), RITUXAN® (rituximab), VECTIBIX® (panitumuamb), and ZEVALIN® (ibritumomab). Many other monoclonal antibodies are currently in clinical trials as monotherapy or in combination with other therapies, showing promising results for the treatment of cancer.

SUMMARY

The present invention provides humanized 31.1 monoclonal antibodies (NEO-300 antibodies). These humanized 31.1 monoclonal antibodies (NEO-300 antibodies) may be used in methods for detecting and treating cancer.

In one embodiment, an isolated antibody that binds to an A33 antigen or an antibody fragment thereof, may comprise at least one heavy chain sequence comprising the amino acid sequence of SEQ ID NO:74, 75, 76, or 77 or one of the variable regions contained therein.

In one embodiment, an isolated antibody that binds to an A33 antigen or an antibody fragment thereof, may comprise at least one heavy chain CDR sequence comprising at least one amino acid sequence of SEQ ID NO:78, 79, 80, 81, 82, or 83.

In one embodiment, an isolated antibody that binds to an A33 antigen or an antibody fragment thereof, may comprise at least one light chain sequence comprising the amino acid sequence of SEQ ID NO:84, 85, 86, 87 or one of the variable regions contained therein.

In one embodiment, an isolated antibody that binds to an A33 antigen or an antibody fragment thereof, may comprise at least one light chain CDR sequence comprising at least one amino acid sequence of SEQ ID NO:88, 89, 90, 91, 92, or 93.

For example, an isolated antibody that binds to an A33 antigen or an antibody fragment thereof, may comprise a heavy chain comprising the amino acid sequence of SEQ ID NO:74 and the light chain amino acid sequence of SEQ ID NO:84; or may comprise a heavy chain comprising the amino acid sequence of SEQ ID NO:75 and the light chain amino acid sequence of SEQ ID NO:85; or may comprise a heavy chain comprising the amino acid sequence of SEQ ID NO:76 and the light chain amino acid sequence of SEQ ID NO:86; or may comprise a heavy chain comprising the amino acid sequence of SEQ ID NO:77 and the light chain amino acid sequence of SEQ ID NO:87.

In another embodiment, the antibody may comprise a heavy chain comprising the CDR1 amino acid sequence of SEQ ID NO:78, the CDR2 amino acid sequence of SEQ ID NO:79, 80, 81, or 82 and the CDR3 amino acid sequence of SEQ ID NO:83.

In another embodiment, the antibody may comprise a heavy chain comprising the CDR1 amino acid sequence of SEQ ID NO:78, the CDR2 amino acid sequence of SEQ ID NO:79, and the CDR3 amino acid sequence of SEQ ID NO:83.

In another embodiment, the antibody may comprise a heavy chain comprising the CDR1 amino acid sequence of SEQ ID NO:78, the CDR2 amino acid sequence of SEQ ID NO:80 and the CDR3 amino acid sequence of SEQ ID NO:83.

In another embodiment, the antibody may comprise a heavy chain comprising the CDR1 amino acid sequence of SEQ ID NO:78, the CDR2 amino acid sequence of SEQ ID NO:81 and the CDR3 amino acid sequence of SEQ ID NO:83.

In another embodiment, the antibody may comprise a heavy chain comprising the CDR1 amino acid sequence of SEQ ID NO:78, the CDR2 amino acid sequence of SEQ ID NO:82 and the CDR3 amino acid sequence of SEQ ID NO:83.

In another embodiment, the antibody may comprise a light chain comprising the CDR1 amino acid sequence of SEQ ID NO:88, 89, or 90, the CDR2 amino acid sequence of SEQ ID NO:91 or 92 and the CDR3 amino acid sequence of SEQ ID NO:93.

In another embodiment, the antibody may comprise a light chain comprising the CDR1 amino acid sequence of SEQ ID NO:88, the CDR2 amino acid sequence of SEQ ID NO:91 and the CDR3 amino acid sequence of SEQ ID NO:93.

In another embodiment, the antibody may comprise a light chain comprising the CDR1 amino acid sequence of SEQ ID NO:89, the CDR2 amino acid sequence of SEQ ID NO:91 and the CDR3 amino acid sequence of SEQ ID NO:93.

In another embodiment, the antibody may comprise a light chain comprising the CDR1 amino acid sequence of SEQ ID NO:90, the CDR2 amino acid sequence of SEQ ID NO:91 and the CDR3 amino acid sequence of SEQ ID NO:93.

In another embodiment, the antibody may comprise a light chain comprising the CDR1 amino acid sequence of SEQ ID NO:88, the CDR2 amino acid sequence of SEQ ID NO:92 and the CDR3 amino acid sequence of SEQ ID NO:93.

In another embodiment, the antibody may comprise a light chain comprising the CDR1 amino acid sequence of SEQ ID NO:89, the CDR2 amino acid sequence of SEQ ID NO:92 and the CDR3 amino acid sequence of SEQ ID NO:93.

In another embodiment, the antibody may comprise a light chain comprising the CDR1 amino acid sequence of SEQ ID NO:90, the CDR2 amino acid sequence of SEQ ID NO:92 and the CDR3 amino acid sequence of SEQ ID NO:93.

In another embodiment, the antibody may comprise a heavy chain comprising the CDR1 amino acid sequence of SEQ ID NO:78, the CDR2 amino acid sequence of SEQ ID NO:79, 80, 81, or 82 and the CDR3 amino acid sequence of SEQ ID NO:83 and a light chain comprising the CDR1 amino acid sequence of SEQ ID NO:88, 89, or 90, the CDR2 amino acid sequence of SEQ ID NO:91 or 92 and the CDR3 amino acid sequence of SEQ ID NO:93.

In another embodiment, the antibody may comprise a heavy chain comprising the CDRs contained in antibody cdr31.1-HC (SEQ ID NO:74) and a light chain comprising the CDRs contained in antibody cdr31.1-LC (SEQ ID NO:84).

In another embodiment, the antibody may comprise a heavy chain comprising the CDRs contained in antibody cdr31.1-HC (SEQ ID NO:74) and a light chain comprising the CDRs contained in antibody abb31.1-LC (SEQ ID NO:85).

In another embodiment, the antibody may comprise a heavy chain comprising the CDRs contained in antibody cdr31.1-HC (SEQ ID NO:74) and a light chain comprising the CDRs contained in antibody sdr31.1-LC (SEQ ID NO:86).

In another embodiment, the antibody may comprise a heavy chain comprising the CDRs contained in antibody cdr31.1-HC (SEQ ID NO:74) and a light chain comprising the CDRs contained in antibody ven31.1-LC (SEQ ID NO:87).

In another embodiment, the antibody may comprise a heavy chain comprising the CDRs contained in antibody abb31.1-HC (SEQ ID NO:75) and a light chain comprising the CDRs contained in antibody cdr31.1-LC (SEQ ID NO:84).

In another embodiment, the antibody may comprise a heavy chain comprising the CDRs contained in antibody abb31.1-HC (SEQ ID NO:75) and a light chain comprising the CDRs contained in antibody abb31.1-LC (SEQ ID NO:85).

In another embodiment, the antibody may comprise a heavy chain comprising the CDRs contained in antibody abb31.1-HC (SEQ ID NO:75) and a light chain comprising the CDRs contained in antibody sdr31.1-LC (SEQ ID NO:86).

In another embodiment, the antibody may comprise a heavy chain comprising the CDRs contained in antibody abb31.1-HC (SEQ ID NO:75) and a light chain comprising the CDRs contained in antibody ven31.1-LC (SEQ ID NO:87).

In another embodiment, the antibody may comprise a heavy chain comprising the CDRs contained in antibody sdr31.1-HC (SEQ ID NO:76) and a light chain comprising the CDRs contained in antibody cdr31.1-LC (SEQ ID NO:84).

In another embodiment, the antibody may comprise a heavy chain comprising the CDRs contained in antibody sdr31.1-HC (SEQ ID NO:76) and a light chain comprising the CDRs contained in antibody abb31.1-LC (SEQ ID NO:85).

In another embodiment, the antibody may comprise a heavy chain comprising the CDRs contained in antibody sdr31.1-HC (SEQ ID NO:76) and a light chain comprising the CDRs contained in antibody sdr31.1-LC (SEQ ID NO:86).

In another embodiment, the antibody may comprise a heavy chain comprising the CDRs contained in antibody sdr31.1-HC (SEQ ID NO:76) and a light chain comprising the CDRs contained in antibody ven31.1-LC (SEQ ID NO:87).

In another embodiment, the antibody may comprise a heavy chain comprising the CDRs contained in antibody ven31.1-HC (SEQ ID NO:77) and a light chain comprising the CDRs contained in antibody cdr31.1-LC (SEQ ID NO:84).

In another embodiment, the antibody may comprise a heavy chain comprising the CDRs contained in antibody ven31.1-HC (SEQ ID NO:77) and a light chain comprising the CDRs contained in antibody abb31.1-LC (SEQ ID NO:85).

In another embodiment, the antibody may comprise a heavy chain comprising the CDRs contained in antibody ven31.1-HC (SEQ ID NO:77) and a light chain comprising the CDRs contained in antibody sdr31.1-LC (SEQ ID NO:86).

In another embodiment, the antibody may comprise a heavy chain comprising the CDRs contained in antibody ven31.1-HC (SEQ ID NO:77) and a light chain comprising the CDRs contained in antibody ven31.1-LC (SEQ ID NO:87).

In another embodiment, the antibody may comprise a heavy chain comprising the variable chain of antibody cdr31.1-HC (amino acids 1 to 118 of SEQ ID NO:74) and a light chain comprising the variable light chain of antibody cdr31.1-LC (amino acids 1 to 107 of SEQ ID NO:84).

In another embodiment, the antibody may comprise a heavy chain comprising the variable chain of antibody cdr31.1-HC (amino acids 1 to 118 of SEQ ID NO:74) and a light chain comprising the variable light chain of antibody abb31.1-LC (amino acids 1 to 107 of SEQ ID NO:85).

In another embodiment, the antibody may comprise a heavy chain comprising the variable chain of antibody cdr31.1-HC (amino acids 1 to 118 of SEQ ID NO:74) and a light chain comprising the variable light chain of antibody sdr31.1-LC (amino acids 1 to 107 of SEQ ID NO:86).

In another embodiment, the antibody may comprise a heavy chain comprising the variable chain of antibody cdr31.1-HC (amino acids 1 to 118 of SEQ ID NO:74) and a light chain comprising the variable light chain of antibody ven31.1-LC (amino acids 1 to 107 of SEQ ID NO:87).

In another embodiment, the antibody may comprise a heavy chain comprising the variable chain of antibody abb31.1-HC (amino acids 1 to 118 of SEQ ID NO:75) and a light chain comprising the variable light chain of antibody cdr31.1-LC (amino acids 1 to 107 of SEQ ID NO:84).

In another embodiment, the antibody may comprise a heavy chain comprising the variable chain of antibody abb31.1-HC (amino acids 1 to 118 of SEQ ID NO:75) and a light chain comprising the variable light chain of antibody abb31.1-LC (amino acids 1 to 107 of SEQ ID NO:85).

In another embodiment, the antibody may comprise a heavy chain comprising the variable chain of antibody abb31.1-HC (amino acids 1 to 118 of SEQ ID NO:75) and a light chain comprising the variable light chain of antibody sdr31.1-LC (amino acids 1 to 107 of SEQ ID NO:86).

In another embodiment, the antibody may comprise a heavy chain comprising the variable chain of antibody abb31.1-HC (amino acids 1 to 118 of SEQ ID NO:75) and a light chain comprising the variable light chain of antibody ven31.1-LC (amino acids 1 to 107 of SEQ ID NO:87).

In another embodiment, the antibody may comprise a heavy chain comprising the variable chain of antibody sdr31.1-HC (amino acids 1 to 118 of SEQ ID NO:76) and a light chain comprising the variable light chain of antibody cdr31.1-LC (amino acids 1 to 107 of SEQ ID NO:84).

In another embodiment, the antibody may comprise a heavy chain comprising the variable chain of antibody sdr31.1-HC (amino acids 1 to 118 of SEQ ID NO:76) and a light chain comprising the variable light chain of antibody abb31.1-LC (amino acids 1 to 107 of SEQ ID NO:85).

In another embodiment, the antibody may comprise a heavy chain comprising the variable chain of antibody sdr31.1-HC (amino acids 1 to 118 of SEQ ID NO:76) and a light chain comprising the variable light chain of antibody sdr31.1-LC (amino acids 1 to 107 of SEQ ID NO:86).

In another embodiment, the antibody may comprise a heavy chain comprising the variable chain of antibody sdr31.1-HC (amino acids 1 to 118 of SEQ ID NO:76) and a light chain comprising the variable light chain of antibody ven31.1-LC (amino acids 1 to 107 of SEQ ID NO:87).

In another embodiment, the antibody may comprise a heavy chain comprising the variable chain of antibody ven31.1-HC (amino acids 1 to 118 of SEQ ID NO:77) and a light chain comprising the variable light chain of antibody cdr31.1-LC (amino acids 1 to 107 of SEQ ID NO:84).

In another embodiment, the antibody may comprise a heavy chain comprising the variable chain of antibody ven31.1-HC (amino acids 1 to 118 of SEQ ID NO:77) and a light chain comprising the variable light chain of antibody abb31.1-LC (amino acids 1 to 107 of SEQ ID NO:85).

In another embodiment, the antibody may comprise a heavy chain comprising the variable chain of antibody ven31.1-HC (amino acids 1 to 118 of SEQ ID NO:77) and a light chain comprising the variable light chain of antibody sdr31.1-LC (amino acids 1 to 107 of SEQ ID NO:86).

In another embodiment, the antibody may comprise a heavy chain comprising the variable chain of antibody ven31.1-HC (amino acids 1 to 118 of SEQ ID NO:77) and a light chain comprising the variable light chain of antibody ven31.1-LC (amino acids 1 to 107 of SEQ ID NO:87).

In another embodiment, the antibody may comprise a heavy chain polypeptide of antibody cdr31.1-HC (SEQ ID NO:74) and a light chain polypeptide of antibody cdr31.1-LC (SEQ ID NO:84).

In another embodiment, the antibody may comprise a heavy chain polypeptide of antibody cdr31.1-HC (SEQ ID NO:74) and a light chain polypeptide of antibody abb31.1-LC (SEQ ID NO:85).

In another embodiment, the antibody may comprise a heavy chain polypeptide of antibody cdr31.1-HC (SEQ ID NO:74) and a light chain polypeptide of antibody sdr31.1-LC (SEQ ID NO:86).

In another embodiment, the antibody may comprise a heavy chain polypeptide of antibody cdr31.1-HC (SEQ ID NO:74) and a light chain polypeptide of antibody ven31.1-LC (SEQ ID NO:87).

In another embodiment, the antibody may comprise a heavy chain polypeptide of antibody abb31.1-HC (SEQ ID NO:75) and a light chain polypeptide of antibody cdr31.1-LC (SEQ ID NO:84).

In another embodiment, the antibody may comprise a heavy chain polypeptide of antibody abb31.1-HC (SEQ ID NO:75) and a light chain polypeptide of antibody abb31.1-LC (SEQ ID NO:85).

In another embodiment, the antibody may comprise a heavy chain polypeptide of antibody abb31.1-HC (SEQ ID NO:75) and a light chain polypeptide of antibody sdr31.1-LC (SEQ ID NO:86).

In another embodiment, the antibody may comprise a heavy chain polypeptide of antibody abb31.1-HC (SEQ ID NO:75) and a light chain polypeptide of antibody ven31.1-LC (SEQ ID NO:87).

In another embodiment, the antibody may comprise a heavy chain polypeptide of antibody sdr31.1-HC (SEQ ID NO:76) and a light chain polypeptide of antibody cdr31.1-LC (SEQ ID NO:84).

In another embodiment, the antibody may comprise a heavy chain polypeptide of antibody sdr31.1-HC (SEQ ID NO:76) and a light chain polypeptide of antibody abb31.1-LC (SEQ ID NO:85).

In another embodiment, the antibody may comprise a heavy chain polypeptide of antibody sdr31.1-HC (SEQ ID NO:76) and a light chain polypeptide of antibody sdr31.1-LC (SEQ ID NO:86).

In another embodiment, the antibody may comprise a heavy chain polypeptide of antibody sdr31.1-HC (SEQ ID NO:76) and a light chain polypeptide of antibody ven31.1-LC (SEQ ID NO:87).

In another embodiment, the antibody may comprise a heavy chain polypeptide of antibody ven31.1-HC (SEQ ID NO:77) and a light chain polypeptide of antibody cdr31.1-LC (SEQ ID NO:84).

In another embodiment, the antibody may comprise a heavy chain polypeptide of antibody ven31.1-HC (SEQ ID NO:77) and a light chain polypeptide of antibody abb31.1-LC (SEQ ID NO:85).

In another embodiment, the antibody may comprise a heavy chain polypeptide of antibody ven31.1-HC (SEQ ID NO:77) and a light chain polypeptide of antibody sdr31.1-LC (SEQ ID NO:86).

In another embodiment, the antibody may comprise a heavy chain polypeptide of antibody ven31.1-HC (SEQ ID NO:77) and a light chain polypeptide of antibody ven31.1-LC (SEQ ID NO:87).

In another embodiment, the antibody may comprise at least one said heavy chain and at least one said light chain. In another embodiment, the antibody may comprise at least one of said heavy chain CDR and at least one of said light chain CDR. In another embodiment, the antibody may comprise at least two of said heavy chain CDRs and at least two of said light chain CDRs. In another embodiment, the antibody may comprise at least three of said heavy chain CDRs and at least three of said light chain CDRs.

In another embodiment, the antibody may comprise at least one heavy chain sequence comprising the amino acid sequence of SEQ ID NO:74, 75, 76, or 77 or one of the variable regions contained therein; at least one CDR sequence comprising at least one amino acid sequence of SEQ ID NO:78, 79, 80, 81, 82, or 83; at least one light chain sequence comprising the amino acid sequence of SEQ ID NO:84, 85, 86, 87 or one of the variable regions contained therein; and/or at least one light chain CDR sequence comprising at least one amino acid sequence of SEQ ID NO:88, 89, 90, 91, 92, or 93.

In another embodiment, the heavy chain may comprise a heavy chain CDR1 of the amino acid sequence of SEQ ID NO:78, at least one heavy chain CDR2 of the amino acid sequence of SEQ ID NOs: 79, 80, 81, or 82; and at least one heavy chain CDR3 of the amino acid sequence of SEQ ID NO:83.

In another embodiment, the light chain may comprise at least one light chain CDR1 of the amino acid sequence of SEQ ID NOs: 88, 89, or 90, at least one light chain CDR2 of the amino acid sequence of SEQ ID NOs: 91 or 92; and a light chain CDR3 of the amino acid sequence of SEQ ID NO:93.

In another embodiment, the antibody or antibody fragment specifically binds the amino acid sequence of SEQ ID NO:10, 11, 12, or 13.

In one embodiment, the antibody or antibody fragment may be recombinant. In another embodiment, the antibody or antibody fragment has anti-tumor activity. In another embodiment, the antibody fragment is a Fab, Fab', F(ab')2, Fv, CDR, paratope, or portion of an antibody that is capable of binding the antigen.

In one embodiment, the antibody may comprise a constant domain. The constant domain may potentiate an effector function, such as ADCC or CDC. For example, the constant domain may comprise or consist of a human IgG1 or human IgG3 constant domain. Said constant domain may be modified to enhance one or more effector functions, such as ADCC or CDC.

In one embodiment, the antibody or fragment may be directly or indirectly conjugated to a label, cytotoxic agent, therapeutic agent, or an immunosuppressive agent. In another embodiment, the antibody may be admixed in a composition with an antibody, label, cytotoxic agent, therapeutic agent, or an immunosuppressive agent.

In another embodiment, the antibody may be administered in combination with an antibody, label, cytotoxic agent, therapeutic agent, or an immunosuppressive agent, simultaneously or sequentially.

In another embodiment, the label may be a chemiluminescent label, paramagnetic label, an MRI contrast agent, fluorescent label, bioluminescent label, or radioactive label.

In another embodiment, the paramagnetic label may be aluminum, manganese, platinum, oxygen, lanthanum, lutetium, scandium, yttrium, or gallium.

In another embodiment, the cytotoxic agent may be a moiety that inhibits DNA, RNA, or protein synthesis, a radionuclide, or ribosomal inhibiting protein.

In another embodiment, the cytotoxic agent may be $^{212}$Bi, $^{131}$I, $^{188}$Re, $^{90}$Y, vindesine, methotrexate, adriamycin, cisplatin, pokeweed antiviral protein, *Pseudomonas* exotoxin A, ricin, diphtheria toxin, ricin A chain, or cytotoxic phospholipase enzyme.

In another embodiment, the therapeutic agent may be a lymphokine or growth factor.

In another embodiment, the immunosuppressive agent may be cyclosporine, leflunomide, methotrexate, azothiprine, mercaptopurine, dactinomycin, tacrolimus, or sirolimus.

In one embodiment, the invention provides a composition comprising an antibody that binds to an A33 antigen or an antibody fragment thereof. In another embodiment, the antibody may comprise at least one heavy chain sequence comprising the amino acid sequence of SEQ ID NO:74, 75, 76, or 77 or one of the variable regions contained therein; at least one CDR sequence comprising at least one amino acid sequence of SEQ ID NO:78, 79, 80, 81, 82, or 83; at least one light chain sequence comprising the amino acid sequence of SEQ ID NO:84, 85, 86, 87 or one of the variable regions contained therein; and at least one light chain CDR sequence comprising at least one amino acid sequence of SEQ ID NO:88, 89, 90, 91, 92, or 93. In another embodiment, the heavy chain may comprise a heavy chain CDR1 of the amino acid sequence of SEQ ID NO:78, at least one heavy chain CDR2 of the amino acid sequence of SEQ ID NOs: 79, 80, 81, or 82; and at least one heavy chain CDR3 of the amino acid sequence of SEQ ID NO:83. In another embodiment, the light chain may comprise at least one light chain CDR1 of the amino acid sequence of SEQ ID NOs: 88, 89, or 90, at least one light chain CDR2 of the amino acid sequence of SEQ ID NOs: 91 or 92; and a light chain CDR3 of the amino acid sequence of SEQ ID NO:93. In another embodiment, the antibody or antibody fragment specifically binds the amino acid sequence of SEQ ID NO:10, 11, 12, or 13. In another embodiment, the composition may further comprise a pharmaceutically acceptable carrier.

In one embodiment, a diagnostic kit may comprise an antibody that binds to an A33 antigen or an antibody fragment thereof. In another embodiment, the antibody may comprise at least one heavy chain sequence comprising the amino acid sequence of SEQ ID NO:74, 75, 76, or 77 or one of the variable regions contained therein; at least one CDR sequence comprising at least one amino acid sequence of SEQ ID NO:78, 79, 80, 81, 82, or 83; at least one light chain sequence comprising the amino acid sequence of SEQ ID NO:84, 85, 86, 87 or one of the variable regions contained therein; and at least one light chain CDR sequence comprising at least one amino acid sequence of SEQ ID NO:88, 89, 90, 91, 92, or 93. In another embodiment, the heavy chain may comprise a heavy chain CDR1 of the amino acid sequence of SEQ ID NO:78, at least one heavy chain CDR2 of the amino acid sequence of SEQ ID NOs: 79, 80, 81, or 82; and at least one heavy chain CDR3 of the amino acid sequence of SEQ ID NO:83. In another embodiment, the light chain may comprise at least one light chain CDR1 of the amino acid sequence of SEQ ID NOs: 88, 89, or 90, at least one light chain CDR2 of the amino acid sequence of SEQ ID NOs: 91 or 92; and a light chain CDR3 of the amino acid sequence of SEQ ID NO:93. In another embodiment, the antibody or antibody fragment specifically binds the amino acid sequence of SEQ ID NO: 10, 11, 12, or 13. In another embodiment, the antibody may be directly or indirectly fixed to a solid phase support. In another embodiment, the solid phase support may be a bead, test tube, sheet, culture dish, or test strip. In another embodiment, the solid phase support may be an array.

In one embodiment, the method for treating cancer may comprise administering an effective amount of an antibody that binds to an A33 antigen or an antibody fragment thereof to a patient in need thereof. In another embodiment, the method for slowing the growth of a tumor may comprise administering an effective amount of an antibody that binds to an A33 antigen or an antibody fragment thereof to a patient in need thereof. In another embodiment, the method for killing tumor cells may comprise administering an effective amount of an antibody that binds to an A33 antigen or an antibody fragment thereof to a patient in need thereof. In another embodiment, the method for promoting tumor regression in a subject may comprise administering an effective amount of an antibody that binds to an A33 antigen or an antibody fragment thereof to a patient in need thereof.

In one embodiment, the composition for treating cancer may comprise an antibody that binds to an A33 antigen or an antibody fragment thereof. In another embodiment, the composition for slowing the growth of a tumor may comprise an effective amount of an antibody that binds to an A33 antigen or an antibody fragment thereof. In another embodiment, the composition for killing tumor cells may comprise an effective amount of an antibody that binds to an A33 antigen or an antibody fragment thereof. In another embodiment, the composition for promoting tumor regression in a subject may comprise an effective amount of an antibody that binds to an A33 antigen or an antibody fragment thereof.

In one embodiment, the invention provides for the use of an antibody that binds to an A33 antigen or an antibody fragment thereof in the preparation of a medicament for treating cancer. In another embodiment, the invention provides for the use of an antibody that binds to an A33 antigen or an antibody fragment thereof in the preparation of a medicament for slowing the growth of a tumor. In another embodiment, the invention provides for the use of an antibody that binds to an A33 antigen or an antibody fragment thereof in the preparation of a medicament for killing tumor cells. In another embodiment, the invention provides for the use an antibody that binds to an A33 antigen or an antibody fragment thereof in the preparation of a medicament for promoting tumor regression.

In another embodiment, the cancer may be lung, breast, pancreas, uterine, esophageal, colorectal, or liver cancer. In another embodiment, the cancer may be pancreas or colorectal cancer. In another embodiment, the antibody may be administered in combination with another antibody, a lymphokine, or a hematopoietic growth factor. In another embodiment, the agent may be administered simultaneously or sequentially with the antibody. In another embodiment, the cancer may be a stage 1, 2, 3 or 4 cancer. In another embodiment, the cancer may have metastasized. In another embodiment, the patient expresses detectable levels of a 31.1 epitope. In another embodiment, the tumor antigen may be detected in a tumor biopsy sample or in the blood, stool, urine or lymph fluid. In another embodiment, the patient may be at risk of cancer. In another embodiment, the patient may be a patient without symptoms.

In one embodiment, the method for detecting an 31.1 epitope comprising (a) contacting a test sample with the antibody or antibody fragment of any one of the claims that binds an 31.1 epitope, and (b) assaying for antibody-epitope complexes, wherein the presence of said epitope may be indicative of a carcinoma.

In one embodiment, the method for detecting the presence of an 31.1 epitope in a patient comprising (a) administering to said patient the antibody or antibody fragment of any one of the claims, wherein said antibody may be labeled, that binds an 31.1 epitope and (b) detecting the presence of an 31.1 epitope; wherein the presence of said epitope may be indicative of a carcinoma wherein said antibody.

In another embodiment, the antibody or antibody or antibody fragment thereof may be conjugated to a label. In another embodiment, the label may be a chemiluminescent label, paramagnetic label, an MRI contrast agent, fluorescent label, bioluminescent label, or radioactive label. In another embodiment, the paramagnetic label may be aluminum, manganese, platinum, oxygen, lanthanum, lutetium, scandium, yttrium, or gallium. In another embodiment, the cancer may be lung, breast, pancreas, uterine, esophageal, colorectal, or liver cancer.

In another embodiment, the patient may be at risk of cancer. In another embodiment, the patient may be a patient without symptoms. In another embodiment, the test sample may be obtained from a patient at risk of cancer. In another embodiment, the test sample may be obtained from a patient without symptoms.

In another embodiment, the antibody may be attached to a solid support. In another embodiment, the solid phase support may be a bead, test tube, sheet, culture dish, or test strip. In another embodiment, the solid support may be an array.

In another embodiment, the sample may be a tissue biopsy, lymph, urine, cerebrospinal fluid, amniotic fluid, inflammatory exudate, blood, serum, stool, or liquid collected from the colorectal tract.

In another embodiment, the antibody-epitope complex may be detected by an assay selected from the group consisting of Western blots, radioimmunoassays, ELISA (enzyme linked immunosorbent assay), "sandwich" immunoassays, lateral flow assay, immunoprecipitation assays, precipitation reactions, gel diffusion precipitation reactions, immunodiffusion assays, agglutination assays, complement-fixation assays, immunohistochemical assays, fluorescent immunoassays, and protein A immunoassays.

In another embodiment, the method may detect colorectal polyps. In another embodiment, the method may further comprise additional testing for the presence of tumors. In another embodiment, the method may detect benign tumors. In another embodiment, the method may detect malignant tumors. In another embodiment, the method may detect metastatic tumors. In another embodiment, the method may detect non-metastatic tumors. In another embodiment, the method may detect pre-cancerous cells that express a cell marker comprising a 31.1 epitope.

In another embodiment, the method may comprise imaging said epitope. In another embodiment, the imaging may be selected from the group consisting of positron emission tomography (PET), CCD low-light monitoring system, x-ray, CT scanning, scintigraphy, photo acoustic imaging, single photon emission computed tomography (SPECT), magnetic resonance imaging (MRI), ultrasound, paramagnetic imaging, and endoscopic optical coherence tomography.

In one embodiment, a method of making antibodies may comprise (a) immunizing an animal with an 31.1 epitope, (b) removing said animal's spleen and prepare a single cell suspension, (c) fusing a spleen cell with a myeloma cell, (d) culturing post-fusion cells in hybridoma selection medium, (e) culture the resultant hybridomas, (f) screening for specific antibody production, and (g) selecting hybridomas which produce the desired antibody.

In one embodiment, a composition may comprise at least two of the following: (a) an antibody or an antibody fragment thereof, that binds a NPC-1 epitope; (b) an antibody or an antibody fragment thereof, that binds a 16C3 epitope, and (c) an antibody or an antibody fragment thereof, that binds a 31.1 epitope.

In one embodiment, a composition for treating cancer may comprise at least two of the following: (a) an antibody or an antibody fragment thereof, that binds a NPC-1 epitope; (b) an antibody or an antibody fragment thereof, that binds a 16C3 epitope, and (c) an antibody or an antibody fragment thereof, that binds a 31.1 epitope.

In one embodiment, a composition for slowing the growth of a tumor may comprise at least two of the following: (a) an antibody or an antibody fragment thereof, that binds a NPC-1 epitope; (b) an antibody or an antibody fragment thereof, that binds a 16C3 epitope, and (c) an antibody or an antibody fragment thereof, that binds a 31.1 epitope.

In one embodiment, a composition for killing tumor cells may comprise at least two of the following: (a) an antibody or an antibody fragment thereof, that binds a NPC-1 epitope; (b) an antibody or an antibody fragment thereof, that binds a 16C3 epitope, and (c) an antibody or an antibody fragment thereof, that binds a 31.1 epitope.

In one embodiment, a composition for promoting tumor regression may comprise at least two of the following: (a) an antibody or an antibody fragment thereof, that binds a NPC-1 epitope; (b) an antibody or an antibody fragment thereof, that binds a 16C3 epitope, and (c) an antibody or an antibody fragment thereof, that binds a 31.1 epitope.

In another embodiment, the composition may comprise three of said antibodies.

In one embodiment, a method for treating cancer may comprise administering an effective amount of a composition may comprise at least two of the following: (a) an antibody or antibody fragment thereof, that binds a NPC-1 epitope; (b) an antibody or antibody fragment thereof, that binds a 16C3 epitope, and (c) an antibody or antibody fragment thereof, that binds a 31.1 epitope to a patient in need thereof.

In one embodiment, a method for slowing the growth of a tumor may comprise administering an effective amount of a composition may comprise at least two of the following: (a) an antibody or antibody fragment thereof, that binds a NPC-1 epitope; (b) an antibody or antibody fragment thereof, that binds a 16C3 epitope, and (c) an antibody or antibody fragment thereof, that binds a 31.1 epitope to a patient in need thereof.

In one embodiment, a method for promoting tumor regression in a subject may comprise administering an effective amount of a composition may comprise at least two of the following: (a) an antibody or antibody fragment thereof, that binds a NPC-1 epitope; (b) an antibody or antibody fragment thereof, that binds a 16C3 epitope, and (c) an antibody or antibody fragment thereof, that binds a 31.1 epitope to a patient in need thereof.

In one embodiment, a method for killing tumor cells may comprise administering an effective amount of a composition may comprise at least two of the following: (a) an antibody or antibody fragment thereof, that binds a NPC-1 epitope; (b) an antibody or antibody fragment thereof, that binds a 16C3 epitope, and (c) an antibody or antibody fragment thereof, that binds a 31.1 epitope to a patient in need thereof.

In one embodiment, a method for detecting a tumor-associated NPC-1 epitope may comprise (a) contacting a test sample with a composition may comprise at least two of the following: (i) an antibody or antibody fragment thereof, that binds a NPC-1 epitope; (ii) an antibody or antibody fragment thereof, that binds a 16C3 epitope, and (iii) an antibody or antibody fragment thereof, that binds a 31.1 epitope to a patient in need thereof, and (b) assaying for antibody-epitope complexes, wherein the presence of said epitope is indicative of a carcinoma.

In one embodiment, a method for detecting the presence of an epitope associated with a carcinoma in a patient comprising (a) administering to said patient a composition may comprise at least two of the following: (i) a labeled antibody, or a fragment thereof, that binds a NPC-1 epitope; (ii) a labeled antibody or antibody fragment thereof, that binds a 16C3 epitope, and (iii) a labeled antibody or antibody fragment thereof, that binds a 31.1 epitope to a patient in need thereof, and (b) detecting the presence of an epitope bound by said antibody, wherein the presence of said epitope is indicative of a carcinoma.

In another embodiment, the method may comprise administration of three of said antibodies. In a further embodiment, the cancer may be lung, breast, pancreas, uterine, esophageal, colorectal, or liver cancer.

In a further embodiment, the antibody or antibody fragment thereof that binds a NPC-1 epitope may comprise a heavy and light chain, wherein said heavy chain is selected from the group consisting of the amino acid sequences of SEQ ID NOs: 19, 20, 29, 30, 36, and 37, optionally may comprise at least one heavy chain CDR sequence of the amino acid sequence of the amino acid sequences of SEQ ID NOs: 21, 22, 23, 31, 32, 33; and the light chain is selected from the group consisting of SEQ ID NOs: 14, 15, 24, 25, 34, and 35, optionally may comprise at least one light chain CDR sequence of the amino acid sequence of SEQ ID NOs: 16, 17, 18, 26, 27, and 28.

In a further embodiment, the antibody or antibody fragment thereof that binds a 16C3 epitope may comprise a heavy and light chain, wherein said heavy chain is selected from the group consisting of the amino acid sequences of SEQ ID NOs: 43, 44, 53, 54, 55, 56, 57, 63, and 64, optionally may comprise at least one heavy chain CDR sequence of the amino acid sequence of the amino acid sequences of SEQ ID NOs: 45, 46, 47, 65, 66, and 67; and the light chain is selected from the group consisting of SEQ ID NOs: 38, 39, 48, 49, 50, 51, 52, 58, and 59, optionally may comprise at least one light chain CDR sequence of the amino acid sequence of SEQ ID NOs: 40, 41, 42, 60, 61, and 62.

In a further embodiment, the antibody or antibody fragment thereof that binds a 31.1 epitope may comprise a heavy and light chain, wherein said heavy chain is selected from the group consisting of the amino acid sequences of SEQ ID NOs: 69, 72, 73, 74, 75, 76, and 77 or one of the variable regions contained therein, optionally may comprise at least one heavy chain CDR sequence of the amino acid sequence of the amino acid sequences of SEQ ID NOs: 78, 79, 80, 81, 82, and 83; and the light chain is selected from the group consisting of SEQ ID NOs: 68, 70, 71, 84, 85, 86 or one of the variable regions contained therein, and 87, optionally may comprise at least one light chain CDR sequence of the amino acid sequence of SEQ ID NOs: 88, 89, 90, 91, 92, and 93.

The invention provides an isolated polypeptide comprising a 31.1 epitope. In one embodiment, the 31.1 epitope may not be sensitive to treatment by glycolytic enzymes. In another embodiment, the A33 antigen may comprise said 31.1 epitope. In another embodiment, 31.1 epitope may be a non-linear epitope. In a further embodiment, the 31.1 epitope may comprise an amino acid sequence with at least 80% homology to the amino acid sequence of SEQ ID NO: 10, 11, 12, or 13.

The invention provides a tumor specific antigen comprising an amino acid sequence with at least 80% homology to the amino acid sequence of SEQ ID NO:10, 11, 12, or 13. In another embodiment, epitope may comprise an amino acid sequence with at least 80% homology to the amino acid sequence of SEQ ID NO: 10, 11, 12, or 13. In a further embodiment, epitope may be a non-linear epitope, optionally comprising the amino acid sequence of SEQ ID NO: 10, 11, 12, or 13.

A tumor specific antigen comprising a 31.1 epitope. In another embodiment, the tumor specific antigen may comprise an amino acid sequence with at least 80% homology to the amino acid sequence of SEQ ID NOs: 10, 11, 12, or 13.

Further aspects of the invention are set forth in the following clauses:

Clause 1. An isolated antibody that binds to an A33 antigen or an antibody fragment thereof, comprising at least one heavy chain sequence comprising the amino acid sequence of SEQ ID NO:74, 75, 76, or 77 or one of the variable regions contained therein.

Clause 2. An isolated antibody that binds to an A33 antigen or an antibody fragment thereof, comprising at least one heavy chain CDR sequence comprising at least one amino acid sequence of SEQ ID NO:78, 79, 80, 81, 82, or 83.

Clause 3. An isolated antibody that binds to an A33 antigen or an antibody fragment thereof, comprising at least one light chain sequence comprising the amino acid sequence of SEQ ID NO:84, 85, 86, 87 or one of the variable regions contained therein.

Clause 4. An isolated antibody that binds to an A33 antigen or an antibody fragment thereof, comprising at least one light chain CDR sequence comprising at least one amino acid sequence of SEQ ID NO:88, 89, 90, 91, 92, or 93.

Clause 5. The antibody of any one of clauses 1-4, wherein said antibody comprises at least one said heavy chain or heavy chain variable region and at least one said light chain or light chain variable region.

Clause 6. The antibody of any one of clauses 1-5, wherein said antibody comprises at least one of said heavy chain CDR and at least one of said light chain CDR.

Clause 7. The antibody of any one of clauses 1-6, wherein said antibody comprises at least two of said heavy chain CDRs and at least two of said light chain CDRs.

Clause 8 The antibody of any one of clauses 1-7, wherein said antibody comprises at least three of said heavy chain CDRs and at least three of said light chain CDRs.

Clause 9. The antibody of any one of clauses 1-8, wherein said antibody comprises at least one heavy chain sequence comprising the amino acid sequence of SEQ ID NO:74, 75, 76, or 77; at least one CDR sequence comprising at least one amino acid sequence of SEQ ID NO:78, 79, 80, 81, 82, or 83; at least one light chain sequence comprising the amino acid sequence of SEQ ID NO:84, 85, 86, 87; and at least one light chain CDR sequence comprising at least one amino acid sequence of SEQ ID NO:88, 89, 90, 91, 92, or 93.

Clause 10. The antibody of any one of clauses 1-10, wherein said heavy chain comprises a heavy chain CDR1 of the amino acid sequence of SEQ ID NO:78, at least one heavy chain CDR2 of the amino acid sequence of SEQ ID NOs: 79, 80, 81, or 82; and at least one heavy chain CDR3 of the amino acid sequence of SEQ ID NO:83.

Clause 11. The antibody of any one of clauses 1-10, wherein said light chain comprises at least one light chain CDR1 of the amino acid sequence of SEQ ID NOs: 88, 89, or 90, at least one light chain CDR2 of the amino acid sequence of SEQ ID NOs: 91 or 92; and a light chain CDR3 of the amino acid sequence of SEQ ID NO:93.

Clause 12. The antibody of any one of clauses 1-11, wherein said antibody or antibody fragment specifically binds the amino acid sequence of SEQ ID NO:10, 11, 12, or 13.

Clause 13. The antibody of any one of clauses 1-12, wherein said antibody or fragment is recombinant.

Clause 14. The antibody of any one of clauses 1-12, wherein the antibody or fragment has anti-tumor activity.

Clause 15. The antibody of any one of clauses 1-12, wherein said fragment is a Fab, Fab', F(ab')2, Fv, CDR, paratope, or portion of an antibody that is capable of binding the antigen.

Clause 16. The antibody of any one of clauses 1-15, wherein said antibody or fragment is directly or indirectly conjugated to a label, cytotoxic agent, therapeutic agent, or an immunosuppressive agent, and/or said antibody potentiates ADCC or CDC, and/or said antibody is of a human IgG1 or human IgG3 isotype.

Clause 17. The antibody of any one of clauses 1-15, wherein said antibody is admixed in a composition with an antibody, label, cytotoxic agent, therapeutic agent, or an immunosuppressive agent.

Clause 18. The antibody of any one of clauses 1-15, wherein said antibody is administered in combination with an antibody, label, cytotoxic agent, therapeutic agent, or an immunosuppressive agent, simultaneously or sequentially.

Clause 19. The antibody of clause 16, 17, or 18, wherein said label is a chemiluminescent label, paramagnetic label, an MRI contrast agent, fluorescent label, bioluminescent label, or radioactive label.

Clause 20. The antibody of clause 19, wherein said paramagnetic label is aluminum, manganese, platinum, oxygen, lanthanum, lutetium, scandium, yttrium, or gallium.

Clause 21. The antibody of clause 16, 17, or 18, wherein the cytotoxic agent is a moiety that inhibits DNA, RNA, or protein synthesis, a radionuclide, or ribosomal inhibiting protein.

Clause 22. The antibody of clause 21, wherein the cytotoxic agent is $^{212}Bi$, $^{131}I$, $^{188}Re$, $^{90}Y$, vindesine, methotrexate, adriamycin, cisplatin, pokeweed antiviral protein, *Pseudomonas* exotoxin A, ricin, diphtheria toxin, ricin A chain, or cytotoxic phospholipase enzyme.

Clause 23. The antibody of clause 16, 17, or 18, wherein said therapeutic agent is a lymphokine or growth factor.

Clause 24. The antibody of clause 16, 17, or 18, wherein said immunosuppressive agent is cyclosporine, letlunomide, methotrexate, azothiprine, mercaptopurine, dactinomycin, tacrolimus, or sirolimus.

Clause 25. A composition comprising the antibody or antibody fragment of any one of clauses 1-24.

Clause 26. The composition of clause 25, wherein said composition further comprises a pharmaceutically acceptable carrier.

Clause 27. A diagnostic kit comprising the antibody or antibody fragment of any one of clauses 1-24.

Clause 28. The kit of clause 27, wherein antibody is directly or indirectly fixed to a solid phase support.

Clause 29. The kit of clause 28, wherein said solid phase support is a bead, test tube, sheet, culture dish, or test strip.

Clause 30. The kit of clause 29, wherein said solid phase support is an array.

Clause 31. A method for treating cancer comprising administering an effective amount of the antibody or antibody fragment of any one of clauses 1-24 to a patient in need thereof. Clause 32. A method for slowing the growth of a tumor comprising administering an effective amount of the antibody or antibody fragment of any one of clauses 1-24 to a patient in need thereof.

Clause 33. A method for killing tumor cells comprising administering an effective amount of the antibody or antibody fragment of any one of clauses 1-24 to a patient in need thereof.

Clause 34. A method for promoting tumor regression in a subject comprising administering an effective amount of the antibody or antibody fragment of any one of clauses 1-24 to a patient in need thereof.

Clause 35. A composition for treating cancer comprising an antibody or antibody fragment thereof of any one of clauses 1-24.

Clause 36. A composition for slowing the growth of a tumor comprising an effective amount of the antibody or antibody fragment of any one of clauses 1-24.

Clause 37. A composition for killing tumor cells comprising an effective amount of the antibody or antibody fragment of any one of clauses 1-24.

Clause 38. A composition for promoting tumor regression in a subject comprising an effective amount of the antibody or antibody fragment of any one of clauses 1-24.

Clause 39. Use of the antibody or antibody fragment thereof of any one of clauses 1-24 in the preparation of a medicament for treating cancer.

Clause 40. Use of the antibody or antibody fragment thereof of any one of clauses 1-24 in the preparation of a medicament for slowing the growth of a tumor.

Clause 41. Use of the antibody or antibody fragment thereof of any one of clauses 1-24 in the preparation of a medicament for killing tumor cells.

Clause 42. Use of the antibody or antibody fragment thereof of any one of clauses 1-24 in the preparation of a medicament for promoting tumor regression.

Clause 43. The composition, use, or method of any one of clauses 31-42, wherein said cancer is lung, breast, pancreas, uterine, esophageal, colorectal, or liver cancer.

Clause 44. The composition, use, or method of clause 43, wherein said cancer is pancreas or colorectal cancer.

Clause 45. The composition, use, or method of any one of clauses 31-42, wherein said antibody is administered in combination with another antibody, a lymphokine, or a hematopoietic growth factor.

Clause 46. The composition, use, or method of any one of clauses 31-42, wherein said agent is administered simultaneously or sequentially with the antibody.

Clause 47. The composition, use, or method of any one of clauses 31-42, wherein said cancer is lung, breast, pancreas, uterine, esophageal, colorectal, or liver cancer.

Clause 48. The composition, use, or method of any one of clauses 31-42, wherein said cancer is a stage 1, 2, 3 or 4 cancer.

Clause 49. The composition, use, or method of any one of clauses 31-42, wherein said cancer has metastasized.

Clause 50. The composition, use, or method of any one of clauses 31-42, wherein the patient expresses detectable levels of a 31.1 epitope.

Clause 51. The composition, use, or method of clause 50, wherein the tumor antigen is detected in a tumor biopsy sample or in the blood, stool, urine or lymph fluid.

Clause 52. The composition, use, or method of any one of clauses 31-42, wherein said patient is at risk of cancer.

Clause 53. The composition, use, or method of any one of clauses 31-42, wherein said patient is a patient without symptoms.

Clause 54. A method for detecting an 31.1 epitope comprising (a) contacting a test sample with the antibody or antibody fragment of any one of clauses 1-24, that binds an 31.1 epitope, and (b) assaying for antibody-epitope complexes, wherein the presence of said epitope is indicative of a carcinoma.

Clause 55. A method for detecting the presence of an 31.1 epitope in a patient comprising (a) administering to said patient the antibody or antibody fragment of any one of clauses 1-24, wherein said antibody is labeled, that binds an 31.1 epitope and (b) detecting the presence of an 31.1 epitope;

wherein the presence of said epitope is indicative of a carcinoma.

Clause 56. The method of clause 54 or 55, wherein said antibody or fragment is conjugated to a label.

Clause 57. The method of clause 56, wherein said label is a chemiluminescent label, paramagnetic label, an MRI contrast agent, fluorescent label, bioluminescent label, or radioactive label.

Clause 58. The method of clause 57, wherein said paramagnetic label is aluminum, manganese, platinum, oxygen, lanthanum, lutetium, scandium, yttrium, or gallium.

Clause 59. The method of clause 54 or 55, wherein said cancer is lung, breast, pancreas, uterine, esophageal, colorectal, or liver cancer.

Clause 60. The method of any one of clauses 54-59, wherein said patient is at risk of cancer.

Clause 61. The method of any one of clauses 54-59, wherein said patient is a patient without symptoms.

Clause 62. The method of any one of clauses 54-59, wherein the test sample is obtained from a patient at risk of cancer.

Clause 63. The method of any one of clauses 54-59, wherein the test sample is obtained from a patient without symptoms.

Clause 64. The method of any one of clauses 54-59, wherein said antibody is attached to a solid support.

Clause 65. The method of clause 64, wherein said solid phase support is a bead, test tube, sheet, culture dish, or test strip.

Clause 66. The method of clause 65, wherein said solid support is an array.

Clause 67. The method of any one of clauses 54-66, wherein said sample is a tissue biopsy, lymph, urine, cerebrospinal fluid, amniotic fluid, inflammatory exudate, blood, serum, stool, or liquid collected from the colorectal tract.

Clause 68. The method of any one of clauses 54-66, wherein the antibody-epitope complex is detected by an assay selected from the group consisting of Western blots, radioimmunoassays, ELISA (enzyme linked immunosorbent assay), "sandwich" immunoassays, lateral flow assay, immunoprecipitation assays, precipitation reactions, gel diffusion precipitation reactions, immunodiffusion assays, agglutination assays, complement-fixation assays, immunohistochemical assays, fluorescent immunoassays, and protein A immunoassays.

Clause 69. The method of any one of clauses 54-68, wherein said method detects colorectal polyps.

Clause 70. The method of any one of clauses 54-68, wherein said method further comprises additional testing for the presence of tumors.

Clause 71. The method of clause 70, wherein said method detects benign tumors.

Clause 72. The method of clause 70, wherein said method detects malignant tumors.

Clause 73. The method of clause 70, wherein said method detects metastatic tumors.

Clause 74. The method of clause 70, wherein said method detects non-metastatic tumors.

Clause 75. The method of any one of clauses 54-74, wherein said method detects pre-cancerous cells that express a cell marker comprising a 31.1 epitope.

Clause 76. The method of any one of clauses 54-75, wherein said method comprises imaging said epitope.

Clause 77. The method of clause 76, wherein said imaging is selected from the group consisting of positron emission tomography (PET), CCD low-light monitoring system, x-ray, CT scanning, scintigraphy, photo acoustic imaging, single photon emission computed tomography (SPECT), magnetic resonance imaging (MRI), ultrasound, paramagnetic imaging, and endoscopic optical coherence tomography.

Clause 78. A method of making antibodies comprising
(a) immunizing an animal with an 31.1 epitope,
(b) removing said animal's spleen and prepare a single cell suspension,
(c) fusing a spleen cell with a myeloma cell,
(d) culturing post-fusion cells in hybridoma selection medium,
(e) culture the resultant hybridomas,
(f) screening for specific antibody production, and
(g) selecting hybridomas which produce the desired antibody.

Clause 79. A composition comprising at least two of the following:
(a) an antibody or an antibody fragment thereof, that binds a NPC-1 epitope;
(b) an antibody or an antibody fragment thereof, that binds a 16C3 epitope, and
(c) an antibody or an antibody fragment thereof, that binds a 31.1 epitope.

Clause 80. A composition for treating cancer comprising at least two of the following:
(a) an antibody or an antibody fragment thereof, that binds a NPC-1 epitope;
(b) an antibody or an antibody fragment thereof, that binds a 16C3 epitope, and
(c) an antibody or an antibody fragment thereof, that binds a 31.1 epitope.

Clause 81. A composition for slowing the growth of a tumor comprising at least two of the following:
(a) an antibody or an antibody fragment thereof, that binds a NPC-1 epitope;
(b) an antibody or an antibody fragment thereof, that binds a 16C3 epitope, and
(c) an antibody or an antibody fragment thereof, that binds a 31.1 epitope.

Clause 82. A composition for killing tumor cells comprising at least two of the following:
(a) an antibody or an antibody fragment thereof, that binds a NPC-1 epitope;
(b) an antibody or an antibody fragment thereof, that binds a 16C3 epitope, and
(c) an antibody or an antibody fragment thereof, that binds a 31.1 epitope.

Clause 83. A composition for promoting tumor regression comprising at least two of the following:
(a) an antibody or an antibody fragment thereof, that binds a NPC-1 epitope;
(b) an antibody or an antibody fragment thereof, that binds a 16C3 epitope, and
(c) an antibody or an antibody fragment thereof, that binds a 31.1 epitope.

Clause 84. The composition of any one of clauses 79-83, wherein said composition comprises three of said antibodies.

Clause 85. The composition of any one of clauses 79-83, wherein said cancer is lung, breast, pancreas, uterine, esophageal, colorectal, or liver cancer.

Clause 86. The composition of any one of clauses 79-83, wherein said antibody or antibody fragment thereof that binds a NPC-1 epitope comprises a heavy and light chain, wherein said heavy chain is selected from the group consisting of the amino acid sequences of SEQ ID NOs: 19, 20, 29, 30, 36, and 37, optionally comprising at least one heavy chain CDR sequence of the amino acid sequence of the amino acid sequences of SEQ ID NOs: 21, 22, 23, 31, 32, 33; and the light chain is selected from the group consisting of SEQ ID NOs: 14, 15, 24, 25, 34, and 35, optionally comprising at least one light chain CDR sequence of the amino acid sequence of SEQ ID NOs: 16, 17, 18, 26, 27, and 28.

Clause 87. The composition of any one of clauses 79-83, wherein said antibody or antibody fragment thereof that binds a 16C3 epitope comprises a heavy and light chain, wherein said heavy chain is selected from the group consisting of the amino acid sequences of SEQ ID NOs: 43, 44, 53, 54, 55, 56, 57, 63, and 64, optionally comprising at least one heavy chain CDR sequence of the amino acid sequence of the amino acid sequences of SEQ ID NOs: 45, 46, 47, 65, 66, and 67; and the light chain is selected from the group consisting of SEQ ID NOs: 38, 39, 48, 49, 50, 51, 52, 58, and 59, optionally comprising at least one light chain CDR sequence of the amino acid sequence of SEQ ID NOs: 40, 41, 42, 60, 61, and 62.

Clause 88. The composition of any one of clauses 79-83, wherein said antibody or antibody fragment thereof that binds a 31.1 epitope comprises a heavy and light chain, wherein said heavy chain is selected from the group consisting of the amino acid sequences of SEQ ID NOs: 69, 72, 73, 74, 75, 76, and 77, optionally comprising at least one heavy chain CDR sequence of the amino acid sequence of the amino acid sequences of SEQ ID NOs: 78, 79, 80, 81, 82, and 83; and the light chain is selected from the group consisting of SEQ ID NOs: 68, 70, 71, 84, 85, 86, and 87, optionally comprising at least one light chain CDR sequence of the amino acid sequence of SEQ ID NOs: 88, 89, 90, 91, 92, and 93.

Clause 89. A method for treating cancer comprising administering an effective amount of a composition comprising at least two of the following:
(a) an antibody or antibody fragment thereof, that binds a NPC-1 epitope;
(b) an antibody or antibody fragment thereof, that binds a 16C3 epitope, and
(c) an antibody or antibody fragment thereof, that binds a 31.1 epitope to a patient in need thereof.

Clause 90. A method for slowing the growth of a tumor comprising administering an effective amount of a composition comprising at least two of the following:
(a) an antibody or antibody fragment thereof, that binds a NPC-1 epitope;
(b) an antibody or antibody fragment thereof, that binds a 16C3 epitope, and
(c) an antibody or antibody fragment thereof, that binds a 31.1 epitope to a patient in need thereof.

Clause 91. A method for promoting tumor regression in a subject comprising administering an effective amount of a composition comprising at least two of the following:
(a) an antibody or antibody fragment thereof, that binds a NPC-1 epitope;
(b) an antibody or antibody fragment thereof, that binds a 16C3 epitope, and
(c) an antibody or antibody fragment thereof, that binds a 31.1 epitope to a patient in need thereof.

Clause 92. A method for killing tumor cells comprising administering an effective amount of a composition comprising at least two of the following:
(a) an antibody or antibody fragment thereof, that binds a NPC-1 epitope;
(b) an antibody or antibody fragment thereof, that binds a 16C3 epitope, and
(c) an antibody or antibody fragment thereof, that binds a 31.1 epitope to a patient in need thereof.

Clause 93. A method for detecting a tumor-associated NPC-1 epitope comprising (a) contacting a test sample with a composition comprising at least two of the following:

(i) an antibody or antibody fragment thereof, that binds a NPC-1 epitope;

(ii) an antibody or antibody fragment thereof, that binds a 16C3 epitope, and (iii) an antibody or antibody fragment thereof, that binds a 31.1 epitope to a patient in need thereof, and (b) assaying for antibody-epitope complexes, wherein the presence of said epitope is indicative of a carcinoma.

Clause 94. A method for detecting the presence of an epitope associated with a carcinoma in a patient comprising (a) administering to said patient a composition comprising at least two of the following:

(i) a labeled antibody, or a fragment thereof, that binds a NPC-1 epitope;

(ii) a labeled antibody or antibody fragment thereof, that binds a 16C3 epitope, and (iii) a labeled antibody or antibody fragment thereof, that binds a 31.1 epitope to a patient in need thereof, and (b) detecting the presence of an epitope bound by said antibody, wherein the presence of said epitope is indicative of a carcinoma.

Clause 95. The method of any one of clauses 89-94, wherein said method comprises administration of three of said antibodies.

Clause 96. The method of any one of clauses 89-94, wherein said cancer is lung, breast, pancreas, uterine, esophageal, colorectal, or liver cancer.

Clause 97. The method of any one of clauses 89-94, wherein said antibody or antibody fragment thereof that binds a NPC-1 epitope comprises a heavy and light chain, wherein said heavy chain is selected from the group consisting of the amino acid sequences of SEQ ID NOs: 19, 20, 29, 30, 36, and 37, optionally comprising at least one heavy chain CDR sequence of the amino acid sequence of the amino acid sequences of SEQ ID NOs: 21, 22, 23, 31, 32, 33; and the light chain is selected from the group consisting of SEQ ID NOs: 14, 15, 24, 25, 34, and 35, optionally comprising at least one light chain CDR sequence of the amino acid sequence of SEQ ID NOs: 16, 17, 18, 26, 27, and 28.

Clause 98. The method of any one of clauses 89-94, wherein said antibody or antibody fragment thereof that binds a 16C3 epitope comprises a heavy and light chain, wherein said heavy chain is selected from the group consisting of the amino acid sequences of SEQ ID NOs: 43, 44, 53, 54, 55, 56, 57, 63, and 64, optionally comprising at least one heavy chain CDR sequence of the amino acid sequence of the amino acid sequences of SEQ ID NOs: 45, 46, 47, 65, 66, and 67; and the light chain is selected from the group consisting of SEQ ID NOs: 38, 39, 48, 49, 50, 51, 52, 58, and 59, optionally comprising at least one light chain CDR sequence of the amino acid sequence of SEQ ID NOs: 40, 41, 42, 60, 61, and 62.

Clause 99. The method of any one of clauses 89-94, wherein said antibody or antibody fragment thereof that binds a 31.1 epitope comprises a heavy and light chain, wherein said heavy chain is selected from the group consisting of the amino acid sequences of SEQ ID NOs: 69, 72, 73, 74, 75, 76, and 77, optionally comprising at least one heavy chain CDR sequence of the amino acid sequence of the amino acid sequences of SEQ ID NOs: 78, 79, 80, 81, 82, and 83; and the light chain is selected from the group consisting of SEQ ID NOs: 68, 70, 71, 84, 85, 86, and 87, optionally comprising at least one light chain CDR sequence of the amino acid sequence of SEQ ID NOs: 88, 89, 90, 91, 92, and 93.

Clause 100. An isolated nucleic acid encoding an antibody according to any one of clauses 1 to 24 or a heavy chain or light chain thereof.

Clause 101. The isolated nucleic acid of clause 100 which is contained in a vector or host cell.

Clause 102. A method of making the antibody of any one of clauses 1-24, comprising expressing a nucleic acid according to clause 100 in a cell or a cell-free translation system, and optionally purifying said antibody.

BRIEF DESCRIPTION OF THE DRAWINGS

FIG. 1A-D depicts amino acid sequences of the variable heavy chain of humanized NEO-303 monoclonal antibody. The variable region for cdr31.1, abb31.1, and sdr31.1 is shown in bold. For each of the four antibody heavy chains depicted the variable region is about 118 amino acids in length, begins at the N-terminus with the sequence "QIQ" and ends with the sequence "VSS." FIG. 1E depicts a sequence alignment between the amino acid sequences of SEQ ID NOs: 74-77 including the CDRs (underlined) (the CDR amino acid sequences are also separately provided in SEQ ID NOs: 78-83). Sequence differences among these four heavy chain sequences are included within the CDR2 region. FIG. 1A shows the polypeptide of SEQ ID NO:74. FIG. 1B shows the polypeptide of SEQ ID NO:75. FIG. 1C shows the polypeptide of SEQ ID NO:76. FIG. 1D shows the polypeptide of SEQ ID NO:77. FIG. 1E shows alignment of SEQ ID NOs:74, 75, 76, and 77, respectively.

FIG. 2A-D depicts amino acid sequences of the variable light chain of humanized NEO-303 monoclonal antibody. The variable region for cdr31.1, abb31.1, and sdr31.1 is shown in bold. For each of the four antibody light chains depicted the variable region is about 107 amino acids in length, begins at the N-terminus with the sequence "SIV" or "SIQ" and ends with the sequence "EIK" or "ELK." FIG. 2E depicts a sequence alignment between the amino acid sequences of SEQ ID NOs: 84-87 including the CDRs (underlined) (the CDR amino acid sequences are also separately provided in SEQ ID NOs: 88-93). Sequence differences among these four light chain sequences are included within the CDR1 region, as well as in the framework 1 (FR1) region (extending from the first amino acid to the amino acid just prior to the start of CDR1 sequence) and framework 4 (FR4) region (starting with the first amino acid C-terminal to the CDR3 sequence and extending to the end of the variable domain). FIG. 2A shows the polypeptide of SEQ ID NO:84. FIG. 2B shows the polypeptide of SEQ ID NO:85. FIG. 2C shows the polypeptide of SEQ ID NO:86. FIG. 2D shows the polypeptide of SEQ ID NO:87. FIG. 2E shows alignment of SEQ ID NOs:84, 85, 86, and 87, respectively.

DETAILED DESCRIPTION OF THE INVENTION

Figure 3:
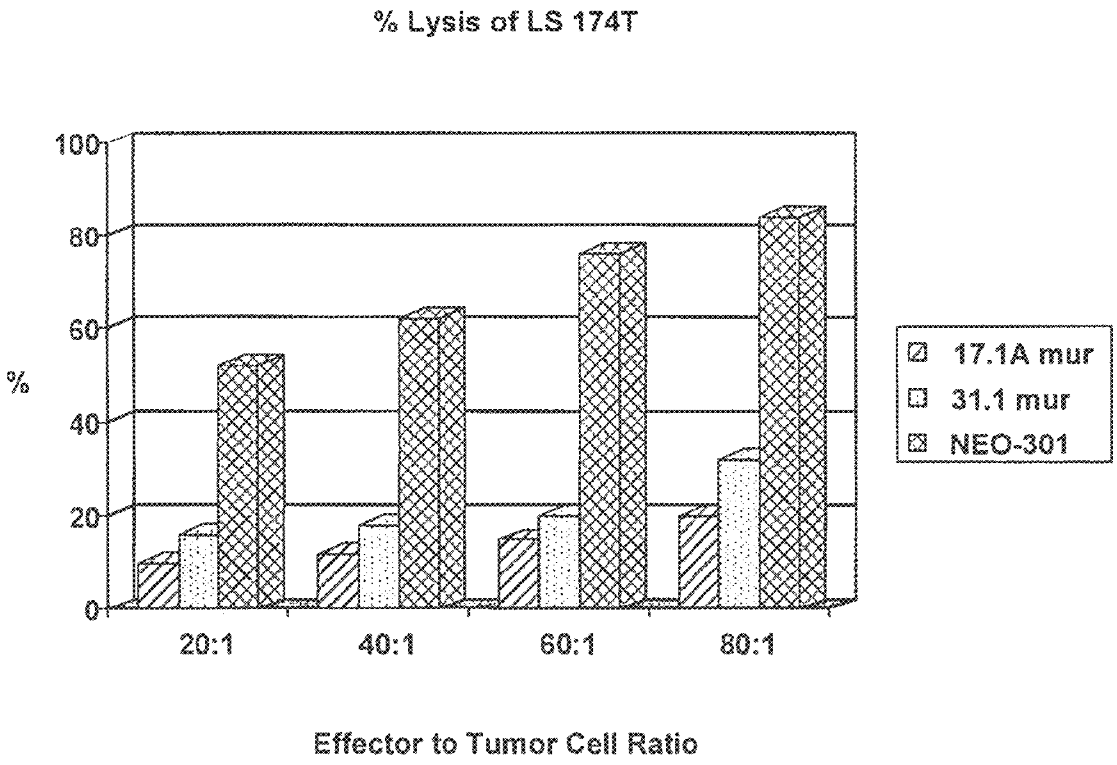
FIG. 3 depicts the effector-to-tumor cell ratio for 17.7A (control), murine 31.1, and NEO-301 antibodies.

In order that the invention herein described may be fully understood, the following detailed description is set forth. Various embodiments of the invention are described in detail and may be further illustrated by the provided examples.

Definitions

Unless defined otherwise, all technical and scientific terms used herein have the same meaning as those commonly understood by one of ordinary skill in the art to which this invention belongs. Although methods and materials similar or equivalent to those described herein may be used in the invention or testing of the present invention, suitable methods and materials are described herein. The materials, methods and examples are illustrative only, and are not intended to be limiting.

As used in the description herein and throughout the claims that follow, the meaning of "a," "an," and "the" includes plural reference unless the context clearly dictates otherwise.

"Amino acid," as used herein refers broadly to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Antibody," as used herein, refers broadly to any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, from all sources, e.g., human, rodent, rabbit, cow, sheep, pig, dog, chicken, are considered to be "antibodies." Antibodies include but are not limited to chimeric antibodies, human antibodies and other non-human mammalian antibodies, humanized antibodies, single chain antibodies (scFvs), camelbodies, nanobodies, IgNAR (single-chain antibodies derived from sharks), small-modular immunopharmaceuticals (SMIPs), and antibody fragments (e.g., Fabs, Fab', $F(ab')_2$.) Numerous antibody coding sequences have been described; and others may be raised by methods well-known in the art. See Streltsov, et al. (2005) *Protein Sci.* 14(11): 2901-9; Greenberg, et al. (1995) *Nature* 374(6518): 168-173; Nuttall, et al. (2001) *Mol Immunol.* 38(4): 313-26; Hamers-Casterman, et al. (1993) *Nature* 363(6428): 446-8; Gill, et al. (2006) *Curr Opin Biotechnol.* 17(6): 653-8.

"Antigen," as used herein, refers broadly to a molecule or a portion of a molecule capable of being bound by an antibody which is additionally capable of inducing an animal to produce an antibody capable of binding to an epitope of that antigen. An antigen may have one epitope, or have more than one epitope. The specific reaction referred to herein indicates that the antigen will react, in a highly selective manner, with its corresponding antibody and not with the multitude of other antibodies which may be evoked by other antigens. Antigens may be tumor specific (e.g., expressed by neoplastic cells of pancreatic and colon carcinoma.)

"Cancer," as used herein, refers broadly to any neoplastic disease (whether invasive or metastatic) characterized by abnormal and uncontrolled cell division causing malignant growth or tumor.

"Chimeric antibody," as used herein, refers broadly to an antibody molecule in which the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug; or the variable region, or a portion thereof, is altered, replaced or exchanged with a variable region having a different or altered antigen specificity.

"Conservatively modified variants," as used herein, applies to both amino acid and nucleic acid sequences, and with respect to particular nucleic acid sequences, refers broadly to conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) may be modified to yield a functionally identical molecule.

"Complementarity determining region," "hypervariable region," or "CDR," as used herein, refers broadly to one or more of the hyper-variable or complementarily determining regions (CDRs) found in the variable regions of light or heavy chains of an antibody. See Kabat, et al. (1987) "*Sequences of Proteins of Immunological Interest*" National Institutes of Health, Bethesda, Md. These expressions include the hypervariable regions as defined by Kabat, et al. (1983) "*Sequences of Proteins of Immunological Interest*" U.S. Dept. of Health and Human Services or the hypervariable loops in 3-dimensional structures of antibodies. Chothia and Lesk (1987) *J Mol. Biol.* 196: 901-917. The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the antibody-antigen interaction. Kashmiri (2005) *Methods* 36: 25-34.

"Control amount," as used herein, refers broadly to a marker can be any amount or a range of amounts to be compared against a test amount of a marker. For example, a control amount of a marker may be the amount of a marker in a patient with a particular disease or condition or a person without such a disease or condition. A control amount can be either in absolute amount (e.g., microgram/ml) or a relative amount (e.g., relative intensity of signals).

"Differentially present," as used herein, refers broadly to differences in the quantity or quality of a marker present in a sample taken from patients having a disease or condition as compared to a comparable sample taken from patients who do not have one of the diseases or conditions. For example, a nucleic acid fragment may optionally be differentially present between the two samples if the amount of the nucleic acid fragment in one sample is significantly different from the amount of the nucleic acid fragment in the other sample, for example as measured by hybridization and/or NAT-based assays. A polypeptide is differentially present between the two samples if the amount of the polypeptide in one sample is significantly different from the amount of the polypeptide in the other sample. It should be noted that if the marker is detectable in one sample and not detectable in the other, then such a marker may be considered to be differentially present. Optionally, a relatively low amount of up-regulation may serve as the marker.

"Diagnostic," as used herein, refers broadly to identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

"Diagnosing," as used herein refers broadly to classifying a disease or a symptom, determining a severity of the disease, monitoring disease progression, forecasting an outcome of a disease and/or prospects of recovery. The term "detecting" may also optionally encompass any of the foregoing. Diagnosis of a disease according to the present invention may, in some embodiments, be affected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject.

"Effective amount," as used herein, refers broadly to the amount of a compound, antibody, antigen, or cells that, when administered to a patient for treating a disease, is sufficient to effect such treatment for the disease. The effective amount may be an amount effective for prophylaxis, and/or an amount effective for prevention. The effective amount may be an amount effective to reduce, an amount effective to prevent the incidence of signs/symptoms, to reduce the severity of the incidence of signs/symptoms, to eliminate the incidence of signs/symptoms, to slow the development of the incidence of signs/symptoms, to prevent the development of the incidence of signs/symptoms, and/or effect prophylaxis of the incidence of signs/symptoms. The "effective amount" may vary depending on the disease and its severity and the age, weight, medical history, susceptibility, and pre-existing conditions, of the patient to be treated. The term "effective amount" is synonymous with "therapeutically effective amount" for purposes of this invention.

"Expression vector," as used herein, refers broadly to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression cassettes which contain only the minimum elements needed for transcription of the recombinant nucleic acid.

"Framework region" or "FR," as used herein, refers broadly to one or more of the framework regions within the variable regions of the light and heavy chains of an antibody. See Kabat, et al. (1987) "*Sequences of Proteins of Immunological Interest*," National Institutes of Health, Bethesda, Md. These expressions include those amino acid sequence regions interposed between the CDRs within the variable regions of the light and heavy chains of an antibody.

"Heterologous," as used herein, refers broadly to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"High affinity," as used herein, refers broadly to an antibody having a KD of at least $10^{-8}$ M, more preferably at least $10^{-9}$ M and even more preferably at least $10^{-10}$ M for a target antigen. However, "high affinity" binding can vary for other antibody isotypes. For example, "high affinity" binding for an IgM isotype refers to an antibody having a KD of at least $10^{-7}$ M, more preferably at least $10^{-8}$ M.

"Homology," as used herein, refers broadly to a degree of similarity between a nucleic acid sequence and a reference nucleic acid sequence or between a polypeptide sequence and a reference polypeptide sequence. Homology may be partial or complete. Complete homology indicates that the nucleic acid or amino acid sequences are identical. A partially homologous nucleic acid or amino acid sequence is one that is not identical to the reference nucleic acid or amino acid sequence. The degree of homology can be determined by sequence comparison. The term "sequence identity" may be used interchangeably with "homology."

"Host cell," as used herein, refers broadly to a cell that contains an expression vector and supports the replication or expression of the expression vector. Host cells may be prokaryotic cells such as *E. coli*, or eukaryotic cells such as yeast, insect (e.g., SF9), amphibian, or mammalian cells such as CHO, HeLa, HEK-293, e.g., cultured cells, explants, and cells in vivo.

"Hybridization," as used herein, refers broadly to the physical interaction of complementary (including partially complementary) polynucleotide strands by the formation of hydrogen bonds between complementary nucleotides when the strands are arranged antiparallel to each other.

"K-assoc" or "Ka", as used herein, refers broadly to the association rate of a particular antibody-antigen interaction, whereas the term "Kdiss" or "Kd," as used herein, refers to the dissociation rate of a particular antibody-antigen interaction. The term "KD", as used herein, is intended to refer to the dissociation constant, which is obtained from the ratio of Kd to Ka (i.e., Kd/Ka) and is expressed as a molar concentration (M). KD values for antibodies can be determined using methods well established in the art.

"Immunoassay," as used herein, refers broadly to an assay that uses an antibody to specifically bind an antigen. The immunoassay may be characterized by the use of specific binding properties of a particular antibody to isolate, target, and/or quantify the antigen.

"Isolated," as used herein, refers broadly to material removed from its original environment in which it naturally occurs, and thus is altered by the hand of man from its natural environment. Isolated material may be, for example, exogenous nucleic acid included in a vector system, exogenous nucleic acid contained within a host cell, or any material which has been removed from its original environment and thus altered by the hand of man (e.g., "isolated antibody").

"Label" or a "detectable moiety" as used herein, refers broadly to a composition detectable by spectroscopic, photochemical, biochemical, immunochemical, chemical, or other physical means.

"Low stringency," "medium stringency," "high stringency," or "very high stringency conditions," as used herein, refers broadly to conditions for nucleic acid hybridization and washing. Guidance for performing hybridization reactions can be found in Ausubel, et al. (2002) *Short Protocols in Molecular Biology* ($5^{th}$ Ed.) John Wiley & Sons, NY. Exemplary specific hybridization conditions include but are not limited to: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C.

"Mammal," as used herein, refers broadly to any and all warm-blooded vertebrate animals of the class Mammalia, including humans, characterized by a covering of hair on the skin and, in the female, milk-producing mammary glands for nourishing the young. Examples of mammals include but are not limited to alpacas, armadillos, capybaras, cats, camels, chimpanzees, chinchillas, cattle, dogs, donkeys, goats, gorillas, hamsters, horses, humans, lemurs, llamas, mice, non-human primates, pigs, rats, sheep, shrews, squirrels, and tapirs. Mammals include but are not limited to bovine, canine, equine, feline, murine, ovine, porcine, primate, and rodent species. Mammal also includes any and all those listed on the Mammal Species of the World maintained by the National Museum of Natural History, Smithsonian Institution in Washington D.C.

"Nucleic acid" or "nucleic acid sequence," as used herein, refers broadly to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones. Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

"Operatively linked", as used herein, refers broadly to when two DNA fragments are joined such that the amino acid sequences encoded by the two DNA fragments remain in-frame.

"Paratope," as used herein, refers broadly to the part of an antibody which recognizes an antigen (e.g., the antigen-binding site of an antibody.) Paratopes may be a small region (e.g., 15-22 amino acids) of the antibody's Fv region and may contain parts of the antibody's heavy and light chains. See Goldsby, et al. *Antigens* (*Chapter* 3) Immunology ($5^{th}$ Ed.) New York: W.H. Freeman and Company, pages 57-75.

"Patient," as used herein, refers broadly to any animal who is in need of treatment either to alleviate a disease state or to prevent the occurrence or reoccurrence of a disease state. Also, "Patient" as used herein, refers broadly to any animal who has risk factors, a history of disease, susceptibility, symptoms, signs, was previously diagnosed, is at risk for, or is a member of a patient population for a disease. The patient may be a clinical patient such as a human or a veterinary patient such as a companion, domesticated, livestock, exotic, or zoo animal. The term "subject" may be used interchangeably with the term "patient".

"Polypeptide," "peptide" and "protein," are used interchangeably and refer broadly to a polymer of amino acid residues. The terms apply to amino acid polymers in which one or more amino acid residue is an analog or mimetic of a corresponding naturally occurring amino acid, as well as to naturally occurring amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer. Polypeptides can be modified, e.g., by the addition of carbohydrate residues to form glycoproteins. The terms "polypeptide," "peptide" and "protein" include glycoproteins, as well as non-glycoproteins.

"Promoter," as used herein, refers broadly to an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation.

"Prophylactically effective amount," as used herein, refers broadly to the amount of a compound that, when administered to a patient for prophylaxis of a disease or prevention of the reoccurrence of a disease, is sufficient to effect such prophylaxis for the disease or reoccurrence. The prophylactically effective amount may be an amount effective to prevent the incidence of signs and/or symptoms. The "prophylactically effective amount" may vary depending on the disease and its severity and the age, weight, medical history, predisposition to conditions, preexisting conditions, of the patient to be treated.

"Prophylaxis," as used herein, refers broadly to a course of therapy where signs and/or symptoms are not present in the patient, are in remission, or were previously present in a patient. Prophylaxis includes preventing disease occurring subsequent to treatment of a disease in a patient. Further, prevention includes treating patients who may potentially develop the disease, especially patients who are susceptible to the disease (e.g., members of a patent population, those with risk factors, or at risk for developing the disease).

"Recombinant" as used herein, refers broadly with reference to a product, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

"Specifically (or selectively) binds" to an antibody or "specifically (or selectively) immunoreactive with," or "specifically interacts or binds," as used herein, refers broadly to a protein or peptide (or other epitope), refers, in some embodiments, to a binding reaction that is determinative of the presence of the protein in a heterogeneous population of proteins and other biologics. For example, under designated immunoassay conditions, the specified antibodies bind to a particular protein at least two times greater than the background (non-specific signal) and do not substantially bind in a significant amount to other proteins present in the sample. Typically a specific or selective reaction will be at least twice background signal or noise and more typically more than about 10 to 100 times background.

"Specifically hybridizable" and "complementary" as used herein, refer broadly to a nucleic acid can form hydrogen bond(s) with another nucleic acid sequence by either traditional Watson-Crick or other non-traditional types. The binding free energy for a nucleic acid molecule with its complementary sequence is sufficient to allow the relevant function of the nucleic acid to proceed, e.g., RNAi activity. Determination of binding free energies for nucleic acid molecules is well known in the art. See, e.g., Turner, et al. (1987) *CSH Symp. Quant. Biol.* LII: 123-33; Frier, et al. (1986) *PNAS* 83: 9373-77; Turner, et al. (1987) *J. Am. Chem. Soc.* 109: 3783-85. A percent complementarity indicates the percentage of contiguous residues in a nucleic acid molecule that can form hydrogen bonds (e.g., Watson-Crick base pairing) with a second nucleic acid sequence (e.g., about at least 5, 6, 7, 8, 9, 10 out of 10 being about at least 50%, 60%, 70%, 80%, 90%, and 100% complementary, inclusive). "Perfectly complementary" or 100% complementarity refers broadly all of the contiguous residues of a nucleic acid sequence hydrogen bonding with the same number of contiguous residues in a second nucleic acid sequence. "Substantial complementarity" refers to polynucleotide strands exhibiting about at least 90% complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically may differ by at least 5 nucleotides.

"Signs" of disease, as used herein, refers broadly to any abnormality indicative of disease, discoverable on examination of the patient; an objective indication of disease, in contrast to a symptom, which is a subjective indication of disease.

"Solid support," "support," and "substrate," as used herein, refers broadly to any material that provides a solid or semi-solid structure with which another material can be attached including but not limited to smooth supports (e.g., metal, glass, plastic, silicon, and ceramic surfaces) as well as textured and porous materials.

"Subjects" as used herein, refers broadly to anyone suitable to be treated according to the present invention include, but are not limited to, avian and mammalian subjects, and are preferably mammalian. Mammals of the present invention include, but are not limited to, canines, felines, bovines, caprines, equines, ovines, porcines, rodents (e.g., rats and mice), lagomorphs, primates, humans. Any mammalian subject in need of being treated according to the present invention is suitable. Human subjects of both genders and at any stage of development (i.e., neonate, infant, juvenile, adolescent, adult) can be treated according to the present invention. The present invention may also be carried out on animal subjects, particularly mammalian subjects such as mice, rats, dogs, cats, cattle, goats, sheep, and horses for veterinary purposes, and for drug screening and drug development purposes. "Subjects" is used interchangeably with "patients."

"Symptoms" of disease as used herein, refers broadly to any morbid phenomenon or departure from the normal in structure, function, or sensation, experienced by the patient and indicative of disease.

"Therapy," "therapeutic," "treating," or "treatment", as used herein, refers broadly to treating a disease, arresting, or reducing the development of the disease or its clinical symptoms, and/or relieving the disease, causing regression of the disease or its clinical symptoms. Therapy encompasses prophylaxis, treatment, remedy, reduction, alleviation, and/or providing relief from a disease, signs, and/or symptoms of a disease. Therapy encompasses an alleviation of signs and/or symptoms in patients with ongoing disease signs and/or symptoms (e.g., tumor growth, metastasis). Therapy also encompasses "prophylaxis". The term "reduced", for purpose of therapy, refers broadly to the clinical significant reduction in signs and/or symptoms. Therapy includes treating relapses or recurrent signs and/or symptoms (e.g., tumor growth, metastasis). Therapy encompasses but is not limited to precluding the appearance of signs and/or symptoms anytime as well as reducing existing signs and/or symptoms and eliminating existing signs and/or symptoms. Therapy includes treating chronic disease ("maintenance") and acute disease. For example, treatment includes treating or preventing relapses or the recurrence of signs and/or symptoms (e.g., tumor growth, metastasis).

"Variable region" or "VR," as used herein, refers broadly to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

"Vector," as used herein, refers broadly to a plasmid, cosmid, phagemid, phage DNA, or other DNA molecule which is able to replicate autonomously in a host cell, and which is characterized by one or a small number of restriction endonuclease recognition sites at which such DNA sequences may be cut in a determinable fashion without loss of an essential biological function of the vector, and into which DNA may be inserted in order to bring about its replication and cloning. The vector may further contain a marker suitable for use in the identification of cells transformed with the vector.

The techniques and procedures are generally performed according to conventional methods well known in the art and as described in various general and more specific references that are cited and discussed throughout the present specification. See, e.g., Sambrook, et al. (2001) *Molec. Cloning: Lab. Manual* [3rd Ed] Cold Spring Harbor Laboratory Press. Standard techniques may be used for recombinant DNA, oligonucleotide synthesis, and tissue culture, and transformation (e.g., electroporation, lipofection).

Enzymatic reactions and purification techniques may be performed according to manufacturer's specifications or as commonly accomplished in the art or as described herein. The nomenclatures utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

A33 Antigen Comprising a 31.1 Epitope

The present invention provides humanized 31.1 monoclonal antibodies. These humanized monoclonal antibodies may be used in methods for detecting and treating cancer.

The 31.1 antibody is an antibody reactive with human colon and pancreatic cancer tissues. The antigen of the 31.1 antibody is human A33 antigen as shown by western blot of immunoprecipitated antigen, mass spectroscopy, dot blot, flow cytometry and ELISA. The 31.1 antibody does not cross react with mouse recombinant A33 in sandwich ELISA and A33 in IHC staining. The 31.1 epitope is non-linear due to the sensitivity to its disruption by detergents and negative binding results on reducing condition in Western Blot. The full length of the A33 amino acid sequence and the peptides identified by mass spectroscopy from LS174T human colon tumor cell IP (immunoprecipitatation) protein are shown below.

```
                                                                 (SEQ ID NO: 10)
  1 MVGKMWPVLW TLCAVRVTVD AISVETPQDV LRASQGKSVT LPCTYHTSTS SREGLIQWDK

 61 LLLTHIERVV IWPFSNKNYI HGELYKNRVS ISNNAEQSDA SITIDQLTMA DNGTYECSVS

121 LMSDLEGNTK SRVRELVEVP PSKPECGIEG ETIIGNNIQL TCQSKEGSPT PQYSWKRYNI

181 LNQEQPLAQP ASGQPVSLKN ISTDTSGYYI CTSSNEEGTQ FCNITVAVRS PSMNVALYVG

241 IAVGVVAALI IIGIIIYCCC CRGKDDNTED KEDARPNREA YEEPPEQLRE LSREREEEDD

301 YRQEEQRSTG RESPDHLDQ
```

The highlighting designates peptide sequences identified by mass spectroscopy from LS 174T 31.1 IP (39% coverage of the total A33 sequence). AS33 is a previously described monoclonal antibody which reacts with the A33 protein. The 31.1 antibody can detect the antigen in 31.1 IP proteins from LS 174T and an engineered recombinant CHO cell line expressing the full length A33 cDNA (A33-CHO), but not in AS33 IP proteins from both cell lines in western blot under non-reducing condition. AS33 binds to the antigen in 31.1 and AS33 IP proteins from LS174T and A33-CHO recombinant cells. Experimental results suggest that 31.1 antibody binds to a different epitope of the A33 antigen compared to commercial AS33 antibody.

Therefore, the humanized 31.1 antibodies described herein may recognize a non-linear (e.g., conformational) epitope in the A33 antigen contained in the following peptide sequence ("31.1 epitope" shown in bold):

(SEQ. ID. NO. 12)

VRLLVLVPPSKPECGIEGETIIGNNIQLTCQSKEGSPTPQYSWKRYNILN

QEQPLAQPASGQPVSLK.

Further, data from overlapping 8mer and 10mer peptide array analysis and PH.D phage display bio-panning suggests the 31.1 epitope on the A33 antigen may be located about residues 168-186 (SPTPQYSWKRYNILNQEQP) (SEQ ID NO:94) of the A33 antigen; and disulfide bridging is needed for the cognate 31.1 epitope conformation. These data support the previous disclosure in U.S. Patent Application Publication No. 2008/0031873 which showed that an engineered point mutation of the A33 cDNA at residue Asn-179 to Asp reduced the binding of 31.1 antibody after transfection into mammalian cells and expression of the mutated recombinant A33 protein.

Thus, the present invention provides for antibodies that bind the A33 antigen (e.g., 31.1 epitope) expressed by colon and pancreatic and other cancers, and their uses in clinical and scientific procedures, including diagnostic procedures. The NEO-300 antibodies that binds the A33 antigen (e.g., 31.1 epitope) are useful both as diagnostic and therapeutic target specific tools for cancer because the NEO-301 antibody effectively inhibited tumor progression in an in vivo model. Additionally, the A33 antigen is a specific biomarker for pancreas, colon and other cancers, and may be measured in biopsied tissue as well as in subject serum and fecal samples. Additionally, immunohistochemistry studies demonstrate that the NEO-300 antibodies may be useful as a tissue biomarker of human pancreas and colon cancer presence and progression, and may also identify other cancers such as uterine and lung cancers. See also WO 2011/163401.

A33 Antigen Polypeptides

A33 is a cancer-specific antigen. The A33 antigen is a cell surface glycoprotein expressed in the small intestine and colonic epithelium. The A33 antigen shares homology with tight-junction associated proteins of the immunoglobulin superfamily including CAR and JAM. A33 antigen is expressed in 95% of colon tumors but not normal intestine or other organs. Ackerman, et al. (2008) *Cancer Immunol Immunother* 57(7): 1017-1027; Garinchesa, et al. (1996) *Int. J. Oncol.* 9(3): 465-71.

The invention provides humanized antibodies that selectiving bind the 31.1 epitope on the A33 antigen polypeptide. Exemplary polypeptides comprising an A33 antigen are provided in SEQ ID NO: 10. Further A33 amino acid sequences derived from full length A33 protein include regions involved in NEO-300 antibody binding to A33 antigen (e.g., SEQ ID NOs: 10, 11, 12, or 13) because, as discussed herein, the 31.1 epitope is believed to be non-linear (e.g., conformational). See also WO 2011/163401.

Nucleic acids encoding polypeptides comprising at least one A33 antigen may be modified using standard molecular biological techniques that result in variants polypeptides comprising at least one A33 antigen including but not limited to deletions, additions and substitutions in the amino acid sequence, that retain the specific antigenicity of the A33 antigen (e.g., the A33 antigen is bound by the 31.1 antibody). Additionally, variant polypeptides comprising at least one A33 antigens may also retain the antigenicity of the A33 antigens (e.g., raise a specific immune response against the A33 antigens, respectively, upon immunization in a subject). The A33 antigen polypeptides may be formulated with a pharmaceutical carrier to manufacture an antigen composition useful as a "cancer vaccine" (e.g., a pharmaceutical composition that elicits a specific immune response against the A33 antigen, that produces anti-tumor antibodies after immunization in a subject).

The A33 antigen polypeptides described herein may be purified from cells that have been altered to express it (e.g., recombinant). DNA sequences encoding the A33 antigen polypeptides may be inserted into an expression vector and then transformed (or transfected) in an appropriate host cell and/or expressed in a transgenic animal. The A33 antigen polypeptides so expressed may then be isolated by methods known in the art. See, e.g., Maniatis, et al. (2001) *Molecular Cloning: A Laboratory Manual* [3rd Ed.] Cold Spring Harbor Laboratory Press.

The polypeptides of the present invention may be biochemically synthesized such as by using standard solid phase techniques. These methods include exclusive solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence) and therefore involves different chemistry. Solid phase peptide synthesis procedures are well known in the art and further described by Stewart (1984) *Solid Phase Peptide Syntheses* [2nd Ed.] Pierce Chemical Company and Benoiton (2005) *Chemistry of Peptide Synthesis* CRC Press. Synthetic peptides may be purified by preparative high performance liquid chromatography and the composition of which may be confirmed via amino acid sequencing. See Creighton (1992) [2nd Ed.] *Proteins, Structures and Molecular Principles* W.H. Freeman and Company; Aguilar (2004) [Ed.] *HPLC of Peptides and Proteins: Methods and Protocols* Humana Press; Simpson (2002) *Protein Sequencing Protocols* [2nd Ed.] Humana Press.

In cases where large amounts of the polypeptides of the present invention are desired, the polypeptides of the present invention may be generated using recombinant techniques such as described by Invitrogen (2002) "*Guide to Baculovirus Expression Vector Systems (BEVs) and Insect Culture Techniques" Instruction Manual*; Hatti-Kaul and Mattiasson (2003) [Eds] *Isolation and Purification of Proteins*; Ahmed (2004) *Principles and Reactions of Protein Extraction, Purification and Characterization* CRC Press. Further recombinant techniques such as described by, for example, Bitter, et al. (1987) *Methods in Enzymol.* 153: 516-544, Studier, et al. (1990) *Methods in Enzymol.* 185: 60-89, Brisson, et al. (1984) *Nature* 310: 511-514, Takamatsu, et al. (1987) *EMBO J.* 6: 307-311, Coruzzi, et al. (1984) *EMBO J.* 3: 1671-1680 and Brogli, et al. (1984) *Science* 224: 838-843, Gurley, et al. (1986) *Mol. Cell. Biol.* 6: 559-565 and Weissbach & Weissbach (1988) *Methods for Plant Molecular Biology*, Academic Press, NY, Section VIII, pages 421-463.

Polypeptide Isolation

The present invention also provides methods for isolation of the A33 antigen polypeptides. For example, relevant cell lines or tumor samples may be obtained from a cancer patient. After homogenization and solubilization in a detergent, the antigen is chromatographically purified. Size-exclusion or affinity chromatography may be used for this, and may be used in conjunction with NEO-300 antibody binding. For example, A33 antigen polypeptides may be immobilized on a solid support (e.g., coupled to resins, magnetic beads) for simple antigen adsorption, washing, and elution from the solid support. The eluted protein is then studied further for antigen presence, characterization, and identification. See Walker (2002) *Protein Protocols Handbook* [2nd Ed.] Humana Press and Cultur (2003) [Ed.] *Protein Purification Protocols* Humana Press.

The antigen isolated in this way may be used for preparing a pharmaceutical using the conventional pharmaceutical excipient and carrier substance. For example, in-vivo administration of the purified antigen in a physiological NaCl solution.

Additionally, the A33 antigen polypeptides according to the invention may serve as an antigen in the identification of activities as part of a high-throughput screening. High-throughput screening methods are known to persons skilled in the art. Wells (2002) *High Throughout Bioanalytical Sample Preparation* Elsevier Health Sciences.

NEO-300 Antibodies Bind 31.1 Epitope on A33 Antigen

The present invention provides humanized antibodies which selectively bind the A33 antigen including but not limited monoclonal and humanized monoclonal antibodies (e.g., NEO-300 monoclonal antibodies, e.g., NEO-301, NEO-302, NEO-303). The antibodies which selectively bind the A33 antigen may be admixed in compositions with pharmaceutical carriers and additional antibodies (e.g., NEO-300 monoclonal antibodies including but not limited to NEO-301, NEO-302, NEO-303). For example, the NEO-301 monoclonal antibody exhibits specificity for binding to colon and pancreatic tumor cells and strong cytotoxicity (e.g., ADCC activity) against colon and pancreatic tumor cells. Arlen, et al. (Nov. 3, 2010) *Journal of Cancer* 1: 209-222. Exemplary antibodies are provided in Table 1.

TABLE 1

Antibodies

| Antibody | Aliases | Antigen | Exemplary SEQ ID NOs | Description |
|---|---|---|---|---|
| NPC-1 | | NPC-1 | | Murine hybridoma that expresses NPC-1 IgG1 (ATCC) |
| NEO-101 | NPC-1C, ensituximab | NPC-1 | Light Chain (SEQ ID NOs: 14, 15)<br>LC CDRs (SEQ ID NOs: 16, 17, 18<br>Heavy Chain (SEQ ID NOs: 19, 20)<br>HC CDRs (SEQ ID NOs: 21, 22, 23) | Chimeric NPC-1 antibody, engineered in CHO-DG44 production cell clone 4B7; targets a variant of MUC5AC |
| NEO-102 | | NPC-1 | Light Chain (SEQ ID NOs: 24, 25)<br>LC CDRs (SEQ ID NOs: 26, 27, 28)<br>Heavy Chain (SEQ ID NOs: 29, 30)<br>HC CDRs (SEQ ID NOs: 31, 32, 33) | Chimeric NPC-1 antibody, engineered in CHO-M production cells, contains 2 amino acid changes in HC constant domain* |
| NEO-103 | | NPC-1 | Light Chain (SEQ ID NOs: 34, 35)<br>Heavy Chain (SEQ ID NOs: 36, 37) | Humanized NPC-1 antibody |
| 16C3 | | 16C3 | Light Chain (SEQ ID NOs: 38, 39)<br>LC CDRs (SEQ ID NOs: 40, 41, 42)<br>Heavy Chain (SEQ ID NOs: 43, 44)<br>HC CDRs (SEQ ID NOs: 45, 46, 47) | Murine hybridoma that expresses 16C3 IgG1 (ATCC) |
| 16C3 | Variant h16C3 antibodies | 16C3 | Light Chain (SEQ ID NOs: 48, 49, 50, 51, 52)<br>Heavy Chain (SEQ ID NOs: 53, 54, 55, 56, 57) | Humanized 16C3 antibody |
| NEO-201 | h16C3-Abb* | 16C3 | Light Chain (SEQ ID NOs: 58, 59)<br>LC CDRs (SEQ ID NOs: 60, 61, 62)<br>Heavy Chain (SEQ ID NOs: 63, 64)<br>HC CDRs (SEQ ID NOs: 65, 66, 67) | Humanized 16C3 antibody |
| NEO-300 Antibodies | | | | |
| 31.1 | | 31.1 | | Chimeric 31.1 antibody, produced in CHO-K cells |
| NEO-301 | 31.1C | 31.1 | Light Chain (SEQ ID NO: 68)<br>Heavy Chain (SEQ ID NO: 69) | Chimeric 31.1 antibody, contains 2 amino acid changes in HC constant domain,* produced in high titer CHO-S cells |
| NEO-302 | | 31.1 | Light Chain (SEQ ID NO: 70, 71)<br>Heavy Chain (SEQ ID NO: 72, 73) | Humanized 31.1 antibody |
| NEO-303 | | 31.1 | Heavy Chain (SEQ ID NOs: 74-77)<br>HC CDRs (SEQ ID NOs: 78-83)<br>Light Chain (SEQ ID NOs: 84-87)<br>LC CDRs (SEQ ID NOs: 88-93) | Humanized 31.1 antibody |

*2 amino acid changes in heavy chain constant domain are Proline at residue 175 to Leucine in CH1 and Methionine at residue 390 to Threonine in CH3. The Leucine and Threonine residues represent more common allotypes in human population and were introduced to reduce potential in vivo antigenicity or toxicity.

Antibodies may comprise of two identical light polypeptide chains of molecular weight approximately 23,000 daltons ("light chain"), and two identical heavy chains of molecular weight 53,000-70,000 ("heavy chain"). See Edelman (1971) *Ann. NY. Acad. Sci.* 190: 5. The four chains are joined by disulfide bonds in a "Y" configuration wherein the light chains bracket the heavy chains starting at the mouth of the "Y" configuration. The "branch" portion of the "Y" configuration is designated the $F_{ab}$ region; the stem portion of the "Y" configuration is designated the Fc region. The amino acid sequence orientation runs from the N-terminal end at the top of the "Y" configuration to the C-terminal end at the bottom of each chain. The N-terminal end possesses the variable region having specificity for the antigen that elicited it, and is about 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e., the antigen eliciting it). There are five known major classes of constant regions that determine the class of the immunoglobulin molecule (e.g., IgG, IgM, IgA, IgD, and IgE corresponding to γ, μ, α, δ, and ε heavy chain constant regions). The constant region or class determines subsequent effector function of the antibody, including activation of complement (Kabat (1976) *Structural Concepts in Immunology and Immunochemistry* [2nd Ed.] pages 413-436; Holt, Rinehart, Winston) and other cellular responses (Andrews, et al. (1980) *Clinical Immunobiology* 1-18; Kohl, et al. (1983) *Immunology* 48: 187) while the variable region determines the antigen with which it will react. Light chains are classified as either κ (kappa) or λ (lambda). Each heavy chain class may be prepared with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells.

Specific binding to an antibody under such conditions may require an antibody that is selected for its specificity for a particular protein. For example, polyclonal antibodies raised to seminal basic protein from specific species such as rat, mouse, or human can be selected to obtain only those polyclonal antibodies that are specifically immunoreactive with seminal basic protein and not with other proteins, except for polymorphic variants and alleles of seminal basic protein. This selection may be achieved by subtracting out antibodies that cross-react with seminal basic protein molecules from other species. A variety of immunoassay formats may be used to select antibodies specifically immunoreactive with a particular protein. For example, solid-phase ELISA immunoassays are routinely used to select antibodies specifically immunoreactive with a protein. See, e.g., Harlow & Lane (1998) *USING ANTIBODIES: A LABORATORY MANUAL* Cold Spring Harbor Laboratory, for a description of immunoassay formats and conditions that can be used to determine specific immunoreactivity. Typically a specific or selective reaction will be at least twice background signal or noise and more typically more than about 10 to 100 times background.

Polyclonal Antibody

Polyclonal antibodies are heterogeneous populations of antibody molecules derived from the sera of animals immunized with an antigen. Polyclonal antibodies which selectively bind the A33 antigen may be made by methods well-known in the art. See, e.g., Howard & Kaser (2007) *Making and Using Antibodies: A Practical Handbook* CRC Press.

Monoclonal Antibody

A monoclonal antibody contains a substantially homogeneous population of antibodies specific to antigens, which population contains substantially similar epitope binding sites. Monoclonal antibodies may be obtained by methods known to those skilled in the art. See, e.g. Kohler and Milstein (1975) *Nature* 256: 495-497; U.S. Pat. No. 4,376,110; Ausubel, et al. [Eds.] (2011) *CURRENT PROTOCOLS IN MOLECULAR BIOLOGY*, Greene Publishing Assoc. and Wiley Interscience, NY.; and Harlow & Lane (1998) *USING ANTIBODIES: A LABORATORY MANUAL* Cold Spring Harbor Laboratory; Colligan, et al. (2005) [Eds.] *Current Protocols in Immunology* Greene Publishing Assoc. and Wiley Interscience, NY. Such antibodies may be of any immunoglobulin class including IgG, IgM, IgE, IgA, GILD and any subclass thereof. A hybridoma producing an antibody of the present invention may be cultivated in vitro, in situ, or in vivo. and A33 antigen antibody which selectively binds the A33 antigen (e.g., exemplary light chain are depicted in SEQ ID NO:68 and heavy chain are depicted in SEQ ID NO:69 and further exemplary light chain are depicted in SEQ ID NO:70, 71 and heavy chain are depicted in SEQ ID NO:72, 73). See also WO 2011/163401. 31.1 monoclonal antibody, described in WO 02/074251 and WO 2006/004950, exhibits specificity for the A33 antigen. The 31.1 monoclonal antibody also exhibits specificity for binding to colon and pancreatic tumor cells and strong cytotoxicity (e.g., ADCC activity) against colon and pancreatic tumor cells. Arlen, et al. (Nov. 3, 2010) Journal of *Cancer* 1: 209-222. An exemplary humanized NEO-300 antibody which selectively binds the A33 antigen (e.g., exemplary heavy chains are depicted in the amino acid sequence of SEQ ID NO:74-78 and light chains are depicted in the amino acid sequences of SEQ ID NO:84-87).

TABLE 2

Pairwise similarities of humanized NEO-301 antibody heavy chains For each pairwise alignment, the similarity (relative to the maximum similarity) and the number of identical amino acids (in % of shorter sequence) is given. Maximum values are underlined.

| | abb31.1-HC (448 aa) SEQ ID NO: 75 | sdr31.1-HC (448 aa) SEQ ID NO: 76 | ven31.1-HC (448 aa) SEQ ID NO: 77 |
|---|---|---|---|
| cdr31.1-HC (448 aa) SEQ ID NO: 74 | 0.985<br>98% | 0.981<br>98% | 0.993<br>98% |
| abb31.1-HC (448 aa) SEQ ID NO: 75 | | <u>1.000</u><br><u>99%</u> | 0.974<br>97% |
| sdr31.1-HC (448 aa) SEQ ID NO: 76 | | | 0.970<br>96% |

The similarity value 1.000 marks only the two most similar sequences, it does not necessarily mean that these sequences are identical.

TABLE 3

Pairwise similarities of humanized NEO-301 antibody light chains For each pairwise alignment, the similarity (relative to the maximum similarity) and the number of identical amino acids (in % of shorter sequence) is given. Maximum values are underlined.

| | abb31.1-LC (214 aa) SEQ ID NO: 85 | sdr31.1-LC (214 aa) SEQ ID NO: 86 | ven31.1-LC (214 aa) SEQ ID NO: 87 |
|---|---|---|---|
| cdr31.1-LC (214 aa) SEQ ID NO: 84 | 0.992<br><u>98%</u> | 0.993<br><u>98%</u> | 0.986<br>97% |
| abb31.1-LC (214 aa) SEQ ID NO: 85 | | <u>1.000</u><br><u>98%</u> | 0.969<br>96% |
| sdr31.1-LC (214 aa) SEQ ID NO: 86 | | | 0.969<br>95% |

The similarity value 1.000 marks only the two most similar sequences, it does not necessarily mean that these sequences are identical.

Chimeric Antibody

Chimeric antibodies are molecules different portions of which are derived from different animal species, such as those having variable region derived from a murine antibody and a human immunoglobulin constant region, which are primarily used to reduce immunogenicity in application and to increase yields in production, for example, where murine monoclonal antibodies have higher yields from hybridomas but higher immunogenicity in humans, such that human murine chimeric monoclonal antibodies are used. Chimeric antibodies and methods for their production are known in the art. See Cabilly, et al. (1984) *Proc. Natl. Acad. Sci. USA* 81: 3273-3277; Morrison, et al. (1994) *Proc. Natl. Acad. Sci.* USA 81: 6851-6855, Boulianne, et al. (1984) *Nature* 312: 643-646; Neuberger, et al. (1985) *Nature* 314: 268-270; European Patent Application 173494 (1986); WO 86/01533 (1986); European Patent Application 184187 (1986); European Patent Application 73494 (1986); Sahagan, et al. (1986) *J. Immunol.* 137: 1066-1074; Liu, et al. (1987) *Proc. Natl. Acad. Sci. USA* 84: 3439-3443; Sun, et al. (1987) *Proc. Natl. Acad. Sci. USA* 84: 214-218; Better, et al. (1988) *Science* 240: 1041-1043; and Harlow & Lane (1998) *USING ANTIBODIES: A LABORATORY MANUAL* Cold Spring Harbor Laboratory; U.S. Pat. No. 5,624,659. Exemplary chimeric antibodies include but are not limited to NEO-301 (31.1C) which selectively binds the A33 antigen (e.g., exemplary light chain are depicted in SEQ ID NO:68 and heavy chain depicted in SEQ ID NO:69). See also WO 2011/163401.

Humanized Antibody

Humanized antibodies are engineered to contain even more human-like immunoglobulin domains, and incorporate only the complementarity-determining regions of the animal-derived antibody. This may be accomplished by examining the sequence of the hyper-variable loops of the variable regions of the monoclonal antibody, and fitting them to the structure of the human antibody chains. See, e.g., U.S. Pat. No. 6,187,287. Likewise, other methods of producing humanized antibodies are now well known in the art. See, e.g., U.S. Pat. Nos. 5,225,539; 5,530,101; 5,585,089; 5,693,762; 6,054,297; 6,180,370; 6,407,213; 6,548,640; 6,632,927; and 6,639,055; Jones, et al. (1986) *Nature* 321: 522-525; Reichmann, et al. (1988) *Nature* 332: 323-327; Verhoeyen, et al. (1988) *Science* 239: 1534-36; and Zhiqiang An (2009) [Ed.] *Therapeutic Monoclonal Antibodies: From Bench to Clinic* John Wiley & Sons, Inc. Examples of humanized antibodies include but are not limited to NEO-302 which selectively binds the A33 antigen (e.g., exemplary light chain are depicted in SEQ ID NO:70-71 and heavy chain are depicted in SEQ ID NO:72-73) and NEO-303 which selectively binds the A33 antigen (e.g., exemplary light chain are depicted in SEQ ID NO:74-77 with heavy chain CDR sequences of SEQ ID NOs: 78-83 and heavy chain are depicted in SEQ ID NO:84-8) with light chain CDR sequences of SEQ ID NOs: 88-93).

Antibody Fragments

In addition to entire immunoglobulins (or their recombinant counterparts), immunoglobulin fragments comprising the epitope binding site (e.g., Fab', $F(ab')_2$, or other fragments) may be synthesized. "Fragment," or minimal immunoglobulins may be designed utilizing recombinant immunoglobulin techniques. For instance "Fv" immunoglobulins for use in the present invention may be produced by synthesizing a fused variable light chain region and a variable heavy chain region. Combinations of antibodies are also of interest, e.g. diabodies, which comprise two distinct Fv specificities. Antigen-binding fragments of immunoglobulins include but are not limited to SMIPs (small molecule immunopharmaceuticals), camelbodies, nanobodies, and IgNAR.

Anti-Idiotypic Antibody

An anti-idiotypic (anti-Id) antibody is an antibody which recognizes unique determinants generally associated with the antigen-binding site of an antibody. An Id antibody may be prepared by immunizing an animal of the same species and genetic type (e.g., mouse strain) as the source of the antibody with the antibody to which an anti-Id is being prepared. The immunized animal will recognize and respond to the idiotypic determinants of the immunizing antibody by producing an antibody to these idiotypic determinants (the anti-Id antibody). See e.g., U.S. Pat. No. 4,699,880. The anti-Id antibody may also be used as an "immunogen" to induce an immune response in yet another animal, producing a so-called anti-anti-Id antibody. The anti-anti-Id may be epitopically identical to the original antibody which induced the anti-Id. Thus, by using antibodies to the idiotypic determinants of an antibody it is possible to identify other clones expressing antibodies of identical specificity. See WO 2011/163401.

Engineered and Modified Antibodies

An antibody of the invention further may be prepared using an antibody having one or more of the VH and/or VL sequences derived from an antibody starting material to engineer a modified antibody, which modified antibody may have altered properties from the starting antibody. An antibody may be engineered by modifying one or more residues within one or both variable regions (i.e., VH and/or VL), for example within one or more CDR regions and/or within one or more framework regions. Additionally or alternatively, an antibody may be engineered by modifying residues within the constant region(s), for example to alter the effector function(s) of the antibody.

One type of variable region engineering that may be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties. See, e.g., Riechmann, et al. (1998) *Nature* 332: 323-327; Jones, et al. (1986) *Nature* 321: 522-525; Queen, et al. (1989) *Proc. Natl. Acad. U.S.A.* 86: 10029-10033; U.S. Pat. Nos. 5,225,539; 5,530,101; 5,585,089; 5,693,762; and 6,180,370.

Suitable framework sequences may be obtained from public DNA databases or published references that include germline antibody gene sequences. For example, germline DNA sequences for human heavy and light chain variable region genes may be found in the "VBase" human germline sequence database (available on the Internet), as well as in Kabat, E. A., et al. (1991) *Sequences of Proteins of Immunological Interest, Fifth Edition*, U.S. Department of Health and Human Services, NIH Publication No. 91-3242; Tomlinson, et al. (1992) "*The Repertoire of Human Germline VH Sequences Reveals about Fifty Groups of VH Segments with Different Hypervariable Loops*" J. Mol. Biol. 227: 776-798; and Cox, et al. (1994) *Eur. J Immunol.* 24: 827-836.

Another type of variable region modification is to mutate amino acid residues within the VH and/or VL CDR 1, CDR2 and/or CDR3 regions to thereby improve one or more binding properties (e.g., affinity) of the antibody of interest. Site-directed mutagenesis or PCR-mediated mutagenesis may be performed to introduce the mutation(s) and the effect on antibody binding, or other functional property of interest, may be evaluated in appropriate in vitro or in vivo assays. Preferably conservative modifications (as discussed herein) may be introduced. The mutations may be amino acid substitutions, additions or deletions, but are preferably substitutions. Moreover, typically no more than one, two, three, four or five residues within a CDR region are altered.

Engineered antibodies of the invention include those in which modifications have been made to framework residues within VII and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues may be identified by comparing the antibody framework sequences to the germline sequences from which the antibody is derived.

In addition or alternative to modifications made within the framework or CDR regions, antibodies of the invention may be engineered to include modifications within the Fe region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties may be attached to the antibody) or be modified to alter its glycosylation, again to alter one or more functional properties of the antibody. Such embodiments are described further below. The numbering of residues in the Fe region is that of the EU index of Kabat.

The hinge region of CH1 may be modified such that the number of cysteine residues in the hinge region is altered, e.g., increased or decreased. See U.S. Pat. No. 5,677,425. The number of cysteine residues in the hinge region of CH1 may be altered to, for example, facilitate assembly of the light and heavy chains or to increase or decrease the stability of the antibody.

The Fe hinge region of an antibody may be mutated to decrease the biological half life of the antibody. More specifically, one or more amino acid mutations may be introduced into the CH2-CH3 domain interface region of the Fc-hinge fragment such that the antibody has impaired Staphylococcyl protein A (SpA) binding relative to native Fc-hinge domain SpA binding. See, e.g., U.S. Pat. No. 6,165,745.

The antibody may be modified to increase its biological half life. Various approaches are possible. For example, one or more of the following mutations may be introduced: T252L, T254S, T256F. See U.S. Pat. No. 6,277,375. Alternatively, to increase the biological half life, the antibody may be altered within the CH1 or CL region to contain a salvage receptor binding epitope taken from two loops of a CH2 domain of an Fc region of an IgG. See U.S. Pat. Nos. 5,869,046 and 6,121,022.

The Fc region may be altered by replacing at least one amino acid residue with a different amino acid residue to alter the effector function(s) of the antibody. For example, one or more amino acids selected from amino acid residues 234, 235, 236, 237, 297, 318, 320 and 322 may be replaced with a different amino acid residue such that the antibody has an altered affinity for an effector ligand but retains the antigen-binding ability of the parent antibody. The effector ligand to which affinity may be altered may be, for example, an Fc receptor or the C1 component of complement. See U.S. Pat. Nos. 5,624,821 and 5,648,260.

The Fc region may be modified to increase the ability of the antibody to mediate antibody dependent cellular cytotoxicity (ADCC) and/or to increase the affinity of the antibody for an Fcy receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. See WO 00/42072. Moreover, the binding sites on human IgG1 for Fc□RI, Fc□RII, Fc□RIII and FcRn have been mapped and variants with improved binding. See Shields, et al. (2001) *J. Biol. Chem.* 276: 6591-6604. Specific mutations at positions 256, 290, 298, 333, 334 and 339 are shown to improve binding to Fc□RIII. Additionally, the following combination mutants are shown to improve Fc□RII binding: T256A/S298A, S298A/E333A, S298A/K224A and S298A/E333A/K334A.

The glycosylation of an antibody may be modified. For example, an aglycoslated antibody may be made (i.e., the antibody lacks glycosylation). Glycosylation may be altered to, for example, increase the affinity of the antibody for antigen. Such carbohydrate modifications may be accomplished by, for example, altering one or more sites of glycosylation within the antibody sequence. For example, one or more amino acid substitutions may be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody may be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications may be accomplished by, for example, expressing the antibody in a host cell with altered glycosylation machinery. Cells with altered glycosylation machinery have been described in the art and may be used as host cells in which to express recombinant antibodies of the invention to thereby produce an antibody with altered glycosylation. See U.S. Patent Application Publication No. 2004/0110704 and Yamane-Ohnuki, et al. (2004) *Biotechnol Bioeng.* 87: 614-22; EP 1,176,195; WO 2003/035835; Shields, et al. (2002) *J. Biol. Chem.* 277: 26733-26740; WO 99/54342; Umana, et al. (1999) *Nat. Biotech.* 17: 176-180; and Tarentino, et al. (1975) *Biochem.* 14: 5516-23.

An antibody may be pegylated to, for example, increase the biological (e.g., serum) half life of the antibody. To pegylate an antibody, the antibody, or antibody fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer).

The invention also provides variants and equivalents that are substantially homologous to the antibodies, antibody fragments, diabodies, SMIPs, camelbodies, nanobodies, IgNAR, polypeptides, variable regions and CDRs set forth herein. These may contain, e.g., conservative substitution mutations, (i.e., the substitution of one or more amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid.

Methods of Engineering Antibodies

Antibodies having VII and VL sequences disclosed herein may be used to create new variant antibodies by modifying the VH and/or VL sequences, or the constant region(s) attached thereto. Thus, the structural features of an variant antibody of the invention, are used to create structurally related variant antibodies that retain at least one functional property of the antibodies of the invention, such as binding to A33 antigen. For example, one or more CDR regions of one NEO-300 variant antibody, or mutations thereof, may be combined recombinantly with known framework regions and/or other CDRs to create additional, recombinantly-engineered, NEO-300 antibodies (e.g., antibodies which bind the A33 antigen e.g., NEO-301, NEO-302, NEO-303)) of the invention, as discussed herein. The starting material for the engineering method may be one or more of the VH and/or VK sequences provided herein, or one or more CDR regions thereof. To create the engineered antibody, it is not necessary to actually prepare (i.e., express as a protein) an antibody having one or more of the VH and/or VK sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein. Standard molecular biology techniques may be used to prepare and express altered antibody sequence.

The antibody encoded by the altered antibody sequence(s) may retain one, some or all of the functional properties of the NEO-300 antibodies (e.g., NEO-301, NEO-302, NEO-303) produced by methods and with sequences provided herein, which functional properties include binding to A33 variant antigen with a specific KD level or less and/or modulating immune cell activity, and/or selectively binding to desired target cells such as, for example, colorectal carcinoma, lung cancer, prostate cancer, pancreas cancer, ovarian cancer, gastric cancer, and liver cancer. The functional properties of the altered antibodies may be assessed using standard assays available in the art and/or described herein.

Mutations may be introduced randomly or selectively along all or part of an NEO-300 antibody coding sequence and the resulting modified or NEO-300 antibodies may be screened for binding activity and/or other desired functional properties. See WO 2002/092780 and WO 2003/074679.

Generation of NEO-300 Antibodies Using Animals

The antibodies of the invention that selectively bind the A33 antigen may be human monoclonal antibodies (e.g., NEO-302 and NEO-303). Such human monoclonal antibodies directed against a A33 antigen may be generated using transgenic or transchromosomic mice carrying parts of the human immune system rather than the mouse system. These transgenic and transchromosomic mice include mice referred to herein as the HuMAb Mouse® and KM Mouse® respectively, and are collectively referred to herein as "human Ig mice." The HuMAb Mouse® (Medarex. Inc.) contains human immunoglobulin gene miniloci that encode unrearranged human heavy (□ and □) and □ light chain immunoglobulin sequences, together with targeted mutations that inactivate the endogenous □ and □□chain loci. See, e.g., Lonberg, et al. (1994) Nature 368(6474): 856-859. Accordingly, the mice exhibit reduced expression of mouse IgM or □, and in response to immunization, the introduced human heavy and light chain transgenes undergo class switching and somatic mutation to generate high affinity human IgG□ monoclonal. Lonberg (1994) handbook of Experimental Pharmacology 113: 49-101; Lonberg and Huszar (1995) *Intern. Rev. Immunol.* 13: 65-93, and Harding and Lonberg (1995) *Ann. NY. Acad. Sci.* 764: 536-546. The preparation and use of the HuMab Mouse®, and the genomic modifications carried by such mice, is further described in Taylor, et al. (1992) *Nucleic Acids Research* 20: 6287-6295; Chen, et al. (1993) *International Immunology* 5: 647-656; Tuaillon, et al. (1993) *Proc. Natl. Acad. Sci. USA* 90: 3720-3724; Choi, et al. (1993) *Nature Genetics* 4: 117-123; Chen, et al. (1993) *EMBO J.* 12: 821-830; Tuaillon, et al. (1994) *J. Immunol.* 152: 2912-2920; Taylor, et al. (1994) *International Immunology* 6: 579-591; and Fishwild, et al. (1996) *Nature Biotechnology* 14: 845-851. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807; WO 92/03918, WO 93/12227, WO 94/25585; WO 97/13852; WO 98/24884; WO 99/45962; and WO 01/14424.

Human NEO-300 antibodies (e.g., NEO-301, NEO-302, NEO-303) of the invention may be raised using a mouse that carries human immunoglobulin sequences on transgenes and transchromosomes, such as a mouse that carries a human heavy chain transgene and a human light chain transchromosome. Such mice, referred to herein as "KM Mice®", are described in detail in WO 02/43478.

Still further, alternative transgenic animal systems expressing human immunoglobulin genes are available in the art and may be used to raise NEO-300 antibodies of the invention. For example, an alternative transgenic system referred to as the Xenomouse (Abgenix, Inc.) may be used; such mice are described in, for example, U.S. Pat. Nos. 5,939,598; 6,075,181; 6,114,598; 6,150,584 and 6,162,963.

Moreover, alternative transchromosomic animal systems expressing human immunoglobulin genes are available in the art and may be used to raise NEO-300 antibodies of the invention. For example, mice carrying both a human heavy chain transchromosome and a human light chain transchromosome, referred to as "TC mice" may be used. See Tomizuka, et al. (2000) *Proc. Natl. Acad Sci. USA* 97: 722-727. Furthermore, cows carrying human heavy and light chain transchromosomes have been described in the art (Kuroiwa, et al. (2002) *Nature Biotechnology* 20: 889-894) and may be used to raise NEO-300 antibodies of the invention.

Human monoclonal antibodies of the invention may also be prepared using phage display methods for screening libraries of human immunoglobulin genes. Such phage display methods for isolating human antibodies are established in the art. See, for example, U.S. Pat. Nos. 5,223,409; 5,403,484; 5,571,698; 5,427,908 5,580,717; 5,969,108; 6,172,197; 5,885,793; 6,521,404; 6,544,731; 6,555,313; 6,582,915 and 6,593,081.

Human monoclonal antibodies of the invention may also be prepared using SCID mice into which human immune cells have been reconstituted such that a human antibody response may be generated upon immunization. See, e.g., U.S. Pat. Nos. 5,476,996 and 5,698,767.

When human Ig mice are used to raise human antibodies of the invention, such mice may be immunized with a purified or enriched preparation of A33 antigen polypeptide, as described by Lonberg, et al. (1994) *Nature* 368(6474): 856-859; Fishwild, et al. (1996) *Nature Biotechnology* 14: 845-851; WO 98/24884 and WO 01/14424. Preferably, the mice will be 6-16 weeks of age upon the first infusion. For example, a purified or recombinant preparation (5-50 □g) of A33 antigen may be used to immunize the human Ig mice intraperitoneally.

Prior experience with various antigens by others has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response may be monitored over the course of the immunization protocol with plasma samples being obtained by retroorbital bleeds. The plasma may be screened by ELISA (as described below), and mice with sufficient titers of NEO-300 human immunoglobulin may be used for fusions. Mice may be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene may be bred together into a single mouse having two different human heavy chain transgenes (HCo7/HCo12). Alternatively or additionally, the KM Mouse® strain may be used.

Generation of Hybridomas Producing Human Monoclonal Antibodies of the Invention

To generate hybridomas producing human monoclonal antibodies of the invention, splenocytes and/or lymph node cells from immunized mice may be isolated and fused to an appropriate immortalized cell line, such as a mouse myeloma cell line. The resulting hybridomas may be screened for the production of antigen-specific antibodies. For example, single cell suspensions of splenic lymphocytes from immunized mice may be fused to one-sixth the number of P3X63-Ag8.653 nonsecreting mouse myeloma cells (ATCC, CRL 1580) with 50% PEG. Cells may be plated at approximately $2\times10^{-5}$ in flat bottom microtiter plate, followed by a two week incubation in selective medium containing 20% fetal Clone Serum, 18% “653” conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and IX HAT (Sigma; the HAT is added 24 hours after the fusion). After approximately two weeks, cells may be cultured in medium in which the HAT is replaced with HT. Individual wells may then be screened by ELISA for human monoclonal IgM and IgG antibodies. Once extensive hybridoma growth occurs, medium may be observed usually after 10-14 days. The antibody secreting hybridomas may be replated, screened again, and if still positive for human IgG, the monoclonal antibodies may be subcloned at least twice by limiting dilution. The stable subclones may then be cultured in vitro to generate small amounts of antibody in tissue culture medium for characterization.

To purify human monoclonal antibodies, selected hybridomas may be grown in two-liter spinner-flasks for monoclonal antibody purification. Supernatants may be filtered and concentrated before affinity chromatography with protein A-Sepharose (Pharmacia, Piscataway, N.J.) Eluted IgG may be checked by gel electrophoresis and high performance liquid chromatography to ensure purity. The buffer solution may be exchanged into PBS, and the concentration may be determined by OD280 using 1.43 extinction coefficient. The monoclonal antibodies may be aliquoted and stored at −80° C.

Polynucleotides Encoding Neo-300 Antibodies

The present invention also provides nucleotides which NEO-300 antibodies described herein. The invention also provides polynucleotides comprising at least one NEO-300 antibody sequence encoding similar polypeptides with different codon usage, altered sequences characterized by mutations, such as deletion, insertion or substitution of one or more nucleotides, either naturally occurring or man induced, either randomly or in a targeted fashion. The present invention also encompasses homologous nucleic acid sequences (e.g., which form a part of a polynucleotide sequence of the present invention), which include sequence regions unique to the polynucleotides of the present invention.

The present invention also provides methods for producing antibodies and fragments thereof. Methods of producing antibodies are well known to those of ordinary skill in the art. For example, methods of producing chimeric antibodies are now well known in the art. See, e.g., U.S. Pat. No. 4,816,567; Morrison, et al. (1984) *PNAS USA* 81: 8651-55; Neuberger, et al. (1985) *Nature* 314: 268-270; Boulianne, et al. (1984) *Nature* 312: 643-46.

For example, antibodies or antigen binding fragments may be produced by genetic engineering. In this technique, as with other methods, antibody-producing cells are sensitized to the desired antigen or immunogen. The messenger RNA isolated from antibody producing cells is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that may be detected by screening with the antigen or immunogen.

Another aspect of the invention pertains to nucleic acid molecules that encode the antibodies of the invention which bind the A33 antigen. The nucleic acids may be present in whole cells, in a cell lysate, or in a partially purified or substantially pure form. A nucleic acid may be isolated by purification away from other cellular components or other contaminants (e.g., other cellular nucleic acids or proteins) by standard techniques, including alkaline/SDS treatment, CsCl banding, column chromatography, agarose gel electrophoresis and others well known in the art. See Ausubel, et al. (2011) *Current Protocols in Molecular Biology* John Wiley & Sons, Inc. A nucleic acid of the invention may be, for example, DNA or RNA and may or may not contain intronic sequences. The nucleic acid may be a cDNA molecule.

Nucleic acids of the invention may be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma may be obtained by standard PCR amplification or cDNA cloning techniques. For antibodies obtained from an immunoglobulin gene library (e.g., using phage display techniques), nucleic acid encoding the antibody may be recovered from the library.

Specifically, degenerate codon substitutions may be achieved by generating, e.g., sequences in which the third position of one or more selected codons is substituted with mixed-base and/or deoxyinosine residues. Batzer, et al. (1991) *Nucleic Acid Res.* 19: 5081; Ohtsuka, et al. (1985) *J. Biol. Chem.* 260: 2605-08; Rossolini, et al. (1994) *Mol. Cell. Probes* 8: 91-98.

Once DNA fragments encoding VH and VL segments are obtained, these DNA fragments may be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker.

The isolated DNA encoding the VH region may be converted to a full-length heavy chain gene by operatively linking the VH-encoding DNA to another DNA molecule encoding heavy chain constant regions (CH1, CH2 and CH3). The sequences of human heavy chain constant region genes are known in the art (see, e.g., Kabat, et al. (1991) *Sequences of Proteins of Immunological Interest*, Fifth Edition, U.S. Department of Health and Human Services, NIH Publication No. 91-3242) and DNA fragments encompassing these regions may be obtained by standard PCR amplification. The heavy chain constant region may be an IgG1, IgG2, IgG3, IgG4, IgA, IgE, IgM, or IgD constant region, but most preferably is an IgG 1 or IgG4 constant region. For a Fab fragment heavy chain gene, the VH-encoding DNA may be operatively linked to another DNA molecule encoding only the heavy chain CH1 constant region.

The isolated DNA encoding the VL region may be converted to a full-length light chain gene (as well as a Fab light chain gene) by operatively linking the VL-encoding DNA to another DNA molecule encoding the light chain constant region, CL. The sequences of human light chain constant region genes are known in the art (see, e.g., Kabat, et al. (1991) *Sequences of Proteins of Immunological Interest* Fifth Edition, U.S. Department of Health and Human Services, NIH Publication No. 91-3242) and DNA fragments encompassing these regions may be obtained by standard PCR amplification. The light chain constant region may be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly4-Ser)_3$, such that the VH and VL sequences may be expressed as a contiguous single-chain protein, with the VL and VII regions joined by the flexible linker. See, e.g., Bird, et al. (1988) *Science* 242: 423-426; Huston, et al. (1988) *Proc. Natl. Acad. Sci. USA* 85: 5879-5883; McCafferty, et al. (1990) *Nature* 348: 552-554.

The present invention also encompasses nucleic acids encoding homologues of NEO-300 antibody polypeptides, such homologues can be at least about 80%, 81%, 82%, 83%, 84%, 85%, 86%, 87%, 88%, 89%, 90%, 91%, 92%, 93%, 94%, 95%, 96%, 97%, 98%, 99% or 100% identical homologous to the amino acid sequences set forth herein, as may be determined using BlastP software of the National Center of Biotechnology Information (NCBI) using default parameters. The present invention also encompasses fragments of the above described polynucleotides and polypeptides having mutations, such as deletions, insertions or substitutions of one or more nucleic acids, either naturally occurring or man induced, either randomly or in a targeted fashion.

Nucleic acid molecules may encode a NEO-300 antibody (e.g., NEO-301, NEO-302, NEO-303), or a functional fragment of said nucleic acid molecule. A "functional fragment" of said nucleic acid includes a fragment of the gene or cDNA encoding said NEO-300 antibody, which fragment is capable of being expressed to produce a NEO-300 antibody capable of binding the A33 antigen. Thus, for example, fragments of the NEO-300 antibody according to the invention which correspond to amino acid residues that contribute to the binding to the A33 antigen. This aspect of the invention also includes differentially spliced isoforms and transcriptional starts of the nucleic acids according to the invention. The nucleic acid molecules according to the invention also comprise fragments, derivatives and allelic variants of the nucleic acid molecules described above that encodes a NEO-300 antibody according to the invention. Methods and materials for making nucleic acids encoding fragments of NEO-300 antibodies are well known in the art. See, e.g., Maniatis, et al. (2001) *Molecular Cloning: A Laboratory Manual* [$3^{rd}$ Ed.] Cold Spring Harbor Laboratory Press.

Antibodies, and fragments thereof, of the invention may also be produced by constructing, using conventional techniques well known to those of ordinary skill in the art, an expression vector containing an operon and a DNA sequence encoding an antibody heavy chain in which the DNA sequence encoding the CDRs required for antibody specificity is derived from a non-human cell source, while the DNA sequence encoding the remaining parts of the antibody chain is derived from a human cell source. Furthermore, the invention relates to vectors, especially plasmids, cosmids, viruses, bacteriophages and other vectors common in genetic engineering, which contain the above-mentioned nucleic acid molecules of the invention. The nucleic acid molecules contained in the vectors may be linked to regulatory elements that ensure the transcription in prokaryotic and eukaryotic cells.

Furthermore, identity refers broadly to the that functional and/or structural equivalence that exists between the nucleic acid molecules concerned or the proteins coded by them. The nucleic acid molecules, which are homologous to the molecules described above and constitute derivatives of these molecules, are generally variations of these molecules, which constitute modifications, which execute the same biological function. At the same time, the variations may occur naturally, for example they may be sequences from other species, or they may be mutants, wherein these mutants may have occurred in a natural manner or have been introduced by objective mutagenesis. The variations may also be synthetically manufactured sequences. The allelic variants may be both naturally occurring variants and also synthetically manufactured variants or variants produced by recombinant DNA techniques. Nucleic acid molecules, which deviate from nucleic acid molecules according to the invention due to degeneration of the genetic code, constitute a special form of derivatives.

Included also within the scope of the invention is any nucleotide sequence that encodes the amino acid sequence of NEO-300 antibody thereof. Because the genetic code is degenerate, more than one codon may be used to encode a particular amino acid. Using the genetic code, one or more different nucleotides may be identified, each of which would be capable of encoding the amino acid. The probability that a particular nucleotide will, in fact, constitute the actual codon encoding sequence may be estimated by considering abnormal base pairing relationships and the frequency with which a particular codon is actually used (to encode a particular amino acid) in eukaryotic or prokaryotic cells expressing a A33 antigen thereof. Such "codon usage rules" are disclosed by Lathe, et al. (1985) *J. Molec. Biol.* 183: 1-12.

Isolation and expression of the NEO-300 antibody or fragments or variants thereof (e.g., NEO-301, NEO-302, NEO-303), of the invention may be effected by well-established cloning procedures using probes or primers constructed based on the NEO-300 antibody nucleic acids sequences disclosed in the application. Related NEO-300 antibody sequences may also be identified from human or other species genomic databases using the sequences disclosed herein and known computer-based search technologies, e.g., BLAST sequence searching. The pseudogenes disclosed herein may be used to identify functional alleles or related genes.

Expression vectors can then be used to infect or transfect host cells for the functional expression of these sequences. These genes and vectors can be made and expressed in vitro or in vivo. One of skill will recognize that desired phenotypes for altering and controlling nucleic acid expression can be obtained by modulating the expression or activity of the genes and nucleic acids (e.g., promoters, enhancers) within the vectors of the invention. Any of the known methods described for increasing or decreasing expression or activity can be used.

The polynucleotide sequences provided herein may be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the polynucleotides is well within the capabilities of one skilled in the art. See, e.g., Maniatis, et al. (2001) *Molecular Cloning: A Laboratory Manual* [3$^{rd}$ Ed.] Cold Spring Harbor Laboratory Press; Swamy (2008) *Laboratory Manual on Biotechnology* Rastogi Publications; Herdewijn (2005) [Ed.] *Methods in Molecular Biolog: Oligonucleotide Synthesis: Methods and Applications* Volume 288 Humana Press; and Rapley (2000) [Ed.] *The Nucleic Acid Protocols Handbook* Humana Press. Double-stranded DNA fragments may then be obtained either by synthesizing the complementary strand and annealing the strands together under appropriate conditions, or by adding the complementary strand using DNA polymerase with an appropriate primer sequence.

Techniques for the manipulation of nucleic acids, such as, for example, for generating mutations in sequences, subcloning, labeling probes, sequencing, hybridization are well described in the scientific and patent literature. See, e.g., Sambrook, et al. (2001) (Eds.) *Molecular Cloning: A Laboratory Manual* (3$^{rd}$ Ed.) Cold Spring Harbor Laboratory; Ausubel, et al. (2011) Ed., *Current Protocols in Molecular Biology*, John Wiley & Sons, Inc., New York; Tijssen (1993) [Ed.] *Laboratory Techniques in Biochemistry and Molecular Biology: Hybridization With Nucleic Acid Probes, Part I, Theory and Nucleic Acid Preparation*, Elsevier, NY.

Hybridization and the strength of hybridization (e.g., the strength of the association between polynucleotides) is impacted by many factors well known in the art including the degree of complementarity between the polynucleotides, and the stringency of the conditions involved, which is affected by such conditions as the concentration of salts, the presence of other components (e.g., the presence or absence of polyethylene glycol), the molarity of the hybridizing strands and the G+C content of the polynucleotide strands, all of which results in a characteristic melting temperature ($T_m$) of the formed hybrid. Techniques of nucleic acid hybridization are disclosed by Sambrook, et al. (2001) (Eds.) *Molecular Cloning: A Laboratory Manual* [3$^{rd}$ Ed.] Cold Spring Harbor Laboratory, and by Hayrnes, et al. (1985) in NUCLEIC ACID HYBRIDIZATION, A PRACTICAL APPROACH (IRL Press, DC). Hybridization wash conditions may include wash solution of 0.2×SSC/0.1% SDS and incubation with rotation for 10 minutes at room temperature, (low stringency wash), wash solution of prewarmed (42° C.) 0.2×SSC/0.1% SDS and incubation with rotation for 15 minutes at 42° C. (medium stringency wash) and wash solution of prewarmed (68° C.) 0.1×SSC/0.1% SDS and incubation with rotation for 15 minutes at 68° C. (high stringency wash). See Ausubel, et al. (2011) [Ed.] *Current Protocols in Molecular Biology* John Wiley & Sons, Inc.

Oligonucleotide primers may be used to amplify nucleic acids encoding a NEO-300 antibody (e.g., NEO-301, NEO-302, NEO-303). The nucleic acids described herein can also be cloned or measured quantitatively using amplification techniques. Amplification methods are also well known in the art, and include, e.g., polymerase chain reaction (PCR) (Innis (1990) [Ed.] *PCR Protocols, a Guide to Methods and Applications*, Academic Press, NY.; Innis (1995) [Ed.] *PCR Strategies*, Academic Press, Inc., NY.); ligase chain reaction (LCR) (Wu (1989) *Genomics* 4: 560; Landegren (1988) *Science* 241: 1077; Barringer (1990) *Gene* 89: 117); transcription amplification (Kwoh (1989) *PNAS* 86: 1173); self-sustained sequence replication (Guatelli (1990) *PNAS* 87: 1874); Q Beta replicase amplification (Smith (1997) *J. Clin. Microbiol.* 35: 1477-91)); automated Q-beta replicase amplification assay (Burg (1996) *Mol. Cell. Probes* 10: 257-71); and other RNA polymerase mediated techniques (e.g., NASBA, Cangene, Mississauga, Ontario). See, also, Berger (1987) *Methods Enzymol.* 152: 307-16; Sambrook, et al. (2001) (Eds.) *Molecular Cloning: A Laboratory Manual* (3$^{rd}$ Ed.) Cold Spring Harbor Laboratory; Ausubel, et al. (2011) [Ed.] *Current Protocols in Molecular Biology*, John Wiley & Sons, Inc., New York; Maniatis, et al. (2001) *Molecular Cloning: A Laboratory Manual* [3$^{rd}$ Ed.] Cold Spring Harbor Laboratory Press; U.S. Pat. Nos. 4,683,195 and 4,683,202; Sooknanan (1995) *Biotechnology* 13: 563-64.

Paradigms to design degenerate primer pairs are well known in the art. For example, a COnsensus-DEgenerate Hybrid Oligonucleotide Primer (CODEHOP) strategy computer program is readily accessible and is directly linked from the BlockMaker multiple sequence alignment site for hybrid primer prediction beginning with a set of related protein sequences, such as the NEO-300 antibody sequences provided herein. See, e.g., Rose (1998) *Nucleic Acids Res.* 26: 1628-35; Singh (1998) *Biotechniques* 24: 318-19.

Polymorphic variants, alleles, and interspecies homologs that are substantially identical to NEO-300 antibodies disclosed herein may be isolated using the nucleic acid probes described herein. Alternatively, expression libraries can be used to clone NEO-300 antibody polypeptides and polymorphic variants, alleles, and interspecies homologs thereof, by detecting expressed homologs immunologically with antisera or purified antibodies made against a A33 antigen polypeptide, which also recognize and selectively bind to the A33 antigen homolog.

Nucleic acids that encode NEO-300 antibody may be generated by amplification (e.g., PCR) of appropriate nucleic acid sequences using appropriate (perfect or degenerate) primer pairs. The amplified nucleic acid can be genomic DNA from any cell or tissue or mRNA or cDNA derived from NEO-300 antibody expressing cells. Methods for expression of heterologous sequences in host cells are well known in the art. See, e.g., Maniatis, et al. (2001) *Molecular Cloning: A Laboratory Manual* [3$^{rd}$ Ed.] Cold Spring Harbor Laboratory Press.

Fusion Proteins Comprising a NEO-300 Antibody

Hybrid protein-coding sequences comprising nucleic acids encoding NEO-300 antibody described herein fused to a translocation sequences may be constructed. These nucleic acid sequences may be operably linked to transcriptional or translational control elements, e.g., transcription and translation initiation sequences, promoters and enhancers, transcription and translation terminators, polyadenylation sequences, and other sequences useful for transcribing DNA into RNA. In construction of recombinant expression cassettes, vectors, and transgenics, a promoter fragment can be employed to direct expression of the desired nucleic acid in all desired cells or tissues.

Fusion proteins may comprise C-terminal or N-terminal translocation sequences. Further, fusion proteins can comprise additional elements, e.g., for protein detection, purification, or other applications. Detection and purification facilitating domains include, e.g., metal chelating peptides such as polyhistidine tracts, histidine-tryptophan modules, or other domains that allow purification on immobilized metals; maltose binding protein; protein A domains that allow purification on immobilized immunoglobulin; or the domain utilized in the FLAGS extension/affinity purification system (Immunex Corp, Seattle Wash.)

The inclusion of a cleavable linker sequences such as Factor Xa (see, e.g., Ottavi, (1998) *Biochimie* 80: 289-93), subtilisin protease recognition motif (see, e.g., Polyak (1997) *Protein Eng.* 10: 615-19); enterokinase (Invitrogen, San Diego, Calif.), between the translocation domain (for efficient plasma membrane expression) and the rest of the newly translated polypeptide may be useful to facilitate purification. For example, one construct can include a polypeptide encoding a nucleic acid sequence linked to six histidine residues followed by a thioredoxin, an enterokinase cleavage site (see, e.g., Williams (1995) *Biochemistry* 34: 1787-97), and an C-terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature. See, e.g., Kroll (1993) *DNA Cell. Biol.* 12: 441-53.

Systems for Recombinant Expression of the NEO-300 Antibody

Vectors contain elements that facilitate manipulation for the expression of a foreign protein within the target host cell. Conveniently, manipulation of sequences and production of DNA for transformation is first performed in a bacterial host (e.g., *E. coli*) and usually vectors will include sequences to facilitate such manipulations, including a bacterial origin of replication and appropriate bacterial selection marker. Selection markers encode proteins necessary for the survival or growth of transformed host cells grown in a selective culture medium. Host cells not transformed with the vector containing the selection gene will not survive in the culture medium. Typical selection genes encode proteins that confer resistance to antibiotics or other toxins, complement auxotrophic deficiencies, or supply critical nutrients not available from complex media. Exemplary vectors and methods for transformation of yeast are described in the art. See, e.g., Burke, et al. (2000) *Methods in Yeast Genetics* Cold Spring Harbor Laboratory Press.

The polypeptide coding sequence of interest may be operably linked to transcriptional and translational regulatory sequences that provide for expression of the polypeptide in yeast cells. These vector components may include, but are not limited to, one or more of the following: an enhancer element, a promoter, and a transcription termination sequence. Sequences for the secretion of the polypeptide may also be included (e.g., a signal sequence).

Expression vectors, either as individual expression vectors or as libraries of expression vectors, comprising the ligand-binding region encoding sequences may be introduced into a genome or into the cytoplasm or a nucleus of a cell and expressed by a variety of conventional techniques, well described in the scientific and patent literature. See, e.g., Sambrook, et al. (2001) [Eds.] *Molecular Cloning: A Laboratory Manual* (3rd Ed.) Cold Spring Harbor Laboratory; Ausubel, et al. (2011) [Ed.] *Current Protocols in Molecular Biology* John Wiley & Sons, Inc.

The nucleic acids can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required. For example, the marker may encode antibiotic resistance (e.g., chloramphenicol, kanamycin, G418, bleomycin, hygromycin) or herbicide resistance (e.g., chlorosulfurone or Basta) to permit selection of those cells transformed with the desired DNA sequences. See, e.g., Ausubel, et al. (2011) [Ed.] *Current Protocols in Molecular Biology* John Wiley & Sons, Inc.; and Walker & Papley (2009) *Molecular Biology and Biotechnology* [5th Ed.] Royal Society of Chemistry. Because selectable marker genes conferring resistance to substrates like neomycin or hygromycin can only be utilized in tissue culture, chemoresistance genes are also used as selectable markers in vitro and in vivo.

To enable cellular expression of the polynucleotides of the present invention, a nucleic acid construct according to the present invention may be used, which includes at least a coding region of one of the above nucleic acid sequences, and further includes at least one cis acting regulatory element. Preferably, the promoter utilized by the nucleic acid construct of the present invention is active in the specific cell population transformed. Promoters are untranslated sequences located upstream (5') to the start codon of a structural gene (generally within about 100 to 1000 bp) that control the transcription and translation of particular nucleic acid sequences to which they are operably linked. Such promoters fall into several classes: inducible, constitutive, and repressible promoters (e.g., that increase levels of transcription in response to absence of a repressor). Inducible promoters may initiate increased levels of transcription from DNA under their control in response to some change in culture conditions (e.g., the presence or absence of a nutrient or a change in temperature.) Examples of cell type-specific and/or tissue-specific promoters are well-known in the art. See Bernardi (2003) [Ed.] *Gene Transfer and Expression in Mammalian Cells* Volume 38 Elsevier Science B.V. The nucleic acid construct of the present invention can further include an enhancer, which can be adjacent or distant to the promoter sequence and can function in up regulating the transcription therefrom.

A second expression vector may be produced using the same conventional means well known to those of ordinary skill in the art, said expression vector containing an operon and a DNA sequence encoding an antibody light chain in which the DNA sequence encoding the CDRs required for antibody specificity is derived from a non-human cell source, preferably a rabbit B-cell source, while the DNA sequence encoding the remaining parts of the antibody chain is derived from a human cell source.

The nucleic acid construct of the present invention may further include an appropriate selectable marker and/or an origin of replication. Preferably, the nucleic acid construct utilized is a shuttle vector, which can propagate both in *E. coli* (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (Carlsbad, Calif.) Examples of retroviral vector and packaging systems are those sold by Clontech (San Diego, Calif.), including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5' LTR promoter.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel (1990) *Gene Expression Technology: Methods in Enzymology* 185, Academic Press, San Diego, Calif. Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired. The expression vectors of the invention can be introduced into host cells to thereby produce proteins or peptides, including fusion proteins or peptides, encoded by nucleic acids as described herein.

The recombinant expression vectors of the invention may be designed for production of variant proteins in prokaryotic or eukaryotic cells. For example, proteins of the invention can be expressed in bacterial cells such as *Escherichia coli*, insect cells (e.g., using baculovirus expression vectors), yeast cells, or mammalian cells. Suitable host cells are discussed further in Goeddel (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, to the amino or C terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin, PreScission, TEV and enterokinase. Typical fusion expression vectors include pGEX (Pharmacia Biotech Inc; Smith and Johnson (1988) *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

The recombinant mammalian expression vector is capable of directing expression of the nucleic acid may be in a particular cell type (e.g., tissue-specific regulatory elements are used to express the nucleic acid). Tissue-specific regulatory elements are known in the art. For efficient production of the protein, it is preferable to place the nucleotide sequences encoding the protein of the invention under the control of expression control sequences optimized for expression in a desired host. For example, the sequences may include optimized transcriptional and/or translational regulatory sequences (e.g., altered Kozak sequences).

One strategy to maximize recombinant protein expression in *E. coli* is to express the protein in a host bacterium with an impaired capacity to proteolytically cleave the recombinant protein. See, e.g., Gottesman (1990) *Gene Expression Technology: Methods in Enzymology* Academic Press, San Diego, Calif. 185: 119-128. Another strategy is to alter the nucleic acid sequence of the nucleic acid to be inserted into an expression vector so that the individual codons for each amino acid are those preferentially utilized in *E. coli*. See, e.g., Wada, et al. (1992) *Nucl. Acids Res.* 20: 2111-2118. Such alteration of nucleic acid sequences of the invention can be carried out by standard DNA synthesis techniques. Another strategy to solve codon bias is by using BL21-codon plus bacterial strains (Invitrogen) or Rosetta bacterial strain (Novagen), these strains contain extra copies of rare *E. coli* tRNA genes.

The expression vector encoding for the protein of the invention may be a yeast expression vector. Examples of vectors for expression in yeast *Saccharomyces cerevisiae* include pYepSec1 (Baldari, et al. (1987) *EMBO J.* 6: 229-234), pMFa (Kurjan and Herskowitz (1982) *Cell* 30: 933-943), pJRY88 (Schultz, et al. (1987) *Gene* 54: 113-123), pYES2 (Invitrogen Corporation, San Diego, Calif.), and picZ (Invitrogen Corp, San Diego, Calif.)

A host cell can be any prokaryotic or eukaryotic cell. For example, protein of the invention can be produced in bacterial cells such as *E. coli*, insect cells, yeast, plant or mammalian cells (e.g., Chinese hamster ovary cells (CHO), COS, HEK293 cells). Other suitable host cells are known to those skilled in the art.

The polypeptides of the present invention can be produced in insect cells using baculovirus expression vectors. Baculovirus vectors available for expression of proteins in cultured insect cells (e.g., SF9 cells) include the pAc series (Smith, et al. (1983) *Mol. Cell. Biol.* 3: 2156-2165) and the pVL series (Lucklow and Summers (1989) *Virology* 170: 31-39). In yet another embodiment, a nucleic acid of the invention is expressed in mammalian cells using a mammalian expression vector. Examples of mammalian expression vectors include pCDM8 (Seed (1987) *Nature* 329: 840) and pMT2PC (Kaufman, et al. (1987) *EMBO J.* 6: 187-195), pIRESpuro (Clontech), pUB6 (Invitrogen), pCEP4 (Invitrogen) pREP4 (Invitrogen), pcDNA3 (Invitrogen). When used in mammalian cells, the expression vector's control functions are often provided by viral regulatory elements. For example, commonly used promoters are derived from polyoma, adenovirus 2, cytomegalovirus, Rous Sarcoma Virus, and simian virus 40. For other suitable expression systems for both prokaryotic and eukaryotic cells see, e.g., Sambrook, et al. (2001) (Eds.) *Molecular Cloning: A Laboratory Manual* ($3^{rd}$ Ed.) Cold Spring Harbor Laboratory.

The expression vectors are transfected into a host cell by convention techniques well known to those of ordinary skill in the art to produce a transfected host cell, said transfected host cell cultured by conventional techniques well known to those of ordinary skill in the art to produce said antibody polypeptides.

The host cell may be co-transfected with the two expression vectors described above, the first expression vector containing DNA encoding an operon and a light chain-derived polypeptide and the second vector containing DNA encoding an operon and a heavy chain-derived polypeptide. The two vectors contain different selectable markers, but preferably achieve substantially equal expression of the heavy and light chain polypeptides. Alternatively, a single vector may be used, the vector including DNA encoding both the heavy and light chain polypeptides. The coding sequences for the heavy and light chains may comprise cDNA, genomic DNA, or both.

The general methods by which the vectors may be constructed, transfection methods required to produce the host cell and culturing methods required to produce the antibodies, and fragments thereof, from said host cells all include conventional techniques. Although preferably the cell line used to produce the antibody is a mammalian cell line, any other suitable cell line, such as a bacterial cell line such as an *E. coli*-derived bacterial strain, or a yeast cell line, may be used.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (2001) [Eds.] *Molecular Cloning A Laboratory Manual* ($3^{rd}$ Ed.) Cold Spring Harbor Laboratory and other laboratory manuals.

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well-known methods for introducing cloned genomic DNA, cDNA, synthetic DNA or other foreign genetic material into a host cell. See, e.g., Sambrook, et al. (2001) (Eds.) *Molecular Cloning: A Laboratory Manual* ($3^{rd}$ Ed.) Cold Spring Harbor Laboratory and Walker & Papley (2009) *Molecular Biology and Biotechnology* [$5^{th}$ Ed.] Royal Society of Chemistry. It is only necessary that the particular genetic engineering procedure used be capable of successfully introducing at least one nucleic acid molecule into the host cell capable of expressing the NEO-300 antibody or antigen-binding fragment thereof.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin, puromycin, blasticidin and methotrexate. Nucleic acids encoding a selectable marker can be introduced into a host cell on the same vector as that encoding protein of the invention or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) protein of the invention. Accordingly, the invention further provides methods for producing proteins of the invention using the host cells of the invention. In one embodiment, the method comprises culturing the host cell of the present invention (into which a recombinant expression vector encoding protein of the invention has been introduced) in a suitable medium such that the protein of the invention is produced. In another embodiment, the method further comprises isolating protein of the invention from the medium or the host cell.

After the expression vector is introduced into the cells, the transfected cells are cultured under conditions favoring expression of the receptor, fragment, or variant of interest, which is then recovered from the culture using standard techniques. Examples of such techniques are well known in the art. See, e.g., WO 00/06593. Similarly, once produced the antibodies may be purified according to standard procedures in the art, such as for example cross-flow filtration, ammonium sulphate precipitation, and affinity column chromatography.

For example, the production of the NEO-300 antibodies described herein, a vector which allows for the insertion of both heavy and light chain genes, with transfection to CHO cells may be used to optimize production. The plasmid vector pRc/CMV that we employed was designed with the intent of achieving high expression of our chimeric monoclonal antibodies. The vector has a cloning site which accepted the heavy and light chain genes, inserting them downstream from the human CMV. The vector allows antibody to be produced at levels greater than 1000 mg/L in bioreactor media, so that therapeutic doses of 250-500 mg may be delivered. Plasmid vectors may carry a dhfr expression unit driven by an enhancer-deficient SV40 early promoter. The vector may be inserted into the CHO-D-SFM (dihydrofolate reductase (dhfr)-deficient Chinese hamster ovary) cells in near serum-free medium supplemented with 1.0 μg/ml of methotrexate (MTX). At the end of the production, cells may be adapted to serum free media before final purification of the antibody.

Labels

The NEO-300 antibodies and fragments thereof described herein may be modified post-translationally to add effector moieties such as chemical linkers, detectable moieties such as for example fluorescent dyes, enzymes, substrates, bioluminescent materials, radioactive materials, chemiluminescent moieties, a cytotoxic agent, radioactive materials, or functional moieties.

A wide variety of entities, e.g., ligands, may be coupled to the oligonucleotides as known in the art. Ligands may include naturally occurring molecules, or recombinant or synthetic molecules. Exemplary ligands include, but are not limited to, avadin, biotin, peptides, peptidomimetics, polylysine (PLL), polyethylene glycol (PEG), mPEG, cationic groups, spermine, spermidine, polyamine, thyrotropin, melanotropin, lectin, glycoprotein, surfactant protein A, mucin, glycosylated polyaminoacids, transferrin, aptamer, imnmunoglobulins (e.g., antibodies), insulin, transferrin, albumin, sugar, lipophilic molecules (e.g., steroids, bile acids, cholesterol, cholic acid, and fatty acids), vitamin A, vitamin E, vitamin K, vitamin B, folic acid, B12, riboflavin, biotin, pyridoxal, vitamin cofactors, lipopolysaccharide, hormones and hormone receptors, lectins, carbohydrates, multivalent carbohydrates, radiolabeled markers, fluorescent dyes, and derivatives thereof. See, e.g., U.S. Pat. Nos. 6,153,737; 6,172,208; 6,300,319; 6,335,434; 6,335,437; 6,395,437; 6,444,806; 6,486,308; 6,525,031; 6,528,631; and 6,559,279.

Additionally, moieties may be added to the NEO-300 antibody to increase half-life in vivo (e.g., by lengthening the time to clearance from the blood stream. Such techniques include, for example, adding PEG moieties (also termed pegilation), and are well-known in the art. See U.S. Patent Application Publication No. 2003/0031671.

An NEO-300 antibody or antigen-binding fragments thereof, described herein may be "attached" to a substrate when it is associated with the solid label through a non-random chemical or physical interaction. The attachment may be through a covalent bond. However, attachments need not be covalent or permanent. Materials may be attached to a label through a "spacer molecule" or "linker group." Such spacer molecules are molecules that have a first portion that attaches to the biological material and a second portion that attaches to the label. Thus, when attached to the label, the spacer molecule separates the label and the biological materials, but is attached to both. Methods of attaching biological material (e.g., label) to a label are well known in the art, and include but are not limited to chemical coupling.

Detectable Labels

The NEO-300 antibody and antigen-binding fragments thereof, described herein may be modified post-translationally to add effector labels such as chemical linkers, detectable labels such as for example fluorescent dyes, enzymes, substrates, bioluminescent materials, radioactive materials, and chemiluminescent labels, or functional labels such as for example streptavidin, avidin, biotin, a cytotoxin, a cytotoxic agent, and radioactive materials. Further exemplary enzymes include, but are not limited to, horseradish peroxidase, acetylcholinesterase, alkaline phosphatase, □-galactosidase and luciferase. Further exemplary fluorescent materials include, but are not limited to, rhodamine, fluorescein, fluorescein isothiocyanate, umbelliferone, dichlorotriazinylamine, phycoerythrin and dansyl chloride. Further exemplary chemiluminescent labels include, but are not limited to, luminol. Further exemplary bioluminescent materials include, but are not limited to, luciferin and aequorin. Further exemplary radioactive materials include, but are not limited to, bismuth-213 ($^{213}Bs$), carbon-14 ($^{14}C$), carbon-11 ($^{11}C$), chlorine-18 ($Cl^{18}$), chromium-51 ($^{51}Cr$), cobalt-57 ($^{57}Co$), cobalt-60 ($^{60}Co$), copper-64 ($^{64}Cu$), copper-67 ($^{67}Cu$), dysprosium-165 ($^{165}Dy$), erbium-169 ($^{169}Er$), fluorine-18 ($^{18}F$), gallium-67 ($^{67}Ga$), gallium-68 ($^{68}Ga$), germanium-68 ($^{68}Ge$), holmium-166 ($^{166}Ho$), indium-111 ($^{111}In$), iodine-125 ($^{125}I$), iodine-123 ($^{124}I$), iodine-124 ($^{124}I$), iodine-131 ($^{131}I$), iridium-192 ($^{192}Ir$), iron-59 ($^{59}Fe$), krypton-81 ($^{81}Kr$), lead-212 ($^{212}Pb$), lutetium-177 ($^{177}Lu$), molybdenum-99 ($^{99}Mo$), nitrogen-13 ($^{13}N$), oxygen-15 ($^{15}O$), palladium-103 ($^{103}Pd$), phosphorus-32 ($^{32}P$), potassium-42 ($^{42}K$), rhenium-186 ($^{186}Re$), rhenium-188 ($^{188}Re$), rubidium-81 ($^{81}Rb$), rubidium-82 ($^{82}Rb$), samarium-153 ($^{153}Sm$), selenium-75 ($^{75}Se$), sodium-24 ($^{24}Na$), strontium-82 ($^{82}Sr$), strontium-89 ($^{89}Sr$), sulfur 35 ($^{35}S$), technetium-99m ($^{99}Tc$), thallium-201 ($^{201}Tl$), tritium ($^{3}H$), xenon-133 ($^{133}Xe$), ytterbium-169 ($^{169}Yb$), ytterbium-177 ($^{177}Yb$), and yttrium-90 ($^{90}Y$).

Cytotoxic Agents

The NEO-300 antibody and antigen-binding fragments thereof, described herein may be conjugated to cytotoxic agents including, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the *vinca* alkaloids, vincristine and vinblastine. Other cytotoxic agents include paclitaxel (TAXOL®), ricin, *pseudomonas* exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, *vinca* alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Toxin conjugated monoclonal antibodies, tumor antigen specific monoclonal antibodies, Erbitux®, Avastin®, Pertuzumab, anti-CD20 antibodies, Rituxan®, ocrelizumab, ofatumumab, DXL625, Herceptin®, or any combination thereof. Toxic enzymes from plants and bacteria such as ricin, diphtheria toxin and *Pseudomonas* toxin may be conjugated to the humanized antibodies, or antigen-binding fragments thereof, to generate cell-type-specific-killing reagents. Youle, et al. (1980) *Proc. Nat'l Acad. Sci. USA* 77: 5483; Gilliland, et al. (1980) *Proc. Nat'l Acad. Sci. USA* 77: 4539; Krolick, et al. (1980) *Proc. Nat'l Acad. Sci. USA* 77: 5419. Other cytotoxic agents include cytotoxic ribonucleases. See U.S. Pat. No. 6,653,104.

The NEO-300 antibody and antigen-binding fragments thereof, described herein may be conjugated to a radionuclide that emits alpha or beta particles (e.g., radioimmunoconjugates). Such radioactive isotopes include but are not limited to beta-emitters such as phosphorus-32 ($^{32}P$), scandium-47 ($^{47}Sc$), copper-67 ($^{67}Cu$), gallium-67 ($^{67}Ga$), yttrium-88 ($^{88}Y$), yttrium-90 ($^{90}Y$), iodine-125 ($^{125}I$), iodine-131 ($^{131}$), samarium-153 ($^{153}Sm$), lutetium-177 ($^{177}Lu$), rhenium-186 ($^{186}Re$), rhenium-188 ($^{188}Re$), and alpha-emitters such as astatine-211 ($^{211}At$), lead-212 ($^{212}Pb$), bismuth-212 ($^{212}Bi$), bismuth-213 ($^{213}Bi$) or actinium-225 ($^{225}Ac$).

Methods are known in the art for conjugating a NEO-300 antibody and antigen-binding fragments thereof, described herein to a label, such as those methods described by Hunter, et al (1962) *Nature* 144: 945; David, et al. (1974) *Biochemistry* 13: 1014; Pain, et al. (1981) *J. Immunol. Meth.* 40: 219; and Nygren (1982) *Histochem, and Cytochem,* 30: 407.

Secondary Agents for Administration or Admixing

The NEO-300 antibodies and fragments thereof described herein may be administered in conjunction with, either simultaneously or sequentially, or admixed with moieties including but not limited to antibodies, fluorescent dyes, enzymes, substrates, bioluminescent materials, radioactive materials, chemiluminescent moieties, a cytotoxic agent, radioactive materials, or functional moieties.

Examples of antibodies that may be admixed or administered in conjunction with a NEO-300 antibody (e.g., NFO-301, NEO-302, NEO-303) includes but are not limited to NPC-1 (NEO-100), 16C3 (NEO-200), and/or 31.1 (NEO-300) antibodies. NPC-1 (NEO-100) antibodies selectively bind a NPC-1 epitope on MUC5AC (SEQ ID NOs: 1-4). 16C3 (NEO-200) antibodies selectively bind 16C3 epitope on CEACAM5/6 (SEQ ID NOs: 5-9). 31.1 (NEO-300) antibodies, as discussed herein, selectively bind 31.1 epitope on A33 antigen (SEQ ID NOs: 10-13). See also WO 2011/163401.

Examples of monoclonal antibodies that may be admixed or administered in conjunction with a NEO-300 antibody (e.g., NEO-301, NEO-302, NEO-303) includes but are not limited to an NPC-1 antibody which selectively binds the NPC-1 antigen (e.g., exemplary light chain are depicted in SEQ ID NO: 14, 15 with CDRs depicted in SEQ ID NO: 16, 17, 18 and heavy chain are depicted in SEQ ID NO: 19, 20 with CDRs depicted in SEQ ID NO:21, 22, 23, exemplary light chain are depicted in SEQ ID NO:24, 25 with CDRs depicted in SEQ ID NO:26, 27, 28 and heavy chain are depicted in SEQ ID NO:29, 30 with CDRs depicted in SEQ ID NO:31, 32, 33, and exemplary light chain are depicted in SEQ ID NO:34, 35 and heavy chain are depicted in SEQ ID NO:36, 37); a 16C3 antibody which selectively binds the 16C3 antigen (e.g., exemplary light chain are depicted in SEQ ID NO:38, 39 with CDRs depicted in SEQ ID NO:40, 41, 42 and heavy chain are depicted in SEQ ID NO:44, 45 with CDRs depicted in SEQ ID NO:45, 46, 47, additional exemplary light chains are depicted in SEQ ID NO:48, 49, 50, 51, 52 and heavy chain are depicted in SEQ ID NO:53, 54, 55, 56, 57, and exemplary light chain are depicted in SEQ ID NO:58, 59 with CDRs depicted in SEQ ID NO:60, 61, 62 and heavy chain are depicted in SEQ ID NO:63, 64 with CDRs depicted in SEQ ID NO:65, 66, 67) and A33 antigen antibody which selectively binds the A33 antigen (e.g., exemplary light chain are depicted in SEQ ID NO:68 and heavy chain are depicted in SEQ ID NO:69 and further exemplary light chain are depicted in SEQ ID NO:71 and heavy chain are depicted in SEQ ID NO:73). See also WO 2011/163401. 31.1 monoclonal antibody, described in WO 02/074251 and WO 2006/004950, exhibits specificity for the A33 antigen.

Examples of humanized antibodies that may be admixed or administered in conjunction with a NEO-300 antibody (e.g., NEO-301, NEO-302, NEO-303) includes but are not limited to NEO-103 which selectively binds the NPC-1 antigen (e.g., exemplary light chain are depicted in SEQ ID NO:34-35 and heavy chain are depicted in SEQ ID NO:36-37), 16C3 (h16C3) which selectively binds the 16C3 antigen (e.g., exemplary light chains are depicted in SEQ ID NOs: 38-52 and heavy chains depicted in SEQ ID NOs: 53-57); NEO-201 (h16C3-Abb*) which selectively binds the 16C3 antigen (e.g, exemplary light chain are depicted in SEQ ID NO:59 with CDRs are depicted in SEQ ID NOs: 60-62, heavy chain are depicted in SEQ ID NO:64 with CDRs are depicted in SEQ ID NOs: 65-67); and NEO-302 which selectively binds the A33 antigen (e.g., exemplary light chain are depicted in SEQ ID NO:70-71 and heavy chain are depicted in SEQ ID NO:72-73). See also WO 2011/163401.

Examples of chimeric antibodies that may be admixed or administered in conjunction with a NEO-300 antibody (e.g., NEO-301, NEO-302, NEO-303) includes but are not limited to NEO-101 (NPC-IC) which selectively binds NPC-1 antigen (e.g., exemplary light chain are depicted in SEQ ID NOs: 14, 15 with CDRS depicted in SEQ ID NOs: 16-18 and heavy chain depicted in SEQ ID NOs: 19, 20 with CDRs depicted in SEQ ID NOs: 21-23); NEO-102 which selectively binds NPC-1 antigen (e.g., exemplary light chain are depicted in SEQ ID NOs: 24, 25 with CDRS depicted in SEQ ID NOs: 26-28 and heavy chain depicted in SEQ ID NOs: 29, 30 with CDRs depicted in SEQ ID NOs: 31-33); and NEO-301 (31.1C) which selectively binds the A33 antigen (e.g., exemplary light chain are depicted in SEQ ID NO:68 and heavy chain depicted in SEQ ID NO:69). See also WO 2011/163401.

NEO-300 antibody (e.g., NEO-301, NEO-302, NEO-303) may be admixed or administered in conjunction with nucleic acids that encode polypeptides for antibodies that bind NPC-1 antigen are provided in SEQ ID NOs: 14, 19, 24, 29, 34, and 36 (encoding the polypeptides of SEQ ID NO: 15, 20, 25, 30, 35, and 37, respectively) including antibody light chains (SEQ ID NO: 14, 24, and 34), antibody heavy chains (SEQ ID NO:15, 25, and 35). Additionally, exemplary NPC-1 antibody polypeptides include humanized light chain (SEQ ID NO:71) and humanized heavy chain (SEQ ID NO:36).

NEO-300 antibody (e.g., NEO-301, NEO-302, NEO-303) may be admixed or administered in conjunction with nucleic acids that encode polypeptides for antibodies that bind 16C3 antigen are provided in SEQ ID NOs: 38, 43, 58, and 100 (encoding the polypeptides of SEQ ID NO:39, 44, 59, and 101, respectively) including antibody light chains (SEQ ID NOs: 38 and 58), antibody heavy chains (SEQ ID NOs: 43 and 63).

NEO-300 antibody (e.g., NEO-301, NEO-302, NEO-303) may be admixed or administered in conjunction with nucleic acids that encode polypeptides for antibodies that bind A33 antigen are provided in SEQ ID NOs: 70 and 72 (encoding the polypeptides of SEQ 1D NO:71 and 73, respectively) including antibody light chains (SEQ ID NO:70), antibody heavy chains (SEQ ID NO:72).

Ligands that may be administered along or admixed with the antibodies and antibody fragments may include naturally occurring molecules, or recombinant or synthetic molecules. Exemplary ligands include, but are not limited to, avadin, biotin, peptides, peptidomimetics, polylysine (PLL), polyethylene glycol (PEG), mPEG, cationic groups, spermine, spermidine, polyamine, thyrotropin, melanotropin, lectin, glycoprotein, surfactant protein A, mucin, glycosylated polyaminoacids, transferrin, aptamer, immunoglobulins (e.g., antibodies), insulin, transferrin, albumin, sugar, lipophilic molecules (e.g., steroids, bile acids, cholesterol, cholic acid, and fatty acids), vitamin A, vitamin E, vitamin K, vitamin B, folic acid, B12, riboflavin, biotin, pyridoxal, vitamin cofactors, lipopolysaccharide, hormones and hormone receptors, lectins, carbohydrates, multivalent carbohydrates, radiolabeled markers, fluorescent dyes, and derivatives thereof. See, e.g., U.S. Pat. Nos. 6,153,737; 6,172,208;

6,300,319; 6,335,434; 6,335,437; 6,395,437; 6,444,806; 6,486,308; 6,525,031; 6,528,631; and 6,559, 279.

Detectable Labels

The NEO-300 antibody and antigen-binding fragments thereof, described herein may be administered with, either simultaneously or sequentially, or admixed with labels such as chemical linkers, detectable labels such as for example fluorescent dyes, enzymes, substrates, bioluminescent materials, radioactive materials, and chemiluminescent labels, or functional labels such as for example streptavidin, avidin, biotin, a cytotoxin, a cytotoxic agent, and radioactive materials. Further exemplary enzymes include, but are not limited to, horseradish peroxidase, acetylcholinesterase, alkaline phosphatase, □-galactosidase and luciferase. Further exemplary fluorescent materials include, but are not limited to, rhodamine, fluorescein, fluorescein isothiocyanate, umbelliferone, dichlorotriazinylamine, phycoerythrin and dansyl chloride. Further exemplary chemiluminescent labels include, but are not limited to, luminol. Further exemplary bioluminescent materials include, but are not limited to, luciferin and aequorin. Further exemplary radioactive materials include, but are not limited to, bismuth-213 ($^{213}$Bs), carbon-14 ($^{14}$C), carbon-11 ($^{11}$C), chlorine-18 ($Cl^{18}$), chromium-51 ($^{51}$Cr), cobalt-57 ($^{57}$Co), cobalt-60 ($^{60}$Co), copper-64 ($^{64}$Cu), copper-67 ($^{67}$Cu), dysprosium-165 ($^{165}$Dy), erbium-169 ($^{169}$Er), fluorine-18 ($^{18}$F), gallium-67 ($^{67}$Ga), gallium-68 ($^{68}$Ga), germanium-68 ($^{68}$Ge), holmium-166 ($^{166}$Ho), indium-111 ($^{111}$In), iodine-125 ($^{125}$I), iodine-123 ($^{124}$I), iodine-124 ($^{124}$I), iodine-131 ($^{131}$I), iridium-192 ($^{192}$Ir), iron-59 ($^{59}$Fe), krypton-81 ($^{81}$Kr), lead-212 ($^{212}$Pb), lutetium-177 ($^{177}$Lu), molybdenum-99 ($^{99}$Mo), nitrogen-13 ($^{13}$N), oxygen-15 ($^{15}$O), palladium-103 ($^{103}$Pd), phosphorus-32 ($^{32}$P), potassium-42 ($^{42}$K), rhenium-186 ($^{186}$Re), rhenium-188 ($^{188}$Re), rubidium-81 ($^{81}$Rb), rubidium-82 ($^{82}$Rb), samarium-153 ($^{153}$Sm), selenium-75 ($^{75}$Se), sodium-24 ($^{24}$Na), strontium-82 ($^{82}$Sr), strontium-89 ($^{89}$Sr), sulfur 35 ($^{35}$S), technetium-99m ($^{99}$Tc), thallium-201 ($^{201}$Tl), tritium ($^{3}$H), xenon-133 ($^{133}$Xe), ytterbium-169 ($^{169}$Yb), ytterbium-177 ($^{177}$Yb), and yttrium-90 ($^{90}$Y)

Cytotoxic Agents

The NEO-300 antibody and antigen-binding fragments thereof, described herein may be administered with, either simultaneously or sequentially, or admixed with cytotoxic agents including, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the *vinca* alkaloids, vincristine and vinblastine. Other cytotoxic agents include paclitaxel (TAXOL®), ricin, *pseudomonas* exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, vinca alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Toxin conjugated monoclonal antibodies, tumor antigen specific monoclonal antibodies, Erbitux®, Avastin®, Pertuzumab, anti-CD20 antibodies, Rituxan®, ocrelizumab, ofatumumab, DXL625, Herceptin®, or any combination thereof. Toxic enzymes from plants and bacteria such as ricin, diphtheria toxin and *Pseudomonas* toxin may be conjugated to the humanized antibodies, or antigen-binding fragments thereof, to generate cell-type-specific-killing reagents. Youle, et al. (1980) *Proc. Nat'l Acad. Sci. USA* 77: 5483; Gilliland, et al. (1980) *Proc. Nat'l Acad. Sci. USA* 77: 4539; Krolick, et al. (1980) *Proc. Nat'l Acad. Sci. USA* 77: 5419. Other cytotoxic agents include cytotoxic ribonucleases. See U.S. Pat. No. 6,653,104.

The NEO-300 antibody and antigen-binding fragments thereof, described herein may be administered with, either simultaneously or sequentially, or admixed with a radionuclide that emits alpha or beta particles (e.g., radioimmunoconjugates). Such radioactive isotopes include but are not limited to beta-emitters such as phosphorus-32 ($^{32}$P), scandium-47 ($^{47}$Sc), copper-67 ($^{67}$Cu), gallium-67 ($^{67}$Ga), yttrium-88 ($^{88}$Y), yttrium-90 ($^{90}$Y), iodine-125 ($^{125}$I), iodine-131 ($^{131}$I), samarium-153 ($^{153}$Sm), lutetium-177 ($^{177}$Lu), rhenium-186 ($^{186}$Re), rhenium-188 ($^{188}$Re), and alpha-emitters such as astatine-211 ($^{211}$At), lead-212 ($^{212}$Pb), bismuth-212 ($^{212}$Bi), bismuth-213 ($^{213}$Bi) or actinium-225 ($^{225}$Ac).

Substrates

The NEO-300 antibody and antigen-binding fragments thereof (e.g., NEO-301, NEO-302, NEO-303), described herein may be attached to a substrate. A number of substrates (e.g., solid supports) known in the art are suitable for use with the NEO-300 antibody and antigen-binding fragments thereof, described herein. The substrate may be modified to contain channels or other configurations. See Fung (2004) [Ed.] *Protein Arrays: Methods and Protocols* Humana Press and Kambhampati (2004) [Ed.]*Protein Microarray Technology* John Wiley & Sons.

Substrate materials include, but are not limited to acrylics, agarose, borosilicate glass, carbon (e.g., carbon nanofiber sheets or pellets), cellulose acetate, cellulose, ceramics, gels, glass (e.g., inorganic, controlled-pore, modified, soda-lime, or functionalized glass), latex, magnetic beads, membranes, metal, metalloids, nitrocellulose, NYLON®, optical fiber bundles, organic polymers, paper, plastics, polyacryloylmorpholide, poly(4-methylbutene), poly(ethylene terephthalate), poly(vinyl butyrate), polyacrylamide, polybutylene, polycarbonate, polyethylene, polyethyleneglycol terephthalate, polyformaldehyde, polymethacrylate, polymethylmethacrylate, polypropylene, polysaccharides, polystyrene, polyurethanes, polyvinylacetate, polyvinylchloride, polyvinylidene difluoride (PVDF), polyvinylpyrrolidinone, rayon, resins, rubbers, semiconductor materials, SEPHAROSE®, silica, silicon, styrene copolymers, TEFLON®, and variety of other polymers.

Substrates need not be flat and can include any type of shape including spherical shapes (e.g., beads) or cylindrical shapes (e.g., fibers). Materials attached to solid supports may be attached to any portion of the solid support (e.g., may be attached to an interior portion of a porous solid support material).

The substrate body may be in the form of a bead, box, column, cylinder, disc, dish (e.g., glass dish, PETRI dish), fiber, film, filter, microtiter plate (e.g., 96-well microtiter plate), multi-bladed stick, net, pellet, plate, ring, rod, roll, sheet, slide, stick, tray, tube, or vial. The substrate may be a singular discrete body (e.g., a single tube, a single bead), any number of a plurality of substrate bodies (e.g, a rack of 10 tubes, several beads), or combinations thereof (e.g., a tray comprises a plurality of microtiter plates, a column filled with beads, a microtiter plate filed with beads).

A NEO-300 antibody or antibody fragment thereof (e.g., NEO-301, NEO-302, NEO-303) described herein may be "attached" to a substrate when it is associated with the solid substrate through a non-random chemical or physical interaction. The attachment may be through a covalent bond. However, attachments need not be covalent or permanent. Materials may be attached to a substrate through a "spacer molecule" or "linker group." Such spacer molecules are molecules that have a first portion that attaches to the biological material and a second portion that attaches to the substrate. Thus, when attached to the substrate, the spacer molecule separates the substrate and the biological materials, but is attached to both. Methods of attaching biological material (e.g., label) to a substrate are well known in the art, and include but are not limited to chemical coupling.

Plates, such as microtiter plates, which support and contain the solid-phase for solid-phase synthetic reactions may be used. Microtiter plates may house beads that are used as the solid-phase. By "particle" or "microparticle" or "nanoparticle" or "bead" or "microbead" or "microsphere" herein is meant microparticulate matter having any of a variety of shapes or sizes. The shape may be generally spherical but need not be spherical, being, for example, cylindrical or polyhedral. As will be appreciated by those in the art, the particles may comprise a wide variety of materials depending on their use, including, but not limited to, cross-linked starch, dextrans, cellulose, proteins, organic polymers including styrene polymers such as polystyrene and methylstyrene as well as other styrene co-polymers, plastics, glass, ceramics, acrylic polymers, magnetically responsive materials, colloids, thoriasol, carbon graphite, titanium dioxide, nylon, latex, and TEFLON®. See e.g., "Microsphere Detection Guide" from Bangs Laboratories, Fishers, Ind.

A NEO-300 antibody or antibody fragment thereof described herein may be attached to on any of the forms of substrates described herein (e.g., bead, box, column, cylinder, disc, dish (e.g., glass dish, PETRI dish), fiber, film, filter, microtiter plate (e.g., 96-well microtiter plate), multi-bladed stick, net, pellet, plate, ring, rod, roll, sheet, slide, stick, tray, tube, or vial). In particular, particles or beads may be a component of a gelling material or may be separate components such as latex beads made of a variety of synthetic plastics (e.g., polystyrene). The label (e.g., streptavidin) may be bound to a substrate (e.g., bead).

Pharmaceutical Compositions

A "pharmaceutical composition" refers to a chemical or biological composition suitable for administration to a mammal. Such compositions may be specifically formulated for administration via one or more of a number of routes, including but not limited to buccal, epicutaneous, epidural, inhalation, intraarterial, intracardial, intracerebroventricular, intradermal, intramuscular, intranasal, intraocular, intraperitoneal, intraspinal, intrathecal, intravenous, oral, parenteral, rectally via an enema or suppository, subcutaneous, subdermal, sublingual, transdermal, and transmucosal. In addition, administration may occur by means of injection, powder, liquid, gel, drops, or other means of administration.

A "pharmaceutical excipient" or a "pharmaceutically acceptable excipient" is a carrier, usually a liquid, in which an active therapeutic agent is formulated. In one embodiment of the invention, the active therapeutic agent is a humanized antibody described herein, or one or more fragments thereof. The excipient generally does not provide any pharmacological activity to the formulation, though it may provide chemical and/or biological stability, and release characteristics. Exemplary formulations may be found, for example, in Grennaro (2005) [Ed.] *Remington: The Science and Practice of Pharmacy* [21st Ed.]

Pharmaceutical compositions typically must be sterile and stable under the conditions of manufacture and storage. The invention contemplates that the pharmaceutical composition is present in lyophilized form. The composition may be formulated as a solution, microemulsion, liposome, or other ordered structure suitable to high drug concentration. The carrier may be a solvent or dispersion medium containing, for example, water, ethanol, polyol (for example, glycerol, propylene glycol, and liquid polyethylene glycol), and suitable mixtures thereof. The invention further contemplates the inclusion of a stabilizer in the pharmaceutical composition.

The NEO-300 antibodies and fragments thereof (e.g., NEO-301, NEO-302, NEO-303), of the present invention thereof may be formulated into pharmaceutical compositions of various dosage forms. To prepare the pharmaceutical compositions of the invention, at least one A33 antigen, anti-NPC-1 antibody, anti-16C3 antibody, or other NEO-300 antibody or antigen-binding fragments thereof, as the active ingredient may be intimately mixed with appropriate carriers and additives according to techniques well known to those skilled in the art of pharmaceutical formulations. See Grennaro (2005) [Ed.]*Remington: The Science and Practice of Pharmacy* [21st Ed.] For example, the antibodies described herein may be formulated in phosphate buffered saline pH 7.2 and supplied as a 5.0 mg/mL clear colorless liquid solution.

Similarly, compositions for liquid preparations include solutions, emulsions, dispersions, suspensions, syrups, and elixirs, with suitable carriers and additives including but not limited to water, alcohols, oils, glycols, preservatives, flavoring agents, coloring agents, and suspending agents. Typical preparations for parenteral administration comprise the active ingredient with a carrier such as sterile water or parenterally acceptable oil including but not limited to polyethylene glycol, polyvinyl pyrrolidone, lecithin, *arachis* oil or sesame oil, with other additives for aiding solubility or preservation may also be included. In the case of a solution, it may be lyophilized to a powder and then reconstituted immediately prior to use. For dispersions and suspensions, appropriate carriers and additives include aqueous gums, celluloses, silicates, or oils.

For each of the recited embodiments, the NEO-300 antibody or antigen-binding fragments thereof, described herein may be administered by a variety of dosage forms. Any biologically-acceptable dosage form known to persons of ordinary skill in the art, and combinations thereof, are contemplated. Examples of such dosage forms include, without limitation, reconstitutable powders, elixirs, liquids, solutions, suspensions, emulsions, powders, granules, particles, microparticles, dispersible granules, cachets, inhalants, aerosol inhalants, patches, particle inhalants, implants, depot implants, injectables (including subcutaneous, intramuscular, intravenous, and intradermal), infusions, and combinations thereof.

In many cases, it will be preferable to include isotonic agents, e.g., sugars, polyalcohols such as mannitol, sorbitol, or sodium chloride in the composition. Prolonged absorption of the injectable compositions may be brought about by including in the composition an agent which delays absorption, e.g., monostearate salts and gelatin. Moreover, the compounds described herein may be formulated in a time release formulation, e.g. in a composition that includes a slow release polymer. The NEO-300 antibody or antigen-binding fragments thereof, may be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

A person of skill in the art would be able to determine an effective dosage and frequency of administration through routine experimentation, for example guided by the disclosure herein and the teachings in Goodman, et al. (2011) *Goodman & Gilman's The Pharmacological Basis of Therapeutics* [$12^{th}$ Ed.]; Howland, et al. (2005) *Lippincott's Illustrated Reviews: Pharmacology* [$2^{nd}$ Ed.]; and Golan, (2008) *Principles of Pharmacology: The Pathophysiologic Basis of Drug Therapy* [$2^{nd}$ Ed.] See, also, Grennaro (2005) [Ed.] *Remington: The Science and Practice of Pharmacy* [$21^{st}$ Ed.]

Routes of Administration

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are intravenous injection or infusion. The administration can be local, where the composition is administered directly, close to, in the locality, near, at, about, or in the vicinity of, the site(s) of disease, e.g., tumor, or systemic, wherein the composition is given to the patient and passes through the body widely, thereby reaching the site(s) of disease. Local administration (e.g., injection) may be accomplished by administration to the cell, tissue, organ, and/or organ system, which encompasses and/or is affected by the disease, and/or where the disease signs and/or symptoms are active or are likely to occur (e.g., tumor site). Administration can be topical with a local effect, composition is applied directly where its action is desired (e.g., tumor site).

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

In further embodiments, the present invention provides kits including one or more containers comprising pharmaceutical dosage units comprising an effective amount of one or more antibodies and fragments thereof of the present invention. Kits may include instructions, directions, labels, marketing information, warnings, or information pamphlets.

Dosages

The amount of NEO-300 antibody and antigen-binding fragments thereof (e.g., NEO-301, NEO-302, NEO-303), in a therapeutic composition according to any embodiments of this invention may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of antibodies, and fragments thereof, calculated to produce the desired therapeutic effect in association with the required pharmaceutical carrier. The specification for the dosage unit forms of the invention are dictated by and directly dependent on the unique characteristics of the antibodies, and fragments thereof, and the particular therapeutic effect to be achieved, and the limitations inherent in the art of compounding such an antibodies, and fragments thereof, for the treatment of sensitivity in individuals. In therapeutic use for treatment of conditions in mammals (e.g., humans) for which the antibodies and fragments thereof of the present invention or an appropriate pharmaceutical composition thereof are effective, the antibodies and fragments thereof of the present invention may be administered in an effective amount. The dosages as suitable for this invention may be a composition, a pharmaceutical composition or any other compositions described herein.

The dosage may be administered as a single dose, a double dose, a triple dose, a quadruple dose, and/or a quintuple dose. The dosages may be administered singularly, simultaneously, and sequentially.

The dosage form may be any form of release known to persons of ordinary skill in the art. The compositions of the present invention may be formulated to provide immediate release of the active ingredient or sustained or controlled release of the active ingredient. In a sustained release or controlled release preparation, release of the active ingredient may occur at a rate such that blood levels are maintained within a therapeutic range but below toxic levels over an extended period of time (e.g., 4 to 24 hours). The preferred dosage forms include immediate release, extended release, pulse release, variable release, controlled release, timed release, sustained release, delayed release, long acting, and combinations thereof, and are known in the art.

It will be appreciated that the pharmacological activity of the compositions may be monitored using standard pharmacological models that are known in the art. Furthermore, it will be appreciated that the compositions comprising a NEO-300 antibody or antigen-binding fragment thereof, may be incorporated or encapsulated in a suitable polymer matrix or membrane for site-specific delivery, or may be functionalized with specific targeting agents capable of effecting site specific delivery. These techniques, as well as other drug delivery techniques are well known in the art. Determination of optimal dosages for a particular situation is within the capabilities of those skilled in the art. See, e.g., Grennaro (2005) [Ed.] *Remington: The Science and Practice of Pharmacy* [21$^{t}$ Ed.]

Methods of Treatment

The NEO-300 antibody or antigen-binding fragment thereof (e.g., NEO-301, NEO-302, NEO-303), described herein may be used in methods for treating cancer, promoting tumor regression, killing tumor cells, activating an immune response against A33 antigen expressing tumor cells (e.g., cytotoxic immune response), activating dendritic cells, or activating antigen-specific immunity comprising administering an effective amount of a NEO-300 antibody or antigen-binding fragment thereof to a subject in need thereof. Further, the NEO-300 antibody or antigen-binding fragment thereof, described herein may be used to manufacture medicaments for use in treating cancer, promoting tumor regression, killing tumor cells, activating an immune response against A33 antigen expressing tumor cells (e.g., cytotoxic immune response), activating dendritic cells, or activating antigen-specific immunity comprising an effective amount of a NEO-300 antibody or antigen-binding fragment thereof described herein. The NEO-300 antibody or antigen-binding fragment thereof, described herein may be admixed with a pharmaceutically acceptable carrier to manufacture a composition for treating cancer, promoting tumor regression, killing tumor cells, activating an immune response against A33 antigen expressing tumor cells (e.g., cytotoxic immune response), activating dendritic cells, or activating antigen-specific immunity comprising an effective amount of a NEO-300 antibody or antigen-binding fragment thereof described herein.

The cancer treated by the NEO-300 antibody or antigen-binding fragment thereof, described herein may be lung, breast, pancreas, uterine, esophageal, colorectal, or liver cancer. The cancer may be a stage 1, 2, 3 or 4 cancer. The cancer may have metastasized. The patient may be a mammal, such as a human, suffering from cancer where tumor cells express A33 antigens, aberrant A33 antigens, and/or tumorigenesis of neoplastic cells expressing a A33 antigen. The amount sufficient to inhibit or reduce the A33 antigen is an amount sufficient to ameliorate the disorder, which may be monitored as a decrease in either cancer progression or tumor mass. For example, NEO-300 antibodies with minimal HAMA and high levels of ADCC may be administered at doses of 200 mg to 400 mg delivered every two weeks I.V. to a patient in need thereof for treating metastatic cancer.

The patient may express detectable levels of A33 antigen as detected, for example, in a tumor biopsy sample or in the blood, stool, urine, or lymph fluid. Further, the patient may be at risk of cancer or a patient without symptoms. The methods described herein may be used on cells, e.g., human cells, in vitro or ex vivo. Alternatively, the method may be performed on cells present in a subject as part of an in vivo (e.g., therapeutic) protocol.

The NEO-300 antibody or antigen-binding fragment thereof, may be admixed with additional chemotherapeutic agents, cytotoxic agent, antibodies (e.g., 31.1 monoclonal antibody), lymphokine, or hematopoietic growth factor. The NEO-300 antibody or antigen-binding fragment thereof, may also be administered in combination with another antibody, a lymphokine, cytotoxic agent (e.g., a moiety that inhibits DNA, RNA, or protein synthesis, a radionuclide, or ribosomal inhibiting protein, e.g., $^{212}Bi$, $^{131}I$, $^{188}Re$, $^{90}Y$, vindesine, methotrexate, adriamycin, cisplatin, pokeweed antiviral protein, *Pseudomonas* exotoxin A, ricin, diphtheria toxin, ricin A chain, or cytotoxic phospholipase enzyme), immunosuppressive agent (e.g., cyclosporine, leflunomide, methotrexate, azothiprine, mercaptopurine, dactinomycin, tacrolimus, or sirolimus) or a hematopoietic growth factor. The NEO-300 antibody or antigen-binding fragment thereof, may be label with a chemiluminescent label, paramagnetic label (e.g., aluminum, manganese, platinum, oxygen, lanthanum, lutetium, scandium, yttrium, or gallium), an MRI contrast agent, fluorescent label, bioluminescent label, or radioactive label. In the methods described herein, the second agent may be administered simultaneously or sequentially with the antibody.

The antigens, antibodies, and nucleic acids described herein may be used in the manufacture of compositions for use in treating cancer and methods of treating cancer including but not limited to solid and soft tumors, such as esophageal carcinoma, renal cancer, cancer of breast, thyroid, spleen, uterus, kidney, colorectal, lung, prostate, testicles, gastric, cervical, bone, skin, brain, head & neck, bladder, head and neck, liver, pancreas, melanoma, osteosarcoma, fibrosarcoma, rhabdomyosarcoma, teratocarcinoma, neuroblastoma, glioma, glioblastoma and hematological malignancies such as acute lymphocytic leukemia, chronic lymphocytic leukemia, acute myelogenous leukemia, chronic myelogenous leukemia, multiple myeloma, Hodgkin's lymphoma and Non-Hodgkin's lymphoma, and wherein the cancer is invasive or metastatic.

The invention provides for methods of treating a subject with pancreas or colon cancer comprising administering a NEO-300 antibody or antigen-binding fragment thereof, to a subject who may be receiving secondary antihyperplastic therapy. Examples of secondary antihyperplastic therapy include chemotherapy, radiotherapy, immunotherapy, phototherapy, cryotherapy, toxin therapy, hormonal therapy, or surgery. Thus, the invention contemplates use of the methods and compositions in conjunction with standard anticancer therapies. The patient to be treated may be of any age. One of skill in the art will recognize the presence and development of other anticancer therapies which may be used in conjugation with the NEO-300 antibody and antigen-binding fragments thereof.

Determination of dose is within the level of ordinary skill in the art. The NEO-300 antibody (e.g., NEO-301, NEO-302, NEO-303) or antigen-binding fragments thereof may be administered for acute treatment, over one week or less, often over a period of one to three days or may be used in chronic treatment, over several months or years. In general, a therapeutically effective amount of the NEO-300 antibody (e.g., NEO-301, NEO-302, NEO-303) or antigen-binding fragments thereof is an amount sufficient to produce a clinically significant change in A33 antigen shed, decreased cancer progression, or decreased tumor size.

Diagnostic Methods

The NEO-300 antibody (e.g., NEO-301, NEO-302, NEO-303) or antigen-binding fragments thereof may be used in diagnostic methods for detecting the presence or absence of an A33 antigen. The NEO-300 antibody (e.g., NEO-301, NEO-302, NEO-303) or antigen-binding fragments thereof may be used in methods comprising (a) contacting a test sample with an antibody, or antibody fragment thereof, that binds a A33 antigen, and (b) assaying for antibody-epitope complexes, wherein the presence of said epitope is indicative of a carcinoma. Further, the NEO-300 antibody (e.g., NEO-301, NEO-302, NEO-303) or antigen-binding fragments thereof may be used in a method for detecting the presence of an A33 antigen in a patient comprising (a) administering to said patient a labeled monoclonal antibody, or antibody fragment thereof, that binds an A33 antigen and (b) detecting the presence of an A33 antigen; wherein the presence of said epitope is indicative of a carcinoma. The antibody-epitope complex may be detected by Western blot, radioimmunoassay, ELISA (enzyme linked immunosorbent assay), "sandwich" immunoassay, lateral flow assay, immunoprecipitation assay, precipitation reaction, gel diffusion precipitation reaction, immunodiffusion assay, agglutination assay, complement-fixation assay, immunohistochemical assay, fluorescent immunoassay, and protein A immunoassay. The sample may be sample is a tissue biopsy, lymph, urine, cerebrospinal fluid, amniotic fluid, inflammatory exudate, blood, serum, stool, or liquid collected from the colorectal tract.

The NEO-300 antibody (e.g., NEO-301, NEO-302, NEO-303) or antigen-binding fragments thereof may be used in diagnostic methods for detecting the presence or absence of an A33 antigen, wherein the presence of the antigen is indicative of cancer including but not limited to lung, breast, pancreas, uterine, esophageal, colorectal, or liver cancer. The diagnostic methods may be used with patients at risk of cancer or patients without symptoms.

The NEO-300 antibody (e.g., NEO-301, NEO-302, NEO-303) or antigen-binding fragments thereof may be recombinant. The fragments of antibodies which selectively bind a A33 antigen may be a Fab, Fab', F(ab')2, Fv, CDR, paratope, or portion of an antibody that is capable of binding the antigen. The NEO-300 antibody (e.g., NEO-301, NEO-302, NEO-303) or antigen-binding fragments thereof may be chimeric, humanized, anti-idiotypic, single-chain, bifunctional, or co-specific. The antibodies which selectively bind a A33 antigen may be or fragment is conjugated to a label, including but not limited to a chemiluminescent label, paramagnetic label (e.g., aluminum, manganese, platinum, oxygen, lanthanum, lutetium, scandium, yttrium, or gallium), an MRI contrast agent, fluorescent label, bioluminescent label, or radioactive label.

Additionally, NEO-300 antibodies or antigen-binding fragments thereof, may be attached to a solid support (e.g., bead, test tube, sheet, culture dish, or test strip) such as an array.

The method may detect colorectal polyps. The method may further comprise additional testing for the presence of tumors including but not limited to benign tumors, malignant tumors, metastatic tumors, and non-metastatic tumors. For example, the diagnostic method may detect pre-cancerous cells that express a cell marker comprising a A33 antigen.

The method may comprise imaging a A33 antigen by positron emission tomography (PET), CCD low-light monitoring system, X-ray, CT scanning, scintigraphy, photo acoustic imaging, single photon emission computed tomography (SPECT), magnetic resonance imaging (MRI), ultrasound, paramagnetic imaging, and endoscopic optical coherence tomography.

The invention also provides a method for genetic diagnosis of a risk for cancer comprising taking a nucleic acid sample from a patient, analyzing said nucleic acid comprising comparing to cancer specific A33 sequence, wherein if the patient's nucleic acid sample matches the cancer specific A33 sequence, the patient is at risk for developing cancer.

The A33 antigens may be used as a cancer biomarker. Detection of the A33 antigens in a biological sample, such as a subject's serum, biopsied neoplastic cells or fecal sample, may be performed by means of the NEO-300 antibody (e.g., NEO-301, NEO-302, NEO-303) or antigen-binding fragments thereof. For example, a biological sample (e.g., a tumor, serum or fecal sample) is obtained from a subject, then A33 antigen is measured (e.g., by ELISA or PCR), and compared with corresponding samples from normal subjects. Measuring methods include any method of nucleic acid detection, for example in situ hybridization using antisense A33 antigen DNA or cRNA oligonucleotide probes, ultra-high throughput sequencing, nanostring technology, microarrays, rolling circle amplification, proximity-mediated ligation, PCR, qRT-PCR ChIP, ChIP-qPCR, or A33 antigen-binding antibodies. Comparatively high levels of A33 antigens indicate the presence and/or severity of pancreas or colon cancer, and may indicate metastasis or poor cancer prognosis.

The NEO-300 antibody (e.g., NEO-301, NEO-302, NEO-303) or antigen-binding fragments thereof may be used in SQUID (Superconducting Quantum Interference Device) techniques for diagnostic methods. The SQUID technique comprises attaching nanoparticles of iron oxide to antibodies, which are then injected into the patient. If a tumor is present, the antibodies with conjugated nanoparticles recognize and bind to the A33 antigen on tumor cells. See, e.g., Hao, et al. (2010) *Journal of Physics* 43: 474004. In a SQUID method, the patient is then surrounded with sensitive magnetic coils in a superconducting quantum interference device (SQUID). A magnetic field is generated and all of the metal nanoparticles align in one direction. When the magnetic field is broken, the nanoparticles emit an electromagnetic signal as they relax back into their original state. By measuring the strength of the signal, it may tell how many metal particles, and therefore how many tumor cells, may be present, and where in the patient the tumor cells are located. See, e.g., Shao, et al. (2010) *Beilstein Journal of Nanotechnology* 1: 142-154.

Samples and Procurement of Samples

The samples used in the methods described herein may be taken from a subject (patient) include but are not limited to a body fluid or secretion including but not limited to blood, serum, urine, plasma, prostatic fluid, seminal fluid, semen, the external secretions of the skin, respiratory, intestinal, and genitourinary tracts, tears, cerebrospinal fluid, sputum, saliva, milk, peritoneal fluid, pleural fluid, cyst fluid, secretions of the breast ductal system (and/or lavage thereof), broncho alveolar lavage, lavage of the reproductive system and lavage of any other part of the body or system in the body; samples of any organ including isolated cell(s) or tissue(s), wherein the cell or tissue can be obtained from an organ selected from, but not limited to lung, colon, ovarian and/or breast tissue; stool or a tissue sample, or any combination thereof. In some embodiments, the term encompasses samples of in vivo cell culture constituents. Prior to be subjected to the diagnostic assay, the sample can optionally be diluted with a suitable diluent.

Numerous well known tissue or fluid collection methods can be utilized to collect the biological sample from the subject in order to determine the level of DNA, RNA and/or polypeptide of the marker of interest in the subject. Examples of tissue or fluid collection methods include, but are not limited to, fine needle biopsy, needle biopsy, core needle biopsy and surgical biopsy (e.g., brain biopsy), and lavage. Regardless of the procedure employed, once a biopsy/sample is obtained the level of the marker may be determined and a diagnosis can thus be made.

Detection of A33 Antigen

The invention provides a method for detecting the A33 antigens of this invention in a biological sample, comprising: contacting a biological sample with an antibody specifically recognizing a A33 antigen according to the present invention and detecting said interaction; wherein the presence of an interaction correlates with the presence of a A33 antigen in the biological sample.

The A33 antigens described herein are non-limiting examples of markers for diagnosing a disease and/or an indicative condition. Each marker of the present invention may be used alone or in combination, for various uses, including but not limited to, prognosis, prediction, screening, early diagnosis, determination of progression, therapy selection and treatment monitoring of a cancer (e.g., pancreas, liver, colorectal, lung, or breast cancer).

The cancers that may be detected using the methods described herein include but are not limited to non-solid and solid tumors, cancer of the breast, prostate, lung, ovary, colon, uterus, stomach, cervix, liver, pancreas, and wherein the cancer may be invasive or metastatic.

The NEO-300 antibody (e.g., NEO-301, NEO-302, NEO-303) or antigen-binding fragments thereof of the present invention may be used alone or in combination, for various uses, including but not limited to, prognosis, prediction, screening, early diagnosis, determination of progression, therapy selection and treatment monitoring of cancers such as non-solid and solid tumors, cancer of the breast, prostate, lung, ovary, colon, uterus, stomach, cervix, liver, pancreas, and wherein the cancer may be invasive or metastatic. Such a combination may optionally comprise any subcombination of markers, and/or a combination featuring at least one other marker, for example a known marker. Furthermore, such a combination may optionally and preferably be used as described above with regard to determining a ratio between a quantitative or semi-quantitative measurement of any marker described herein to any other marker described herein, and/or any other known marker, and/or any other marker.

Markers of the present invention may optionally be used alone or in combination with known markers for lung cancer, including but not limited to NPC-1, 16C3, CEA, CA15-3, beta-2-microglobulin, CA19-9, TPA, and/or in combination with the known proteins for the variant marker as described herein.

Markers of the present invention might optionally be used alone or in combination with known markers for ovarian cancer, including but not limited to NPC-1, 16C3, CEA, CA125 (Mucin 16), CA72-4TAG, CA-50, CA 54-61, CA-195 and CA 19-9 in combination with CA-125, and/or in combination with the known proteins for the variant marker as described herein.

Markers of the present invention might optionally be used alone or in combination with known markers for colon cancer, including but not limited to NPC-1, 16C3, CEA, CA 19-9, CA50, and/or in combination with the known proteins for the variant marker as described herein.

Typically the level of the marker in a biological sample obtained from the subject is different (i.e., increased or decreased) from the level of the same marker in a similar sample obtained from a healthy individual (examples of biological samples are described herein).

Determining the level of the same marker in normal tissues of the same origin may be effected along-side to detect an elevated expression and/or amplification and/or a decreased expression, of the marker as opposed to the normal tissues.

The present invention also provides methods, uses, devices and assays for the diagnosis of cancers such as non-solid and solid tumors, cancer of the breast, prostate, lung, ovary, colon, uterus, stomach, cervix, liver, pancreas, and wherein the cancer may be invasive or metastatic. Optionally a plurality of markers may be used with the present invention. The plurality of markers may optionally include a markers described herein, and/or one or more known markers. The plurality of markers is preferably then correlated with the disease or condition. For example, such correlation may optionally comprise determining the concentration of each of the plurality of markers, and individually comparing each marker concentration to a threshold level. Optionally, if the marker concentration is above or below the threshold level (depending upon the marker and/or the diagnostic test being performed), the marker concentration correlates with the disease or condition. Optionally and preferably, a plurality of marker concentrations correlates with the disease or condition.

Alternatively, such correlating may optionally comprise determining the concentration of each of the plurality of markers, calculating a single index value based on the concentration of each of the plurality of markers, and comparing the index value to a threshold level. Also, such correlating may optionally comprise determining a temporal change in at least one of the markers, and wherein the temporal change is used in the correlating step.

Such correlating may optionally comprise determining whether at least "X" number of the plurality of markers has a concentration outside of a predetermined range and/or above or below a threshold (as described above). The value of "X" may optionally be one marker, a plurality of markers or all of the markers; alternatively or additionally, rather than including any marker in the count for "X", one or more specific markers of the plurality of markers may optionally be required to correlate with the disease or condition (according to a range and/or threshold).

Correlating may optionally comprise determining whether a ratio of marker concentrations for two markers is outside a range and/or above or below a threshold. Optionally, if the ratio is above or below the threshold level and/or outside a range, the ratio correlates with the disease or condition. Optionally, a combination of two or more these correlations may be used with a single panel and/or for correlating between a plurality of panels. Optionally, the method distinguishes a disease or condition with a sensitivity of at least 70% at a specificity of at least 85% when compared to normal subjects. As used herein, sensitivity relates to the number of positive (diseased) samples detected out of the total number of positive samples present; specificity relates to the number of true negative (non-diseased) samples detected out of the total number of negative samples present. Preferably, the method distinguishes a disease or condition with a sensitivity of at least 80% at a specificity of at least 90% when compared to normal subjects. More preferably, the method distinguishes a disease or condition with a sensitivity of at least 90% at a specificity of at least 90% when compared to normal subjects. Also more preferably, the method distinguishes a disease or condition with a sensitivity of at least 70% at a specificity of at least 85% when compared to subjects exhibiting symptoms that mimic disease or condition symptoms.

A marker panel may be analyzed in a number of fashions well known to those of skill in the art. For example, each member of a panel may be compared to a "normal" value, or a value indicating a particular outcome. A particular diagnosis/prognosis may depend upon the comparison of each marker to this value; alternatively, if only a subset of markers is outside of a normal range, this subset may be indicative of a particular diagnosis/prognosis. The skilled artisan will also understand that diagnostic markers, differential diagnostic markers, prognostic markers, time of onset markers, disease or condition differentiating markers, may be combined in a single assay or device. Markers may also be commonly used for multiple purposes by, for example, applying a different threshold or a different weighting factor to the marker for the different purpose(s).

The panels may comprise markers for the following purposes: diagnosis of a disease; diagnosis of disease and indication if the disease is in an acute phase and/or if an acute attack of the disease has occurred; diagnosis of disease and indication if the disease is in a non-acute phase and/or if a non-acute attack of the disease has occurred; indication whether a combination of acute and non-acute phases or attacks has occurred; diagnosis of a disease and prognosis of a subsequent adverse outcome; diagnosis of a disease and prognosis of a subsequent acute or non-acute phase or attack; disease progression (for example for cancer, such progression may include for example occurrence or recurrence of metastasis).

The above diagnoses may also optionally include differential diagnosis of the disease to distinguish it from other diseases, including those cancers such as non-solid and solid tumors, cancer of the breast, prostate, lung, ovary, colon, uterus, stomach, cervix, liver, pancreas, and wherein the cancer may be invasive or metastatic that may feature one or more similar or identical symptoms.

One or more diagnostic or prognostic indicators are correlated to a condition or disease by merely the presence or absence of the indicator(s). In other embodiments, threshold level(s) of a diagnostic or prognostic indicator(s) can be established, and the level of the indicator(s) in a patient sample can simply be compared to the threshold level(s). The sensitivity and specificity of a diagnostic and/or prognostic test depends on more than just the analytical "quality" of the test—they also depend on the definition of what constitutes an abnormal result. In practice, Receiver Operating Characteristic curves, or "ROC" curves, are typically calculated by plotting the value of a variable versus its relative frequency in "normal" and "disease" populations, and/or by comparison of results from a subject before, during and/or after treatment.

A33 antigens may be featured as a biomarker for detecting cancers such as non-solid and solid tumors, cancer of the breast, prostate, lung, ovary, colon, uterus, stomach, cervix, liver, pancreas, and wherein the cancer may be invasive or metastatic.

The present invention optionally and preferably encompasses any amino acid sequence or antibody fragment thereof encoded by a nucleic acid sequence corresponding to A33 antigens as described herein. Any oligopeptide or peptide relating to such an amino acid sequence or antibody fragment thereof may optionally also (additionally or alternatively) be used as a biomarker.

The present invention provides a method for detecting a polynucleotide of this invention in a biological sample, using NAT based assays, comprising: hybridizing the isolated nucleic acid molecules or oligonucleotide fragments of at least about a minimum length to a nucleic acid material of a biological sample and detecting a hybridization complex; wherein the presence of a hybridization complex correlates with the presence of the polynucleotide in the biological sample. Non-limiting examples of methods or assays are described herein. The present invention also relates to kits based upon such diagnostic methods or assays.

Additionally, the NEO-300 antibody (e.g., NEO-301, NEO-302, NEO-303) or antigen-binding fragments thereof may be used to detect the 31.1 epitope on A33 antigen as a specific biomarker for pancreas and colon cancer, and can be measured in biopsied tissue as well as in subject serum and fecal samples, as described herein. Additionally, diagnostic procedures used to detect colorectal cancer including but not limited to fecal occult blood test (FOBT), colonoscopy, computed tomographic colonography (virtual colonoscopy) [detects colorectal lesions larger than 6 mm in diameter with the same sensitivity as colonoscopy], flexible sigmoidoscopy, double-contrast barium enema, and digital rectal examination. Winawer, et al. (1997) *Am J. Gastoenterology* 112: 594-642; Blum (1995) *Eur. J. Canc.* 31: 1369-72; Ransohoff & Sandler (2002) *N. Engl. J. Med.* 346: 346-44; Bruzzi (2002) *N. Engl. J. Med.* 346: 1672-74; and Laghi, et al. (2002) *Am. J. Surg.* 183: 124-31.

Immunoassays

The NEO-300 antibody and antigen-binding fragments thereof that bind the A33 antigen, may be used in immunoassays to qualitatively or quantitatively detect and analyze markers in a sample. This method comprises providing an NEO-300 antibody (e.g., NEO-301, NEO-302, NEO-303) or antigen-binding fragments thereof, contacting a sample with the antibody; and detecting the presence of a complex of the antibody bound to the marker in the sample.

An A33 antigen may be detected and/or quantified using any of a number of well recognized immunological binding assays using a NEO-300 antibody (e.g., NEO-301, NEO-302, NEO-303) or antigen-binding fragments thereof. Useful assays include, for example, an enzyme immune assay (EIA) such as enzyme-linked immunosorbent assay (ELISA), a radioimmunoassay (RIA), a Western blot assay, or a slot blot assay. See, e.g., U.S. Pat. Nos. 4,366,241;

4,376,110; 4,517,288; and 4,837,168. Generally, a sample obtained from a subject can be contacted with the antibody specifically binds the A33 antigen.

Optionally, the antibody can be fixed to a solid support to facilitate washing and subsequent isolation of the complex, prior to contacting the antibody with a sample. Examples of solid supports include but are not limited to glass or plastic in the form of, e.g., a microtiter plate, a stick, a bead, or a microbead. Antibodies may be attached to a solid support.

After incubating the sample with antibodies, the mixture is washed and the antibody-marker complex formed may be detected. This can be accomplished by incubating the washed mixture with a detection reagent. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations. Usually the assays will be carried out at ambient temperature, although they can be conducted over a range of temperatures (e.g., 10° C.–40° C.).

The immunoassay can be used to determine a test amount of a marker in a sample from a subject. First, a test amount of a marker in a sample may be detected using the immunoassay methods described above. If a marker is present in the sample, it will form an antibody-marker complex with an antibody specifically binds the marker under suitable incubation conditions described above. The amount of an antibody-marker complex can optionally be determined by comparing to a standard. As noted above, the test amount of marker need not be measured in absolute units, as long as the unit of measurement can be compared to a control amount and/or signal. Several immunoassays are known in the art and the NEO-300 antibody (e.g., NEO-301, NEO-302, NEO-303) or antigen-binding fragments thereof described herein may be used in such immunoassays including but not limited to radio-immunoassay (RIA), enzyme linked immunosorbent assay (ELISA), lateral flow assay, magnetic immunoassay, immunoblot, Western blot, immunoprecipitation assays, immunohistochemical analysis, and fluorescence activated cell sorting (FACS). See Wild, (2008) [Ed.] *The Immunoassay Handbook* [3rd Ed.] Elsevier.

Radio-Imaging Methods

The NEO-300 antibody and antigen-binding fragments thereof that bind the A33 antigen, may be used in radio-imaging methods to diagnosis cancer including pancreatic and colorectal cancer, or monitor the progression of tumors. These methods include but are not limited to, positron emission tomography (PET) single photon emission computed tomography (SPECT). Both of these techniques are non-invasive, and can be used to detect and/or measure a wide variety of tissue events and/or functions, such as detecting cancerous cells for example. SPECT may optionally be used with two labels simultaneously. See U.S. Pat. No. 6,696,686.

Commercial Applications and Methods

The present invention further provides for the production of NEO-300 antibody (e.g., NEO-301, NEO-302, NEO-303) or antigen-binding fragments thereof to reach commercial quantities. The NEO-300 antibody (e.g., NEO-301, NEO-302, NEO-303) or antigen-binding fragments thereof may be produced on a large scale, stored if necessary, and supplied to hospitals, clinicians or other healthcare facilities.

Methods of production, storage, and distribution of NEO-300 antibody (e.g., NEO-301, NEO-302, NEO-303) or antigen-binding fragments thereof may be produced by the methods disclosed herein. Following production, the NEO-300 antibody (e.g., NEO-301, NEO-302, NEO-303) or antigen-binding fragments thereof may be harvested, purified, and optionally stored prior to a patient's treatment. For example, once a patient presents with an indication such as, for example, pancreatic, colorectal, esophageal, oral, or breast cancer, a NEO-300 antibody (e.g., NEO-301, NEO-302, NEO-303) or antigen-binding fragments thereof may be ordered and provided in a timely manner. Accordingly, the present invention relates to methods of producing A33 antigen to attain antibodies on a commercial scale, pharmaceutical compositions comprising antibodies and antigen binding fragments thereof which selectively bind to A33 antigen, as well as methods of providing (i.e., producing, optionally storing, and selling) antibodies and antigen binding fragments thereof which selectively bind to A33 antigen to hospitals and clinicians. The production of NEO-300 antibody (e.g., NEO-301, NEO-302, NEO-303) or antigen-binding fragments thereof may be scaled up for commercial use.

The present invention also provides for methods of conducting a pharmaceutical business comprising establishing a distribution system for distributing the preparation for sale or may include establishing a sales group for marketing the pharmaceutical preparation.

All publications (e.g., Non-Patent Literature), patents, patent application publications, and patent applications mentioned in this specification are indicative of the level of skill of those skilled in the art to which this invention pertains. All such publications (e.g., Non-Patent Literature), patents, patent application publications, and patent applications are herein incorporated by reference to the same extent as if each individual publication, patent, patent application publication, or patent application was specifically and individually indicated to be incorporated by reference.

EXAMPLES

The invention now being generally described, it will be more readily understood by reference to the following examples, which are included merely for purposes of illustration of certain aspects and embodiments of the present invention, and are not intended to limit the invention.

Example 1

Characterization of A33 Antigen

The 31.1 antibody is reactive with human colon and pancreatic cancer tissues and is believed to bind the A33 antigen but its epitope was unknown. To confirm and identify the antigen bound by the 31.1 antibody, the A33 antigen was tested under various conditions for binding to the 31.1 antibody. As discussed herein, the 31.1 antibody was confirmed to bind human A33 antigen as demonstrated by Western blot, immunoprecipitation (IP), mass spectroscopy, dot blot, flow cytometry, and ELISA. Further, the epitope is non-linear due to the sensitivity to detergents and negative binding results on reducing condition in western Blot.

Controls

An A33 antigen expression cell line was made by transfecting a vector comprising a full length of A33 cDNA into an A33 negative CHO cell line. A33 expressing CHO cells were selected and used as positive control cells (A33-CHO). AS33 antibody, which binds to A33 antigen, was purified from hybridoma cells. A33-CHO cells and AS33 antibody were used as positive control antibody in this study.

The 31.1 antibody binds to A33-CHO in a dose-dependent manner but does not bind the parent CHO cells in Flow Cytometry. Different concentrations of 31.1-biotin antibody were added to 100 □l of A33-CHO or CHO cells at $1\times10^6$ cell/ml in PBS in 96 well plates and incubated at room temperature for 30 minutes. After washing cells 3 times with PBS, 100 □l of diluted streptavidin-FITC was added to the cells and incubated for another 30 minutes at room temperature. After washing three times with PSB, the cells were analyzed by Guava ExpressPro program in Guava Easycyte instrument. Human IgG-biotin was used as isotype control. The results showed dose-dependent 31.1 antibody binding to the A33-CHO cells.

The 31.1 antibody may detect the antigen in 31.1 IP proteins from LS 174T and A33-CHO, but not in AS33 IP proteins from both cells in Western Blot under non-reducing condition. AS33 binds to the antigen in 31.1 and AS33 IP proteins from LS174T and A33-CHO. However, 31.1 did not detect 31.1 IP protein under reducing condition by Western blotting, suggesting that the 31.1 epitope is non-linear or conformational.

The 31.1 antibody can also detect 31.1 IP proteins specifically by Dot Blot. 2 □l 31.1 IP proteins were added to nitrocellulose paper. After air drying the paper, 31.1-biotin was incubated with the blocked and washed paper for 30 minutes at room temperature. Streptavidin-HRP was incubated with washed paper for another 30 minutes at room temperature. The washed paper was incubated with ECL reagent for 1 minute, covered with Saran wrap and exposed X-ray film in a dark room.

31.1 antibody-captured human recombinant A33 can be detected by AS33 antibody in sandwich ELISA. The plate was coated with 31.1 at 10 □g/ml for 1 hour at 37° C. and blocked with 1% milk, 5 mM EDTA-TBS; after washing plate with TBST, human recombinant A33 antigen was added to the plate and incubated for 1 hour at room temperature. After three washes with TBST, different concentrations of AS33-biotin was added to the plate and incubated for 1 hour at room temperature. Streptavidin-HRP was added to the washed plate and incubated for another 1 hour at room temperature. TMB was added to the washed the plate for 20 minutes at room temperature. The plate was read at 450 nm immediately after adding 1N HCL to stop the reaction. The results demonstrated 31.1 captured A33 antigen comprises the antigen, which can be detected with AS33 antibody, suggesting 31.1 and AS33 antibodies target different epitopes of the A33 antigen.

Characterization of A33 Antigen

Heat treatment: transferring 5 μl (microliters) ddH2O diluted LS 174T 31.1 IP protein (1:1 diluted) into PCR tubes; total 5 tubes. Placing 4 tubes into preheated 100° C. wells in PCR machine and removing one tube each time at 5, 15, 30, and 60 minutes. The tube without heating is 0 minutes.

Protease digestion: mixing 3 μl of Pronase E (1 mg/ml) or ddH2O with 3 μl LS174T IP protein and incubating the mix at 37° C. for 24 hours. ddH2O treatment was used for control. For perioxidate oxidation: Mixing 2 μl of 40 mM perioxidate oxidation (dissolved in 50 mM sodium acetate) with 2 μl LS 74T 31.1 IP protein and incubating the mix at room temperature for 60 minutes. 50 mM sodium acetate was used as digestion buffer control. For 2ME and DTT treatment: Adding 1 μl 2-ME or 1 μl of DTT (1M) to 4 μl LS174T 31.1 IP protein and incubating the mix at 95° C. for 5 minutes. ddH2O was used for controls.

The treated samples were tested by Dot Blot. 2 μl treated 31.1 IP proteins were added to nitrocellulose paper. After air drying the paper, 31.1-biotin was incubated with the blocked and washed paper for 30 minutes at room temperature. Streptavidin-HRP was incubated with washed paper for another 30 minutes at room temperature. The washed paper was incubated with ECL reagent for 1 min. covered with Saran wrap and exposed X-ray film in dark room. LS174T 31.1 IP protein was used for positive control in this Dot Blot experiment. The results demonstrated 31.1 antigen is heat resistant (99 degrees C. for 5 minutes) and sensitive to the treatment of Protease, Periodate oxidation and reducing reagents (2-ME and DTT). It suggested 31.1 antigen is protein and disulfide bonds may be necessary for maintaining the conformation that is recognized by 31.1 antibody.

The 31.1 antibody does not cross react with mouse recombinant A33 in sandwich ELISA and IHC staining. Western blot studies suggest that the 31.1 targeted antigen has a molecular weight of about 37-50 Kd. Further, mass spectroscopy results from 31.1 IP proteins from LS 174T suggested A33 may be the targeted protein. 31.1 IP protein sample was separated on two 4-15% precast SDS-PAGE gels. The band between 37 kD and 50 kD was cut out from one gel for mass spectroscopy and another gel was used for Western blot probed with 31.1-biotin.

Identification of 31.1 Epitope on A33 Antigen

The full length of A33 amino acid sequence and the peptides from LS174T IP protein below, where the highlight shows the peptide sequences from LS174T 31.1 IP which are bound by the 31.1 monoclonal antibody (39% coverage of the total A33 sequence was identified) (a predicted 31.1 epitope is shown in bold).

(SEQ ID NO: 10)

1 MVGKMWPVLW TLCAVRVTVD AISVETPQDV LRASQGKSVT LPCTYHTSTS SREGLIQWDK

61 LLLTHTERVV IWPFSNKNYI HGELYKNRVS ISNNAEQSDA SITIDQLTMA DNGTYECSVS

121 LMSDLEGNTK SRVRLLVLVP PSKPECGIEG ETIIGNNIQL TCQSKEGSPT PQYSWKRYNI

181 LNQEQPLAQP ASGQPVSLKN ISTDTSGYYI CTSSNEEGTQ FCNITVAVRS PSMNVALYVG

241 IAVGVVAALI IIGIIIYCCC CRGKDDNTED KEDARPNREA YEEPPEQLRE LSREREEEDD

301 YRQEEQRSTG RESPDHLDQ

The 31.1 antibody detected the antigen in 31.1 IP proteins from LS174T and A33-CHO, but not in AS33 IP proteins from both cells in Western blot under non-reducing condition. AS33 binds to the antigen in 31.1 and AS33 IP proteins from LS 174T and A33-CHO, which suggested that 31.1 and AS33 antibodies target different epitopes of A33 antigen. As the 31.1 antibody may not detect 31.1 IP protein in reducing condition, this suggests that the 31.1 antibody's epitope is non-linear epitope.

Thus, the epitope on the A33 antigen bound by 31.1 antibody was found to be heat resistant at 99° C. for 5 minutes, up to 15 minutes, but binding was lost after 30 and 60 minutes of heating. The 31.1 antigen was further characterized by protease and periodate oxidation treatment. The results suggests that 31.1 antigen is protease and periodate oxidation sensitive protein. The 31.1 antigen was found to be sensitive to 2-mercaptoethanol and DTT (both well-known reducing agents) in western blot and dot blot. Therefore, the 31.1 epitope bound by the 31.1 antibody on the A33 antigen is believed to be a non-linear epitope due to the observation of band disappear on reducing condition with 2-ME and DTT on Western blot and dot blot.

The epitope on the A33 antigen bound by 31.1 antibody was not sensitive to deglycosylation was found with treatment with N-glycanase (PNGase F), O-glycanase, sialidase, and neuraminidase. In contrast, the NPC-1 antigen is sensitive to both sialidase and neuraminidase treatment. The deglycosylation results suggest that no carbohydrate moieties are involves 31.1 antibody binding to the 31.1 epitope.

Example 2

Monoclonal NEO-300 Antibodies Directed Against Immunogenic Tumor Specific Protein The NEO-301 antibodies described herein were developed against immunogenic tumor proteins (Tumor Specific Antigens/TSA's) that are expressed in human cancers as described in Example 1. The NEO-300 antibodies described herein may be used for the early recognition of A33 as a diagnostic marker, and the targeting of such markers for the destruction of the tumor, primarily through ADCC. The NEO-300 antibodies described herein may be used in the detecting and treatment of colon and pancreas cancer (e.g., the NEO-300 antibodies induce apoptosis of cancer and pancreatic tumor cells). The NEO-300 antibodies, i.e., murine 31.1 appeared for the most part to be IgG2a's. The NEO-301 antibody underwent chimerization (NEO-301) and humanization (NEO-302). The resulting monoclonal antibodies were found to switch their isotypes to an IgG1 subsequent to chimerization or humanization, when expressed in CHO cells. These chimeric monoclonals were not only more efficient in controlling tumor growth but minimized the development of a HAMA response. Because of the specificity of the NEO-300 antibodies (chimeric NEO-300) in targeting well defined immunogenic proteins that were expressed on the tumor cell membrane, they lack of cross reactivity to normal tissue, have relatively low toxicity when delivered intravenously, show rapid targeting of tumor cell populations (4-6 hours in vitro) and destroy xenograft transplants (in vivo) within days of delivery. Further, it is possible to combine the NEO-300 antibodies with immunostimulants such as GMCSF and IL-2 (fusion proteins) or conjugate them with alpha and beta-emitters.

The chimeric or humanized NEO-300 antibodies (e.g., NEO-301), when administered intravenously in high therapeutic doses, can initiate tumor destruction within hours of IV administration. They circulate with a half life exceeding 10 days and show a localization index of better than 10:1, where the concentration of the monoclonal antibody fixed to the tumor is tenfold or greater than what remains in circulation.

Method Used to Determine Antibody Dependent Cell Cytotoxicity (ADCC)

A 4 hr. $^{51}$Cr or $^{111}$In release assay was used to measure antibody dependent cell cytotoxicity. The target cells, whether colon carcinoma, pancreatic carcinoma or lung squamous cancer cell lines, were obtained from the American Type Culture Collection (ATCC) in Rockville Md. Target cells were labeled with 200 μCi sodium $^{51}$chromate or the equivalent in radiolabelled indium in 0.2 ml fetal calf serum for 1 hour. Target cells, ($1\times10^4$ in 50 μl) were added to 96 U-bottom wells assay plates containing effector mononuclear cells. Effector to target cell ratios' of 100, 50, and 25 were assayed in the presence of the NEO-301 monoclonal antibody compared to normal IgG at monoclonal antibody concentrations of 2.5-5.0 μg/well. The plates were incubated for 4 hours at 37° C. in a humidified atmosphere containing 5% $CO_2$. Supernatants were harvested for gamma counting using Skatron Harvester Frames. Experiments were carried out in triplicate. Specific lysis was calculated. It appeared that 5.0 g/well of the NEO-301 antibodies produced optimum results and that the 100:1 E:T ratio produced the highest range of tumor destruction over a 4-6 hour period of time. Spontaneous release was determined by measuring the radioactivity released from target cells incubated in medium alone. Total releasable radioactivity was obtained after treatment with 2.5% Triton X-100. Another method of tabulating data is in terms of "lytic units". Such units can be calculated where one lytic unit is defined as the number of cells required to lyse 15% of a population of $5\times10^3$ target cells in a 6-hour assay. Lytic unit values are then expressed as mean±standard error of the mean. The MTT assay is a similar laboratory test for antibody cytotoxicity using a standard colorimetric assay (an assay which measures changes in color) for measuring cellular proliferation (cell growth). The amount of yellow MTT (3-(4,5-Dimethylthiazol-2-yl)-2,5-diphenyltetrazolium bromide) oxidized to purple formazan (see figure) is measured spectrophotometrically. This oxidation takes place only when mitochondrial reductase enzymes are active, and thus conversion is directly related to the number of viable cells. The production of purple formazan in cells treated with an agent is measured relative to the production in control cells, and a dose-response curve can be generated.

These methods provide the capability for accurately quantifying the intensity of their staining capabilities, and the % of reactive cells expressing the relevant cell surface target antigen. The binding of the monoclonal antibodies have varied with the tumor population studied, but combinations of NEO-301 antibodies have shown that tumor recognition can be optimized to offer a superior response. ADCC was used as an in vitro assay for tumor cytotoxicity demonstrating that the NEO-301 antibodies were associated with a 50-60% or better rate of tumor cell destruction. This process was found to occur in vitro, over a 4-6 hour period of time. The rate of destruction of tumor cells was tested by a chromium or indium release assay.

In an analysis of the ability of a carbohydrate monoclonal antibody such as CA 17.1A to induce apoptosis in colon cancer cells, was compared to NEO-301 (which binds the 31.1 epitope on A33 antigen). The results are shown in FIG. 3.

To evaluate the specificity of the ADCC response to several tumor types and to controls, NEO-301, CA 19.9 (a carbohydrate monoclonal antibody showing activity in pancreatic neoplasms as well as some colorectal lesions) and UPC-10 (a myeloma antibody was used as the control) were examined for their ability to lyse pancreatic and colon cancer cell lines.

TABLE 4

In[111] labeled target cells, antibodies used at 5 □g/ml, human PBMC used as effector cells, 4 hour incubation at 37° C. before harvest.

| Target | Effector:Target Ratio | % Specific ADCC Activity (±SEM) NEO-301 | CA 19-9 | UPC-10 negative control |
|---|---|---|---|---|
| SW1463 | 100:1 | 51.0 ± 1.3 | 2.0 ± 1.2 | 3.4 ± 0.8 |
| | 50:1 | 36.0 ± 1.0 | 1.9 ± 0.1 | 1.1 ± 0.8 |
| | 25:1 | 24.4 ± 1.7 | 1.6 ± 0.3 | 1.3 ± 0.2 |
| AsPC-1 | 100:1 | 30.3 ± 1.3 | 19.5 ± 0.4 | 3.2 ± 0.9 |
| | 50:1 | 19.3 ± 1.3 | 1.4 ± 0.4 | 0.6 ± 0.5 |
| | 25:1 | 12.7 ± 0.1 | 3.3 ± 1.1 | −06 ± 1.9 |
| H441 | 100:1 | 5.0 ± 0.4 | 0.6 ± 3.0 | 3.0 ± 1.2 |
| | 50:1 | 5.2 ± 3.6 | 1.8 ± 0.6 | −0.5 ± 0.4 |
| | 25:1 | 6.7 ± 0.6 | 1.0 ± 0.2 | 0.1 ± 0.5 |
| MCF-7 | 100:1 | 2.4 ± 0.3 | 2.5 ± 0.5 | 2.6 ± 0.8 |
| | 50:1 | 2.4 ± 0.5 | 1.7 ± 0.1 | 1.8 ± 0.3 |
| | 25:1 | 2.8 ± 0.4 | 2.5 ± 0.2 | 1.7 ± 0.1 |

TABLE 5

Chimeric NEO-301 monoclonal antibody in a secondary study indicates the strong ADCC activity of chimeric NEO-301 monoclonal antibody against colon and pancreatic cancer cell lines.

| Tumor Cell Line | Effector:Target Ratio | % Specific Killing Neg. Control | NEO-301 |
|---|---|---|---|
| SW1463 (Colorectal) | 100:1 | 3.4 | 51.0 |
| | 50:1 | 1.1 | 36.0 |
| | 25:1 | 1.3 | 24.4 |
| AsPC-1 (Pancreatic) | 100:1 | 3.2 | 30.3 |
| | 50:1 | 0.6 | 19.3 |
| | 25:1 | −0.6 | 12.7 |
| MCF-7 (Breast) | 100:1 | 2.6 | 2.4 |
| | 50:1 | 1.8 | 2.4 |
| | 25:1 | 1.7 | 2.8 |

In order to evaluate the potential for a clinical response initiated by NEO-301 (chimeric NEO-300), an in vivo murine model was designed. A therapeutic situation was used to evaluate the effect of the antibody on fully established tumors in mice. Control animals (nude mice) were primed by injecting 2 million of either human colon adenocarcinoma or pancreatic adenocarcinoma cells (obtained from ATCC) into the hind legs of the animals. Each animal (7per group) were studied for the appearance and progression of tumor cell growth. At 10 days following injection, clinical tumor masses appeared from 2-3 cm in diameter and progressed so that within 10 to 15 days each animal was limping and having difficulty in functioning. At the end of following week each animal appeared pre terminal. The experiment was then repeated, to test the ability of the monoclonals to control tumor growth by indicating regression of the established tumor mass. Groups were divided to receive the 2 million cancer cells noted above, by subcutaneous injections in the leg. On the 10th day of the experiment one group was given 400 μg of non-specific human IgG with human effector cells intraperitoneally. This was performed as a negative control to rule out the ability of nonspecific IgG in the presence of effector cells to elicit an apoptotic effect on the growing human tumor. A second injection of antibody was given on day 11. The second group that received tumor cells was given the therapeutic antibody NEO-301 without the potential benefit of effector cells. This second arm was employed to evaluate if any additional mechanism other than NK cell activity induced tumor destruction. The third group received both intraperitoneal monoclonal antibody plus human effector cells. It became readily apparent that without the proper monoclonal antibody, non-specific human IgG in conjunction with human effector cells had no response on tumor growth and the masses appearing on the animals' upper leg continued progressing. Therapeutic monoclonals given without effector cells did have some capability of controlling growth of tumor suggesting that a "second", but lesser mechanism than ADCC might be coming into play. The NEO-300 antibody may act secondarily act as TRAIL ligands initiating apoptosis defined by annexin V binding. When the more detailed animal study was performed evaluating the NEO-301 antibody alone and in combination with effector cells to evaluate the initiation of tumor destruction thru a number of different means including its primary function in ADCC. See FIGS. 4, 5, and 6.

The effect of NEO-301 on the induction of apoptosis as defined by annexin V binding was examined. At the time of cell death, just prior to DNA destruction by the apoptosome, phosphoinosityl serine is transported to the surface of the tumor cell membrane where it binds to annexin V tagged with a fluorescent signal.

Figure 4:
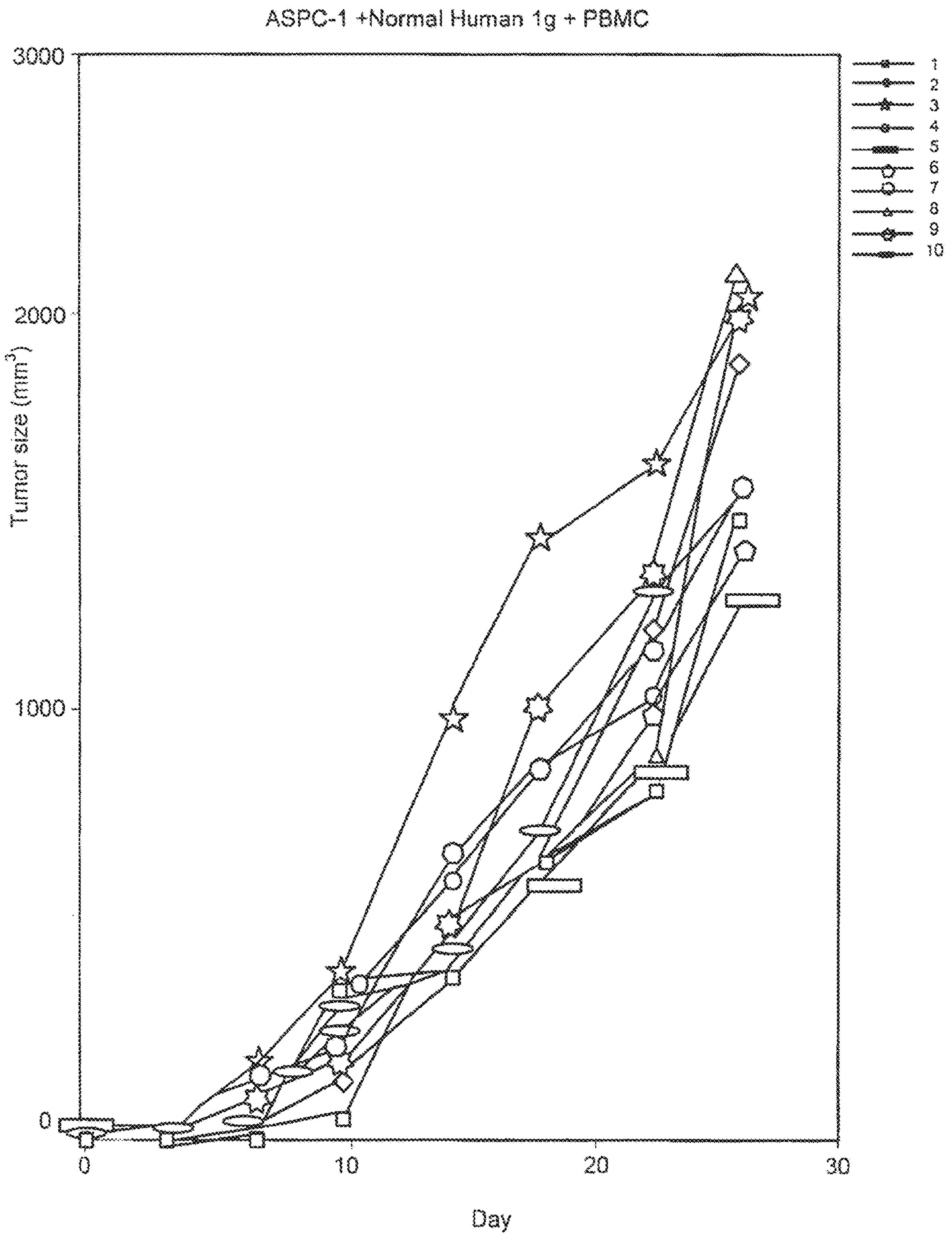
FIG. 4 depicts a control study of tumor growth showing no effect of human IgG on tumor growth over 30 days.

FIG. 4 depicts a control using normal IgG to substitute for the NEO-301 monoclonal antibody.

Figure 5:
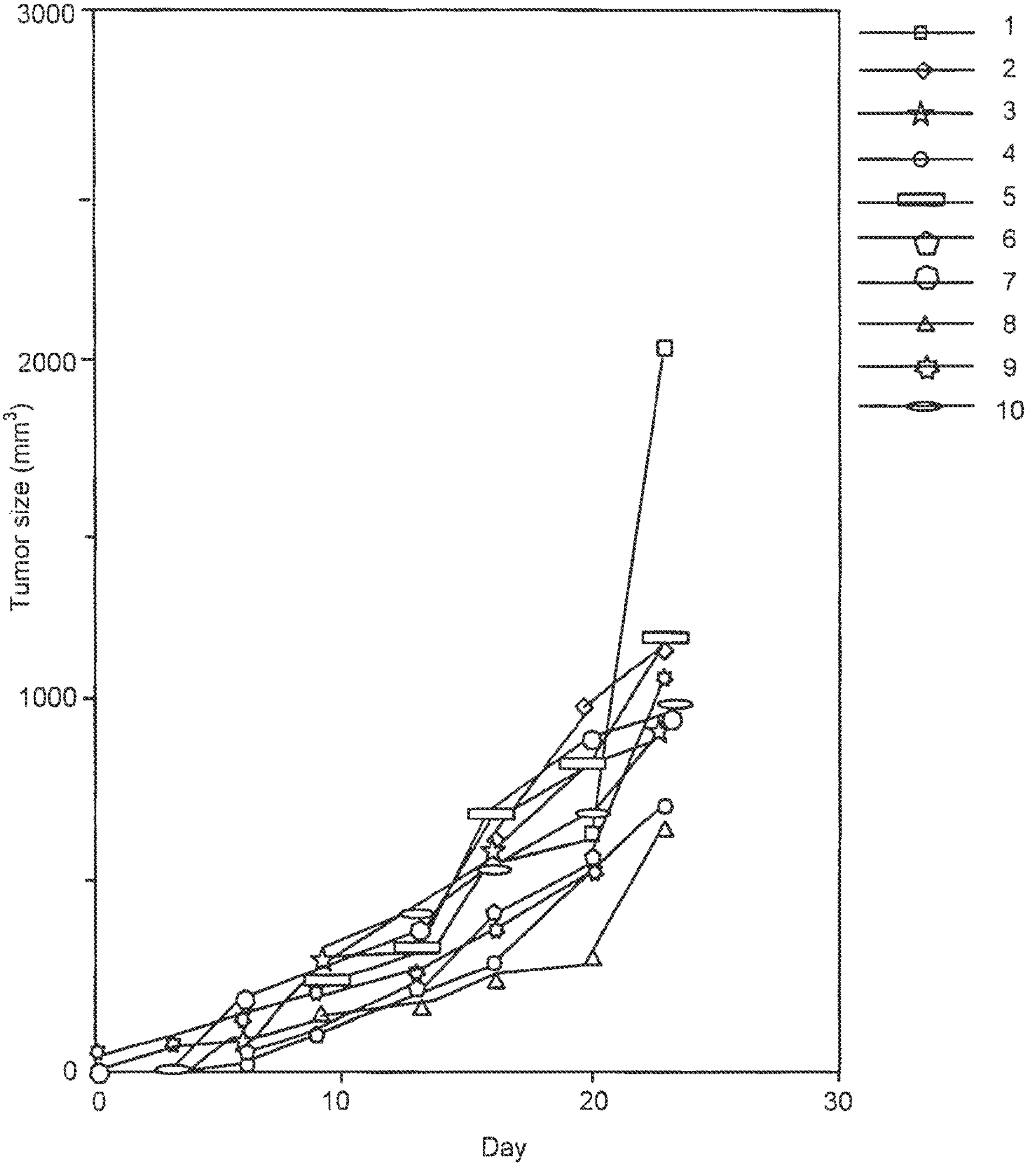
FIG. 5 depicts slowing of tumor growth after chimeric NEO-301 administration alone (monotherapy) over 30 days.

FIG. 5 depicts the slowing of tumor growth observed when NEO-301 monoclonal antibody is administered in the absence of human effector cells.

Figure 6:
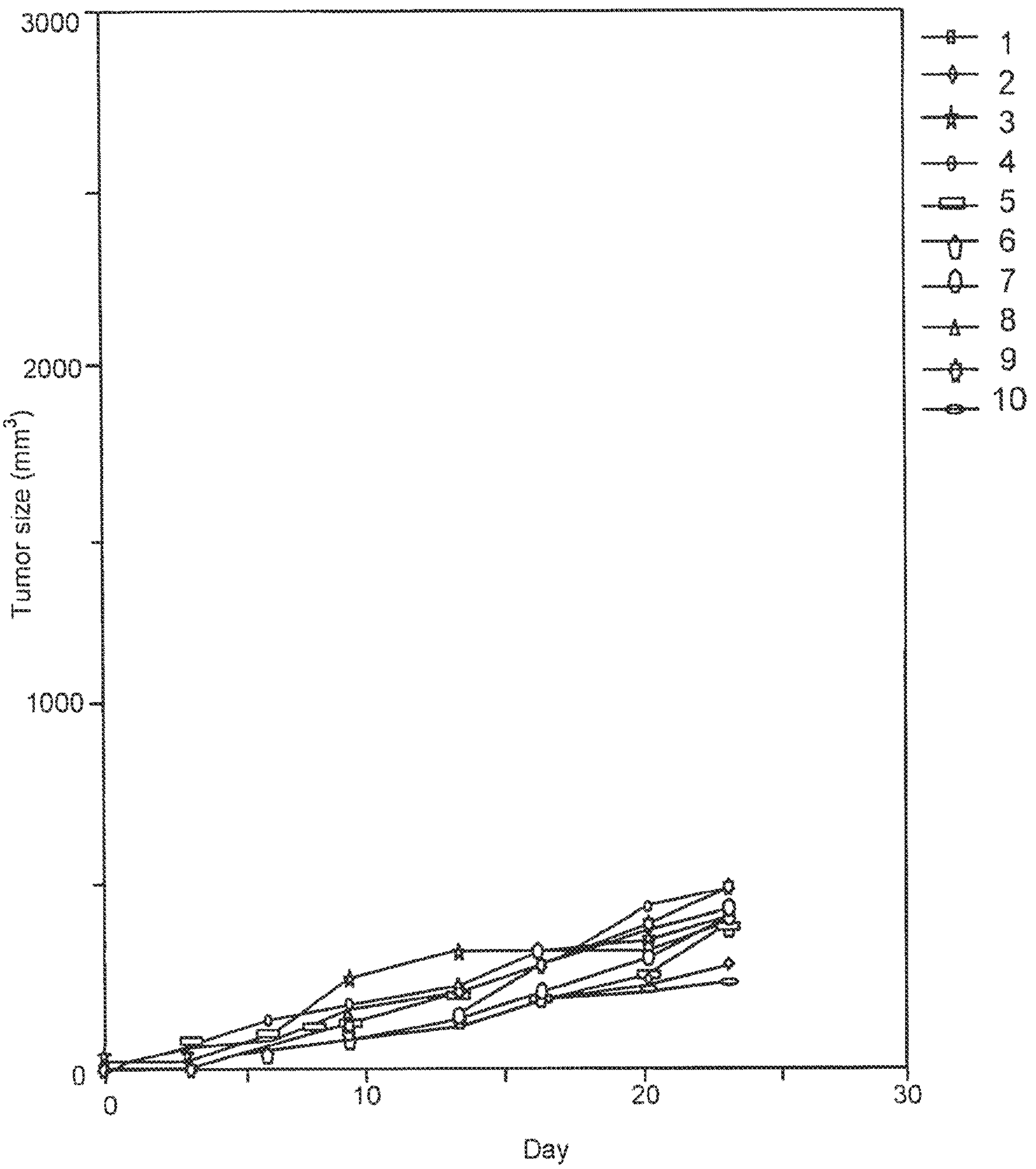
FIG. 6 depicts slowing of tumor growth after chimeric NEO-301 administration with human effector cells [PMNC (polymorphonuclear cells) (combination therapy)] over 30 days.

FIG. 6 depicts the ability of NEO-301 monoclonal antibody given in combination with human effector cells to slow growth of human tumors.

The results of the shift in phosphoinosityl serine to the outer cell membrane was observed in where treated and untreated pancreatic cancer cells were compared for the degree of annexin V binding. Examination of the data showed that the untreated group had an apoptosis rate of about 18.22%. This was found to have increased to 36.83% of the cells undergoing apoptosis in the treated group.

The effect of NEO-301 on VEGF expression was examined and it was demonstrated that a significant diminution in the level of these surface growth factors similar to what is seen with Herceptin (Table 6).

TABLE 6

Antibody suppression of VEGF production by PACA-2 cells by both NEO-301 and Herceptin.

| Antibody (□m/ml) | VEGF | % inhibition |
|---|---|---|
| Herceptin (100) | 116.9 | 43.3 |
| Herceptin (50) | 166.7 | 19.1 |
| NEO-301 (100) | 93.3 | 54.8 |
| NEO-301 (50) | 121.4 | 41.3 |
| 0 | 206.0 | 0 |

Based on these results, NEO-300 antibodies, alone or in combination with chemotherapy, may be used for the treatment of cancers that have failed standard chemotherapy. Further, the NEO-300 antibodies may be produced in a mammalian cell line such as CHO (dhfr-) at over 1000 mg/L of bioreactor fluid that contains no fetal calf serum. Both plasmid vectors carry a dhfr expression unit driven by an enhancer-deficient SV40 early promoter. The vector is inserted into the CHO-D-SFM (dihydrofolate reductase (dhfr)-deficient Chinese hamster ovary) cells in near serum-free medium supplemented with 1 □g/ml of MTX. At the end of the production, cells have to be adapted to serum free media before final purification of the antibody can occur.

In a single patient study with NEO-301 (chimeric NEO-300) against hepatic metastasis from pancreatic cancer, the HAMA response became minimally elevated in contrast to pretreatment levels. After 2 doses of the chimeric monoclonal antibody at 25 mg and 50 mg IV the serum marker for Ca 19.9 fell from 3000U to 300U. The HAMA prior to therapy was 5 nanogms/ml prior to administration of the monoclonal antibody and rose to 7 nanogms/L 2 weeks after the second and final dose was given. Further, the NEO-301 antibody demonstrates a minimal HAMA response and high levels of ADCC. Thus, doses of NEO-300 antibody of about 200 mg to 400 mg may be delivered every two weeks I.V. to patient and may be effective in controlling metastatic pancreatic or colorectal cancer.

Example 3

This example describes humanization of the chimeric 31.1 antibody (NEO-301) described in the foregoing examples. Humanization was carried out in order to produce an antibody having a lower risk for inducing immune responses when used in vivo in humans for therapeutic or diagnostic purposes.

Four humanized heavy chain sequences were produced (shown in FIGS. 1A-D) and four light chain sequences were produced (shown in FIGS. 2A-D). Coding sequences for each were synthesized and subcloned into PcDNA3.1(+) vector.

Methods for 31.1 Screening:

Human IgG ELISA, rH-GPA33 Binding ELISA, cell Flow Cytometry (LS174T or AsPAC1), IHC staining (LS174T FFPE, tumor FFPE and Frozen tumor sections) and Coomassie blue staining of SDS-PAGE gel were used for the screening. Antibody in the culture supernatant was purified by Protein A/G purification in the column and dissolved in PBS buffer after three times dialysis. Aliquots of the antibodies were kept at −20 degrees C. for storage.

Sixteen antibodies were tested comprising combinations of different designed humanized 31.1 HC and LC, along with the further construct A-31.1, chimeric 31.1 and murine 31.1, as shown in Table 5 below. Each combination was produced by transient transfection by using Expi293 Expression System Kit (Gibco, cat # A14635). The 6 days culture supernatants from 2 mL transient transfection were used for initial screening to examine the function of those antibodies; chimeric 31.1 lot #3310 was used for reference standard. Methods of Human IgG ELISA, rH-GPA33 Binding ELISA, LS 174T cell Flow Cytometry, IHC staining on LS 174T FFPE sections and Coomassic blue staining of SDS-PAGE gel were used for the initial screening. The antibody production from different combinations and results of screening are summarized in Table 5. 31.1 Catalent lot #3310 is chimeric 31.1 and used as a positive control.

TABLE 5

Summary of humanized 31.1 production and functions from different combinations of humanized 31.1 antibody chains in transient transfection

| Sample ID | Description | Yield (ug/mL) H IgG ELISA | OD Value of rH-GPA33 Binding ELISA (2 ug/mL of 31.1) | MFI LS174T Flow (0.37 ug/mL) | H-Score of IHC LS174T FFPE (20 ug/mL) |
|---|---|---|---|---|---|
| 1 | cdr-HC + cdr-LC | 260.1 | 0.80 | 878 | 0 |
| 2 | cdr-HC + abb-LC | 260.1 | 0.86 | 821 | 0 |
| 3 | cdr-HC + sdr-LC | 360.5 | 0.29 | 520 | 0 |
| 4 | cdr-HC + ven-LC | 165.5 | 1.27 | 726 | 0 |
| 5 | abb-HC + cdr-LC | 340.3 | 0.85 | 804 | 240/100* |
| 6 | abb-HC + abb-LC | 558 | 0.74 | 628 | 230/240 |
| 7 | abb-HC + sdr-LC | 617.1 | 0.20 | 481 | 120 |
| 8 | abb-HC + ven-LC | 280.5 | 1.20 | 934 | 125 |
| 9 | sdr-HC + cdr-LC | 712.3 | 0.07 | 6.65 | 150 |
| 10 | sdr-HC + abb-LC | 697.3 | 0.07 | 6.2 | 240/115 |
| 11 | sdr-HC + sdr-LC | 826.2 | 0.06 | 5.6 | 160 |
| 12 | sdr-HC + ven-LC | 390.8 | 0.06 | 10.6 | 30 |
| 13 | ven-HC + cdr-LC | 420.5 | 1.27 | 1149 | 20 |
| 14 | ven-HC + abb-LC | 295.9 | 1.44 | 1060 | 125/30 |
| 15 | ven-HC + sdr-LC | 650.1 | 0.46 | 689 | 90 |

TABLE 5-continued

Summary of humanized 31.1 production and functions from different combinations of humanized 31.1 antibody chains in transient transfection

| Sample ID | Description | Yield (ug/mL) H IgG ELISA | OD Value of rH-GPA33 Binding ELISA (2 ug/mL of 31.1) | MFI LS174T Flow (0.37 ug/mL) | H-Score of IHC LS174T FFPE (20 ug/mL) |
|---|---|---|---|---|---|
| 16 | ven-HC + ven-LC | 209.5 | 1.74 | 966 | 0/0 |
| 17 | A-31.1 | 3.1 | 0.06 | 7.6 | 0 |
| 18 | Chimeric 31.1 | 10.5 | 0.38 | 116 | 70 |
| 19 | Mouse 31.1 | 102 | UD | UD | 0 |
| | 31.1Catalent Lot#3310 | | 0.99 | 985 | 0 |

*repeat results

The humanized IgG productions varied from 165.5 ug/mL to 826.2 ug/mL except A-31.1 and chimeric 31.1. 102 ug/mL murine IgG was obtained. Comparable binding capabilities with Chimeric 31.1 lot 3310 tested by rHGPA33 binding ELISA and LS174T flow cytometry were observed in cdr-HC, abb-HC and ven-HC combination with four different LC except sdr-HC.

Positive staining on LS 174T FFPE tissue blocks were obtained in a few of the supernatants with poor reproducibility except one supernatant from abb-HC and abb-LC.

Figure 7:
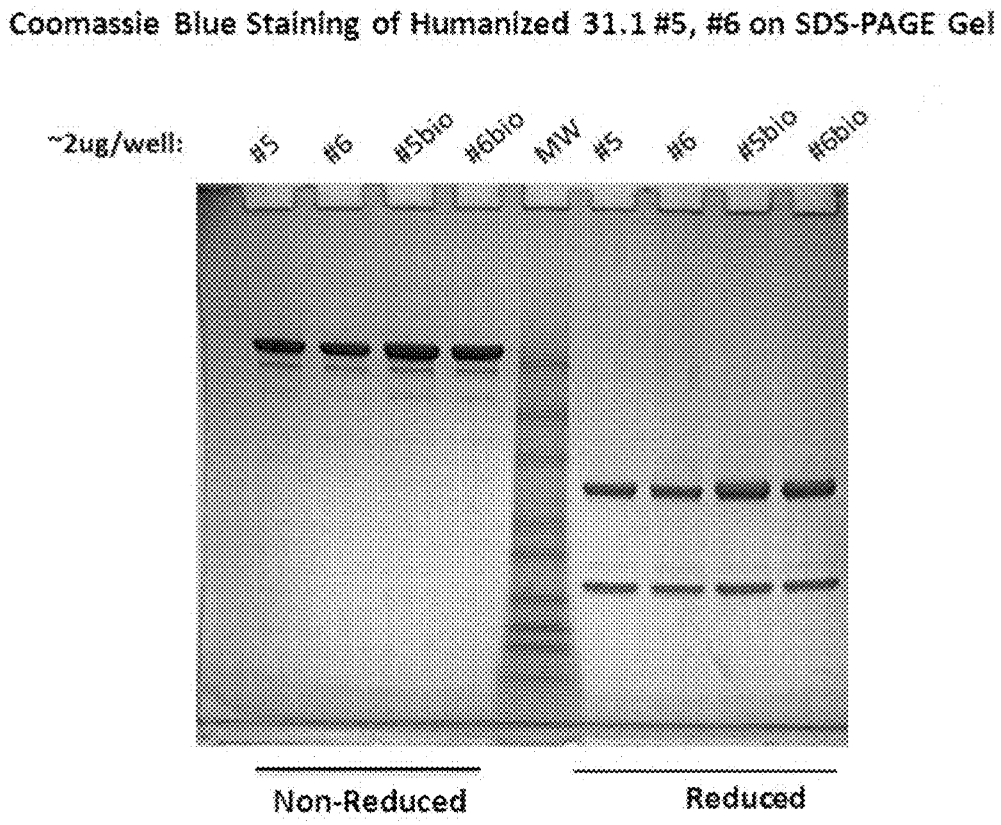
FIG. 7 shows Coomassie blue staining of two humanized 31.1 antibodies, namely #5 and #6, under non-reduced and reduced conditions.

Based on the initial screening results, antibody #5 (abb31.1-HC+cdr31.1-LC, i.e., SEQ ID NOs:75 and 84) and antibody #6 (abb31.1-HC-abb31.1-LC, i.e., SEQ ID NOs:75 and 85) were selected for future characterization. Additional antibody was produced by 240 mL volume transient transfection (120 mL×2 flask, each). The reason for selection #5 and #6 is that both antibodies worked in IHC staining on FFPE LS174T sections with relatively high antibody production, moderate rH-GPA33 binding and MFI in Flow Cytometry. Coomassie blue staining of SDS-PAGE gel was to use to examine the purity and integrity of purified antibodies #5, #6 and biotinlyated #5, #6. As shown in FIG. 7, the good purity of those antibodies was observed in non-reducing conditions (left), and integrity of light chain and heavy chain was shown in the reducing condition (right) on all tested antibodies.

Figure 8:
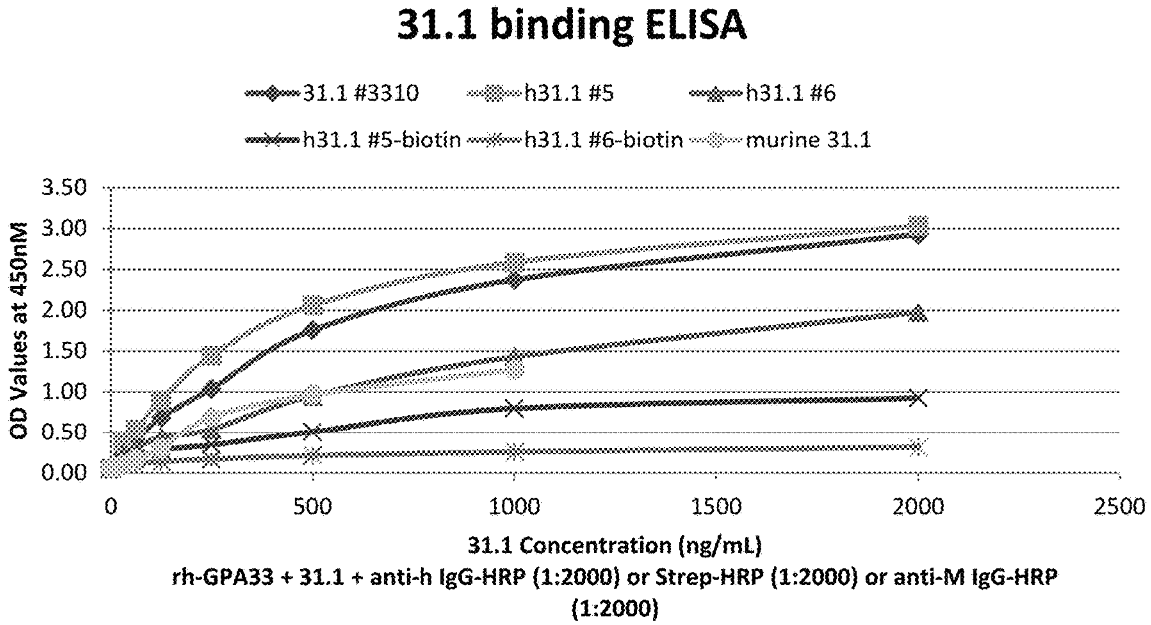
FIG. 8 shows the results of EISA assays using two humanized 31.1 antibodies, namely #5 and #6, as well as biotinylated forms thereof.

The function of humanized 31.1 #5, #6 and biotinylated #5, #6 were tested by rH-GPA33 binding ELISA and Flow Cytometry. The chimeric 31.1 and murine 31.1 were used as control. The results from binding ELISA are shown in FIG. 8. The same binding capacity of h31.1 #5 and chimeric 31.1 was obtained in binding ELISA and was confirmed by Flow Cytometry on both pancreatic cell line (AsPC-1) and colon cancer cell line (LS 174T). The results from both function in vitro assays are summarized in Table 6.

TABLE 6

Binding ELISA and flow cytometry results using chimeric 31.1 antibody, humanized 31.1 #5, #6 and biotinylated #5, #6.

| | EC50 from binding ELISA (ng/mL) | EC 50 from Flow Cytometry (ng/mL) AsPC-1 | EC50 from Flow Cytometry (ng/mL) AsPC-1 | EC50 from Flow Cytometry (ng/mL) LS-174T |
|---|---|---|---|---|
| Chi 31.1 #3310 | 696.9 | 140.88 | 96.65 | 77.73 |
| H 31.1 #5 | 396.4 | 235.05 | 122.5 | 62.53 |
| H 31.1 #6 | 1234.7 | 276.08 | 151.6 | 80.91 |

TABLE 6-continued

Binding ELISA and flow cytometry results using chimeric 31.1 antibody, humanized 31.1 #5, #6 and biotinylated #5, #6.

| | EC50 from binding ELISA (ng/mL) | EC 50 from Flow Cytometry (ng/mL) AsPC-1 | EC50 from Flow Cytometry (ng/mL) AsPC-1 | EC50 from Flow Cytometry (ng/mL) LS-174T |
|---|---|---|---|---|
| H31.1 #5-biotin | 679.2 | 407.88 | UD | UD |
| H31.1 #6-biotin | 12790.3 | 367.56 | UD | UD |
| Murine 31.1 | 633.2 | UD | 97.43 | 62.82 |

IHC staining was carried out with biotinylated h31.1#5 and #6. There was no binding on colon cancer and small intestine cancer FFPE tissue blocks, the same as chimeric 31.1.

After examining the second round of h31.1 characterization and function, it was observed that there was aggregation in #5 and no binding of 31.1 in IHC staining on FFPE tissue blocks. A third round of transient transfection was performed to yield enough humanized 31.1 for function analysis both in vitro and in vivo.

Functional Analysis of h31.1 from combination of #11 & #16

To obtain enough humanized 31.1 material to thoroughly function analysis including animal study, h31.1 antibody #16 combination of heavy and light chain vectors (ven31.1-HC+ven31.1-LC, i.e., SEQ ID NOs:77 and 87) was selected due to the high affinity in binding ELISA and flow cytometry and used for 480 mL transient transfection (240 mL×2 Flasks). For control, 31.1 antibody #11 (sdr31.1-HC+sdr31.1-LC, i.e., SEQ ID NOs:76 and 86) was used for transient transfection due to the result from the first round transient transfection; high yield without binding ability in binding ELISA and Flow Cytometry.

Figure 9:
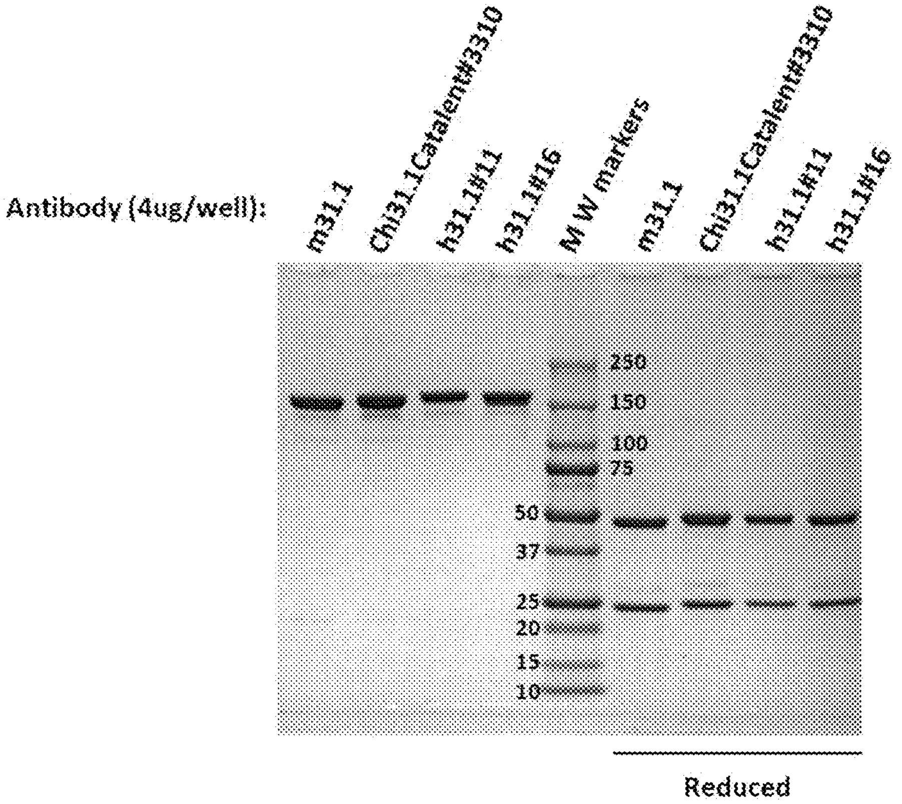
FIG. 9 shows Coomassie blue staining of two humanized 31.1 antibodies, namely #1 and #16, under non-reduced and reduced conditions.

After protein A/G purification, no aggregation was observed in h31.1 antibody #11 and h31.1 antibody #16. Total 149.6 mg h31.1 antibody #16 (4.4 mg/mL×34 mL) and 121 mg h31.1 antibody #11 (5.5 mg/mL X22 mL) were produced. The purity and integrity antibody are shown in FIG. 9; non-reducing condition on the left, reducing condition on the right. Murine 31.1 and chi 31.1 lot #3310 were used as reference.

Figure 10:
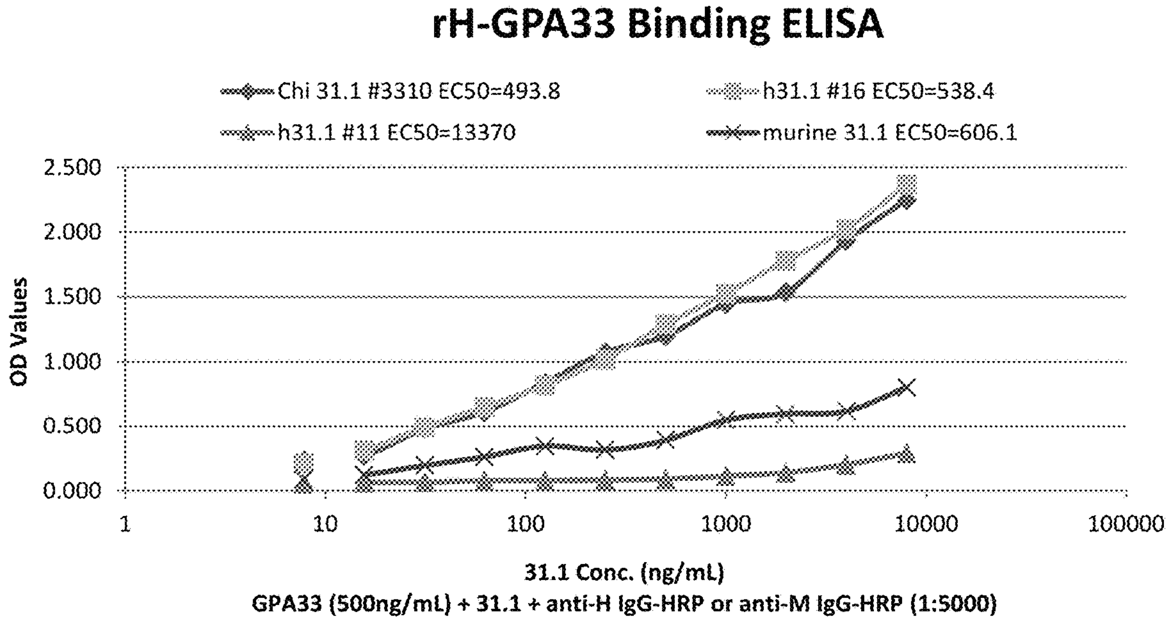
FIG. 10 shows the results of ELISA assays using two humanized 31.1 antibodies, namely #11 and #16.

Comparable dose-dependent binding affinity of humanized h31.1 antibody 31.1 #16 with chimeric 31.1 antibody lot #3310 was observed in rH-GPA33 binding ELISA and Flow Cytometry, as shown in FIG. 10 (ELISA results) and Table 7 (flow cytometry results).

TABLE 7

Reproducible flow cytometry results in two separate experiments using murine 31.1 antibody (m31.1), chimeric 31.1 antibody (Chi31.1), humanized h31.1 antibody 31.1 #11, and humanized h31.1 antibody #16.

| 31.1 conc. | MFI of h31.1 Binding to AspC-1 by Flow Cytometry | | | | | | | |
|---|---|---|---|---|---|---|---|---|
| (ng/ml) | m31.1 | m31.1 | Chi31.1 | Chi31.1 | h31.1#11 | h31.1#11 | h31.1#16 | h31.1#16 |
| 5000 | 1101 | 1114 | 1148 | 1170 | 117 | 117 | 1242 | 1289 |
| 1666.7 | 1327 | 1330 | 1292 | 1247 | 38.9 | 39 | 1417 | 1530 |
| 555.6 | 1396 | 1322 | 1264 | 1323 | 16.2 | 16.6 | 1515 | 1545 |
| 185.2 | 1045 | 1049 | 1056 | 1081 | 8.2 | 8.2 | 1040 | 1046 |
| 61.7 | 562 | 552 | 634 | 619 | 5.9 | 5.3 | 487 | 466 |
| 20.6 | 226 | 216 | 269 | 262 | 4 | 4 | 182 | 181 |
| 6.9 | 86 | 81 | 104 | 103 | 3.6 | 3.6 | 72 | 69 |
| 2.3 | 40 | 37 | 48 | 46 | 3.4 | 3.5 | 29.9 | 30.2 |
| 0 | 4.2 | 4.7 | 3.8 | 3.6 | 3.6 | 3.6 | 3.6 | 3.5 |

Figure 11:
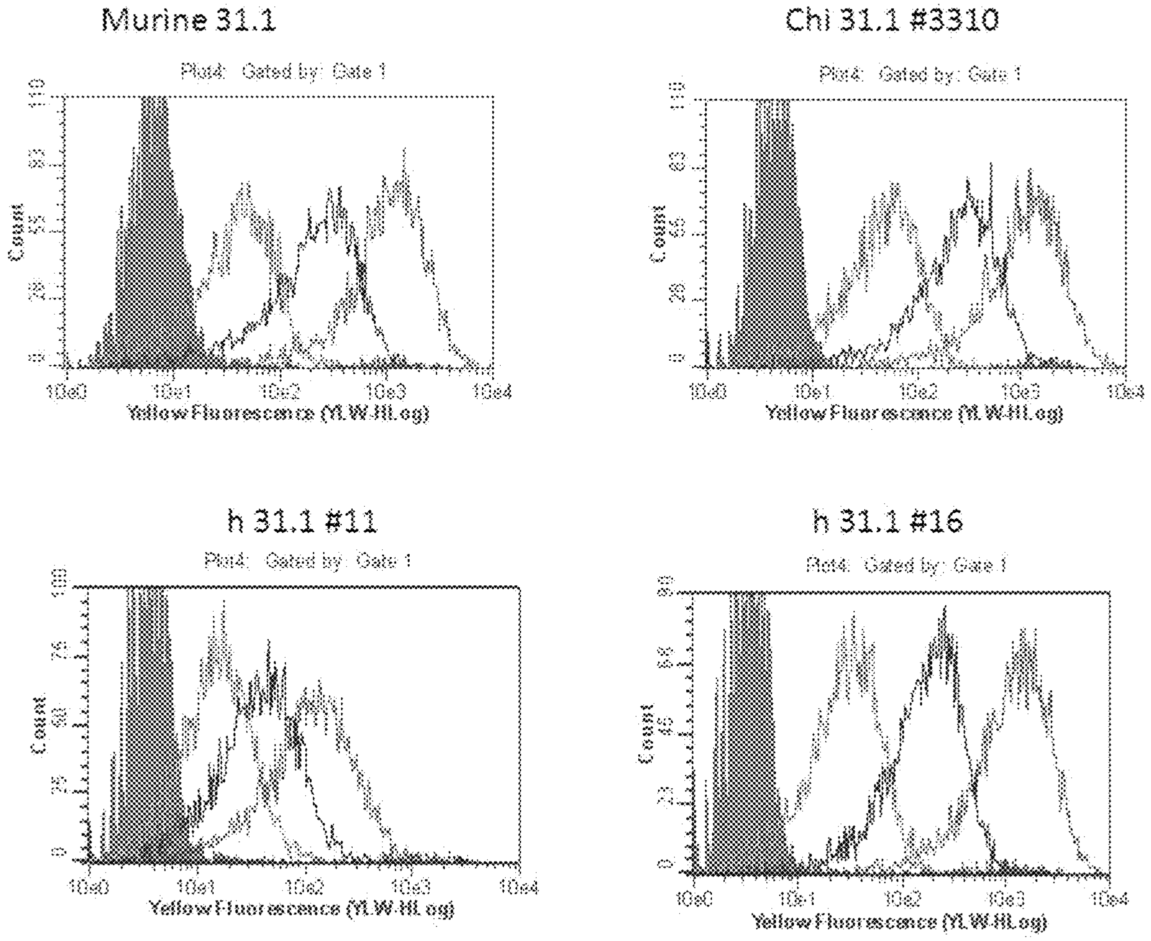
FIG. 11 shows flow cytometry results obtained using two humanized 31.1 antibodies, namely #11 and #16, to stain AsPC-1 cells (pancreatic cancer cell line).

The representative 31.1 binding to AsPC-1 cells by Flow Cytometry with concentration of 5000 ng/mL (rightmost curve), 185 ng/mL (third curve from left) and 20.6 ng/mL (second curve from left) and human IgG control (red, leftmost) are shown in FIG. 11.

Figure 12:
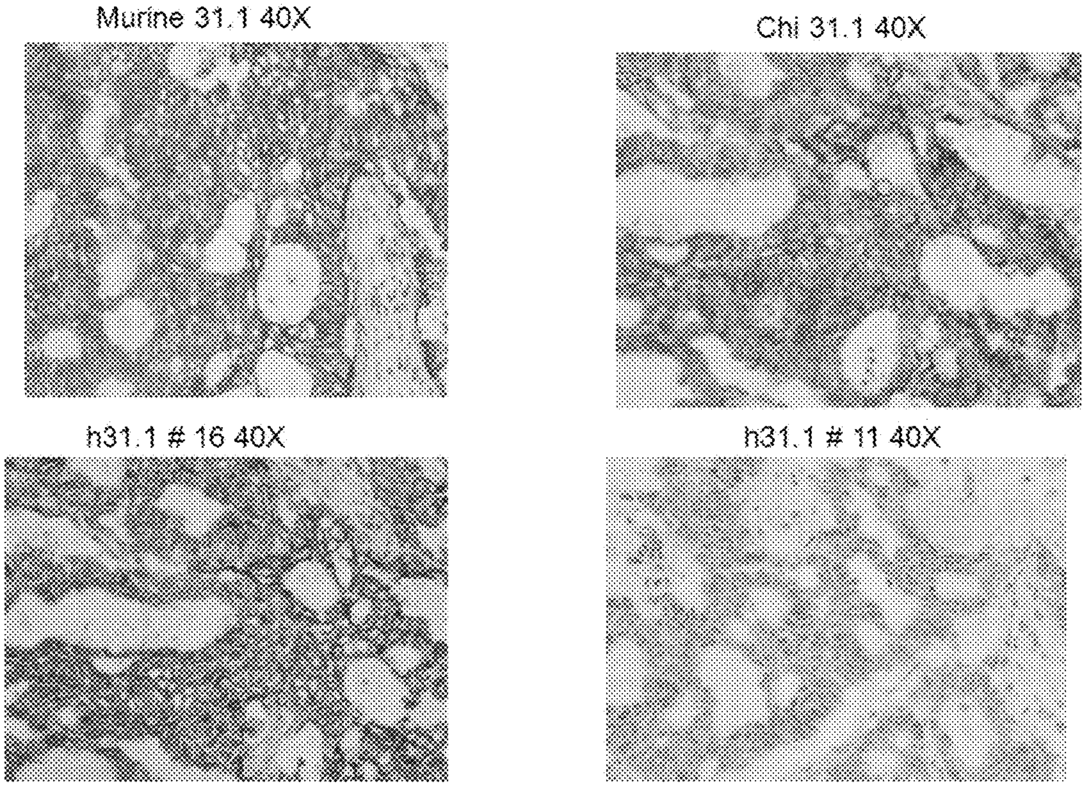
FIG. 12 shows the results of immunohistochemical staining of frozen colon cancer metastasis to liver samples by using humanized 31.1 #11 and #16.

There were no positive IHC staining on FFPE tumor tissue sections with murine 31.1, chimeric 31.1, and humanized 31.1, which confirmed our previous finding. Positive IHC staining was observed when applying these three antibodies on frozen tumor sections. Comparable results were observed among murine 31.1, chimeric 31.1 and humanized 31.1 antibody #16, humanized 31.1 antibody #11 was used as negative control. The raw data, picture and summary of the results are listed in Table 8 and FIG. 12.

TABLE 8

Summary of IHC results.

| | Postive #/Panc ca # | Positive#/Colon ca # |
|---|---|---|
| m31.1 | 2/5 | 4/4 |
| Chi 31.1 | 2/5 | 3/3 |
| h31.1 #16 | 2/5 | 4/4 |
| h31.1 #11 | 0/4 | 0/4 |

Figure 13:
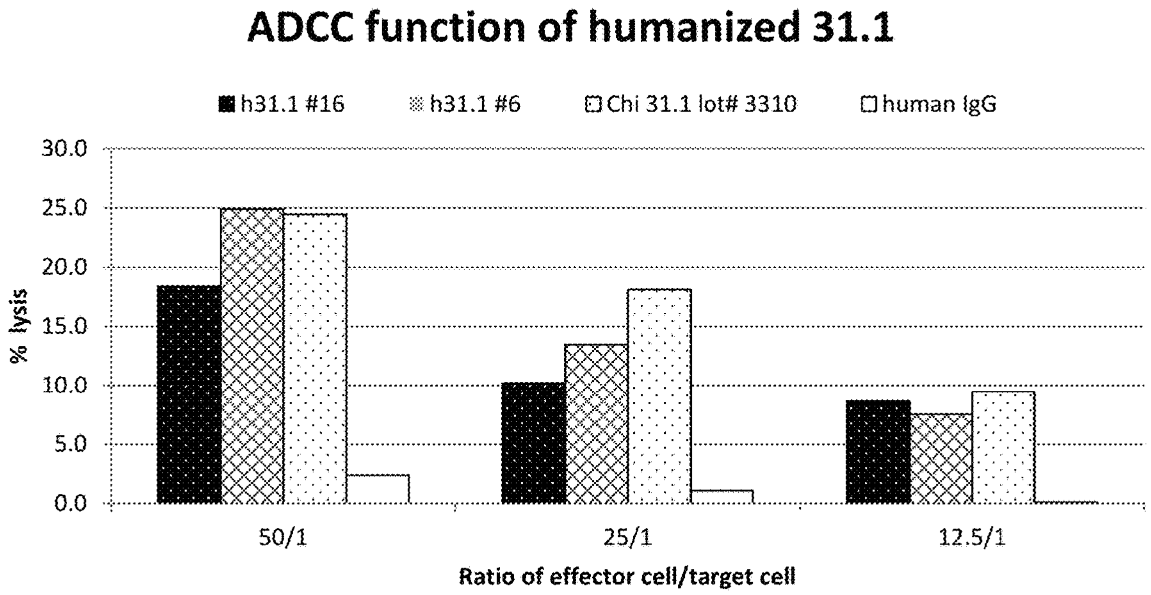
FIG. 13 shows the ADCC function of humanized 31.1 antibodies #16 (leftmost bar in each group), #6 (second bar from left in each group), chimeric 31.1 (third bar from left in each group) and human IgG control (rightmost bar in each group).

Tumor killing function of h31.1 from a combination of antibody #6 and antibody #16 along with chimeric 31.1 was tested by ADCC assay using pancreatic cancer cell line AsPC-1 as target cells, human IgG as negative control. As shown in FIG. 13, comparable tumor specific lysis was obtained from antibody #16 and #6 compared with chimeric 31.1, indicating the humanization of 31.1 did not adversely affect the 31.1 binding and ADCC function in vitro.

Figure 14:
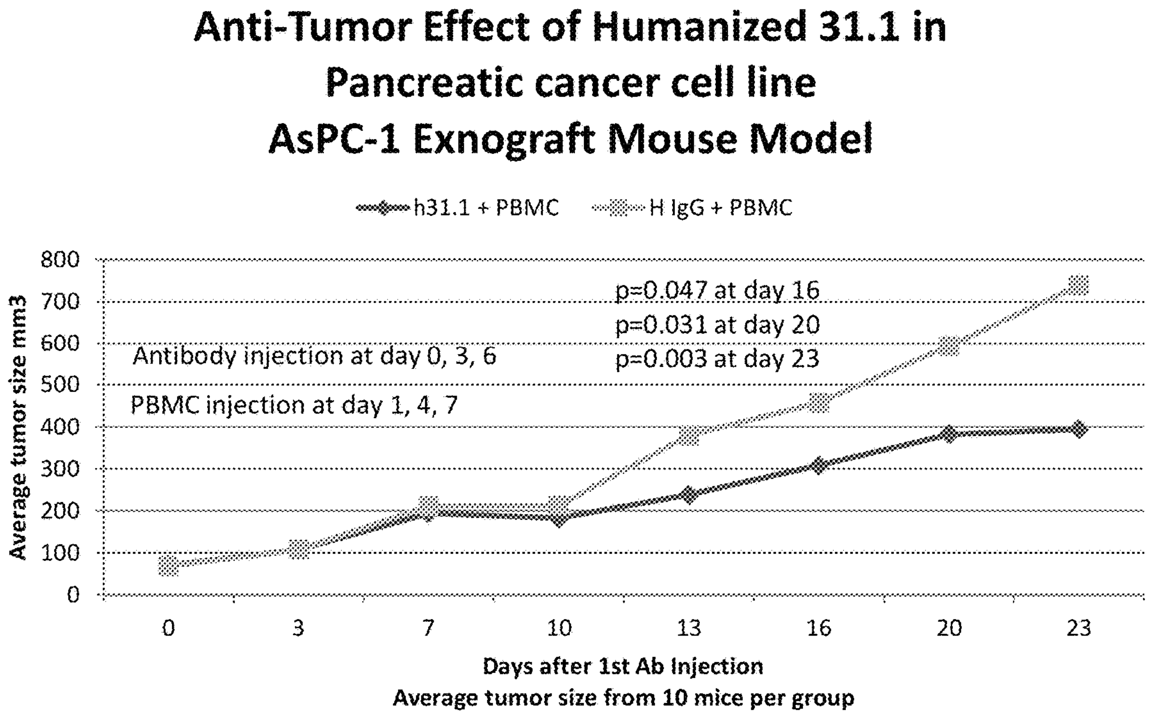
FIG. 14 shows the anti-tumor effect of humanized 31.1 antibody #16 (lower line) in an AsPC-1 (pancreatic cancer) xenograft model, as compared to a human IgG control (upper line). Antibody was injected at day 0, 3, and 6, and PMBC were injected at days 1, 4, and 7. Average tumor size was markedly decreased in mice injected with humanized 31.1 antibody #16.

H31.1 ADCC function in vivo was tested on AsPC-1 xenograft mouse model with h31.1 antibody #16. Significant tumor volume reduction was obtained from day 16 up to day 23 with p values from 0.047 to 0.003 after three antibody injections following PBMCs injections within 7 days compared to H IgG and PMBC injections as shown in FIG. 14.

All publications, patents and patent applications are herein incorporated by reference in their entirety to the same extent as if each individual publication, patent or patent application was specifically and individually indicated to be incorporated by reference in its entirety.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of reducing the incidence of or treating a cancer that expresses the A33 antigen, comprising administering an effective amount of an antibody or fragment thereof that binds to said A33 antigen to a subject in need thereof, wherein said antibody or fragment thereof comprises:

a) a heavy chain comprising the variable chain of antibody cdr31.1-HC (amino acids 1 to 118 of SEQ ID NO:74) and a light chain comprising the variable light chain of antibody cdr31.1-LC (amino acids 1 to 107 of SEQ ID NO:84);

b) a heavy chain comprising the variable chain of antibody cdr31.1-HC (amino acids 1 to 118 of SEQ ID NO:74) and a light chain comprising the variable light chain of antibody abb31.1-LC (amino acids 1 to 107 of SEQ ID NO:85);

c) a heavy chain comprising the variable chain of antibody cdr31.1-HC (amino acids 1 to 118 of SEQ ID NO:74) and a light chain comprising the variable light chain of antibody sdr31.1-LC (amino acids 1 to 107 of SEQ ID NO:86);

d) a heavy chain comprising the variable chain of antibody cdr31.1-HC (amino acids 1 to 118 of SEQ ID NO:74) and a light chain comprising the variable light chain of antibody ven31.1-LC (amino acids 1 to 107 of SEQ ID NO:87);

e) a heavy chain comprising the variable chain of antibody abb31.1-HC (amino acids 1 to 118 of SEQ ID NO:75) and a light chain comprising the variable light chain of antibody cdr31.1-LC (amino acids 1 to 107 of SEQ ID NO:84);

f) a heavy chain comprising the variable chain of antibody abb31.1-HC (amino acids 1 to 118 of SEQ ID NO:75) and a light chain comprising the variable light chain of antibody abb31.1-LC (amino acids 1 to 107 of SEQ ID NO:85);

g) a heavy chain comprising the variable chain of antibody abb31.1-HC (amino acids 1 to 118 of SEQ ID NO:75) and a light chain comprising the variable light chain of antibody sdr31.1-LC (amino acids 1 to 107 of SEQ ID NO:86);

h) a heavy chain comprising the variable chain of antibody abb31.1-HC (amino acids 1 to 118 of SEQ ID NO:75) and a light chain comprising the variable light chain of antibody ven31.1-LC (amino acids 1 to 107 of SEQ ID NO:87);

i) a heavy chain comprising the variable chain of antibody sdr31.1-HC (amino acids 1 to 118 of SEQ ID NO:76) and a light chain comprising the variable light chain of antibody cdr31.1-LC (amino acids 1 to 107 of SEQ ID NO:84);

j) a heavy chain comprising the variable chain of antibody sdr31.1-HC (amino acids 1 to 118 of SEQ ID NO:76) and a light chain comprising the variable light chain of antibody abb31.1-LC (amino acids 1 to 107 of SEQ ID NO:85);

k) a heavy chain comprising the variable chain of antibody sdr31.1-HC (amino acids 1 to 118 of SEQ ID NO:76) and a light chain comprising the variable light chain of antibody sdr31.1-LC (amino acids 1 to 107 of SEQ ID NO:86);

l) a heavy chain comprising the variable chain of antibody sdr31.1-HC (amino acids 1 to 118 of SEQ ID NO:76) and a light chain comprising the variable light chain of antibody ven31.1-LC (amino acids 1 to 107 of SEQ ID NO:87);

m) a heavy chain comprising the variable chain of antibody ven31.1-HC (amino acids 1 to 118 of SEQ ID NO:77) and a light chain comprising the variable light chain of antibody cdr31.1-LC (amino acids 1 to 107 of SEQ ID NO:84);

n) a heavy chain comprising the variable chain of antibody ven31.1-HC (amino acids 1 to 118 of SEQ ID NO:77) and a light chain comprising the variable light chain of antibody abb31.1-LC (amino acids 1 to 107 of SEQ ID NO:85);

o) a heavy chain comprising the variable chain of antibody ven31.1-HC (amino acids 1 to 118 of SEQ ID NO:77) and a light chain comprising the variable light chain of antibody sdr31.1-LC (amino acids 1 to 107 of SEQ ID NO:86);

p) a heavy chain comprising the variable chain of antibody ven31.1-HC (amino acids 1 to 118 of SEQ ID NO:77) and a light chain comprising the variable light chain of antibody ven31.1-LC (amino acids 1 to 107 of SEQ ID NO:87);

q) a heavy chain polypeptide of antibody cdr31.1-HC (SEQ ID NO:74) and a light chain polypeptide of antibody cdr31.1-LC (SEQ ID NO:84);

r) a heavy chain polypeptide of antibody cdr31.1-HC (SEQ ID NO:74) and a light chain polypeptide of antibody abb31.1-LC (SEQ ID NO:85);

s) a heavy chain polypeptide of antibody cdr31.1-HC (SEQ ID NO:74) and a light chain polypeptide of antibody sdr31.1-LC (SEQ ID NO:86);

t) a heavy chain polypeptide of antibody cdr31.1-HC (SEQ ID NO:74) and a light chain polypeptide of antibody ven31.1-LC (SEQ ID NO:87);

u) a heavy chain polypeptide of antibody abb31.1-HC (SEQ ID NO:75) and a light chain polypeptide of antibody cdr31.1-LC (SEQ ID NO:84);

v) a heavy chain polypeptide of antibody abb31.1-HC (SEQ ID NO:75) and a light chain polypeptide of antibody abb31.1-LC (SEQ ID NO:85);

w) a heavy chain polypeptide of antibody abb31.1-HC (SEQ ID NO:75) and a light chain polypeptide of antibody sdr31.1-LC (SEQ ID NO:86);

x) a heavy chain polypeptide of antibody abb31.1-HC (SEQ ID NO:75) and a light chain polypeptide of antibody ven31.1-LC (SEQ ID NO:87);

y) a heavy chain polypeptide of antibody sdr31.1-HC (SEQ ID NO:76) and a light chain polypeptide of antibody cdr31.1-LC (SEQ ID NO:84);

z) a heavy chain polypeptide of antibody sdr31.1-HC (SEQ ID NO:76) and a light chain polypeptide of antibody abb31.1-LC (SEQ ID NO:85);

aa) a heavy chain polypeptide of antibody sdr31.1-HC (SEQ ID NO:76) and a light chain polypeptide of antibody sdr31.1-LC (SEQ ID NO:86);

bb) a heavy chain polypeptide of antibody sdr31.1-HC (SEQ ID NO:76) and a light chain polypeptide of antibody ven31.1-LC (SEQ ID NO:87);

cc) a heavy chain polypeptide of antibody ven31.1-HC (SEQ ID NO:77) and a light chain polypeptide of antibody cdr31.1-LC (SEQ ID NO:84);

dd) a heavy chain polypeptide of antibody ven31.1-HC (SEQ ID NO:77) and a light chain polypeptide of antibody abb31.1-LC (SEQ ID NO:85);

ee) a heavy chain polypeptide of antibody ven31.1-HC (SEQ ID NO:77) and a light chain polypeptide of antibody sdr31.1-LC (SEQ ID NO:86); or ff) a heavy chain polypeptide of antibody ven31.1-HC (SEQ ID NO:77) and a light chain polypeptide of antibody ven31.1-LC (SEQ ID NO:87).

2. The method of claim 1, wherein said antibody or antibody fragment specifically binds the amino acid sequence of one or more of SEQ ID NOs:10, 11, 12, or 13.

3. The method of claim 1, wherein said antibody or antibody fragment has anti-tumor activity, is a human IgG1 or human IgG3 antibody, or is a Fab, Fab', F(ab')2, Fv, CDR, paratope, or portion of an antibody that is capable of binding the antigen, is directly or indirectly conjugated to a label, cytotoxic agent, therapeutic agent, or an immunosuppressive agent, and/or potentiates ADCC or CDC.

4. The method of claim 1, wherein said antibody or antibody fragment is admixed in a composition with another antibody, label, cytotoxic agent, therapeutic agent, or an immunosuppressive agent, is administered in combination with an antibody, label, cytotoxic agent, therapeutic agent, or an immunosuppressive agent, simultaneously or sequentially, wherein said label is optionally a chemiluminescent label, paramagnetic label, an MM contrast agent, fluorescent label, bioluminescent label, or radioactive label, wherein said paramagnetic label is optionally paramagnetic label is aluminum, manganese, platinum, oxygen, lanthanum, lutetium, scandium, yttrium, or gallium, wherein the cytotoxic agent is optionally a moiety that inhibits DNA, RNA, or protein synthesis, a radionuclide, ribosomal inhibiting protein, $^{212}Bi$, $^{131}I$, $^{188}Re$,$^{90}Y$, vindesine, methotrexate, adriamycin, cisplatin, pokeweed antiviral protein, *Pseudomonas* exotoxin A, ricin, diphtheria toxin, ricin A chain, or cytotoxic phospholipase enzyme, wherein optionally said therapeutic agent is a lymphokine or growth factor, and/or wherein optionally wherein said immunosuppressive agent is cyclosporine, leflunomide, methotrexate, azothiprine, mercaptopurine, dactinomycin, tacrolimus, or sirolimus.

5. The method of claim 1, wherein said antibody or antibody fragment is administered in a pharmaceutically acceptable carrier.

6. The method of claim 1, further comprising detecting the 31.1 epitope in a tumor sample, lymph, urine, cerebrospinal fluid, amniotic fluid, inflammatory exudate, blood, serum, stool, or liquid collected from the colorectal tract.

7. The method of claim 6, wherein the presence of said 31.1 epitope is indicative of a carcinoma, optionally lung, breast, pancreas, uterine, esophageal, colorectal, or liver cancer.

8. The method of claim 6, wherein said 31.1 epitope is detected in vitro by an assay selected from the group consisting of Western blot, radioimmunoassays, ELISA (enzyme linked immunosorbent assay), "sandwich" immunoassays, lateral flow assay, immunoprecipitation assays, precipitation reactions, gel diffusion precipitation reactions, immunodiffusion assays, agglutination assays, complement-fixation assays, immunohistochemical assays, fluorescent immunoassays, and protein A immunoassays, or is detected in vivo by a method comprising positron emission tomography (PET), CCD low-light monitoring system, x-ray, CT scanning, scintigraphy, photo acoustic imaging, single photon emission computed tomography (SPECT), magnetic resonance imaging (MM), ultrasound, paramagnetic imaging, and endoscopic optical coherence tomography.

9. The method of claim 1, wherein said antibody or antibody fragment comprises (a) a heavy chain variable region comprising amino acids 1-118 of SEQ ID NO: 77, and (b) a light chain variable region comprising amino acids 1-107 of SEQ ID NO: 87.

10. The method of claim 1, wherein said antibody or antibody fragment is humanized.

11. The method of claim 1, wherein the light chain of said antibody comprises SEQ ID NO: 87 and the heavy chain of said antibody comprises SEQ ID NO: 77.

12. The method of claim 1, wherein said antibody or antibody fragment specifically binds the amino acid sequence of at least one of SEQ ID NOs:10, 11, 12, or 13.

13. The method of claim 1, wherein said antibody or antibody fragment has anti-tumor activity.

14. The method of claim 1, wherein said antibody or antibody fragment comprises a human IgG1 or human IgG3 constant region.

15. The method of claim 1, wherein said antibody or antibody fragment is an Fab, Fab', or F(ab')2.

16. The method of claim 1, wherein said antibody or antibody fragment is directly or indirectly conjugated to a label, cytotoxic agent, therapeutic agent, or an immunosuppressive agent.

17. The method of claim 1, wherein said antibody or antibody fragment potentiates ADCC.

18. The method of claim 1, wherein said antibody or antibody fragment potentiates CDC.

* * * * *